United States Patent
Engler et al.

(10) Patent No.: US 12,187,992 B2
(45) Date of Patent: Jan. 7, 2025

(54) METHOD AND DEVICE FOR EARLY CANCER SCREENING

(71) Applicant: The Regents of the University of California, Oakland, CA (US)

(72) Inventors: Adam Engler, San Diego, CA (US); Afsheen Banisadr, La Jolla, CA (US); Pranjali Beri, La Jolla, CA (US); Alexander Fuhrmann, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 610 days.

(21) Appl. No.: 17/180,492

(22) Filed: Feb. 19, 2021

(65) Prior Publication Data

US 2021/0253987 A1    Aug. 19, 2021

Related U.S. Application Data

(60) Provisional application No. 62/978,658, filed on Feb. 19, 2020.

(51) Int. Cl.
| | |
|---|---|
| *C12M 3/00* | (2006.01) |
| *A61P 35/00* | (2006.01) |
| *C12M 1/12* | (2006.01) |
| *C12N 5/071* | (2010.01) |
| *G01N 33/574* | (2006.01) |

(52) U.S. Cl.
CPC ............ *C12M 21/08* (2013.01); *C12M 25/02* (2013.01); *C12N 5/0679* (2013.01); *G01N 33/574* (2013.01); *A61P 35/00* (2018.01)

(58) Field of Classification Search
None
See application file for complete search history.

(56) References Cited

U.S. PATENT DOCUMENTS

2017/0298316 A1* 10/2017 Kennedy, III ......... C12M 23/14

OTHER PUBLICATIONS

Thompson et al (Thompson TJ, Han B. Analysis of adhesion kinetics of cancer cells on inflamed endothelium using a microfluidic platform. Biomicrofluidics. 2018;12(4):042215. Published Jun. 8, 2018. doi:10.1063/1.5025891) (Year: 2018).*
Fuhrmann et al (Metastatic State of Cancer Cells May Be Indicated by Adhesion Strength, Biophys J. Feb. 28, 2017; 112(4): 736-745) (Year: 2017).*
Pijuan et al (In vitro Cell Migration, Invasion, and Adhesion Assays: From Cell Imaging to Data Analysis Front. Cell Dev. Biol., Jun. 14, 2019). (Year: 2019).*
Khalil et al (Review of Cell Adhesion Studies for Biomedical and Biological Applications. Int J Mol Sci. 2015;16(8):18149-18184. Published Aug. 5, 2015), (Year: 2015).*
Wagner et al. (Adhesion of hematopoietic progenitor cells to human mesenchymal stem cells as a model for cell-cell interaction. Exp Hematol. 2007;35(2):314-325), (Year: 2007).*
Fu et al (Shear assay measurements of cell adhesion on biomaterials surfaces, Materials Science and Engineering, 29, (2009) 1293-1301), (Year: 2009).*
Peel et al. (Effect of cell-cell interactions on the observable strength of adhesion of sheets of cells. Ann Biomed Eng. 1999;27(2):236-246). (Year: 1999).*
Beri et al. Migratory Propensity of Metastatic Breast Cancer Cells as a Function of Adhesion Strength. Presentation at BMES—Biomedical Engineering Society annual meeting, Phoenix, AZ, Oct. 14, 2017.
Fuhrmann et al. Metastatic State of Cancer Cells May Be Indicated by Adhesion Strength. Biophys J. Feb. 28, 2017;112(4):736-745.
Boettiger, David, "Quantitative Measurements of Integrin-Mediated Adhesion to Extracellular Matrix," Methods of Enzymology, 2007, 426, pp. 1-25.
Fischer et al., "Tumor cell adhesion and migration supported by interaction of a receptor-protease complex with its inhibitor," The Journal of Clinical Investigation, 1999, 104, pp. 1213-1221.
Fuhrmann et al., "Cation Type Specific Cell Remodeling Regulates Attachment Strength," PLoS One, 2014, vol. 9, Issue 7, e102424.
Lu et al., "Microfluidic Shear Devices for Quantitative Analysis of Cell Adhesion," Analytical Chemistry, 2004, vol. 76, No. 18, pp. 5257-5264.
Palmer et al., "Single cell adhesion measuring apparatus (SCAMA): application to cancer cell lines of different metastatic potential and voltage-gated Na+ channel expression," Eur Biophys J, 2008, 37, pp. 359-368.
Reticker-Flynn et al., "A combinatorial extracellular matrix platform identifies cell-extracellular matrix interactions that correlate with metastasis," Nature Communications, 2012, 3, 12 pages.

* cited by examiner

*Primary Examiner* — Laura B Goddard
*Assistant Examiner* — Sarah A Alsomairy
(74) *Attorney, Agent, or Firm* — Foley & Lardner LLP

(57) ABSTRACT

The present disclosure provides a device for assessing adhesion strength of a cancer cell and methods of using the same.

9 Claims, 30 Drawing Sheets

Specification includes a Sequence Listing.

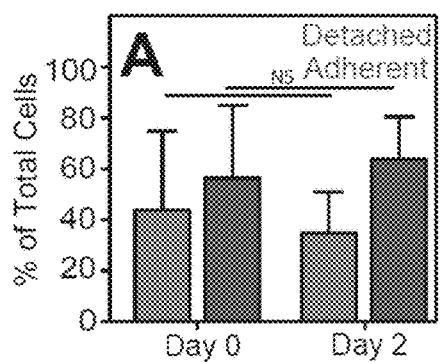
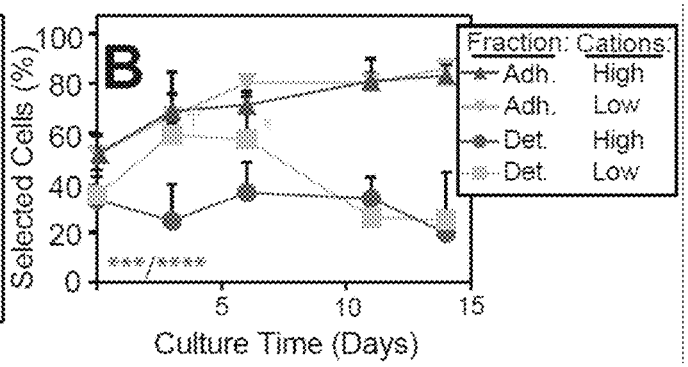
FIG. 2A
FIG. 2B
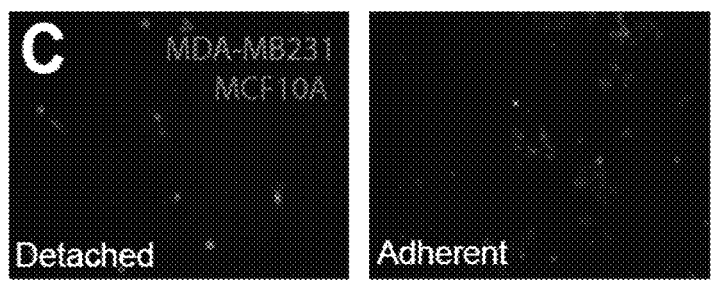
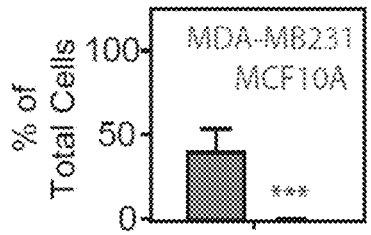
FIG. 2C
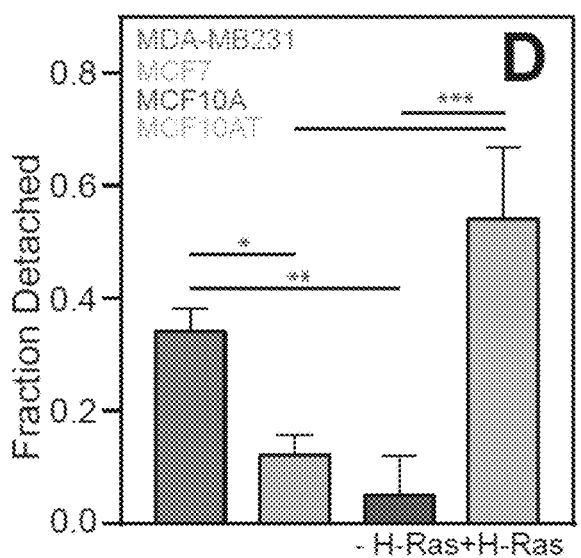
FIG. 2D

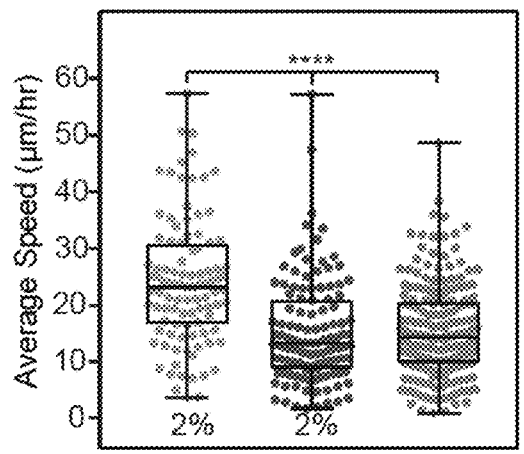
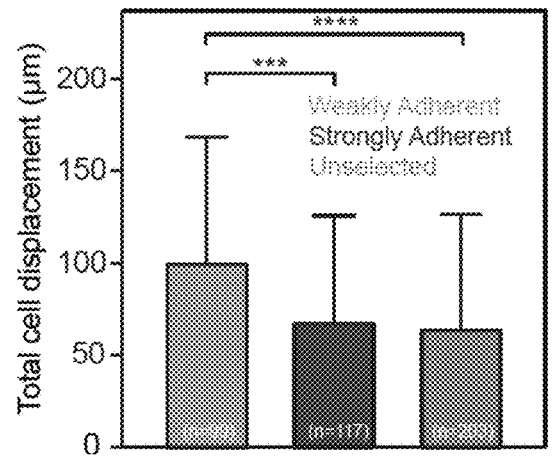
FIG. 3A    FIG. 3B
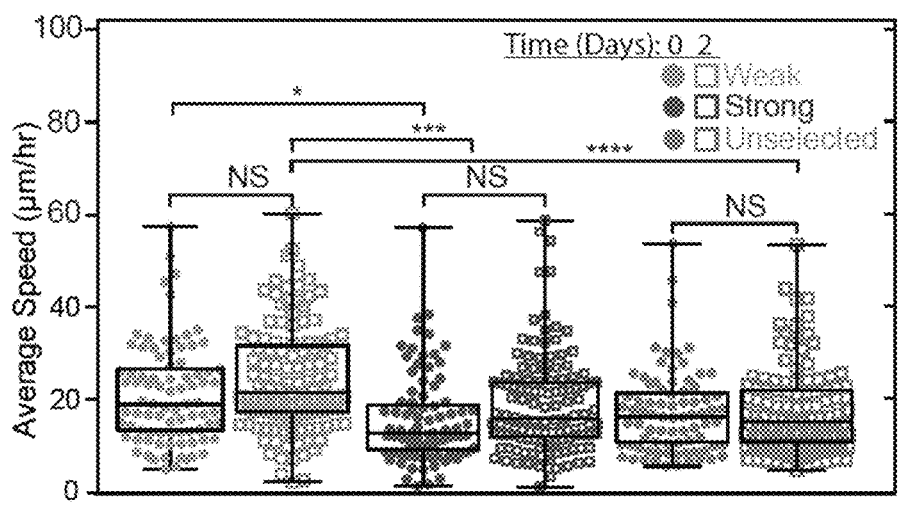
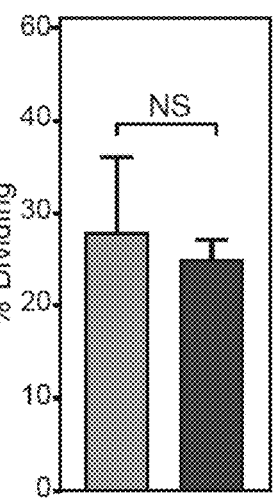
FIG. 3C    FIG. 3D

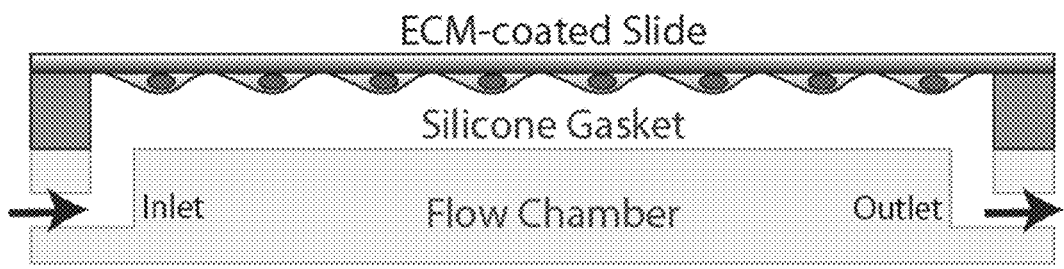
FIG. 7B
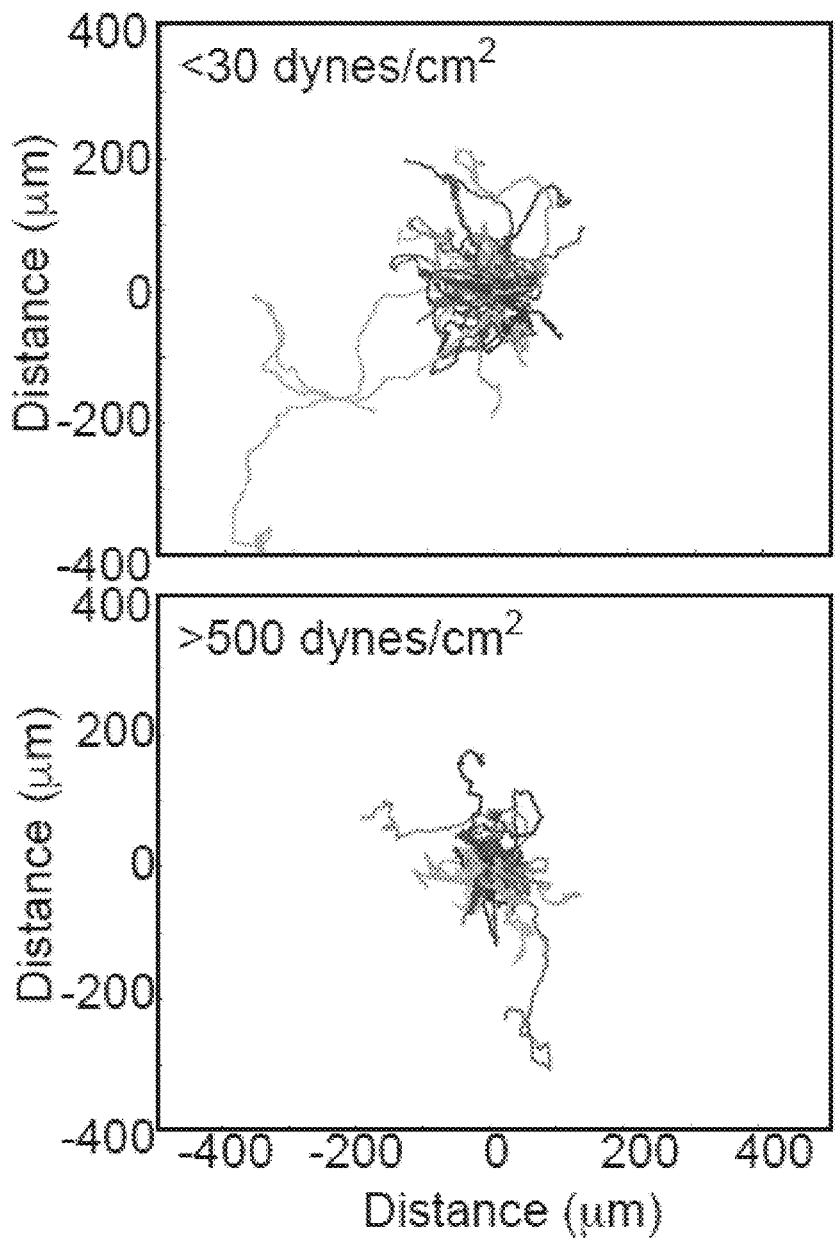
FIG. 8A
FIG. 8B

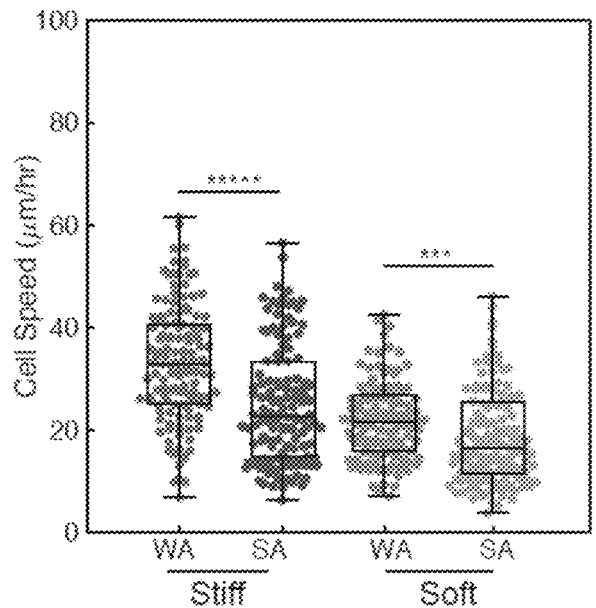 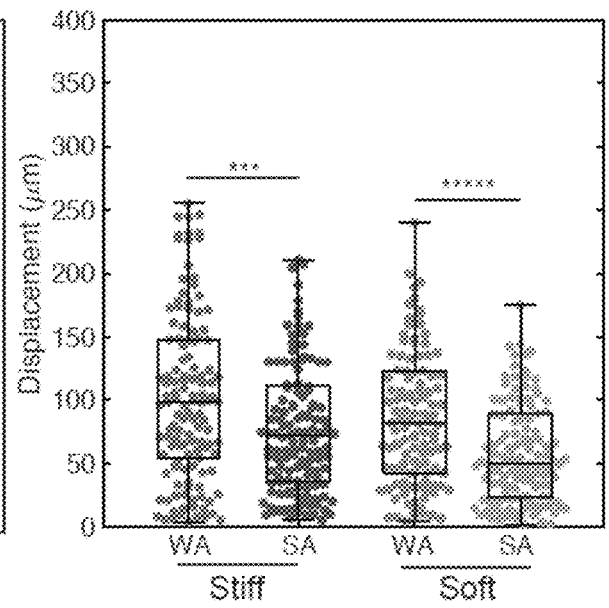
FIG. 10A      FIG. 10B
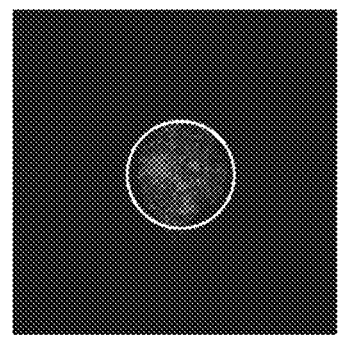 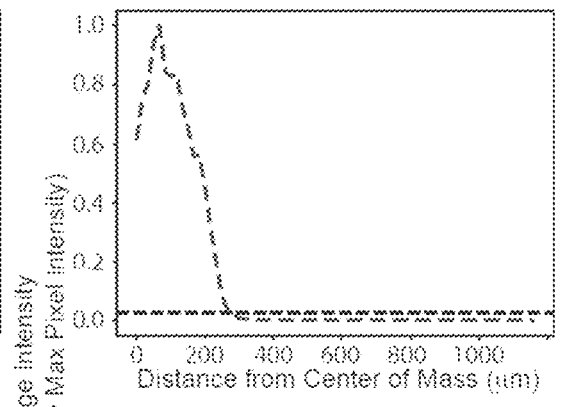
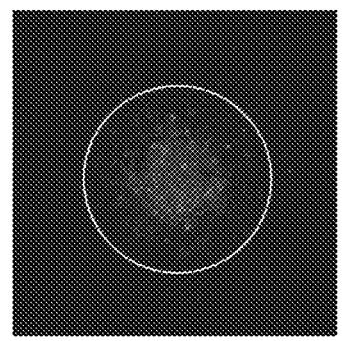 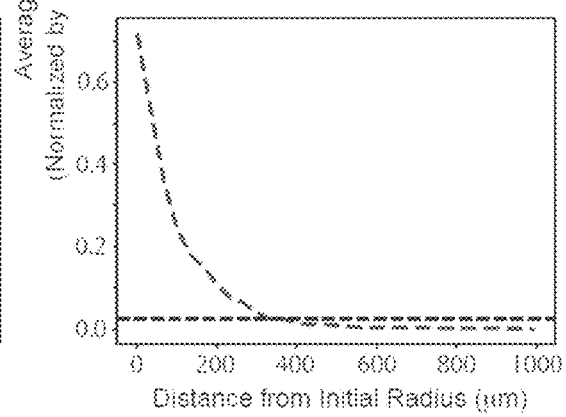
FIG. 11

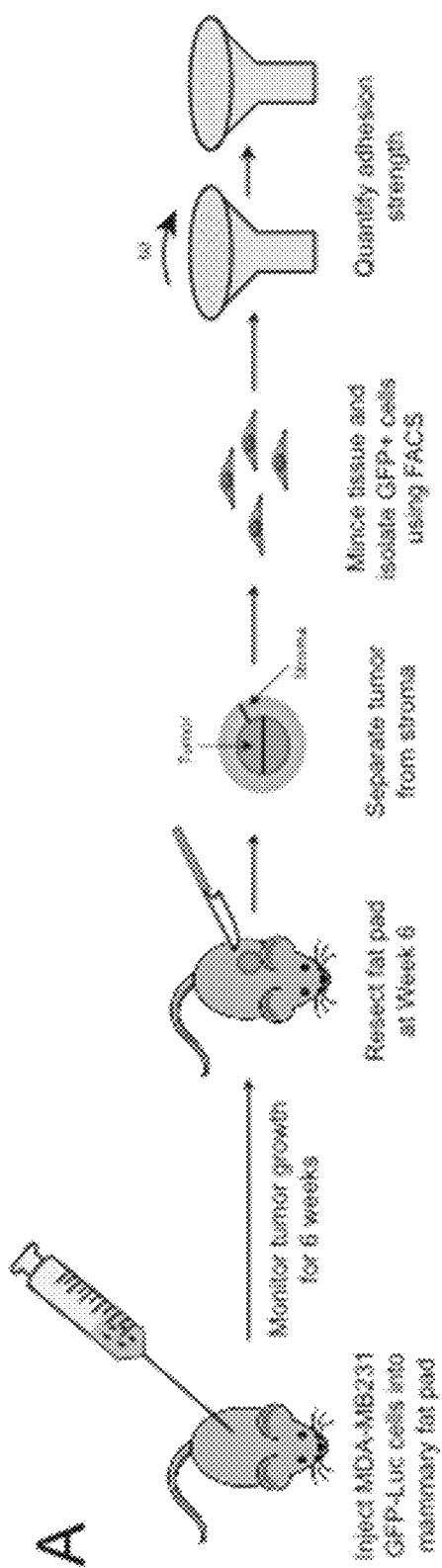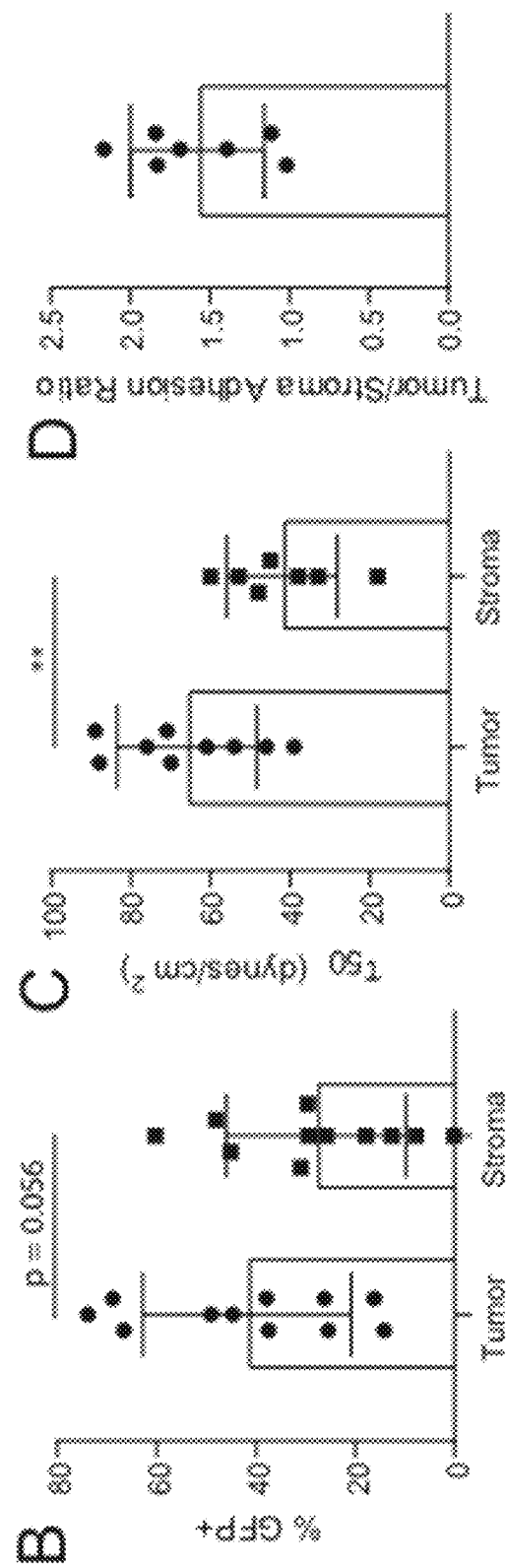
FIGS. 32A-32D

METHOD AND DEVICE FOR EARLY CANCER SCREENING

CROSS-REFERENCE TO RELATED APPLICATION

This application claims priority to U.S. Provisional Application No. 62/978,658, filed Feb. 19, 2020, the entire content of which is incorporated herein by reference.

STATEMENT OF GOVERNMENT SUPPORT

This invention was made with government support under Grant No. CA217735 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 6, 2021, is named 114198-5021_SL.txt and is 2,996 bytes in size.

FIELD OF THE DISCLOSURE

The disclosure relates generally to cancer and more specifically to a methods and a device for assessing adhesion strength and metastatic potential of cancer cells.

BACKGROUND OF THE DISCLOSURE

The high mortality rate associated with cancer is due to metastasis from a primary tumor to a distal site (1, 2). Patient outcomes typically scale with rate of cell dissemination from the tumor, resulting in lower five-year survival rates for aggressive tumors such as invasive ductal carcinoma (1). However, determining cell dissemination rate from a tumor is difficult due to heterogeneity, i.e., cells in the same tumor have different propensities for forming secondary metastases (3-5). Furthermore, there are no universal biochemical markers that predict metastatic potential across solid tumors (4, 6); next generation assays that use these biomarkers typically only surveil cells post-intravasation.

Metastases are the cause of 90% of human cancer deaths,[17] can occur more than 10 years beyond primary tumor resection,[18] and are not infrequent.[1-3] Progress in identifying cells primed to metastasize and in assessing metastatic risk has been slow. This may be due in part to the lack of consistent molecular prognostic markers Therefore, a need exists for a device for monitoring tumor stroma for individual metastatic cells to determine metastatic potential along with compositions or methods using the same.

SUMMARY OF THE DISCLOSURE

Tumors are heterogeneous and comprised of cells with different dissemination abilities. Despite significant effort, there is no universal biological marker that serves as a metric for metastatic potential of solid tumors. Common to disseminating cells from such tumors, however, is the need to modulate their adhesion as they detach from the tumor and migrate through stroma to intravasate. Applicant has discovered that adhesion strength is heterogeneous even amongst cancer cells within a given population, and using a parallel plate flow chamber, these populations were separated and sorted into weakly and strongly adherent groups; when cultured under stromal conditions, this adhesion phenotype was stable over multiple days, sorting cycles, and common across all epithelial tumor lines investigated. Weakly adherent cells displayed increased migration in both 2D and 3D migration assays; this was maintained for several days in culture. Subpopulations did not show differences in expression of proteins involved in the focal adhesion complex but did exhibit intrinsic focal adhesion assembly as well as contractile differences that resulted from differential expression of genes involved in microtubules, cytoskeleton linkages, and motor activity. In human breast tumors, expression of genes associated with the weakly adherent population resulted in worse progression-free and disease-free intervals. Thus, Applicant has determined that adhesion strength is a stable marker for migration and metastatic potential within a given tumor population and that the fraction of weakly adherent cells present within a tumor acts as a physical marker for metastatic potential.

Accordingly, in one aspect, the present disclosure provides a device for assessing adhesion strength of a cancer cell or population of cells or tumor tissue The device comprises, consists essentially of, or alternatively consists of, a solid substrate comprising, consisting essentially of, or alternatively consisting of, a surface (such as a first surface) coated with an extracellular matrix (ECM) protein, a housing having comprising, consisting essentially of, or alternatively consisting of an inlet and an outlet, the housing being configured to be sealingly attached to the surface (such as the first surface) of the solid substrate, thereby forming a flow channel within the housing, and a collection chamber disposed in fluid communication with the outlet, the collection chamber being configured to capture weakly adherent cells. In various embodiments, the solid substrate is formed from glass or polysulfone or both.

In various embodiments, the inner surface of the flow channel is at least partially coated with ECM. In various embodiments, the ECM coating forms at least a part of the inner surface of the flow channel is at least partially coated with the ECM protein. In various embodiments, the inner surface of the flow channel. In various embodiments, the solid substrate is formed from glass or polysulfone or both. In various embodiments, the device also includes (such as, further comprises) a gasket disposed between the solid substrate and the housing, thereby forming a fluid-tight seal. In various embodiments, the device also includes (such as, further comprises) a reservoir containing a shear buffer, the reservoir being provided in fluid communication with the inlet, wherein the shear buffer is configured to flow through flow channel in contact with the ECM protein. In various embodiments, the shear buffer comprises, consists essentially of, or alternatively consists of phosphate-buffered saline (PBS)+MgCa (i.e., PBS comprising $Mg^{2+}$ and $Ca^{2+}$, either of which is at its physiological cation concentration, for example the blood or serum cation concentration). In various embodiments, the shear buffer comprises, consists essentially of, or alternatively consists of 0.5 mM $Mg^{2+}$ and 1 mM $Ca^{2+}$ in PBS. In various embodiments, the shear buffer comprises, consists essentially of, or alternatively consists of 0.5 mM $MgCl_2$ and 1 mM $CaCl_2$) in PBS.

In various embodiments, the solid substrate further comprises a cell culture (such as the cancer cell, population thereof or tumor sample) adhered to the ECM protein. In various embodiments, the cell culture comprises, consists essentially of, or alternatively consists of cancer cells obtained from a tumor biopsy from a subject. In various embodiments, the cancer cell, population, or tumor sample is a solid tumor, e.g., a carcinoma or a sarcoma that can be isolated from a tumor biopsy of a subject. In various embodiment, the cancer cell is an epithelial cancer cell. In various embodiments, the cancer cell, population or tumor comprises, consists essentially of, or consists of a breast cancer cell, a prostate cancer cell, or a lung cancer cell. In various embodiments, the tumor biopsy is from a primary tumor or a metastatic tumor. Additionally or alternatively, the subject is suspected of developing a metastatic cancer and is an animal, e.g. a mammal such as a canine, feline, equine, bovine, or a human patient In another aspect, the disclosure provides a method of assessing adhesion strength of a cancer cell, population of tumor. The method includes, comprises, consists essentially of, or alternatively consists of, culturing the cell, population or tumor on the device as described herein, e.g. a solid substrate coated with an extracellular matrix (ECM) protein, such as the solid substrate of the device as provided herein, sealingly attaching the solid substrate to a housing to form a flow channel over the cultured cancer cell, population or tumor, flowing a shear buffer through the flow channel, collecting the buffer (for example, after flowing through the flow channel), and counting the cancer cells within the collected buffer. In various embodiments, the number of cancer cells within the collected buffer correlates (such as positively correlates) to metastatic potential of the cancer cell, e.g., the higher the number of cell the greater the likelihood of metastasis.

Also provided is a method of assessing adhesion strength of a population of cancer cells or tumor. The method comprises, consists essentially of, or consists of culturing a population of cancer cells or tumor on a solid substrate coated with an extracellular matrix (ECM) protein; sealingly attaching the solid substrate to a housing to form a flow channel over the population of cancer cells or tumor; flowing a shear buffer through the flow channel; collecting the buffer after flowing through the flow channel; and counting the cancer cells within the collected buffer. In various embodiments, the number of cancer cells within the collected buffer correlates to the adhesion strength of the cancer cell population, that is, the lower the number of cells the lower the adhesion strength. In one aspect, the device as described herein can be used to perform this method. In various embodiments, the cancer cell population or tumor sample is a solid tumor, e.g., a carcinoma or a sarcoma that can be isolated from a tumor biopsy of a subject. In various embodiment, the cancer cell is an epithelial cancer cell. In various embodiments, the cancer cell, population or tumor comprises a breast cancer cell, a prostate cancer cell, or a lung cancer cell. The cells can be animal, mammalian, e.g., feline, canine or human.

In various embodiments, the method further comprises counting the number of cancer or tumor cells cultured on the solid substrate, for example in the culturing step or after the flowing step. In further embodiments, the method comprises determining the percentage of cancer cell number in the collected buffer over the total number of cancer cells initially cultured on the solid substrate. Additionally or alternatively, the percentage correlates to adhesion strength of the cancer cell population. In further embodiments, the method comprises determining the ratio of the number of cancer cells in the collected buffer versus the number of cells on the solid substrate after the flowing step. Additionally or alternatively, the ratio correlates to adhesion strength of the cancer cell population.

In various embodiments, the shear buffer comprises, consists essentially of, or alternatively consists of phosphate-buffered saline (PBS)+MgCa (i.e., PBS comprising $Mg^{2+}$ and $Ca^{2+}$, each of which is at its physiological cation concentration, for example the serum cation concentration). In various embodiments, the shear buffer comprises, consists essentially of, or alternatively consists of 0.5 mM $Mg^{2+}$ and 1 mM $Ca^{2+}$ in PBS. In various embodiments, the shear buffer comprises, consists essentially of, or alternatively consists of 0.5 mM $MgCl_2$ and 1 mM $CaCl_2$) in PBS.

In various embodiments, the cell culture comprises, consists essentially of, or alternatively consists of cancer cells obtained from a tumor biopsy from a subject, e.g., a solid tumor such as a carcinoma or sarcoma. In various embodiments, the cancel cell population is isolated from a tumor biopsy of a subject. In various embodiments, the tumor biopsy is from a primary tumor or a metastatic tumor. In various embodiment, the cancer cell is an epithelial cancer cell. In various embodiments, the cancer cell population comprises, or consists essentially of, or consists of a population from the group of: breast cancer cells, prostate cancer cells, or lung cancer cells. In one aspect, the device as described herein can be used to perform this method. In various embodiments, the solid substrate is formed from glass or polysulfone or both.

In one aspect, provided is a method for selecting a therapy for treating cancer. The method comprises, consists essentially of, or alternatively consists of culturing a first population of cancer cells on a first solid substrate coated with an extracellular matrix (ECM) protein in the presence of the therapy; separately culturing a second population of the cancer cells on a second solid substrate coated with the extracellular matrix (ECM) protein in the absence of the therapy; attaching (for example, sealingly attaching) the first and second solid substrates to a housing to form a flow channel over the cancer cell populations; flowing a shear buffer through the flow channels of the populations; collecting the buffer after flowing through the flow channels of the populations; and determining the number of cancer cells of the populations within the collected buffer. In various embodiments, less cells counted in the presence of the therapy as compared to the number of cells cultured in the absence of the therapy identifies the therapy as suitable for treating cancer or metastatic cancer. In various embodiments, the cancer is a metastatic cancer. In one aspect, the device as described herein can be used to perform this method. In various embodiments, the cancer cell, population, or tumor sample is a solid tumor, e.g., a carcinoma or a sarcoma that can be isolated from a tumor biopsy of a subject. In various embodiment, the cancer cell is an epithelial cancer cell. In various embodiments, the cancer cell, population or tumor comprises a breast cancer cell, a prostate cancer cell, or a lung cancer cell. The cells can be animal, mammalian, e.g., feline, canine or human.

In yet a further aspect, provided is a method for treating a cancer patient. The method comprises, consists essentially of, or alternatively consists of administering to the patient a cancer therapy, for example in an effective amount of. In various embodiments, the patient was selected for the therapy by a method comprising, consisting essentially of, or alternatively consisting of determining gene expression of one or more genes in a biological sample of the patient. In various embodiments, the therapy is suitable for treating a cancer metastasis.

In various embodiments, the one or more genes are selected from Neuroblast Differentiation-Associated Protein AHNAK (AHNAK), A-Kinase Anchoring Protein 13 (AKAP13), A-Kinase Anchoring Protein 9 (AKAP9), ALMS1 Centrosome And Basal Body Associated Protein (ALMS1), APC Regulator Of WNT Signaling Pathway (APC), Assembly Factor For Spindle Microtubules (ASPM), ATM Serine/Threonine Kinase (ATM), Baculoviral IAP Repeat Containing 6 (BIRC6), Bcl2 Modifying Factor (BMF), BRCA2 DNA Repair Associated (BRCA2), BUB1 Mitotic Checkpoint Serine/Threonine Kinase B (BUB1B), Coiled-Coil Domain Containing 88A (CCDC88A), Cyclin A1 (CCNA1), Cyclin B1 (CCNB1), Cyclin B2 (CCNB2), Cyclin F (CCNF), Cell Division Cycle 25B (CDC25B), CDC42 Binding Protein Kinase Alpha (CDC42BPA), CDC42 Effector Protein 2 (CDC42EP2), Cell Division Cycle 45 (CDC45), Cell Division Cycle 6 (CDC6), Centromere Protein E (CENPE), Centromere Protein F (CENPF), Centromere Protein J (CENPJ), Centrosomal Protein 192 (CEP192), Centrosomal Protein 350 (CEP350), Centrosomal Protein 97 (CEP97), Cytoskeleton Associated Protein 2 (CKAP2), Cytoskeleton Associated Protein 5 (CKAP5), Centriolin (CNTRL), DNA Cross-Link Repair 1B (DCLRE1B), Desmoplakin (DSP), Dystonin (DST), Denticleless E3 Ubiquitin Protein Ligase Homolog (DTL), Dynein Cytoplasmic 1 Heavy Chain 1 (DYNC1H1), Dynein Cytoplasmic 2 Heavy Chain 1 (DYNC2H1), E2F Transcription Factor 1 (E2F1), Extra Spindle Pole Bodies Like 1, Separase (ESPL1), Filaggrin (FLG), FERM Domain Containing 6 (FRMD6), Growth Arrest Specific 2 Like 3 (GAS2L3), GTP Binding Protein Overexpressed In Skeletal Muscle (GEM), GEN1 Holliday Junction 5' Flap Endonuclease (GEN1), G Protein Signaling Modulator 2 (GPSM2), G2 And S-Phase Expressed 1 (GTSE1), Histone Deacetylase 4 (HDAC4), HECT And RLD Domain Containing E3 Ubiquitin Protein Ligase 2 (HERC2), Hyaluronan Mediated Motility Receptor (HMMR), Huntingtin (HTT), Protein TALPID3 (KIAA0586), Kinesin Family Member 11 (KIF11), Kinesin Family Member 14 (KIF14), Kinesin Family Member 18A (KIF18A), Kinesin Family Member 18B (KIF18B), Kinesin Family Member 20A (KIF20A), Kinesin Family Member 20B (KIF20B), Kinesin Family Member 4A (KIF4A), Kinetochore Localized Astrin (SPAG5) Binding Protein (KNSTRN), Keratin 17 (KRT17), Keratin 81 (KRT81), Microtubule Actin Crosslinking Factor 1 (MACF1), Microtubule Associated Protein 1B (MAP1B), Minichromosome Maintenance Complex Component 2 (MCM2), Minichromosome Maintenance Complex Component 3 (MCM3), Midasin AAA ATPase 1 (MDN1), Myosin Heavy Chain 15 (MYH15), Myosin VA (MYOSA), Myosin IXA (MYO9A), Neuron Navigator 1 (NAV1), NudE Neurodevelopment Protein 1 (NDE1), NIMA Related Kinase 2 (NEK2), Pro-Apoptotic WT1 Regulator (PAWR), Proliferating Cell Nuclear Antigen (PCNA), Pericentrin (PCNT), Phosphodiesterase 4D Interacting Protein (PDE4DIP), Pseudopodium Enriched Atypical Kinase 1 (PEAK1), Pleckstrin Homology, MyTH4 And FERM Domain Containing H2 (PLEKHH2), Polo Like Kinase 2 (PLK2), Proline And Serine Rich Coiled-Coil 1 (PSRC1), Protein Tyrosine Phosphatase Non-Receptor Type 14 (PTPN14), RAN Binding Protein 2 (RANBP2), RB Binding Protein 6, Ubiquitin Ligase (RBBP6), RCSD Domain Containing 1 (RCSD1), Receptor Accessory Protein 4 (REEP4), Replication Timing Regulatory Factor 1 (RIF1), Serum Amyloid A1 (SAA1), Sodium Channel And Clathrin Linker 1 (SCLT1), SET Domain Containing 2, Histone Lysine Methyltransferase (SETD2), SH3 And PX Domains 2A (SH3PXD2A), Solute Carrier Family 7 Member 11 (SLC7A11), Sperm Associated Antigen 5 (SPAG5), Spectrin Beta, Non-Erythrocytic 1 (SPTBN1), Spectrin Repeat Containing Nuclear Envelope Protein 1 (SYNE1), Spectrin Repeat Containing Nuclear Envelope Protein 2 (SYNE2), Transforming Acidic Coiled-Coil Containing Protein 3 (TACC3), DNA Topoisomerase II Alpha (TOP2A), Tripartite Motif Containing 59 (TRIM59), TTK Protein Kinase (TTK), Ubiquitin Protein Ligase E3 Component N-Recognin 4 (UBR4), or Utrophin (UTRN). In various embodiments, the one or more genes are selected from GAS2L3, SYNE2, AKAP9, KIF14, DYNC1H1, or MYO9A.

In various embodiments, the biological sample is a tumor biopsy. In various embodiments, the cancer has metastatic potential. In various embodiment, the cancer is an epithelial cancer, e.g., a carcinoma or a sarcoma that can be isolated from a tumor biopsy of a subject. In various embodiments, the cancer cell, population or tumor comprises a breast cancer cell, a prostate cancer cell, or a lung cancer cell. The cells can be animal, mammalian, e.g., feline, canine or human. In various embodiments, the cancer is a breast cancer, a prostate cancer, or a lung cancer.

In various embodiments, the therapy comprises, or consists essentially of, or consists of administering to the patient a microtubule-targeting drug, for example, an effective amount of the microtubule-targeting drug. In various embodiments, the therapy comprises, consists essentially of, or alternatively consists of administration of nocodazole, paclitaxel, or both, for example in an effective amount. In various embodiments, the patient was selected for the therapy if the biological sample of the patient comprises a cancer cell expressing one or more of the genes. In various embodiments, the patient was selected for the therapy if the biological sample of the patient comprises, consists essentially of, or consists of a cancer cell expressing one or more genes selected from GAS2L3, SYNE2, AKAP9, KIF14, DYNCIH1, or MYO9A.

In various embodiments, the method further comprises determining one or more of the following of the biological sample: a lower adhesion strength compared to the rest of the cells in the cell population or a non-metastatic control; a higher migration speed compared to the rest of the cells in the cell population or a non-metastatic control; an inhibition effect on migration upon contacting a microtubule-targeting drug; a higher percentage of cell displacement compared to the rest of the cells in the cell population or a non-metastatic control; a higher number of focal adhesions compared to the rest of the cells in the cell population or a non-metastatic control; a higher contractility compared to the rest of the cells in the cell population or a non-metastatic control; a higher invasion compared to the rest of the cells in the cell population or a non-metastatic control; or expression of one or more of the genes.

In a further aspect, provided is a kit, or a composition, or a system, for example for use in a method as disclosed herein. In various embodiments, the kit or composition or system comprises, or consists essentially of, or consists of a device as disclosed herein and optional instruction for use.

BRIEF DESCRIPTION OF THE DRAWINGS

FIG. 1C shows the average speed of cells isolated from the microfluidic device compared to an unselected population.

FIGS. 2A-2D are graphical and pictorial diagrams showing that low cation PPFC accurately and precisely sorts cancer cell populations that are stable long-term. FIG. 2A shows that MDA-MB231 populations were sorted at day 0, remixed, and then resorted at day 2. Differences between weakly (indicated as "Detached" as the left bar for each day)

and strongly (indicated as "Adherent" as the right bar for each day) adherent populations were assessed by two-tailed unpaired t-test (n=3). FIG. 2B shows adherent cells post-sort were cultured in high cations for 3, 6, 11, and 14 days and resorted. Cells that detached were cultured in high cations (the line connecting the triangles and the line connecting the solid circles) or low cations (the line connecting the inverted triangles and the line connecting the squares) mirroring stroma prior to resorting. Differences between weakly and strongly adherent populations as a function of culture time and condition were assessed by two-way ANOVA with Tukey test for multiple comparisons (n=3). For time and condition, ANOVA showed *$p<0.001$ and **$p<0.0001$, respectively as indicated at the corner of the plot. Individual comparisons to their counterpart cation conditions are indicated in the plot with †714 $p<0.1$, and *$p<0.05$. FIG. 2C shows images of cells from the flow-through (detached) and remaining on the plate (adherent) after exposure to shear along with quantification of the percentage of cells that detached relative to plated cells from each line (left bar, MDA-MB231; and right bar, MCF10A). n=3. ***$p<0.001$ for two-tailed unpaired t-test between lines. FIG. 2D shows a plot showing the fraction of detached cells from MDA-MB231 (the first bar from the left), MCF7 (the second bar from the left), and MCF10A (the third bar from the left) and their H-Ras transformed counterparts MCF10AT (the fourth bar from the left) after exposure to 250 dynes/cm$^2$ of shear stress.

FIGS. 3A-3H are graphical and pictorial diagrams showing sorted populations of single cells and spheroids exhibit and sustain different migration patterns. FIG. 3A shows average speed and FIG. 3B shows total displacement plotted for MDA-MB231 cells sorted by the indicated shear stress and allowed to migrate on collagen gels for 24 hours. Percentages in FIG. 3A reflect the portion of each population that detaches or remains adherent at a given stress. n=3 biological replicates for the number of cells per condition inset in the bars in FIG. 3B. In either of FIG. 3A and FIG. 3B, the data from left to right represent results from the weakly adherent group, the strongly adherent group and the unselected group, respectively. FIG. 3C shows average speed was measured after initial isolation and after 2 days. n=3 biological replicates. The left two sets of plotting represent results from the weakly adherent group; the middle two sets represent results from the strongly adherent group; while the right two sets represent results from the unselected group. FIG. 3D shows a plot showing the percentage of dividing cells on a collagen gel over 24 hours for cells selected by the indicated shear stress. n=3 biological replicates. The left bar represent the weakly adherent group while the right bar represent the strongly adherent group. FIG. 3E shows a schematic of tumor spheroid formation (top) and subsequent dissemination (bottom) in a collagen gel. FIG. 3F shows Brightfield images at the time of spheroid embedding in a collagen gel and fluorescent image 24 hours later. Dashed line indicates the average radius of disseminating cells. Plots of (FIG. 3G) maximum and (FIG. 3H) normalized average outward radial migration of cells selected by indicated shear (see FIG. 11 for radius measurements). In either of FIG. 3G and FIG. 3H, the data from left to right represent results from the weakly adherent group, the strongly adherent group and the unselected group, respectively. One-way ANOVA with Tukey test for multiple comparisons was used to indicate significance where *$p<0.05$, $p<0.01$, *$p<0.001$, ***$p<0.0001$, and N.S.=not significant.

FIG. 4A shows a comparison of the expression of common focal adhesion proteins in strongly adherent (SA) and weakly adherent (WA) cells. FIG. 4B shows representative images of focal adhesions (pointed by arrows) in SA and WA cells when subjected to with or without cation conditions. FIG. 4C shows focal adhesion density and FIG. 4D shows total area per cell area is plotted for the indicated sorting and cation conditions. In either of FIG. 4C and FIG. 4D, the left two sets of data provide results from the weakly adherent group, while the right two sets of data provide results from the strongly adherent group. n=3 biological replicates and >50 cells/condition. One-way ANOVA, with Tukey's multiple comparison test was performed for the indicated comparisons with $p<0.01$, *$p<0.001$, and **$p<0.0001$. FIG. 4E shows Brightfield and traction stress plots for cells from the indicated shear conditions. Scale bar is 10 microns. FIG. 4F shows plot of normalized strain energy for WA and SA cells. n=3 biological replicates and >30 cells/condition. A two-tailed unpaired t-test between lines indicated $p<0.01$, *$p<0.001$, and **$p<0.0001$.

FIG. 5A shows differences in gene expression between weakly and strongly adherent MDA-MB231 cells. FIG. 5B shows hierarchical clustering of differentially expressed genes between weakly and strongly adherent cells. Vertical bars indicate clustering of genes that are upregulated in strongly adherent cells and weakly adherent cells. FIG. 5C shows genes ontology terms that are upregulated in the weakly adherent subpopulation. Cytoskeletal and microtubule gene ontology terms, as well as proteins that bind to these components, were significantly upregulated in weakly adherent cells. FIG. 5D shows expressions of genes upregulated in cytoskeleton and motor activity, normalized to strongly adherent subpopulation. FIG. 5E shows validation of RNA seq gene expression differences via qPCR for select genes. For each gene, the left bar indicates data obtained from the weakly adherent group, while the right bar indicates data obtained from the strongly adherent group. *$p<0.05$ and $p<0.01$ for two-tailed unpaired t-test between weakly and strongly adherent cells. FIG. 5F shows average speed of weakly and strongly adherent cells when treated with microtubule-targeting drugs. At identical concentrations of nocodazole (0.2 ug/mL) and paclitaxel (0.5 ug/mL), weakly adherent cells (left three bars) displayed a significant decrease in migration speed, while the strongly adherent cells (right three bars) demonstrated no change. One-way ANOVA, with Tukey's multiple comparison test was performed for the indicated comparisons with $p<0.01$, *$p<0.001$, and **$p<0.0001$.

FIG. 6A shows progression-free interval and FIG. 6B shows disease-free interval of TNBC patients with Stage I-III tumors. Patients with gene expression that resembled strongly adherent and weakly adherent cells were compared. Genes were restricted to those associated with highlighted GO terms in FIG. 5C, resulting in a cohort of 100 genes.

FIGS. 7A-7C are pictorial diagrams showing PPFC assembly and use. FIG. 7A shows and exemplary exploded parts diagram of the flow chamber. Arrows indicate fluid direction. FIG. 7B shows and exemplary assembled crosssection schematic of the flow chamber with cell locations shown and fluid flow indicated. FIG. 7C shows an exemplary image of an assembled flow chamber (dashed lines).

FIGS. 8A and 8B are graphical diagrams showing a series of rose plots of post-sort cells. Rose plots of MDA-MB231 cells (each tracked to visualize their paths) selected at <30 or >500 dynes/cm$^2$. n=3 biological replicates and 250 cells/condition shown.

FIG. 9A shows average speed and FIG. 9B shows total displacement of MCF10A and MCF10AT cells sorted for the indicated fractions and allowed to migrate on collagen gels for 8 hours. For each panel, the left data set provides results from the weakly adherent group, while the right data set provides results from the strongly adherent group. n=3 biological replicates and >90 cells/condition. A two-tailed unpaired t-test between lines indicated **$p<0.0001$ and ***$p<0.00001$.

FIGS. 10A and 10B are graphical diagrams showing sorted populations of MDA-MB231 cells display migratory differences under different substrate stiffnesses. FIG. 10A shows average speed and FIG. 10B shows total displacement over 24 hours is plotted for MDA-MB231 weakly and strongly adherent cells on soft (300 Pa) and stiff (1.8 kPa) collagen-coated polyacrylamide gels. A two-tailed unpaired t-test between lines indicated **$p<0.0001$ and ***$p<0.00001$.

FIG. 11 is a series of graphical and pictorial diagrams showing determining spheroid invasive front. To automate the detection process for the leading edge of a spheroid embedded in and migrating through a collage gel, image analysis code was written to identify the radial intensity of the spheroid and surround matrix. When that line drops to within 2% of baseline, the average radius of the spheroid is calculated. The invasive ratio is then calculated. Examples of image used to determine the threshold for average radius (top) and the calculation of average radius after 24 hours (bottom) are displayed.

FIG. 12A shows average speed and FIG. 12B shows total displacement plotted for NCI-H1299 lung carcinoma cells sorted by the indicated shear stress and allowed to migrate on collagen gels for 24 hours. For each figure, the left data set provides results from the weakly adherent group; while the middle data set provides results from the strongly adherent group; and the right one provides results from the unselected group. Percentages in FIG. 12A reflect the portion of each population that detaches or remains adherent at a given stress. n=3 biological replicates for the number of cells per condition inset in the bars in FIG. 12B. One-way ANOVA with Tukey test for multiple comparisons was used to indicate significance where $p<0.01$, *$p<0.001$, and ***$p<0.0001$.

FIG. 13A shows focal adhesion density and FIG. 13B shows total area per cell area is plotted for the indicated sorting and cation conditions for MDA-MB231 cells cultured on collagen. For each figure, the left two data sets provide results from the weakly adherent group; while the right two data sets provide results from the strongly adherent group. Solid squares indicate no cations provided and open squares indicate cations added. n=3 biological replicates and >50 cells/condition. One-way ANOVA with Tukey's multiple comparison test was performed for the indicated comparisons with $p<0.01$, *$p<0.001$, and ****$p<0.0001$.

FIG. 16A provides image (left) and schematic (right) of the spinning disc adhesion assay. Note the chamber size is 1 L, making it less than ideal for cell collection. Cells plated on coverslips placed at the top of the spinning disc are exposed to a radial shear profile. FIG. 16B shows cell density plotted as a function of coverslip position. Inset images provide heat maps of cell density where hot colors indicate high density; most cells detach at the edge where shear is highest.

FIG. 16C provides plots of normalized cell density vs. applied shear stress for the indicated human cell lines spun in PBS (the lines connecting open squares) or PBS+MgCa (the lines connecting solid hourglass shaped marks). Tau50 (dashed lines) indicate the average adhesion strength. Shear was applied for 5 minutes in all cases.

FIG. 17A provides rose plots of cell migration trajectories for the indicated cell lines and shear stress selection conditions. Each trajectory represents an individual cell path as observed over 24 hours. FIG. 17B provides total cell displacement over 24 hours for the indicated cell lines, shear stress selection conditions, and substrates. FIG. 17C provides an illustration of the transwell migration assay at left and graphs of cell density for the indicated cell lines and shear stress selection conditions at right. Cell density on the insert ceiling (top) and bottom of the well (bottom) are shown separately.  $p<0.01$, *$p<0.001$. Each set of bars provides, from left to right, data obtained from the unselected MCF10A cells, the unselected MDAMB231 cells, MDAM1B231 cells having >15 dynes/cm$^2$, and MDAMB231 cells having >45 dynes/cm$^2$.

FIG. 18A shows a micro-fluidic flow chamber with pump and collection tube. Dashed box indicates the zoomed in region at right. Dye has been added for visualization. FIG. 18B shows a macro-fluidic flow chamber with pump and collection tube. Dashed box indicates the zoomed in region at right. Both devices can be used in sterile conditions.

FIG. 20A provides 2D Rose plots and FIG. 20B provides scatter plots of weakly adherent and unselected MDAMB231 cells cultured in 2.4 mg/mL collage gel (n~20). Rose plots are shown in microns with individual cells tracks.

FIG. 21A provides fluorescent and bright-field images of GFP-labeled xenograft tumors in situ. Scale bars=5 mm.

T=Tumor. Black and white arrowheads denote the metastases. FIG. 21A provides quantification of local (MG-invasive) and regional (Peritoneum-invasive) invasion of xenograft tumors. G3BP2 siRNA increases Twist1 nuclear localization, as described in ref.[37]

FIG. 22A shows a conical tube containing 2 patient biopsies. FIG. 22B provides a Brightfield image showing individual adherent cells in monolayer after enzymatic isolation.

FIG. 23A provides a Brightfield image of cells (dots) with lines to indicate transitions between soft and stiff substrate regions of step-gradient hydrogels (bottom). Double-headed arrows indicate the distance relative to the closest gradient or boundary. Atomic force microscopy (AFM) map is also shown (center) with corresponding color map (top). Position is indicated in microns. FIG. 23B provides a plot of average substrate stiffness versus position for step-gradient hydrogels (n>3). Error bars represent standard deviation. FIG. 23C provides MDA-MB-231 cell speed on soft or stiff side of step-gradient hydrogels. Data is shown for cells sorted by adhesion strength, i.e. weakly (WA) vs. strongly (SA), and cells on softer (open) vs. stiffer (closed) regions. (n>144 cells for each condition from triplicate experiments). $*p<0.05$, $*p<10^{-3}$, $**p<10^{-4}$ determined by one-way ANOVA with Tukey test for multiple comparisons for the indicated comparisons. In FIG. 23D, for adhesion sorted MDA-MB-231 cells that encounter the step-gradient, the fraction of durotactic (bottom section of the bar), anti-durotactic (center section of the bar), and adurotactic (top section of the bar) behavior is plotted. Data represents n=45 of 144 WA cells and 88 of 237 cells that crossed the gradient over triplicate experiments. Comparisons made using a Fisher's exact test for the same migration behavior between WA and SA cells, $*p<0.05$. In FIG. 23E, at 0 and 24 hours, probability density function of MDA-MB-231 cell distribution (calculated using the unbounded kernel density function) versus hydrogel position is shown for weakly (the lines having a higher peak on the soft section at left) vs. strongly (the lines having a lower peak on the soft section at left) adherent cells from triplicate experiments. The stiffer region is shaded in gray. Blue arrow indicates a peak in the strongly adherent cell distribution at 24 hours.

In FIG. 24A, PC-3 (left) and NCI-H1299 (right) cell speed on soft or stiff side of step-gradient hydrogels is plotted. Data is shown for cells sorted by adhesion strength, i.e. weakly (WA) vs. strongly (SA), and cells on softer (open) vs. stiffer (closed) regions. (n>200 cells for each condition from triplicate experiments). In FIG. 24B, for adhesion sorted PC-3 and NCI-H1299 cells that encounter the step-gradient, the fraction of durotactic (the bottom section of the bar), anti-durotactic (the center section of the bar), and adurotactic (the top section of the bar) behavior is plotted. Data represents n=82 of 210 WA PC-3 cells and 86 of 246 SA PC-3 cells and n=142 of 231 WA NCI-H1229 cells and 112 of 247 SA NCI-H1299 cells over triplicate experiments; those not counted did not interact with the gradient. In FIG. 24C, at 0 and 24 hours, PC-3 and NCI-H1299 cell probability density versus hydrogel position is shown for weakly (the higher lines at the left panels) vs. strongly (the lower lines at the left panels) adherent cells from triplicate experiments. The stiffer region is shaded in gray. Arrow indicates a peak in the strongly adherent cell distribution at 24 hours. $*p<0.05$, $p<10^{-2}$, $p<10^{-4}$, $***p<10^{-5}$ determined by one-way ANOVA with Tukey test for multiple comparisons for the indicated cell speed comparisons and a Fisher's exact for durotactic frequencies for the indicated comparisons.

In FIG. 25A, traction force, normalized to cell area, plotted for PC-3 cells on soft or stiff single-modulus (left) hydrogels and NCI-H1299 cells on stiff hydrogels (right). Data is shown for weakly (WA) vs. strongly (SA) adherent cells, and open circles for PC-3 cells on soft (n>47 for PC-3, n>15 for NCI-H1299). $*p<0.05$, $p<0.01$, $*p<0.001$, and $****p<0.0001$ via one-way ANOVA with Tukey test for multiple comparisons for the indicated comparisons. In FIG. 25B, instantaneous cell speed is plotted as a function of position relative to the step-gradient for adhesion sorted weakly (left) and strongly (right) adherent MDA-MB-231 (the bottom line at −50 μm of the distance to boundary in the left panel/the middle line at −50 μm of the distance to boundary in the right panel), PC-3 (the middle line at −50 μm of the distance to boundary in the left panel/the top line at −50 μm of the distance to boundary in the right panel), and NCI-H1299 (the top line at −50 μm of the distance to boundary in the left panel/the bottom line at −50 μm of the distance to boundary in the right panel) cells. Negative values are on the soft substrate and positive on the stiff. Average speed±standard error of the mean is plotted for n>144 cells for each condition from triplicate experiments.

In FIG. 26A, representative images of FAs in weakly and strongly adherent MDA-MB-231 cells on soft or stiff single modulus hydrogels. Paxillin is shown and highlighted in the inset images (dashed boxes indicating which regions are magnified) by arrowheads that point to representative paxillin adhesions. Scale bar is 10 μm. In FIG. 26B, FA area (top) and number of FAs normalized to cell area (bottom) are plotted for the indicated sorting and elasticities. n>20 cells/condition from triplicate experiments. In FIG. 26C, cytokine expression for WA and SA cells, normalized to loading controls, is plotted±standard deviation for 105 cytokines found in cell culture media collected from WA and SA MDA-MB-231 cells plated onto soft (0.35 kPa) and stiff (1.8 kPa) hydrogels for 24 hours. Specific cytokines expressed above background noise are noted with corresponding error bars from triplicate media collections; dashed arrows link cytokine names with their respective data. No data was statistically different between substrate stiffness or adhesion mechanotype based on one-way ANOVA with Tukey test for multiple comparisons. In FIG. 26D, post-selection weakly and strongly adherent MDA-MB-231 cells were plated onto hydrogels of indicated stiffness and subjected to a shear stress gradient. Adhesion strength or $\tau_{50}$, i.e. the shear stress at which 50% of the population detaches from the substrate, is plotted±standard deviation. $*p<0.05$, $p<0.01$, $*p<0.001$, and $****p<0.0001$ via one-way ANOVA with Tukey test for multiple comparisons for the indicated comparisons.

In FIG. 27A, traction force, normalized to cell area, is plotted for MDA-MB-231 cells on single-modulus hydrogels. Data is shown for weakly (WA) vs. strongly (SA) adherent cells, (n>50). $*p<0.05$ determined by one-way ANOVA with Tukey test for multiple comparisons. In FIG. 27B, schematic of bond lifetime versus force with bond states for weakly (WA) versus strongly (SA) adherent cells as used in the computational model. In FIG. 27C, force/FA versus substrate elasticity for catch (solid lines) and slip bonds (dashed lines) comparing 30 pN max SF force (the bottom two lines at 1 kPa of elasticity) and 45 pN max SF force (the top two lines at 1 kPa of elasticity), predicted by computational model. In FIG. 27D, average FA lifetime plotted versus substrate elasticity for the same simulations, i.e., comparing 30 pN max SF force (the top and bottom lines at 1 kPa of elasticity) and 45 pN max SF force (the second top line and the bottom line at 1 kPa of elasticity). In FIG. 27E, schematic of cells migrating over a step-gradient. For durotactic cells, higher tractions and longer bond lifetimes on the stiff side drive adhesion maturation and net migration towards the stiffer substrate. For adurotactic cells, tractions balance across the boundary due to longer bond lifetimes on the soft side of the step-gradient. In FIG. 27F, histogram of all X component forces simulated over 1 hour for a cell fixed at a step-gradient, comparing 30 pN max SF force (the higher peak) and 45 pN max SF force (the lower peak). Inset shows model cell with protruding stress fibers and X component force (arrow pointing to the right), Y component force (arrow pointing to the top), and resultant force (arrow pointing to the top right). In FIG. 27G, X and Y component forces versus max SF force for slip bonds (top) and catch bonds (bottom) from the computational model. In each panel, the upper line reflects $F_x$ while the lower line reflects $F_y$. $F_x$ and $F_y$ are illustrated in the inset for FIG. 27F. Error bars represent standard deviation.

In FIG. 28A, schematic of rigidity sensing in cells where softer catch bonds, i.e. strongly adherent cells, leads to asymmetric adhesion maturation at the step-gradient whereas stiffer bonds in weakly adherent cells break and prevent rigidity sensing. This occurs in four phases: i) integrin binding, ii) assembly and force production, iii) adhesion growth and stress fiber recruitment, and iv) cell movement. In FIG. 28B, diagram indicates the decision logic for the computational durotaxis model described in FIGS. 27 and 29. Gray indicates initial conditions, which feed in to the force on adhesions equations. Adhesion outcomes and cell migration are also included. Arrows indicate the decision logic with notes about each pathway indicated above or to the side of the decision. In FIG. 28C, comparison of catch (left) and slip (right) bond dynamics, Force/FA (top) and average FA lifetime (bottom) as a function of max SF force for ECM stiffnesses fixed at 0.35 (the upper lines at 30 pN for the top panels and the bottom left panel) or 1.8 kPa (the lower lines at 30 pN for the top panels and the bottom left panel). The gray region highlights where force is greater and bond lifetime is also greater or equal than it is on soft, which corresponds to the onset of durotactic behavior. In FIG. 28D, model cell durotaxis on gradients with a different stiffness range at 0 and 24 hours, model cell probability density versus simulated hydrogel position is shown for cells with 45 pN (the upper line at 0 μm in the bottom panel) vs. 30 pN (the lower line at 0 μm in the bottom panel) max SF force. The stiffer region is shaded in gray (30 kPa) vs. the softer region in white (10 kPa); values were chosen to mirror prostate tumor gradients rather than mammary tumor gradients to which model parameters were otherwise tuned. In FIG. 28E, model cell durotaxis on gradients of different magnitude but same stiffness range. (Left) At 0 and 24 hours, model cell probability density versus simulated hydrogel position is shown for cells with 45 pN (Weakly Adherent) vs. 30 pN (Strongly Adherent) max SF force. The stiffer region is shaded in gray (1.8 kPa) vs. the softer region in white (0.35 kPa); gradient slope was changes as indicated. All previous simulations use 145 Pa/μm² (the lower peak in the top right panel and the lower line at 0 μm in the bottom right panel) but plots here also include gradients 3-(48 Pa/μm², the top peaks) and 5-fold shallower (29 Pa/μm², the middle peaks). (Right) Instantaneous cell velocities±S.E.M. for the indicated gradients (145 Pa/μm², the middle line at 40 μm in the top panel and the top line at ~60 μm in the bottom panel; 48 Pa/μm², the top line at 40 μm in the top panel and the bottom line at ~60 μm in the bottom panel; and 29 Pa/μm², the bottom line at 40 μm in the top panel and the middle line at ~60 μm in the bottom panel) and WA (top) or SA (bottom).

In FIG. 29A, model cell speed on simulated on soft or stiff side of step-gradient is plotted. Data is shown for cells of differing max SF force, i.e. 45 pN (left datasets for each SF force group) vs. 30 pN (right datasets for each SF force group), and cells on softer (open) vs. stiffer (closed) regions. (n=100 cells for each simulation). In FIG. 29B, average traction force per focal adhesion, as determined from the computational model, is plotted for 45 pN (left datasets for each SF force group) and 30 pN (right datasets for each SF force group) max SF force (n=100 cells for each condition). *p<0.05, p<10⁻², *p<10⁻³, ****p<10⁻⁴ determined by one-way ANOVA with Tukey test for multiple comparisons for the indicated comparisons in FIGS. 29A-29B. In FIG. 29C, for model cells that encounter the step-gradient, the fraction of durotactic (the bottom sections of the bars), anti-durotactic (the center sections of the bars), and adurotactic (the top sections of the bars) behavior is plotted. Data represents n=44 of 100 and 36 of 100 cells simulated at 45 and 30 pN, respectively; those not counted did not interact with the gradient. Comparisons made using a Fisher's exact test for the same migration behavior between 30 and 45 pN conditions, *p<0.05 and **p<0.01. In FIG. 29D, at 0 and 24 hours, model cell fraction versus simulated hydrogel position is shown for cells with 45 pN (the line having the lower peak in the bottom panel) vs. 30 pN (the line having the higher peak in the bottom panel) max SF force. The stiffer region is shaded in gray. Arrow indicates a peak in the 30 pN cell distribution at 24 hours. *p<0.05, p<10⁻², **p<10⁻⁴ determined by paired student t-test for the indicated comparisons unless otherwise stated.

In FIG. 30A, model cell fraction versus simulated hydrogel position as predicted for 30 (the line having the highest peak in the bottom panel), 35 (the second highest line at −50 μm in the bottom panel), 40 (the second highest line at about −25 μm in the bottom panel)), and 45 pN (the highest line at −50 μm in the bottom panel) max SF forces at t=0 and t=24 hours. Durotactic tendency increased with decreasing max SF force. In FIG. 30B, weakly adherent MDA-MB-231 cell speed on soft or stiff side of step-gradient hydrogels for cells is plotted. Data is shown for blebbistatin treated and nontreated cells, i.e. DMSO vs. 100 μM, and cells on softer (open) vs. stiffer (closed) regions. (n>245 cells for each condition from triplicate experiments). *p<10⁻³, **p<10⁻⁴ determined by one-way ANOVA with Tukey test for multiple comparisons for the indicated comparisons. In FIG. 30C, for treated and nontreated weakly adherent MDA-MB-231 cells that encounter the step-gradient, the fraction of durotactic (the bottom section of each bar), anti-durotactic (the center section of each bar), and adurotactic (the top section of each bar) behavior is plotted. Data represents n=154 of 256 DMSO-treated and 167 of 245 Blebbistatin-treated cells over triplicate experiments; those not counted did not interact with the gradient. Comparisons made using a Fisher's exact test for the same migration behavior between treated and DMSO, *p<0.05. In FIG. 30D, weakly adherent MDA-MB-231 cell fraction was plotted versus hydrogel position for blebbistatin treatment of 100 µM (the highest line at about 60 µm in the top panel and the highest line at about 30 µm in the bottom panel), 10 µM (the lowest line at about 60 µm in the top panel and the second highest line at about 30 µm in the bottom panel), 1 µM (the second lowest line at about 60 µm in the top panel and the second lowest line at about 30 µm in the bottom panel), or DMSO (the second highest line at about 60 µm in the top panel and the lowest line at about 30 µm in the bottom panel) at t=3 and t=27 hours. In FIG. 30E, strongly adherent MDA-MB-231 cell fraction was plotted versus hydrogel position for LPA treatment of 10 µM (the middle line at about −50 µm in the left panel and the lowest line at about 0 µm in the right panel), 1 µM (the lowest line at about −50 µm in the left panel and the highest line at about 0 µm in the right panel), or DMSO (the highest line at about −50 m in the left panel and the middle line at about 0 µm in the right panel) at t=3 and t=24 hours.

In FIG. 31A, migration speed of mammary epithelial cell lines MCF10A and H-Ras transformed MCF10A cells (i.e. MCF10AT) as well as metastatic MDAMB231 are plotted. Cells were first sorted into weakly and strongly adherent population (<30 and >500 dynes/cm$^2$, respectively). In FIG. 31B, migration speed of adhesion sorted cells from the metastatic lung cell line NCI-H1299 and in FIG. 31C, the metastatic prostate cell line PC-3. For each panel, the left dataset is for the weakly adherent group while the right dataset is for the strongly adherent group. A two-tailed unpaired t-test between lines indicated **p<10$^{-4}$ and ***p<10$^{-5}$.

FIGS. 32A-32D provide that unsorted cell injections show local invasion of weakly adherent cells. FIG. 32A provides schematic of injection protocol approved in IACUC protocol S11102. FIG. 32B provides percentage of GFP positive human tumor cells in the mouse host. FIG. 32C provides population average adhesion strength, measured by spinning disc assay. FIG. 32D provides animal matched ratio of tumor:stromal adhesion strength for GFP+ tumor cells. **p<0.01 by one-way ANOVA with repeated measures.

FIG. 33A provides experimental time course. FIG. 33B provides IVIS imaging of tumor development. FIG. 33C provides plot of excised tumor to total body weight for each animal. FIG. 33D provides fluorescent images of mouse lungs showing GFP+ secondary tumors (arrowheads) for the unsorted and weakly and strongly adherent cells. FIG. 33E provides number of total lung metastases per animal and FIG. 33F provides the number normalized to unsorted animals within the same injection cohort. #p<0.1, ***p<0.001 for one-way ANOVA with repeated measures.

DETAILED DESCRIPTION OF THE DISCLOSURE

Figure 1A:
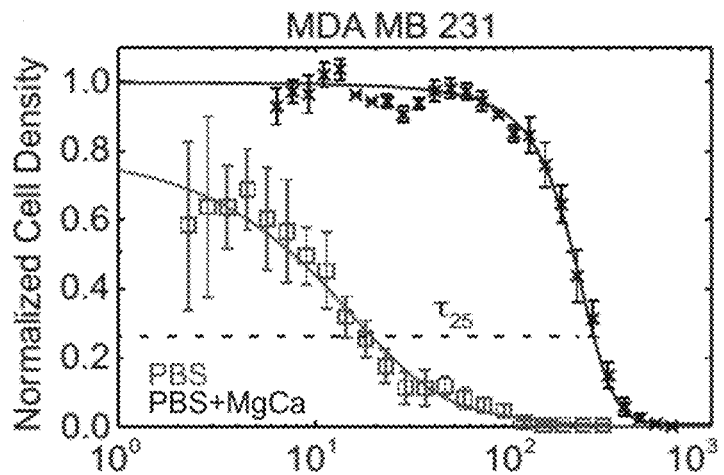
FIGS. 1A-1C are graphical diagrams showing adhesion strength plots for MDA-MB231 cells (FIG. 1A) and MCF7 cells (FIG. 1B) with (upper line) and without (lower line) $Mg^{2+}$ and $Ca^{2+}$.

The present disclosure is based on the observation that weakly adherent cancer cells are more metastatic, so a higher percentage of cells found within a tumor that detach in these conditions correlates to higher likelihood of metastasis.

Metastasis is a complex process in which cancer cells migrate from the primary tumor, invade into the vasculature, and travel to distant parts of the body to establish secondary tumors. Cells with a greater metastatic potential have a proclivity for leading migration away from the primary tumor. The cancer cell population within the tumor displays heterogeneity in metastatic potential, which can be quantified by measuring adhesion strength of the cancer cell population. Using a microfluidic adhesion assay to isolated weakly adherent metastatic breast cancer cells, an increase was shown in migratory propensity of weakly adherent cells in comparison to an unselected cell population.

Definitions

As it would be understood, the section or subsection headings as used herein is for organizational purposes only and are not to be construed as limiting or separating or both limiting and separating the subject matter described.

Before the present compositions and methods are described, it is to be understood that this disclosure is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, one or more steps, and both one or more methods and one or more steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

"Optional" or "optionally" means that the subsequently described circumstance may or may not occur, so that the description includes instances where the circumstance occurs and instances where it does not.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

As used herein, "and/or" refers to and encompasses any and all possible combinations of one or more of the associated listed items, as well as the lack of combinations when interpreted in the alternative ("or").

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the embodiments described herein are merely exemplary and that equivalents of such are known in the art.

The practice of the present technology will employ, unless otherwise indicated, conventional techniques of tissue culture, immunology, molecular biology, microbiology, cell biology, and recombinant DNA, which are within the skill of the art. See, e.g., Green and Sambrook eds. (2012) Molecular Cloning: A Laboratory Manual, $4^{th}$ edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press); MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, $6^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) In Vitro Transcription and Translation Protocols, $2^{nd}$ edition; Guisan ed. (2006) Immobilization of Enzymes and Cells; Perbal (1988) A Practical Guide to Molecular Cloning, $2^{nd}$ edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, $4^{th}$ edition; and Herzenberg et al. eds (1996) Weir's Handbook of Experimental Immunology, $5^{th}$ edition; and the more recent editions each thereof available at the time of filing.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods and materials are now described.

The term "subject", which is used interchangeably with "patient", refers to any individual or patient to which the subject methods are performed. Generally, the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, sport animals, pets, etc., and primates (including monkeys, chimpanzees, orangutans and gorillas) are included within the definition of subject. In some embodiments, the subject is suspected of having a disease as disclosed herein or is suspected of developing a disease. In further embodiments, the disease is a cancer. In some embodiments, the subject has a primary cancer, for example the subject is diagnosed with a primary cancer. In various embodiment, the cancer is an epithelial cancer, a sarcoma or a carcinoma. In yet further embodiments, the disease is a metastatic cancer. Accordingly, the subject may be diagnosed with a primary cancer and is suspect of having a metastatic cancer or is suspected of developing a metastatic cancer. In one embodiment, the subject is diagnosed with a primary breast cancer cell and is suspect of having a metastatic cancer in the lung or is suspected of developing a metastatic cancer in the lung.

As used herein, the term "animal" refers to living multicellular vertebrate organisms, a category that includes, for example, mammals and birds. The term "mammal" includes both human and non-human mammals.

A subject "in need" of treatment with the disclosure's methods includes a subject that is "suffering from disease," i.e., a subject that is experiencing and/or exhibiting one or more symptoms of the disease, and a subject "at risk" of the disease. A subject "in need" of treatment includes animal models of the disease. A subject "at risk" of disease refers to a subject that is not currently exhibiting disease symptoms and is predisposed to expressing one or more symptoms of the disease. This predisposition may be genetic based on family history, genetic factors, environmental factors such as exposure to detrimental compounds present in the environment, etc. It is not intended that the present disclosure be limited to any particular signs or symptoms. Thus, it is intended that the present disclosure encompass subjects that are experiencing any range of disease, from sub-clinical symptoms to full-blown disease, wherein the subject exhibits at least one of the indicia (e.g., signs and symptoms) associated with the disease.

As used herein, the terms "treating," "treatment" and the like are used herein to mean obtaining a desired pharmacologic or physiologic effect or both. In some embodiments, the effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder. In one aspect, treatment is the arrestment of the development of symptoms of the disease or disorder, e.g., a cancer. In some embodiments, they refer to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. When the disease is cancer, the following clinical end points are non-limiting examples of treatment: reduction in tumor burden, slowing of tumor growth, longer overall survival, longer time to tumor progression, inhibition of metastasis or a reduction in metastasis of the tumor. In one aspect, treatment excludes prophylaxis.

In one embodiment, the term "disease" or "disorder" as used herein refers to a cancer or a tumor (which are used interchangeably herein), a status of being diagnosed with such disease, a status of being suspect of having such disease, or a status of at high risk of having such disease.

As used herein, the term "cancer" refers to a plurality of cancer cells that may or may not be metastatic, such as prostate cancer, liver cancer, bladder cancer, skin cancer (e.g., cutaneous, melanoma, basal cell carcinoma, Kaposi's sarcoma, etc.), ovarian cancer, breast cancer, lung cancer, cervical cancer, pancreatic cancer, colon cancer, stomach cancer, esophagus cancer, mouth cancer, tongue cancer, gum cancer, muscle cancer, heart cancer, bronchial cancer, testis cancer, kidney cancer, endometrium cancer, and uterus cancer. Cancer may be a primary cancer, recurrent cancer, and/or metastatic cancer. The place where a cancer starts in the body is called the "primary cancer" or "primary site." If cancer cells spread to another part of the body the new area of cancer is called a "secondary cancer" or a "metastasis." "Recurrent cancer" means the presence of cancer after treatment and after a period of time during which the cancer cannot be detected. The same cancer may be detected at the primary site or somewhere else in the body, e.g., as a metastasis. In some embodiments, the cancer is an epithelial cancer. In further embodiments, the cancer is a mammary epithelial cancer. In some embodiments, the terms cancer and tumor are used interchangeably.

A cancer can be categorized in to various types, optionally based on its origin or location or both, such as those accessible at www.cancer.org/cancer/all-cancer-types.html or www.cancer.net/cancer-types or both. In some embodiments, the term "of the same cancer type" refers to cancer cells located in the same organ or tissue. In some embodiments, the term "of the same cancer type" refers to cancer cells of substantially the same morphology or phenotype or both.

In some embodiments, "a cancer cell" as used herein may refer to one or more cancer cell(s). Additionally or alternatively, "a cancer cell" as used herein may also refer to a progeny of the cancer cell, or a cell population comprising the cancer cell, or a cell population comprising the progeny, or a cell population comprising the cancer cell and the progeny thereof.

As used herein, the term "cancer cell" refers to a cell undergoing early, intermediate or advanced stages of multi-step neoplastic progression as previously described (Pitot et al., Fundamentals of Oncology, 15-28 (1978)). This includes cells in early, intermediate and advanced stages of neoplastic progression including "pre-neoplastic" cells (i.e., "hyperplastic" cells and dysplastic cells), and neoplastic cells in advanced stages of neoplastic progression of a dysplastic cell.

As used herein, a "metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

As used herein, the terms "sample" and "biological sample" refer to any sample suitable for the methods provided by the present disclosure. In one embodiment, the biological sample of the present disclosure is a tissue sample, e.g., a biopsy specimen such as samples from needle biopsy (i.e., biopsy sample). In some embodiment, a biological sample is a biopsy specimen from a cancer or a tumor. In further embodiment, a biological sample is a biopsy specimen from a primary cancer or a primary tumor.

In some embodiments, a biological sample is a blood sample, a plasma sample or a serum sample.

Reference herein to "normal samples" or "corresponding normal samples" means biological samples of the same type as the biological sample obtained from a subject. In various embodiments, the corresponding normal sample is a sample obtained from a healthy individual or an individual free of a disease or an individual not in need of a treatment. Such corresponding normal samples can, but need not be, from an individual that is age-matched or of the same sex or both age and gender matched as the individual providing the sample being examined.

As used herein, the term "marker" or "biomarker" in the context of an analyte means any antigen, molecule or other chemical or biological entity that is specifically found in circulation or associated with a particular tissue (e.g., tumor cells) that it is desired to be identified in a biological sample.

As used herein, the terms "reduce" and "inhibit" are used together because it is recognized that, in some cases, a decrease can be reduced below the level of detection of a particular assay, for example by about 5%, about 10%, about 15%, about 20%, about 25%, about 30%, about 40%, about 50%, about 60%, about 70%, about 80%, about 85%, about 90%, about 95%, about 99%, or about 100% of the reference level. As such, it may not always be clear whether the expression level or activity is "reduced" below a level of detection of an assay, or is completely "inhibited." Nevertheless, it will be clearly determinable, following a treatment according to the present methods.

In some embodiments, the terms "increase" and "upregulate" are used interchangeably and refer to a higher level of detection based on an assay, for example by about 5%, about 10%, about 15%, about 20%, about 25%, about 30%, about 40%, about 50%, about 60%, about 70%, about 80%, about 85%, about 90%, about 95%, about 99%, about 100%, about 2 folds, about 3 folds, about 4 folds, about 5 folds, about 10 folds, or more higher than the reference level. Nevertheless, it will be clearly determinable, following a treatment according to the present methods.

A cancer therapy is exemplified as disclosed herein, such as administration of an anti-cancer agent, an anti-metastatic cancer therapy, an ablative therapy, cryoablation, thermal ablation, radiotherapy, chemotherapy, radiofrequency ablation, electroporation, alcohol ablation, high intensity focused ultrasound, a photodynamic therapy, administration of monoclonal antibodies, immunotherapy, administration of immunotoxins, and etc.

As used herein, an anti-cancer agent refers to any drug or compound used for anticancer treatment. These include any drug that renders or maintains a clinical symptom or diagnostic marker of tumors and cancer, alone or in combination with other compounds, that reduces or maintains a state of remission, reduction, remission, prevention or remission. In some embodiments, the agent is an RNA and/or a DNA. In some embodiments, the agent is a protein or a polypeptide. In some embodiments, the agent is a chemical compound. Examples of anticancer agents include angiogenesis inhibitors such as angiostatin K1-3, DL-adifluoromethyl-ornithine, endostatin, fumagillin, genistein, minocycline, staurosporine, and (+)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine b-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenzimidazole I-b-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; humanised or mouse/human chimeric monoclonal antibodies against defined cancer associated structures (such as Trastuzumab, Rituximab, Cetuximab, Bevacizumab, Alemtuzumab); and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-a, rapamycin, thapsigargin, and bikunin, and derivatives (as defined for imaging agents) thereof.

As used herein, an ablative therapy is a treatment destroying or ablating cancer tumors. In one embodiment, the ablative therapy does not require invasive surgery. In other embodiments, the ablative therapy refers to removal of a tumor via surgery. In some embodiments, the step ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g. IL-2, interferon's, cytokine inducers).

In some embodiments, a method as disclosed herein further includes the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

A "composition" is intended to mean a combination of active agent and another compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers.

Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

The compositions used in accordance with the disclosure can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions are administered in a manner compatible with the dosage formulation and in such amount as is therapeutically or prophylactically effective. The formulations are easily administered in a variety of dosage forms, such as the type of injectable solutions described herein.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

"Therapeutically effective amount" of a drug or an agent refers to an amount of the drug or the agent that is an amount sufficient to obtain a pharmacological response such as passive immunity; or alternatively, is an amount of the drug or agent that, when administered to a patient with a specified disorder or disease, is sufficient to have the intended effect, e.g., treatment, alleviation, amelioration, palliation or elimination of one or more manifestations of the specified disorder or disease in the patient. A therapeutic effect does not necessarily occur by administration of one dose, and may occur only after administration of a series of doses. Thus, a therapeutically effective amount may be administered in one or more administrations.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at cancer.gov. Typically, a patient is given a subsequent chemotherapy regimen because the patient did not shown a positive clinical or sub-clinical response to the first line therapy or the first line therapy has stopped.

The term "suitable for a therapy" or "suitably treated with a therapy" shall mean that the patient is likely to exhibit one or more desirable clinical outcomes as compared to patients having the same disease and receiving the same therapy but possessing a different characteristic that is under consideration for the purpose of the comparison. In one aspect, the characteristic under consideration is a genetic polymorphism or a somatic mutation. In another aspect, the characteristic under consideration is expression level of a gene or a polypeptide. In one aspect, a more desirable clinical outcome is relatively higher likelihood of or relatively better tumor response such as tumor load reduction. In another aspect, a more desirable clinical outcome is relatively longer overall survival. In yet another aspect, a more desirable clinical outcome is relatively longer progression free survival or time to tumor progression. In yet another aspect, a more desirable clinical outcome is relatively longer disease free survival. In further another aspect, a more desirable clinical outcome is relative reduction or delay in tumor recurrence. In another aspect, a more desirable clinical outcome is relatively decreased metastasis. In another aspect, a more desirable clinical outcome is relatively lower relative risk. In yet another aspect, a more desirable clinical outcome is relatively reduced toxicity or side effects. In some embodiments, more than one clinical outcomes are considered simultaneously. In one such aspect, a patient possessing a characteristic, such as a genotype of a genetic polymorphism, can exhibit more than one more desirable clinical outcomes as compared to patients having the same disease and receiving the same therapy but not possessing the characteristic. As defined herein, the patient is considered suitable for the therapy. In another such aspect, a patient possessing a characteristic can exhibit one or more desirable clinical outcome but simultaneously exhibit one or more less desirable clinical outcome. The clinical outcomes will then be considered collectively, and a decision as to whether the patient is suitable for the therapy will be made accordingly, taking into account the patient's specific situation and the relevance of the clinical outcomes. In some embodiments, progression free survival or overall survival is weighted more heavily than tumor response in a collective decision making.

A "tumor response" (TR) refers to a tumor's response to therapy. A "complete response" (CR) to a therapy refers to the clinical status of a patient with evaluable but non-measurable disease, whose tumor and all evidence of disease have disappeared following administration of the therapy. In this context, a "partial response" (PR) refers to a response that is anything less than a complete response. "Stable disease" (SD) indicates that the patient is stable following the therapy. "Progressive disease" (PD) indicates that the tumor has grown (i.e. become larger) or spread (i.e. metastasized to another tissue or organ) or the overall cancer has gotten worse following the therapy. For example, tumor growth of more than 20 percent since the start of therapy typically indicates progressive disease. "Non-response" (NR) to a therapy refers to status of a patient whose tumor or evidence of disease has remained constant or has progressed.

"Overall Survival" (OS) refers to the length of time of a cancer patient remaining alive following a cancer therapy.

"Progression free survival" (PFS) or "Time to Tumor Progression" (TTP) refers to the length of time following a therapy, during which the tumor in a cancer patient does not grow. Progression-free survival includes the amount of time a patient has experienced a complete response, partial response or stable disease.

"Disease free survival" refers to the length of time following a therapy, during which a cancer patient survives with no signs of the cancer or tumor.

"Time to Tumor Recurrence (TTR)" refers to the length of time, following a cancer therapy such as surgical resection or chemotherapy, until the tumor has reappeared (come back). The tumor may come back to the same place as the original (primary) tumor or to another place in the body.

"Relative Risk" (RR), in statistics and mathematical epidemiology, refers to the risk of an event (or of developing a disease) relative to exposure. Relative risk is a ratio of the probability of the event occurring in the exposed group versus a non-exposed group.

The term "determining" or "identifying" is to associate or affiliate a patient closely to a group or population of patients who likely experience the same or a similar clinical response to a therapy.

The term "selecting" a patient for a therapy refers to making an indication that the selected patient is suitable for the therapy. Such an indication can be made in writing by, for instance, a handwritten prescription or a computerized report making the corresponding prescription or recommendation.

When a genetic marker or polymorphism "is used as a basis" for identifying or selecting a patient for a treatment described herein, the genetic marker or polymorphism is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of the genetic marker or polymorphism in a clinical setting is a clear indication that this parameter was used as a basis for initiating, continuing, adjusting and/or ceasing administration of the treatments described herein.

"Having the same cancer" is used when comparing one patient to another or alternatively, one patient population to another patient population. For example, the two patients or patient population will each have or be suffering from colon cancer.

A "normal cell corresponding to the tumor tissue type" refers to a normal cell from a same tissue type as the tumor tissue. A non-limiting examples is a normal lung cell from a patient having lung tumor, or a normal colon cell from a patient having colon tumor.

The term "amplification" or "amplify" as used herein means one or more methods known in the art for copying a target nucleic acid, thereby increasing the number of copies of a selected nucleic acid sequence. Amplification can be exponential or linear. A target nucleic acid can be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods can be used either in place of, or together with, PCR methods.

The term "complement" as used herein means the complementary sequence to a nucleic acid according to standard Watson/Crick base pairing rules. A complement sequence can also be a sequence of RNA complementary to the DNA sequence or its complement sequence, and can also be a cDNA. The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

As used herein, the term "hybridize" or "specifically hybridize" refers to a process where two complementary nucleic acid strands anneal to each other under appropriately stringent conditions. Hybridizations are typically conducted with probe-length nucleic acid molecules. Nucleic acid hybridization techniques are well known in the art. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

"Primer" as used herein refers to an oligonucleotide that is capable of acting as a point of initiation of synthesis when placed under conditions in which primer extension is initiated (e.g., primer extension associated with an application such as PCR). The primer is complementary to a target nucleotide sequence and it hybridizes to a substantially complementary sequence in the target and leads to addition of nucleotides to the 3'-end of the primer in the presence of a DNA or RNA polymerase. The 3'-nucleotide of the primer should generally be complementary to the target sequence at a corresponding nucleotide position for optimal expression and amplification. An oligonucleotide "primer" can occur naturally, as in a purified restriction digest or can be produced synthetically. The term "primer" as used herein includes all forms of primers that can be synthesized including, peptide nucleic acid primers, locked nucleic acid primers, phosphorothioate modified primers, labeled primers, and the like.

Primers are typically between about 5 and about 100 nucleotides in length, such as between about 15 and about 60 nucleotides in length, such as between about 20 and about 50 nucleotides in length, such as between about 25 and about 40 nucleotides in length. In some embodiments, primers can be at least 8, at least 12, at least 16, at least 20, at least 25, at least 30, at least 35, at least 40, at least 45, at least 50, at least 55, at least 60 nucleotides in length. An optimal length for a particular primer application can be readily determined in the manner described in H. Erlich, PCR Technology. Principles and Application for DNA Amplification (1989).

"Probe" as used herein refers to nucleic acid that interacts with a target nucleic acid via hybridization. A probe can be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or unlabeled, or modified in any of a number of ways well known in the art. A probe can specifically hybridize to a target nucleic acid.

Probes can be DNA, RNA or a RNA/DNA hybrid. Probes can be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes can comprise modified nucleobases, modified sugar moieties, and modified internucleotide linkages. A probe can be fully complementary to a target nucleic acid sequence or partially complementary. A probe can be used to detect the presence or absence of a target nucleic acid. Probes are typically at least about 10, 15, 21, 25, 30, 35, 40, 50, 60, 75, 100 nucleotides or more in length.

"Detecting" as used herein refers to determining the presence of a nucleic acid of interest in a sample or the presence of a protein of interest in a sample. Detection does not require the method to provide 100% sensitivity and/or 100% specificity.

"Detectable label" as used herein refers to a molecule or a compound or a group of molecules or a group of compounds used to identify a nucleic acid or protein of interest. In some cases, the detectable label can be detected directly. In other cases, the detectable label can be a part of a binding pair, which can then be subsequently detected. Signals from the detectable label can be detected by various means and will depend on the nature of the detectable label. Detectable labels can be isotopes, fluorescent moieties, colored substances, and the like. Examples of means to detect detectable label include but are not limited to spectroscopic, photochemical, biochemical, immunochemical, electromagnetic, radiochemical, or chemical means, such as fluorescence, chemifluorescence, or chemiluminescence, or any other appropriate means.

"TaqMan® PCR detection system" as used herein refers to a method for real time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, preferably, a human. In an exemplary embodiment, the sample is a biopsy sample.

"Target nucleic acid" as used herein refers to segments of a chromosome, a complete gene with or without intergenic sequence, segments or portions a gene with or without intergenic sequence, or sequence of nucleic acids to which probes or primers are designed. Target nucleic acids can include wild type sequences, nucleic acid sequences containing mutations, deletions or duplications, tandem repeat regions, a gene of interest, a region of a gene of interest or any upstream or downstream region thereof. Target nucleic acids can represent alternative sequences or alleles of a particular gene. Target nucleic acids can be derived from genomic DNA, cDNA, or RNA. As used herein, target nucleic acid can be native DNA or a PCR-amplified product.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segments with a high frequency of complementary base sequences. Exemplary hybridization conditions are as follows. High stringency generally refers to conditions that permit hybridization of only those nucleic acid sequences that form stable hybrids in 0.018 M NaCl at 65° C. High stringency conditions can be provided, for example, by hybridization in 50% formamide, 5×Denhardt's solution, 5×SSC (saline sodium citrate) 0.2% SDS (sodium dodecyl sulfate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2×SSC, 0.2% SDS, at 65° C. Low stringency refers to conditions equivalent to hybridization in 10% formamide, 5×Denhardt's solution, 6×SSC, 0.2% SDS, followed by washing in 1×SSC, 0.2% SDS, at 50° C.

As used herein the term "substantially identical" refers to a polypeptide or nucleic acid exhibiting at least 50%, 75%, 85%, 90%, 95%, or even 99% identity to a reference amino acid or nucleic acid sequence over the region of comparison. For polypeptides, the length of comparison sequences will generally be at least 20, 30, 40, or 50 amino acids or more, or the full length of the polypeptide. For nucleic acids, the length of comparison sequences will generally be at least 10, 15, 20, 25, 30, 40, 50, 75, or 100 nucleotides or more, or the full length of the nucleic acid.

As used herein, a weakly adherent cancer cell as used herein refers to cancer cells that can be detached or removed from a tumor tissue or a cell culture substrate by a shear stress, for example, created by a moving fluid, such as blood or shear buffer. In some embodiments, the weakly adherent cancer cells are the top 1% or the top 2% or the top 5% or the top 10% of the cell population, which are detached or removed from the tumor tissue or the cell culture substrate to its liquid environment upon increasing the shear stress or the time of applying the shear stress or both. In some embodiments, a weakly adherent cancer cell is a cancer cell which can be detached or removed from a tumor tissue or a cell culture to the liquid environment thereof under a certain shear stress for a certain time period.

In some embodiments, the shear stress is about 1 dynes/$cm^2$ to about 2000 dynes/$cm^2$, including any ranges or numbers therebetween, such as about 5 dynes/$cm^2$ to about 40 dynes/$cm^2$, about 10 dynes/$cm^2$, or about 15 dynes/$cm^2$, or about 16 dynes/$cm^2$, or about 17 dynes/$cm^2$, or about 18 dynes/$cm^2$, or about 19 dynes/$cm^2$, or about 20 dynes/$cm^2$, or about 21 dynes/$cm^2$, or about 22 dynes/$cm^2$, or about 23 dynes/$cm^2$, or about 24 dynes/$cm^2$, or about 25 dynes/$cm^2$, or about 26 dynes/$cm^2$, or about 27 dynes/$cm^2$, or about 28 dynes/$cm^2$, or about 29 dynes/$cm^2$, or about 30 dynes/$cm^2$, or about 31 dynes/$cm^2$, or about 32 dynes/$cm^2$, or about 33 dynes/$cm^2$, or about 34 dynes/$cm^2$, or about 35 dynes/$cm^2$, or about 36 dynes/$cm^2$, or about 37 dynes/$cm^2$, or about 38 dynes/$cm^2$, or about 39 dynes/$cm^2$. In one aspect, these are measured using the methods as described herein.

In some embodiments, the time period of applying the shear stress to the cells can be also about 1 minute to about 1 day including ranges and numbers there between, for example, for about 2 minutes, for about 3 minutes, for about 4 minutes, for about 5 minutes, for about 6 minutes, for about 7 minutes, for about 8 minutes, for about 9 minutes, for about 10 minutes, for about 11 minutes, for about 12 minutes, for about 13 minutes, for about 14 minutes, for about 15 minutes, for about 16 minutes, for about 17 minutes, for about 18 minutes, for about 19 minutes, for about 20 minutes, for about 21 minutes, for about 22 minutes, for about 23 minutes, for about 24 minutes, for about 25 minutes, for about 26 minutes, for about 27 minutes, for about 28 minutes, for about 29 minutes, for about 0.5 hour, for about 1 hour, for about 2 hours or longer.

Compared to weakly adherent cancer cells, a strongly adherent cancer cell cannot be detached or removed from a tumor tissue or a cell culture substrate by a shear stress easily. Accordingly, at the shear stress and the time period where the weakly adherent cancer cells detached or removed from a tumor tissue or a cell culture substrate, the strongly adherent cells remain attached to the tumor tissue or the culture substrate, such as a glass slide.

In some embodiments, the strongly adherent cancer cells are the bottom 1% or the bottom 2% or the bottom 5% or the bottom 10% of the cell population, which are detached or removed from the tumor tissue or the cell culture substrate to its liquid environment upon increasing the shear stress or the time of applying the shear stress or both. In some embodiments, a strongly adherent cancer cell is a cancer cell which can only be detached or removed from a tumor tissue or a cell culture to the liquid environment thereof when the shear stress reaches or exceeds a certain limit, or when applying the shear stress for a time period longer than a certain limit, or both.

In some embodiments, the shear stress limit is about 20 dynes/cm$^2$ to about 2000 dynes/cm$^2$, including any ranges or numbers therebetween, such as about 20 dynes/cm$^2$, or about 21 dynes/cm$^2$, or about 22 dynes/cm$^2$, or about 23 dynes/cm$^2$, or about 24 dynes/cm$^2$, or about 25 dynes/cm$^2$, or about 26 dynes/cm$^2$, or about 27 dynes/cm$^2$, or about 28 dynes/cm$^2$, or about 29 dynes/cm$^2$, or about 30 dynes/cm$^2$, or about 31 dynes/cm$^2$, or about 32 dynes/cm$^2$, or about 33 dynes/cm$^2$, or about 34 dynes/cm$^2$, or about 35 dynes/cm$^2$, or about 36 dynes/cm$^2$, or about 37 dynes/cm$^2$, or about 38 dynes/cm$^2$, or about 39 dynes/cm$^2$, or about 40 dynes/cm$^2$, or about 41 dynes/cm$^2$, or about 42 dynes/cm$^2$, or about 43 dynes/cm$^2$, or about 44 dynes/cm$^2$, or about 45 dynes/cm$^2$, or about 50 dynes/cm$^2$, or about 55 dynes/cm$^2$, or about 60 dynes/cm$^2$, or about 65 dynes/cm$^2$, or about 70 dynes/cm$^2$, or about 75 dynes/cm$^2$, or about 80 dynes/cm$^2$, or about 85 dynes/cm$^2$, or about 90 dynes/cm$^2$, or about 95 dynes/cm$^2$, or about 100 dynes/cm$^2$, or about 200 dynes/cm$^2$, or about 300 dynes/cm$^2$, or about 400, dynes/cm$^2$, or about 500, dynes/cm$^2$, or about 600 dynes/cm$^2$, or about 700 dynes/cm$^2$, or about 800 dynes/cm$^2$, or about 900 dynes/cm$^2$, or about 1000 dynes/cm$^2$, or about 1500 dynes/cm$^2$, or about 2000 dynes/cm$^2$.

In some embodiments, the limit of the time period is about 1 minute to about 1 day including ranges and numbers there between, for example, for about 2 minutes, for about 3 minutes, for about 4 minutes, for about 5 minutes, for about 6 minutes, for about 7 minutes, for about 8 minutes, for about 9 minutes, for about 10 minutes, for about 11 minutes, for about 12 minutes, for about 13 minutes, for about 14 minutes, for about 15 minutes, for about 16 minutes, for about 17 minutes, for about 18 minutes, for about 19 minutes, for about 20 minutes, for about 21 minutes, for about 22 minutes, for about 23 minutes, for about 24 minutes, for about 25 minutes, for about 26 minutes, for about 27 minutes, for about 28 minutes, for about 29 minutes, for about 0.5 hour, for about 1 hour, for about 2 hours, for about 3 hours, for about 4 hours, for about 5 hours, for about 6 hours, for about 7 hours, for about 8 hours, for about 1 day, for about 2 days, for about 3 days, for about 1 week, for about 1 month or longer.

It is noted that using the methods, systems, or devices as disclosed herein, the shear stress and time period to detach a weakly adherent cancer cell can be selected or adjusted by one of skill in the art based on the cancer cell type.

As used herein, adhesion strength refers to the interfacial strength between a cancer cell and an extracellular matrix or a substrate optionally coated with an extracellular matrix protein. Methods of assessing such strength is disclosed herein.

A "solid substrate" refers to, for example, a material having a rigid or semi-rigid surface or surfaces, which may be regular or irregular in geometric configuration, and may take the form of beads, resins, gels, spheres, microspheres, particles, fibres or other geometric configurations or physical forms.

In some embodiments, the terms "first" "second" "third" "fourth" or similar in a component name are used to distinguish and identify more than one components sharing certain identity in their names. For example, "first solid substrate" and "second solid substrate" are used to distinguishing two solid substrates.

As used herein, an extracellular matrix (ECM) is a three-dimensional network consisting of extracellular macromolecules and minerals, such as collagen, enzymes, glycoproteins and hydroxyapatite that provide structural and biochemical support to surrounding cells. Because multicellularity evolved independently in different multicellular lineages, the composition of ECM varies between multicellular structures; however, cell adhesion, cell-to-cell communication and differentiation are common functions of the ECM. See, for example, Theocharis et al. Advanced Drug Delivery Reviews. 97: 4-27; Bonnans et al. Nature Reviews. Molecular Cell Biology. 15 (12): 786-801; Michel et al. The New Phytologist. 188 (1): 82-97; or Abedin et al. rends in Cell Biology. 20 (12): 734-42. Accordingly, an ECM protein refers to a protein existing in an ECM. Exemplified ECM proteins include collagen (such as any of types I to XIV), elastin, fibronectin, or laminin. In some embodiments, an ECM protein as used herein is coated on a substrate, facilitating cell adherence to the substrate.

A shear buffer as used herein refers to a buffer in which the cells are immersed while being applied with a shear stress. In some embodiments, the shear buffer is a buffer solution having a pH or an osmotic pressure or both not disrupting a cell. In one embodiment, the shear buffer comprises, consists essentially of, or alternatively consists of phosphate-buffered saline (PBS). In one embodiment, the shear buffer is phosphate-buffered saline (PBS). In various embodiments, the shear buffer comprises, consists essentially of, or alternatively consists of phosphate-buffered saline (PBS)+MgCa (i.e., PBS comprising Mg$^{2+}$ and Ca$^{2+}$, each of which is at its physiological cation concentration, for example the serum cation concentration). In various embodiments, the shear buffer comprises, consists essentially of, or alternatively consists of 0.5 mM Mg$^{2+}$ and 1 mM Ca$^{2+}$ in PBS. In various embodiments, the shear buffer comprises, consists essentially of, or alternatively consists of 0.5 mM MgCl$_2$ and 1 mM CaCl$_2$) in PBS.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. As used herein, the term "isolated cell" generally refers to a cell that is substantially separated from other cells of a tissue.

The terms "polynucleotide", "nucleic acid" and "oligonucleotide" are used interchangeably and refer to a polymeric form of nucleotides of any length, either deoxyribonucleotides or ribonucleotides or analogs thereof.

Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" refers to a polynucleotide containing at least one open reading frame (ORF) that is capable of encoding a particular polypeptide or protein after being transcribed and translated.

The term "express" refers to the production of a gene product. As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Detectable label", "label", "detectable marker" or "marker" are used interchangeably, including, but not limited to radioisotopes, fluorochromes, chemiluminescent compounds, dyes, and proteins, including enzymes. Detectable labels can also be attached to a polynucleotide, polypeptide, antibody or composition described herein.

As used herein, the term "label" or a detectable label intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6th ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

As used herein, a purification label or maker refers to a label that may be used in purifying the molecule or component that the label is conjugated to, such as an epitope tag (including but not limited to a Myc tag, a human influenza hemagglutinin (HA) tag, a FLAG tag), an affinity tag (including but not limited to a glutathione-S transferase (GST), a poly-Histidine (His) tag, Calmodulin Binding Protein (CBP), or Maltose-binding protein (MBP)), or a fluorescent tag.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

As used herein, an "antibody" includes whole antibodies and any antigen-binding fragment or a single chain thereof. Thus, the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the $V_L$, $V_H$, $C_L$ and $C_H$, domains; a F(ab')$_2$ fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "AHNAK" is a polynucleotide (such as a gene, a DNA, an mRNA or any hybrid thereof) that encodes a Neuroblast Differentiation-Associated Protein AHNAK. The nucleotide sequence, amino acid sequence, structure and other information relating to AHNAK and its *Homo sapiens* (human) AHNAK protein can be found at uniprot.org/uniprot/Q09666 and www.genecards.org/cgi-bin/carddisp.pl?gene=AHNAK, each of which is incorporated herein in its entirety by reference.

The term "AKAP13" is a polynucleotide (such as a gene, a DNA, an mRNA or any hybrid thereof) that encodes an A-Kinase Anchoring Protein 13. The nucleotide sequence, amino acid sequence, structure and other information relating to AKAP13 and its *Homo sapiens* (human) AKAP13 protein can be found at uniprot.org/uniprot/Q12802 and www.genecards.org/cgi-bin/carddisp.pl?gene=AKAP13, each of which is incorporated herein in its entirety by reference.

The term "AKAP9" is a polynucleotide (such as a gene, a DNA, an mRNA or any hybrid thereof) that encodes an A-Kinase Anchoring Protein 9. The nucleotide sequence, amino acid sequence, structure and other information relating to AKAP9 and its *Homo sapiens* (human) AKAP9 protein can be found at uniprot.org/uniprot/Q99996 and www.genecards.org/cgi-bin/carddisp.pl?gene=AKAP9, each of which is incorporated herein in its entirety by reference.

The term "ALMS1" is a polynucleotide (such as a gene, a DNA, an mRNA or any hybrid thereof) that encodes an ALMS1 Centrosome And Basal Body Associated Protein. The nucleotide sequence, amino acid sequence, structure and other information relating to ALMS1 and its *Homo sapiens* (human) ALMS1 protein can be found at uniprot.org/uniprot/Q8TCU4 and www.genecards.org/cgi-bin/carddisp.pl?gene=ALMS1, each of which is incorporated herein in its entirety by reference.

The term "APC" is a polynucleotide (such as a gene, a DNA, an mRNA or any hybrid thereof) that encodes an APC Regulator Of WNT Signaling Pathway, also known as Adenomatous polyposis coli protein. The nucleotide sequence, amino acid sequence, structure and other information relating to APC and its *Homo sapiens* (human) APC protein can be found at uniprot.org/uniprot/P25054 and www.genecards.org/cgi-bin/carddisp.pl?gene=APC, each of which is incorporated herein in its entirety by reference.

The term "ASPM" is a polynucleotide (such as a gene, a DNA, an mRNA or any hybrid thereof) that encodes an Assembly Factor For Spindle Microtubules. The nucleotide sequence, amino acid sequence, structure and other information relating to ASPM and its *Homo sapiens* (human) ASPM protein can be found at uniprot.org/uniprot/Q8IZT6 and www.genecards.org/cgi-bin/carddisp.pl?gene=ASPM, each of which is incorporated herein in its entirety by reference.

The term "ATM" is a polynucleotide (such as a gene, a DNA, an mRNA or any hybrid thereof) that encodes an ATM Serine/Threonine Kinase. The nucleotide sequence, amino acid sequence, structure and other information relating to ATM and its *Homo sapiens* (human) ATM protein can be found at uniprot.org/uniprot/Q13315 and www.genecards.org/cgi-bin/carddisp.pl?gene=ATM, each of which is incorporated herein in its entirety by reference.

The term "BIRC6" is a polynucleotide (such as a gene, a DNA, an mRNA or any hybrid thereof) that encodes a Baculoviral IAP Repeat Containing 6. The nucleotide sequence, amino acid sequence, structure and other information relating to BIRC6 and its *Homo sapiens* (human) BIRC6 protein can be found at uniprot.org/uniprot/Q9NR09 and www.genecards.org/cgi-bin/carddisp.pl?gene=BIRC6, each of which is incorporated herein in its entirety by reference.

The term "BMF" is a polynucleotide (such as a gene, a DNA, an mRNA or any hybrid thereof) that encodes a Bcl2 Modifying Factor. The nucleotide sequence, amino acid sequence, structure and other information relating to BMF and its *Homo sapiens* (human) BMF protein can be found at uniprot.org/uniprot/Q96LC9 and www.genecards.org/cgi-bin/carddisp.pl?gene=BMF, each of which is incorporated herein in its entirety by reference.

The term "BRCA2" is a polynucleotide (such as a gene, a DNA, an mRNA or any hybrid thereof) that encodes a BRCA2 DNA Repair Associated. The nucleotide sequence, amino acid sequence, structure and other information relating to BRCA2 and its *Homo sapiens* (human) BRCA2 protein can be found at uniprot.org/uniprot/P51587 and www.genecards.org/cgi-bin/carddisp.pl?gene=BRCA2, each of which is incorporated herein in its entirety by reference.

The term "BUB1B" is a polynucleotide (such as a gene, a DNA, an mRNA or any hybrid thereof) that encodes a BUB1 Mitotic Checkpoint Serine/Threonine Kinase B. The nucleotide sequence, amino acid sequence, structure and other information relating to BUB1B and its *Homo sapiens* (human) BUB1B protein can be found at uniprot.org/uniprot/O60566 and www.genecards.org/cgi-bin/carddisp.pl?gene=BUB1B, each of which is incorporated herein in its entirety by reference.

The term "CCDC88A" is a polynucleotide (such as a gene, a DNA, an mRNA or any hybrid thereof) that encodes a Coiled-Coil Domain Containing 88A. The nucleotide sequence, amino acid sequence, structure and other information relating to CCDC88A and its *Homo sapiens* (human) CCDC88A protein can be found at uniprot.org/uniprot/Q3V6T2 and www.genecards.org/cgi-bin/carddisp.pl?gene=CCDC88A, each of which is incorporated herein in its entirety by reference.

The term "CCNA1" is a polynucleotide (such as a gene, a DNA, an mRNA or any hybrid thereof) that encodes a Cyclin A1. The nucleotide sequence, amino acid sequence, structure and other information relating to CCNA1 and its *Homo sapiens* (human) CCNA1 protein can be found at uniprot.org/uniprot/P78396 and www.genecards.org/cgi-bin/carddisp.pl?gene=CCNA1, each of which is incorporated herein in its entirety by reference.

The term "CCNB1" is a polynucleotide (such as a gene, a DNA, an mRNA or any hybrid thereof) that encodes a Cyclin B1. The nucleotide sequence, amino acid sequence, structure and other information relating to CCNB1 and its *Homo sapiens* (human) CCNB1 protein can be found at uniprot.org/uniprot/P14635 and www.genecards.org/cgi-bin/carddisp.pl?gene=CCNB1, each of which is incorporated herein in its entirety by reference.

The term "CCNB2" is a polynucleotide (such as a gene, a DNA, an mRNA or any hybrid thereof) that encodes a Cyclin B2. The nucleotide sequence, amino acid sequence, structure and other information relating to CCNB2 and its *Homo sapiens* (human) CCNB2 protein can be found at uniprot.org/uniprot/O95067 and www.genecards.org/cgi-bin/carddisp.pl?gene=CCNB2, each of which is incorporated herein in its entirety by reference.

The term "CCNF" is a polynucleotide (such as a gene, a DNA, an mRNA or any hybrid thereof) that encodes a Cyclin F. The nucleotide sequence, amino acid sequence, structure and other information relating to CCNF and its *Homo sapiens* (human) CCNF protein can be found at uniprot.org/uniprot/P41002 and www.genecards.org/cgi-bin/carddisp.pl?gene=CCNF, each of which is incorporated herein in its entirety by reference.

The term "CDC25B" is a polynucleotide (such as a gene, a DNA, an mRNA or any hybrid thereof) that encodes a Cell Division Cycle 25B, also known as M-Phase Inducer Phosphatase 2. The nucleotide sequence, amino acid sequence, structure and other information relating to CDC25B and its *Homo sapiens* (human) CDC25B protein can be found at uniprot.org/uniprot/P30305 and www.genecards.org/cgi-bin/carddisp.pl?gene=CDC25B, each of which is incorporated herein in its entirety by reference.

The term "CDC42BPA" is a polynucleotide (such as a gene, a DNA, an mRNA or any hybrid thereof) that encodes a CDC42 Binding Protein Kinase Alpha. The nucleotide sequence, amino acid sequence, structure and other information relating to CDC42BPA and its *Homo sapiens* (human) CDC42BPA protein can be found at uniprot.org/uniprot/Q5VT25 and www.genecards.org/cgi-bin/carddisp.pl?gene=CDC42BPA, each of which is incorporated herein in its entirety by reference.

The term "CDC42EP2" is a polynucleotide (such as a gene, a DNA, an mRNA or any hybrid thereof) that encodes a CDC42 Effector Protein 2. The nucleotide sequence, amino acid sequence, structure and other information relating to CDC42EP2 and its *Homo sapiens* (human) CDC42EP2 protein can be found at uniprot.org/uniprot/O14613 and www.genecards.org/cgi-bin/carddisp.pl?gene=CDC42EP2, each of which is incorporated herein in its entirety by reference.

The term "CDC45" is a polynucleotide (such as a gene, a DNA, an mRNA or any hybrid thereof) that encodes a Cell Division Cycle 45. The nucleotide sequence, amino acid sequence, structure and other information relating to CDC45 and its *Homo sapiens* (human) CDC45 protein can be found at uniprot.org/uniprot/O75419 and www.genecards.org/cgi-bin/carddisp.pl?gene=CDC45, each of which is incorporated herein in its entirety by reference.

The term "CDC6" is a polynucleotide (such as a gene, a DNA, an mRNA or any hybrid thereof) that encodes a Cell Division Cycle 6. The nucleotide sequence, amino acid sequence, structure and other information relating to CDC6 and its *Homo sapiens* (human) CDC6 protein can be found at uniprot.org/uniprot/Q99741 and www.genecards.org/cgi-bin/carddisp.pl?gene=CDC6, each of which is incorporated herein in its entirety by reference.

The term "CENPE" is a polynucleotide (such as a gene, a DNA, an mRNA or any hybrid thereof) that encodes a Centromere Protein E. The nucleotide sequence, amino acid sequence, structure and other information relating to CENPE and its *Homo sapiens* (human) CENPE protein can be found at uniprot.org/uniprot/Q02224 and www.genecards.org/cgi-bin/carddisp.pl?gene=CENPE, each of which is incorporated herein in its entirety by reference.

The term "CENPF" is a polynucleotide (such as a gene, a DNA, an mRNA or any hybrid thereof) that encodes a Centromere Protein F. The nucleotide sequence, amino acid sequence, structure and other information relating to CENPF and its *Homo sapiens* (human) CENPF protein can be found at uniprot.org/uniprot/P49454 and www.genecards.org/cgi-bin/carddisp.pl?gene=CENPF, each of which is incorporated herein in its entirety by reference.

The term "CENPJ" is a polynucleotide (such as a gene, a DNA, an mRNA or any hybrid thereof) that encodes a Centromere Protein J. The nucleotide sequence, amino acid sequence, structure and other information relating to CENPJ and its *Homo sapiens* (human) CENPJ protein can be found at uniprot.org/uniprot/Q9HC77 and www.genecards.org/cgi-bin/carddisp.pl?gene=CENPJ, each of which is incorporated herein in its entirety by reference.

The term "CEP192" is a polynucleotide (such as a gene, a DNA, an mRNA or any hybrid thereof) that encodes a Centrosomal Protein 192. The nucleotide sequence, amino acid sequence, structure and other information relating to CEP192 and its *Homo sapiens* (human) CEP192 protein can be found at uniprot.org/uniprot/Q8TEP8 and www.genecards.org/cgi-bin/carddisp.pl?gene=CEP192, each of which is incorporated herein in its entirety by reference.

The term "CEP350" is a polynucleotide (such as a gene, a DNA, an mRNA or any hybrid thereof) that encodes a Centrosomal Protein 350. The nucleotide sequence, amino acid sequence, structure and other information relating to CEP350 and its *Homo sapiens* (human) CEP350 protein can be found at uniprot.org/uniprot/Q5VT06 and www.genecards.org/cgi-bin/carddisp.pl?gene=CEP350, each of which is incorporated herein in its entirety by reference.

The term "CEP97" is a polynucleotide (such as a gene, a DNA, an mRNA or any hybrid thereof) that encodes a Centrosomal Protein 97. The nucleotide sequence, amino acid sequence, structure and other information relating to CEP97 and its *Homo sapiens* (human) CEP97 protein can be found at uniprot.org/uniprot/Q8IW35 and www.genecards.org/cgi-bin/carddisp.pl?gene=CEP97, each of which is incorporated herein in its entirety by reference.

The term "CKAP2" is a polynucleotide (such as a gene, a DNA, an mRNA or any hybrid thereof) that encodes a Cytoskeleton Associated Protein 2. The nucleotide sequence, amino acid sequence, structure and other information relating to CKAP2 and its *Homo sapiens* (human) CKAP2 protein can be found at uniprot.org/uniprot/Q8WWK9 and www.genecards.org/cgi-bin/carddisp.pl?gene=CKAP2, each of which is incorporated herein in its entirety by reference.

The term "CKAP5" is a polynucleotide (such as a gene, a DNA, an mRNA or any hybrid thereof) that encodes a Cytoskeleton Associated Protein 5. The nucleotide sequence, amino acid sequence, structure and other information relating to CKAP5 and its *Homo sapiens* (human) CKAP5 protein can be found at uniprot.org/uniprot/Q14008 and www.genecards.org/cgi-bin/carddisp.pl?gene=CKAP5, each of which is incorporated herein in its entirety by reference.

The term "CNTRL" is a polynucleotide (such as a gene, a DNA, an mRNA or any hybrid thereof) that encodes a Centriolin. The nucleotide sequence, amino acid sequence, structure and other information relating to CNTRL and its *Homo sapiens* (human) CNTRL protein can be found at uniprot.org/uniprot/Q7Z7A1 and www.genecards.org/cgi-bin/carddisp.pl?gene=CNTRL, each of which is incorporated herein in its entirety by reference.

The term "DCLRElB" is a polynucleotide (such as a gene, a DNA, an mRNA or any hybrid thereof) that encodes a DNA Cross-Link Repair 1B. The nucleotide sequence, amino acid sequence, structure and other information relating to DCLRElB and its *Homo sapiens* (human) DCLRElB protein can be found at uniprot.org/uniprot/Q9H816 and www.genecards.org/cgi-bin/carddisp.pl?gene=DCLRE1B, each of which is incorporated herein in its entirety by reference.

The term "DSP" is a polynucleotide (such as a gene, a DNA, an mRNA or any hybrid thereof) that encodes a Desmoplakin. The nucleotide sequence, amino acid sequence, structure and other information relating to DSP and its *Homo sapiens* (human) DSP protein can be found at uniprot.org/uniprot/P15924 and www.genecards.org/cgi-bin/carddisp.pl?gene=DSP, each of which is incorporated herein in its entirety by reference.

The term "DST" is a polynucleotide (such as a gene, a DNA, an mRNA or any hybrid thereof) that encodes a Dystonin. The nucleotide sequence, amino acid sequence, structure and other information relating to DST and its *Homo sapiens* (human) DST protein can be found at uniprot.org/uniprot/Q03001 and www.genecards.org/cgi-bin/carddisp.pl?gene=DST, each of which is incorporated herein in its entirety by reference.

The term "DTL" is a polynucleotide (such as a gene, a DNA, an mRNA or any hybrid thereof) that encodes a Denticleless E3 Ubiquitin Protein Ligase Homolog. The nucleotide sequence, amino acid sequence, structure and other information relating to DTL and its *Homo sapiens* (human) DTL protein can be found at uniprot.org/uniprot/Q9NZJ0 and www.genecards.org/cgi-bin/carddisp.pl?gene=DTL, each of which is incorporated herein in its entirety by reference.

The term "DYNC1H1" is a polynucleotide (such as a gene, a DNA, an mRNA or any hybrid thereof) that encodes a Dynein Cytoplasmic 1 Heavy Chain 1. The nucleotide sequence, amino acid sequence, structure and other information relating to DYNC1H1 and its *Homo sapiens* (human) DYNC1H1 protein can be found at uniprot.org/uniprot/Q14204 and www.genecards.org/cgi-bin/carddisp.pl?gene=DYNC1H1, each of which is incorporated herein in its entirety by reference.

The term "DYNC2H1" is a polynucleotide (such as a gene, a DNA, an mRNA or any hybrid thereof) that encodes a Dynein Cytoplasmic 2 Heavy Chain 1. The nucleotide sequence, amino acid sequence, structure and other information relating to DYNC2H1 and its *Homo sapiens* (human) DYNC2H1 protein can be found at uniprot.org/uniprot/Q8NCM8 and www.genecards.org/cgi-bin/carddisp.pl?gene=DYNC2H1, each of which is incorporated herein in its entirety by reference.

The term "E2F1" is a polynucleotide (such as a gene, a DNA, an mRNA or any hybrid thereof) that encodes an E2F Transcription Factor 1. The nucleotide sequence, amino acid sequence, structure and other information relating to E2F1 and its *Homo sapiens* (human) E2F1 protein can be found at uniprot.org/uniprot/Q01094 and www.genecards.org/cgi-bin/carddisp.pl?gene=E2F1, each of which is incorporated herein in its entirety by reference.

The term "ESPL1" is a polynucleotide (such as a gene, a DNA, an mRNA or any hybrid thereof) that encodes an Extra Spindle Pole Bodies Like 1, Separase. The nucleotide sequence, amino acid sequence, structure and other information relating to ESPL1 and its *Homo sapiens* (human) ESPL1 protein can be found at uniprot.org/uniprot/Q14674 and www.genecards.org/cgi-bin/carddisp.pl?gene=ESPL1, each of which is incorporated herein in its entirety by reference.

The term "FLG" is a polynucleotide (such as a gene, a DNA, an mRNA or any hybrid thereof) that encodes a Filaggrin. The nucleotide sequence, amino acid sequence, structure and other information relating to FLG and its *Homo sapiens* (human) FLG protein can be found at uniprot.org/uniprot/P20930 and www.genecards.org/cgi-bin/carddisp.pl?gene=FLG, each of which is incorporated herein in its entirety by reference.

The term "FRMD6" is a polynucleotide (such as a gene, a DNA, an mRNA or any hybrid thereof) that encodes an FERM Domain Containing 6. The nucleotide sequence, amino acid sequence, structure and other information relating to FRMD6 and its *Homo sapiens* (human) FRMD6 protein can be found at uniprot.org/uniprot/Q96NE9 and www.genecards.org/cgi-bin/carddisp.pl?gene=FRMD6, each of which is incorporated herein in its entirety by reference.

The term "GAS2L3" is a polynucleotide (such as a gene, a DNA, an mRNA or any hybrid thereof) that encodes a Growth Arrest Specific 2 Like 3. The nucleotide sequence, amino acid sequence, structure and other information relating to GAS2L3 and its *Homo sapiens* (human) GAS2L3 protein can be found at uniprot.org/uniprot/Q86XJ1 and www.genecards.org/cgi-bin/carddisp.pl?gene=GAS2L3, each of which is incorporated herein in its entirety by reference.

The term "GEM" is a polynucleotide (such as a gene, a DNA, an mRNA or any hybrid thereof) that encodes a GTP Binding Protein Overexpressed In Skeletal Muscle. The nucleotide sequence, amino acid sequence, structure and other information relating to GEM and its *Homo sapiens* (human) GEM protein can be found at uniprot.org/uniprot/P55040 and www.genecards.org/cgi-bin/carddisp.pl?gene=GEM, each of which is incorporated herein in its entirety by reference.

The term "GEN1" is a polynucleotide (such as a gene, a DNA, an mRNA or any hybrid thereof) that encodes a GEN1 Holliday Junction 5' Flap Endonuclease. The nucleotide sequence, amino acid sequence, structure and other information relating to GEN1 and its *Homo sapiens* (human) GEN1 protein can be found at uniprot.org/uniprot/Q17RS7 and www.genecards.org/cgi-bin/carddisp.pl?gene=GEN1, each of which is incorporated herein in its entirety by reference.

The term "GPSM2" is a polynucleotide (such as a gene, a DNA, an mRNA or any hybrid thereof) that encodes a G Protein Signaling Modulator 2. The nucleotide sequence, amino acid sequence, structure and other information relating to GPSM2 and its *Homo sapiens* (human) GPSM2 protein can be found at uniprot.org/uniprot/P81274 and www.genecards.org/cgi-bin/carddisp.pl?gene=GPSM2, each of which is incorporated herein in its entirety by reference.

The term "GTSE1" is a polynucleotide (such as a gene, a DNA, an mRNA or any hybrid thereof) that encodes a G2 And S-Phase Expressed 1. The nucleotide sequence, amino acid sequence, structure and other information relating to GTSE1 and its *Homo sapiens* (human) GTSE1 protein can be found at uniprot.org/uniprot/Q9NYZ3 and www.genecards.org/cgi-bin/carddisp.pl?gene=GTSE1, each of which is incorporated herein in its entirety by reference.

The term "HDAC4" is a polynucleotide (such as a gene, a DNA, an mRNA or any hybrid thereof) that encodes a Histone Deacetylase 4. The nucleotide sequence, amino acid sequence, structure and other information relating to HDAC4 and its *Homo sapiens* (human) HDAC4 protein can be found at uniprot.org/uniprot/P56524 and www.genecards.org/cgi-bin/carddisp.pl?gene=HDAC4, each of which is incorporated herein in its entirety by reference.

The term "HERC2" is a polynucleotide (such as a gene, a DNA, an mRNA or any hybrid thereof) that encodes an HECT And RLD Domain Containing E3 Ubiquitin Protein Ligase 2. The nucleotide sequence, amino acid sequence, structure and other information relating to HERC2 and its *Homo sapiens* (human) HERC2 protein can be found at uniprot.org/uniprot/O95714 and www.genecards.org/cgi-bin/carddisp.pl?gene=HERC2, each of which is incorporated herein in its entirety by reference.

The term "HMMR" is a polynucleotide (such as a gene, a DNA, an mRNA or any hybrid thereof) that encodes a Hyaluronan Mediated Motility Receptor. The nucleotide sequence, amino acid sequence, structure and other information relating to HMMR and its *Homo sapiens* (human) HMMR protein can be found at uniprot.org/uniprot/O75330 and www.genecards.org/cgi-bin/carddisp.pl?gene=HMMR, each of which is incorporated herein in its entirety by reference.

The term "HTT" is a polynucleotide (such as a gene, a DNA, an mRNA or any hybrid thereof) that encodes a Huntingtin. The nucleotide sequence, amino acid sequence, structure and other information relating to HTT and its *Homo sapiens* (human) HTT protein can be found at uniprot.org/uniprot/P42858 and www.genecards.org/cgi-bin/carddisp.pl?gene=HTT, each of which is incorporated herein in its entirety by reference.

The term "KIAA0586" is a polynucleotide (such as a gene, a DNA, an mRNA or any hybrid thereof) that encodes a Protein TALPID3. The nucleotide sequence, amino acid sequence, structure and other information relating to KIAA0586 and its *Homo sapiens* (human) KIAA0586 protein can be found at uniprot.org/uniprot/Q9BVV6 and www.genecards.org/cgi-bin/carddisp.pl?gene=KIAA0586, each of which is incorporated herein in its entirety by reference.

The term "KIF11" is a polynucleotide (such as a gene, a DNA, an mRNA or any hybrid thereof) that encodes a Kinesin Family Member 11. The nucleotide sequence, amino acid sequence, structure and other information relating to KIF11 and its *Homo sapiens* (human) KIF11 protein can be found at uniprot.org/uniprot/P52732 and www.genecards.org/cgi-bin/carddisp.pl?gene=KIF11, each of which is incorporated herein in its entirety by reference.

The term "KIF14" is a polynucleotide (such as a gene, a DNA, an mRNA or any hybrid thereof) that encodes a Kinesin Family Member 14. The nucleotide sequence, amino acid sequence, structure and other information relating to KIF14 and its *Homo sapiens* (human) KIF14 protein can be found at uniprot.org/uniprot/Q15058 and www.genecards.org/cgi-bin/carddisp.pl?gene=KIF14, each of which is incorporated herein in its entirety by reference.

The term "KIF18A" is a polynucleotide (such as a gene, a DNA, an mRNA or any hybrid thereof) that encodes a Kinesin Family Member 18A. The nucleotide sequence, amino acid sequence, structure and other information relating to KIF18A and its *Homo sapiens* (human) KIF18A protein can be found at uniprot.org/uniprot/Q8NI77 and www.genecards.org/cgi-bin/carddisp.pl?gene=KIF18A, each of which is incorporated herein in its entirety by reference.

The term "KIF18B" is a polynucleotide (such as a gene, a DNA, an mRNA or any hybrid thereof) that encodes a Kinesin Family Member 18B. The nucleotide sequence, amino acid sequence, structure and other information relating to KIF18B and its *Homo sapiens* (human) KIF18B protein can be found at uniprot.org/uniprot/Q86Y91 and www.genecards.org/cgi-bin/carddisp.pl?gene=KIF18B, each of which is incorporated herein in its entirety by reference.

The term "KIF20A" is a polynucleotide (such as a gene, a DNA, an mRNA or any hybrid thereof) that encodes a Kinesin Family Member 20A. The nucleotide sequence, amino acid sequence, structure and other information relating to KIF20A and its *Homo sapiens* (human) KIF20A protein can be found at uniprot.org/uniprot/O95235 and www.genecards.org/cgi-bin/carddisp.pl?gene=KIF20A, each of which is incorporated herein in its entirety by reference.

The term "KIF20B" is a polynucleotide (such as a gene, a DNA, an mRNA or any hybrid thereof) that encodes a Kinesin Family Member 20B. The nucleotide sequence, amino acid sequence, structure and other information relating to KIF20B and its *Homo sapiens* (human) KIF20B protein can be found at uniprot.org/uniprot/Q96Q89 and www.genecards.org/cgi-bin/carddisp.pl?gene=KIF20B, each of which is incorporated herein in its entirety by reference.

The term "KIF4A" is a polynucleotide (such as a gene, a DNA, an mRNA or any hybrid thereof) that encodes a Kinesin Family Member 4A. The nucleotide sequence, amino acid sequence, structure and other information relating to KIF4A and its *Homo sapiens* (human) KIF4A protein can be found at uniprot.org/uniprot/O95239 and www.genecards.org/cgi-bin/carddisp.pl?gene=KIF4A, each of which is incorporated herein in its entirety by reference.

The term "KNSTRN" is a polynucleotide (such as a gene, a DNA, an mRNA or any hybrid thereof) that encodes a Kinetochore Localized Astrin (SPAG5) Binding Protein. The nucleotide sequence, amino acid sequence, structure and other information relating to KNSTRN and its *Homo sapiens* (human) KNSTRN protein can be found at uniprot.org/uniprot/Q9Y448 and www.genecards.org/cgi-bin/carddisp.pl?gene=KNSTRN, each of which is incorporated herein in its entirety by reference.

The term "KRT17" is a polynucleotide (such as a gene, a DNA, an mRNA or any hybrid thereof) that encodes a Keratin 17. The nucleotide sequence, amino acid sequence, structure and other information relating to KRT17 and its *Homo sapiens* (human) KRT17 protein can be found at uniprot.org/uniprot/Q04695 and www.genecards.org/cgi-bin/carddisp.pl?gene=KRT17, each of which is incorporated herein in its entirety by reference.

The term "KRT81" is a polynucleotide (such as a gene, a DNA, an mRNA or any hybrid thereof) that encodes a Keratin 81. The nucleotide sequence, amino acid sequence, structure and other information relating to KRT81 and its *Homo sapiens* (human) KRT81 protein can be found at uniprot.org/uniprot/Q14533 and www.genecards.org/cgi-bin/carddisp.pl?gene=KRT81, each of which is incorporated herein in its entirety by reference.

The term "MACF1" is a polynucleotide (such as a gene, a DNA, an mRNA or any hybrid thereof) that encodes a Microtubule Actin Crosslinking Factor 1. The nucleotide sequence, amino acid sequence, structure and other information relating to MACF1 and its *Homo sapiens* (human) MACF1 protein can be found at uniprot.org/uniprot/Q9UPN3 and www.genecards.org/cgi-bin/carddisp.pl?gene=MACF1, each of which is incorporated herein in its entirety by reference.

The term "MAP1B" is a polynucleotide (such as a gene, a DNA, an mRNA or any hybrid thereof) that encodes a Microtubule Associated Protein 1B. The nucleotide sequence, amino acid sequence, structure and other information relating to MAP1B and its *Homo sapiens* (human) MAP1B protein can be found at uniprot.org/uniprot/P46821 and www.genecards.org/cgi-bin/carddisp.pl?gene=MAP1B, each of which is incorporated herein in its entirety by reference.

The term "MCM2" is a polynucleotide (such as a gene, a DNA, an mRNA or any hybrid thereof) that encodes a Minichromosome Maintenance Complex Component 2. The nucleotide sequence, amino acid sequence, structure and other information relating to MCM2 and its *Homo sapiens* (human) MCM2 protein can be found at uniprot.org/uniprot/P49736 and www.genecards.org/cgi-bin/carddisp.pl?gene=MCM2, each of which is incorporated herein in its entirety by reference.

The term "MCM3" is a polynucleotide (such as a gene, a DNA, an mRNA or any hybrid thereof) that encodes a Minichromosome Maintenance Complex Component 3. The nucleotide sequence, amino acid sequence, structure and other information relating to MCM3 and its *Homo sapiens* (human) MCM3 protein can be found at uniprot.org/uniprot/P25205 and www.genecards.org/cgi-bin/carddisp.pl?gene=MCM3, each of which is incorporated herein in its entirety by reference.

The term "MDN1" is a polynucleotide (such as a gene, a DNA, an mRNA or any hybrid thereof) that encodes a Midasin AAA ATPase 1. The nucleotide sequence, amino acid sequence, structure and other information relating to MDN1 and its *Homo sapiens* (human) MDN1 protein can be found at uniprot.org/uniprot/Q9NU22 and www.genecards.org/cgi-bin/carddisp.pl?gene=MDN1, each of which is incorporated herein in its entirety by reference.

The term "MYH15" is a polynucleotide (such as a gene, a DNA, an mRNA or any hybrid thereof) that encodes a Myosin Heavy Chain 15. The nucleotide sequence, amino acid sequence, structure and other information relating to MYH15 and its *Homo sapiens* (human) MYH15 protein can be found at uniprot.org/uniprot/Q9Y2K3 and www.genecards.org/cgi-bin/carddisp.pl?gene=MYH15, each of which is incorporated herein in its entirety by reference.

The term "MYO5A" is a polynucleotide (such as a gene, a DNA, an mRNA or any hybrid thereof) that encodes a Myosin VA. The nucleotide sequence, amino acid sequence, structure and other information relating to MYO5A and its *Homo sapiens* (human) MYO5A protein can be found at uniprot.org/uniprot/Q9Y4I1 and www.genecards.org/cgi-bin/carddisp.pl?gene=MYO5A, each of which is incorporated herein in its entirety by reference.

The term "MYO9A" is a polynucleotide (such as a gene, a DNA, an mRNA or any hybrid thereof) that encodes a Myosin IXA. The nucleotide sequence, amino acid sequence, structure and other information relating to MYO9A and its *Homo sapiens* (human) MYO9A protein can be found at uniprot.org/uniprot/B2RTY4 and www.genecards.org/cgi-bin/carddisp.pl?gene=MYO9A, each of which is incorporated herein in its entirety by reference.

The term "NAV1" is a polynucleotide (such as a gene, a DNA, an mRNA or any hybrid thereof) that encodes a Neuron Navigator 1. The nucleotide sequence, amino acid sequence, structure and other information relating to NAV1 and its *Homo sapiens* (human) NAV1 protein can be found at uniprot.org/uniprot/Q8NEY1 and www.genecards.org/cgi-bin/carddisp.pl?gene=NAV1, each of which is incorporated herein in its entirety by reference.

The term "NDE1" is a polynucleotide (such as a gene, a DNA, an mRNA or any hybrid thereof) that encodes a NudE Neurodevelopment Protein 1. The nucleotide sequence, amino acid sequence, structure and other information relating to NDE1 and its *Homo sapiens* (human) NDE1 protein can be found at uniprot.org/uniprot/Q9NXR1 and www.genecards.org/cgi-bin/carddisp.pl?gene=NDE1, each of which is incorporated herein in its entirety by reference.

The term "NEK2" is a polynucleotide (such as a gene, a DNA, an mRNA or any hybrid thereof) that encodes an NIMA Related Kinase 2. The nucleotide sequence, amino acid sequence, structure and other information relating to NEK2 and its *Homo sapiens* (human) NEK2 protein can be found at uniprot.org/uniprot/P51955 and www.genecards.org/cgi-bin/carddisp.pl?gene=NEK2, each of which is incorporated herein in its entirety by reference.

The term "PAWR" is a polynucleotide (such as a gene, a DNA, an mRNA or any hybrid thereof) that encodes a Pro-Apoptotic WT1 Regulator. The nucleotide sequence, amino acid sequence, structure and other information relating to PAWR and its *Homo sapiens* (human) PAWR protein can be found at uniprot.org/uniprot/Q62627 and www.genecards.org/cgi-bin/carddisp.pl?gene=PAWR, each of which is incorporated herein in its entirety by reference.

The term "PCNA" is a polynucleotide (such as a gene, a DNA, an mRNA or any hybrid thereof) that encodes a Proliferating Cell Nuclear Antigen. The nucleotide sequence, amino acid sequence, structure and other information relating to PCNA and its *Homo sapiens* (human) PCNA protein can be found at uniprot.org/uniprot/P12004 and www.genecards.org/cgi-bin/carddisp.pl?gene=PCNA, each of which is incorporated herein in its entirety by reference.

The term "PCNT" is a polynucleotide (such as a gene, a DNA, an mRNA or any hybrid thereof) that encodes a Pericentrin. The nucleotide sequence, amino acid sequence, structure and other information relating to PCNT and its *Homo sapiens* (human) PCNT protein can be found at uniprot.org/uniprot/O95613 and www.genecards.org/cgi-bin/carddisp.pl?gene=PCNT, each of which is incorporated herein in its entirety by reference.

The term "PDE4DIP" is a polynucleotide (such as a gene, a DNA, an mRNA or any hybrid thereof) that encodes a Phosphodiesterase 4D Interacting Protein. The nucleotide sequence, amino acid sequence, structure and other information relating to PDE4DIP and its *Homo sapiens* (human) PDE4DIP protein can be found at uniprot.org/uniprot/Q5VU43 and www.genecards.org/cgi-bin/carddisp.pl?gene=PDE4DIP, each of which is incorporated herein in its entirety by reference.

The term "PEAK1" is a polynucleotide (such as a gene, a DNA, an mRNA or any hybrid thereof) that encodes a Pseudopodium Enriched Atypical Kinase 1. The nucleotide sequence, amino acid sequence, structure and other information relating to PEAK1 and its *Homo sapiens* (human) PEAK1 protein can be found at uniprot.org/uniprot/Q9H792 and www.genecards.org/cgi-bin/carddisp.pl?gene=PEAK1, each of which is incorporated herein in its entirety by reference.

The term "PLEKHH2" is a polynucleotide (such as a gene, a DNA, an mRNA or any hybrid thereof) that encodes a Pleckstrin Homology, MyTH4 And FERM Domain Containing H2. The nucleotide sequence, amino acid sequence, structure and other information relating to PLEKHH2 and its *Homo sapiens* (human) PLEKHH2 protein can be found at uniprot.org/uniprot/Q8IVE3 and www.genecards.org/cgi-bin/carddisp.pl?gene=PLEKHH2, each of which is incorporated herein in its entirety by reference.

The term "PLK2" is a polynucleotide (such as a gene, a DNA, a mRNA or any hybrid thereof) that encodes a Polo Like Kinase 2. The nucleotide sequence, amino acid sequence, structure and other information relating to PLK2 and its *Homo sapiens* (human) PLK2 protein can be found at uniprot.org/uniprot/Q9NYY3 and www.genecards.org/cgi-bin/carddisp.pl?gene=PLK2, each of which is incorporated herein in its entirety by reference.

The term "PSRC1" is a polynucleotide (such as a gene, a DNA, an mRNA or any hybrid thereof) that encodes a Proline And Serine Rich Coiled-Coil 1. The nucleotide sequence, amino acid sequence, structure and other information relating to PSRC1 and its *Homo sapiens* (human) PSRC1 protein can be found at uniprot.org/uniprot/Q6PGN9 and www.genecards.org/cgi-bin/carddisp.pl?gene=PSRC1, each of which is incorporated herein in its entirety by reference.

The term "PTPN14" is a polynucleotide (such as a gene, a DNA, an mRNA or any hybrid thereof) that encodes a Protein Tyrosine Phosphatase Non-Receptor Type 14. The nucleotide sequence, amino acid sequence, structure and other information relating to PTPN14 and its *Homo sapiens* (human) PTPN14 protein can be found at uniprot.org/uniprot/Q15678 and www.genecards.org/cgi-bin/carddisp.pl?gene=PTPN14, each of which is incorporated herein in its entirety by reference.

The term "RANBP2" is a polynucleotide (such as a gene, a DNA, an mRNA or any hybrid thereof) that encodes a RAN Binding Protein 2. The nucleotide sequence, amino acid sequence, structure and other information relating to RANBP2 and its *Homo sapiens* (human) RANBP2 protein can be found at uniprot.org/uniprot/P49792 and www.genecards.org/cgi-bin/carddisp.pl?gene=RANBP2, each of which is incorporated herein in its entirety by reference.

The term "RBBP6" is a polynucleotide (such as a gene, a DNA, an mRNA or any hybrid thereof) that encodes a RB Binding Protein 6, Ubiquitin Ligase. The nucleotide sequence, amino acid sequence, structure and other information relating to RBBP6 and its *Homo sapiens* (human) RBBP6 protein can be found at uniprot.org/uniprot/Q7Z6E9 and www.genecards.org/cgi-bin/carddisp.pl?gene=RBBP6, each of which is incorporated herein in its entirety by reference.

The term "RCSD1" is a polynucleotide (such as a gene, a DNA, an mRNA or any hybrid thereof) that encodes an RCSD Domain Containing 1 or CapZ-interacting protein. The nucleotide sequence, amino acid sequence, structure and other information relating to RCSD1 and its *Homo sapiens* (human) RCSD1 protein can be found at uniprot.org/uniprot/Q6JBY9 and www.genecards.org/cgi-bin/carddisp.pl?gene=RCSD1, each of which is incorporated herein in its entirety by reference.

The term "REEP4" is a polynucleotide (such as a gene, a DNA, an mRNA or any hybrid thereof) that encodes a Receptor Accessory Protein 4. The nucleotide sequence, amino acid sequence, structure and other information relating to REEP4 and its *Homo sapiens* (human) REEP4 protein can be found at uniprot.org/uniprot/Q9H6H4 and www.genecards.org/cgi-bin/carddisp.pl?gene=REEP4, each of which is incorporated herein in its entirety by reference.

The term "RIF1" is a polynucleotide (such as a gene, a DNA, an mRNA or any hybrid thereof) that encodes a Replication Timing Regulatory Factor 1. The nucleotide sequence, amino acid sequence, structure and other information relating to RIF1 and its *Homo sapiens* (human) RIF1 protein can be found at uniprot.org/uniprot/Q5UIP0 and www.genecards.org/cgi-bin/carddisp.pl?gene=RIF1, each of which is incorporated herein in its entirety by reference.

The term "SAA1" is a polynucleotide (such as a gene, a DNA, an mRNA or any hybrid thereof) that encodes a Serum Amyloid A1. The nucleotide sequence, amino acid sequence, structure and other information relating to SAA1 and its *Homo sapiens* (human) SAA1 protein can be found at uniprot.org/uniprot/P0DJI8 and www.genecards.org/cgi-bin/carddisp.pl?gene=SAA1, each of which is incorporated herein in its entirety by reference.

The term "SCLT1" is a polynucleotide (such as a gene, a DNA, an mRNA or any hybrid thereof) that encodes a Sodium Channel And Clathrin Linker 1. The nucleotide sequence, amino acid sequence, structure and other information relating to SCLT1 and its *Homo sapiens* (human) SCLT1 protein can be found at uniprot.org/uniprot/Q96NL6 and www.genecards.org/cgi-bin/carddisp.pl?gene=SCLT1, each of which is incorporated herein in its entirety by reference.

The term "SETD2" is a polynucleotide (such as a gene, a DNA, an mRNA or any hybrid thereof) that encodes an SET Domain Containing 2, Histone Lysine Methyltransferase. The nucleotide sequence, amino acid sequence, structure and other information relating to SETD2 and its *Homo sapiens* (human) SETD2 protein can be found at uniprot.org/uniprot/Q9BYW2 and www.genecards.org/cgi-bin/carddisp.pl?gene=SETD2, each of which is incorporated herein in its entirety by reference.

The term "SH3PXD2A" is a polynucleotide (such as a gene, a DNA, an mRNA or any hybrid thereof) that encodes an SH3 And PX Domains 2A. The nucleotide sequence, amino acid sequence, structure and other information relating to SH3PXD2A and its *Homo sapiens* (human) SH3PXD2A protein can be found at uniprot.org/uniprot/Q5TCZ1 and www.genecards.org/cgi-bin/carddisp.pl?gene=SH3PXD2A, each of which is incorporated herein in its entirety by reference.

The term "SLC7A11" is a polynucleotide (such as a gene, a DNA, an mRNA or any hybrid thereof) that encodes a Solute Carrier Family 7 Member 11. The nucleotide sequence, amino acid sequence, structure and other information relating to SLC7A11 and its *Homo sapiens* (human) SLC7A11 protein can be found at uniprot.org/uniprot/Q9UPY5 and www.genecards.org/cgi-bin/carddisp.pl?gene=SLC7A11, each of which is incorporated herein in its entirety by reference.

The term "SPAG5" is a polynucleotide (such as a gene, a DNA, an mRNA or any hybrid thereof) that encodes a Sperm Associated Antigen 5. The nucleotide sequence, amino acid sequence, structure and other information relating to SPAG5 and its *Homo sapiens* (human) SPAG5 protein can be found at uniprot.org/uniprot/Q96R06 and www.genecards.org/cgi-bin/carddisp.pl?gene=SPAG5, each of which is incorporated herein in its entirety by reference.

The term "SPTBN1" is a polynucleotide (such as a gene, a DNA, an mRNA or any hybrid thereof) that encodes a Spectrin Beta, Non-Erythrocytic 1. The nucleotide sequence, amino acid sequence, structure and other information relating to SPTBN1 and its *Homo sapiens* (human) SPTBN1 protein can be found at uniprot.org/uniprot/Q01082 and www.genecards.org/cgi-bin/carddisp.pl?gene=SPTBN1, each of which is incorporated herein in its entirety by reference.

The term "SYNE1" is a polynucleotide (such as a gene, a DNA, an mRNA or any hybrid thereof) that encodes a Spectrin Repeat Containing Nuclear Envelope Protein 1. The nucleotide sequence, amino acid sequence, structure and other information relating to SYNE1 and its *Homo sapiens* (human) SYNE1 protein can be found at uniprot.org/uniprot/Q8NF91 and www.genecards.org/cgi-bin/carddisp.pl?gene=SYNE1, each of which is incorporated herein in its entirety by reference.

The term "SYNE2" is a polynucleotide (such as a gene, a DNA, an mRNA or any hybrid thereof) that encodes a Spectrin Repeat Containing Nuclear Envelope Protein 2. The nucleotide sequence, amino acid sequence, structure and other information relating to SYNE2 and its *Homo sapiens* (human) SYNE2 protein can be found at uniprot.org/uniprot/Q8WXH0 and www.genecards.org/cgi-bin/carddisp.pl?gene=SYNE2, each of which is incorporated herein in its entirety by reference.

The term "TACC3" is a polynucleotide (such as a gene, a DNA, an mRNA or any hybrid thereof) that encodes a Transforming Acidic Coiled-Coil Containing Protein 3. The nucleotide sequence, amino acid sequence, structure and other information relating to TACC3 and its *Homo sapiens* (human) TACC3 protein can be found at uniprot.org/uniprot/Q9Y6A5 and www.genecards.org/cgi-bin/carddisp.pl?gene=TACC3, each of which is incorporated herein in its entirety by reference.

The term "TOP2A" is a polynucleotide (such as a gene, a DNA, an mRNA or any hybrid thereof) that encodes a DNA Topoisomerase II Alpha. The nucleotide sequence, amino acid sequence, structure and other information relating to TOP2A and its *Homo sapiens* (human) TOP2A protein can be found at uniprot.org/uniprot/P11388 and www.genecards.org/cgi-bin/carddisp.pl?gene=TOP2A, each of which is incorporated herein in its entirety by reference.

The term "TRIM59" is a polynucleotide (such as a gene, a DNA, an mRNA or any hybrid thereof) that encodes a Tripartite Motif Containing protein 59 or a Tripartite Motif Containing 59. The nucleotide sequence, amino acid sequence, structure and other information relating to TRIM59 and its *Homo sapiens* (human) TRIM59 protein can be found at uniprot.org/uniprot/Q8IWR1 and www.genecards.org/cgi-bin/carddisp.pl?gene=TRIM59, each of which is incorporated herein in its entirety by reference.

The term "TTK" is a polynucleotide (such as a gene, a DNA, an mRNA or any hybrid thereof) that encodes a TTK Protein Kinase. The nucleotide sequence, amino acid sequence, structure and other information relating to TTK and its *Homo sapiens* (human) TTK protein can be found at uniprot.org/uniprot/P33981 and www.genecards.org/cgi-bin/carddisp.pl?gene=TTK, each of which is incorporated herein in its entirety by reference.

The term "UBR4" is a polynucleotide (such as a gene, a DNA, an mRNA or any hybrid thereof) that encodes a Ubiquitin Protein Ligase E3 Component N-Recognin 4. The nucleotide sequence, amino acid sequence, structure and other information relating to UBR4 and its *Homo sapiens* (human) UBR4 protein can be found at uniprot.org/uniprot/Q5T4S7 and www.genecards.org/cgi-bin/carddisp.pl?gene=UBR4, each of which is incorporated herein in its entirety by reference.

The term "UTRN" is a polynucleotide (such as a gene, a DNA, an mRNA or any hybrid thereof) that encodes a Utrophin. The nucleotide sequence, amino acid sequence, structure and other information relating to UTRN and its *Homo sapiens* (human) UTRN protein can be found at uniprot.org/uniprot/P46939 and www.genecards.org/cgi-bin/carddisp.pl?gene=UTRN, each of which is incorporated herein in its entirety by reference.

MODES FOR CARRYING OUT THE DISCLOSURE

Biophysical markers, such as cell deformability, are an emerging alternative to assess metastatic potential (7-12). Physical prognostic markers have focused on cell separation from blood using deformability[26] or force,[27] while commercially available molecular systems, e.g. CellSearch, use EpCAM antibody-based methods. These devices offer the advantages of speed and low cost, but they rely on detection of extravasated cells in the blood. Assays based on these metrics focus largely on characterizing the physical properties of already circulating cells rather than understanding how cancer cells physically interact with and adhere to the extracellular matrix (ECM) at the onset of invasion. Because early detection is critical in preventing metastases[5] and surveillance of extravasated cells in blood may allow some cells to already engraft, there is an unmet need for technology to monitor tumor stroma for individual metastatic cells, which could be missed with histological analyses. Moreover, such histological analysis may not even be possible if the molecular markers exemplified herein do not apply to a given tumor type.

While molecular markers may be less universal, the underlying process of metastasis can be compartmentalized into a series of discrete physical events required for all solid tumors.[5] Given that all cancer cells must interact with the ECM to initiate metastasis, understanding variations in these interactions can serve as an early indicator of metastatic ability. For optimal cell migration into adjacent parenchyma, cells must turnover their focal adhesions to move through the tissue effectively; extremely unstable or stable adhesion can arrest migration as the cell can never establish contractile forces or unbind and retract rear portions of the cell (13). Thus, migration speed is a function of the strength of attachment and is maximized when migrating cells can cycle their adhesions (13, 14). Indeed, invasive cancer cells have more dynamic focal adhesions than their non-invasive counterparts (15), and decreased adhesion strength corresponds to increased metastatic potential (16). As a result, the adhesion of cancer cells to ECM proteins is becoming an accepted metric for metastatic potential (17, 18).

Many assays have been developed to demonstrate how adhesion differs in metastatic cells compared to their non-metastatic counterparts (17, 19-21). However, such assays are either low throughput or not quantitative. It is also difficult to assess adhesive heterogeneity within a single cancer line using these methods (22). It was previously demonstrated that metastatic breast cancer cells display lower cell-ECM adhesion strength than their non-metastatic counterparts using a spinning-disk shear assay (23, 24), especially when cells are exposed to an environment whose low cation concentration mirrors stroma (25, 26). An inherent heterogeneity was observed in adhesion strength in multiple lineages including breast, prostate, and lung cancer cell lines (23). A parallel plate flow chamber is further disclosed here to isolate distinct fractions of cells from a heterogeneous population. Cells were isolated by applying a uniform shear stress to the cell population in the presence of stromal concentrations of Mg and Ca cations (25, 26).

Within a given tumor line as a non-limiting example, significant adhesion heterogeneity was observed and it was found that the more weakly adherent fraction displays increased migration in both 2D and 3D. Without wishing to be bound by the theory, this is due to the increased contractility and focal adhesion disassembly present in weakly adherent cells, resulting from transcriptomic expression differences in cytoskeletal components. Together, these data suggest that intrinsic differences in adhesion strength of cells within a population can act as markers of intra-tumoral heterogeneity in metastatic potential and be exploited to biophysically fractionate subpopulations.

Limited studies have focused on metastatic cell isolation from stroma making the instant disclosure unique; those studies often propose separations that typically exploit xenogeneic properties[29,30] rather than a property intrinsic to a metastasizing cell; this would limit clinical utility. However the approach as disclosed herein uniquely relies on physical principles applied to cancer,[6] and more specifically leverages the observation that when testing the adhesome, only a subset of highly metastatic cells exhibit invasive behavior in stromal-like niche[11]; noninvasive cancer cells do not exhibit invasive characteristics regardless of niche conditions as assessed using a spinning disc assay.[11]

In one aspect, given the universal physical stages of metastasis as disclosed herein, provided is a technology to assess a physical marker (cell adhesion) which is known to regulate metastasis,[8-10] especially at initial stages of detachment and dissemination.[28] Accordingly, the present disclosure provides a device or a method for determining metastatic potential of a tumor. In various embodiments, the device is a parallel plate flow chamber that is capable of sorting cancer cells based on their ability to adhere to the environment. In some embodiments, adhesion is modulated by epithelial tissue-specific buffers.

Figure 15:
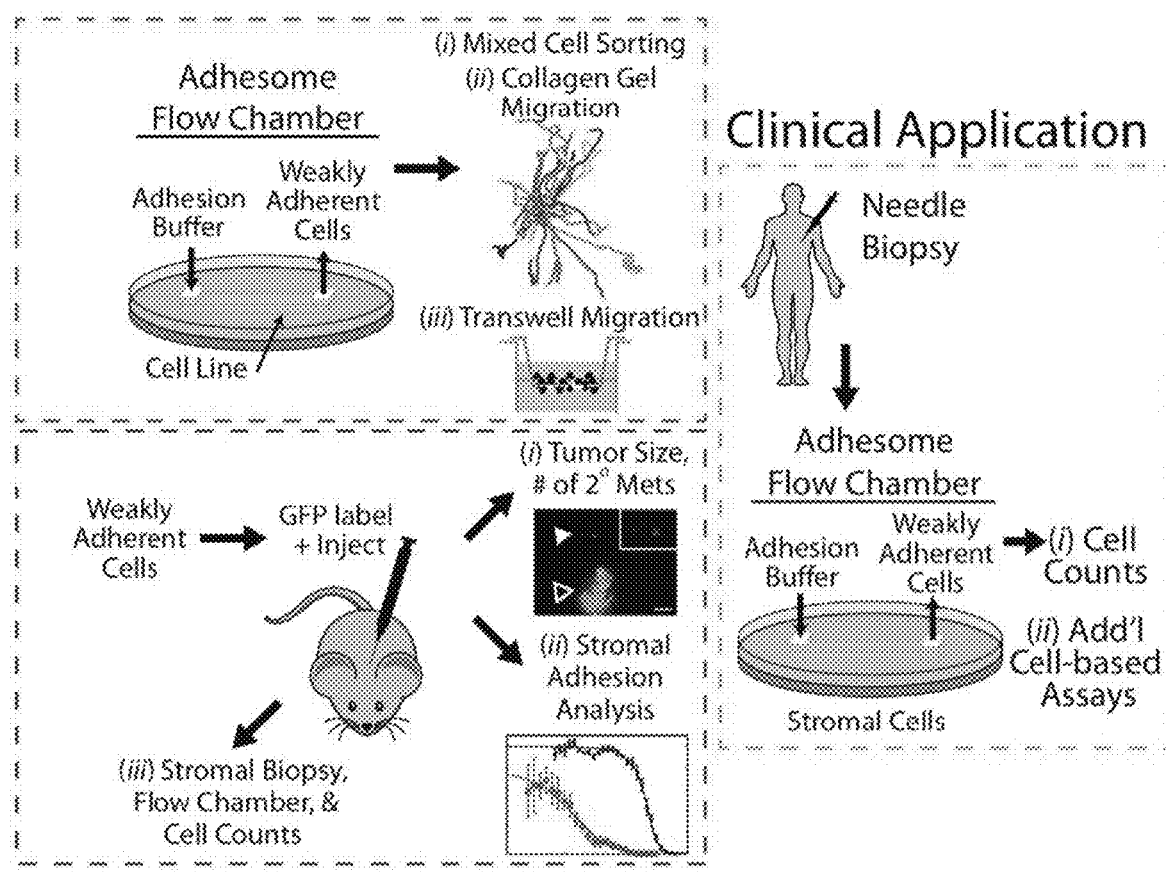
FIG. 15 summarizes a non-limiting experimental approach to test adhesome technology (i.e., the technology as disclosed herein). At left are schematics and experimental design. As indicated in the left top panel, cell lines were used directly in the methods and devices as disclosed herein. As indicated in the left bottom panel, weakly adherent cells from a metastatic cell line is injected and the stroma is analyzed. At right, the schematic identifies how the technology could be used in a clinical setting.

Since cells can remain dormant in stroma for a significant amount of time[18] but may circulate for a short time frame, stromal based detection technology as disclosed herein offers several distinct capabilities: (1) stromal-based detection could provide ongoing tumor surveillance that is capable of assessing metastatic risk earlier than blood-based assays. (2) It offers direct monitoring of tissue stroma for patients at highest cancer risk, e.g. family history, genetic risk factors, or prior incidence of cancer, which could be more precise and identify specific location(s) where cells exhibited a metastatic signature. (3) The technology may better assess how therapies target and prevent tumor dissemination into the stroma; additional molecular analyses of isolated weakly adherent cells are also possible. This stromal-based assay should require only a needle biopsy performed in clinic, making sample collection not significantly more difficult than a blood draw (FIG. 15, right). In various embodiments, a method as disclosed herein may be used in combination with one or more other cancer-detection technologies, such as assessing expression of a molecular prognostic marker in a biological sample of a subject, for example, expression of estrogen receptor, CD24, CD44, CD133, C-X-C Motif Chemokine Receptor 4 (CXCR4), Aldehyde Dehydrogenase Family Member (ALDH), Epithelial Cell Adhesion Molecule (EpCAM), SRY-Box Transcription Factor 2 (SOX2) among many others have been used as cancer stem-like cell markers; evaluating a genetic risk factors of a subject; detecting a circulating tumor cell or a component thereof, such as a circulating tumor nucleotides; or considering family history or prior incidence of cancer of a subject.

Heterogeneity in cancer cell adhesion strength indicates variable metastatic potential in stromal-like conditions. This fluidic-based separation method as disclosed herein provides the ability to sort metastatic cells based on this potential, which stratifies motility rates that inversely scale with adhesion strength. These data imply potential prognostic capabilities of this assay for surveilling tumor stroma post resection as a readout of recurrence free survival time. In addition, the sorted metastatic cells can be used in selecting a therapy suitable for treating the metastatic cancer cells.

Due to the highly heterogeneous nature of tumor cells, both within a given tumor as well as across tumors from different patients, it is difficult to assess tumor aggressiveness and the likelihood of metastasis. In addition, there are no universal biochemical markers that can be utilized to determine metastatic potential. The emergence of biophysical markers is a new approach to identify the most aggressive subpopulations of the tumor population. Common cell-ECM interactions of early dissemination of cancer cells of different tumor origins and subsequent ECM deformation reflect the importance of identifying biophysical markers as metrics for metastatic potential (1, 2). To accomplish this, a parallel plate flow chamber was utilized to study the correlation between decreased adhesion strength of cells to ECM proteins and their subsequent metastatic potential. In conjunction with previous studies (23), the present disclosure demonstrates that metastatic cancer cells are significantly less adherent than their non-metastatic counterparts. This is demonstrated by the ability to select for MDA-MB231 cells over MCF10A cells from a mixed population. It was also found that weak adhesion can serve as a potential marker for metastatic potential, which was demonstrated by the greater percent detachments of MDA-MB231 and MCF10AT cells in comparison to MCF7 and MCF10A cells at the same shear stress.

This study also identified heterogeneity in adhesion strength of cells within a metastatic cancer cell population, especially under stromal-like cation conditions, which may be linked to heterogeneity in metastatic potential of cells within a tumor population or circulating tumor cells or both. This notion is supported by the observations that weakly adherent MDA-536 MB231 cells exhibited increased migration in comparison to their strongly adherent counterparts. These differences in migration exist in both 2D and 3D environments, which indicates that the weakly adherent subpopulation represents the cells that are more likely to leave the primary tumor and establish secondary metastases (48-50). The stability of this increased migratory propensity for multiple days post-sorting further demonstrates the intrinsic nature of this phenotype. In addition, recapitulating this phenotype in metastatic lung cancer cells suggests that adhesion strength is broadly involved in the more migratory subpopulations within tumors from multiple epithelial backgrounds.

The ability to select this more migratory subpopulation of the cell line stems from differences in focal adhesion disassembly between the weakly adherent and strongly adherent cells. Faster focal adhesion disassembly of weakly adherent cells is consistent with previous findings that link quicker focal adhesion disassembly to more migratory cell lines (15, 51, 52). In addition, weakly adherent cells are more contractile than their strongly adherent counterparts, where increased contractility has also been linked to increased migration and more aggressive cancers (39, 40). Differences in migration, focal adhesion assembly, and contractility can be tied to inherent transcriptomic differences between weakly and strongly adherent cells; genes linked to the cytoskeleton, specifically to microtubules, as well as motor proteins involved in vesicular transport and contraction showed significant differential expression. When human breast cancer patients were compared with gene expression signatures that resembled the weakly and strongly adherent cells for the genes of interest. Decreased progression-free and disease-free intervals were observed, implying that tumors resembling the weakly adherent fraction are more aggressive. Several standard cancer therapy drugs (nocodazole, taxols, etc.) target microtubules in order to reduce the growth and spread of aggressive tumors, indicating that differences in microtubules and the cytoskeleton could explain the heterogeneity of tumor cell populations. These findings were confirmed by treating weakly adherent cells to nocodazole and paclitaxel and it was found that their migration speed reduced to that of the strongly adherent cells, whose speed was unaffected by both drugs. Therefore, targeting the cytoskeleton is potentially an important method of restricting the motility of highly aggressive subpopulations early in tumor development and suppressing the migratory populations that were observed (53).

This disclosure reveals a strategy to identify distinct subpopulations via shear separation that can be implemented to study the dissemination of cells from a variety of epithelial cancers. Comparing weakly adherent cell populations across multiple metastatic cell lines of various tumor origins could enable the identification of similarities amongst the most aggressive subpopulation in an effort to identify more universal targeted treatments. Lastly, this shear assay can be adapted to study diseases with a similar adhesion component, highlighting the versatility of this technique.

Accordingly, the present disclosure relies upon assessment of adhesion strength using differences between the tumor and stromal niche, namely the 10-fold difference in cation concentrations to directly sort cells and assess metastatic risk based on the number of cells with a given adhesive signature. Lower stromal cations have been associated with increasingly metastatic and aggressive tumors in vivo, suggesting that exceedingly invasive cells are more sensitive to cation-mediated changes in adhesion.

Accordingly, disclosed herein are micro- and macro-fluidic flow chambers that could capture weakly adherent cells. Flow within these channels exhibit behavior based on Poiseuille flow. A microfluidic flow chamber was developed for experiments where biopsy size could be small, e.g., clinical application, or where the number of cells required for an assay is low. Test chambers were fabricated using a reverse casting method. An exemplary fluid channel was created with dimensions of 100 µm tall, 4 cm wide, and 3 cm long in polydimethylsiloxane (PDMS); a built-in inlet and outlet supply and collect cell culture media or shear buffer, i.e., PBS or PBS+MgCa. Cells are attached to an ECM-coated microscope slide that is bonded with the channel. Cells are loaded into the device, cultured for 6 hours, and then sheared for 5 minutes in adhesion buffer (with or without cations). Since the device fits a standard microscope slide, experiments can be performed in massively parallel arrays. Though each device may be for a single use, hundreds can be cast off of one master, making it reproducible, cost effective, and high throughput, all of which are important for translation.

In one aspect, provided is a device for assessing adhesion strength of a cancer cell or a population thereof, such as a micro fluidic flow chamber as disclosed herein or a macro fluidic flow chamber as disclosed herein.

In various embodiments, the device includes (such as comprises, or consists essentially of, or consists of) a housing having (such as comprising, or consisting essentially of, or consisting of) an inlet and an outlet, where the housing is configured to be sealingly attached to a solid substrate, such as a glass slide or a polysulfone based slide or plate. In various embodiments, disposed within the housing is a collection chamber in fluid communication with the outlet, where the collection chamber is configured to collect cells (such as to capture weakly adherent cells) contained in the flow through buffer for counting. In various embodiments, a gasket, such as a silicone gasket, is provided around a periphery of the solid substrate such that a fluid-tight (such as water-tight) seal is formed between the solid substrate and the housing, thereby forming a flow chamber. In various embodiments, the device further comprises a reservoir containing a shear buffer, the reservoir being provided in fluid communication with the inlet, wherein the shear buffer is configured to flow through the flow channel in contact with the ECM protein.

In various embodiments, a surface of the solid substrate is coated with an extracellular matrix (ECM) protein (such as a collagen or a fibronectin or both) configured to allow cells to adhere thereto. In further embodiments, the housing is being configured to be sealingly attached to the surface of the solid substrate, thereby forming a flow channel within the housing. In some embodiments, the ECM coated surface forms at least a part of the inner surface of the flow channel, such as about 1%, or about 2%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100% of the inner surface of the flow channel. In some embodiments, the inner surface of the flow channel is at least partially coated with the ECM protein, such as about 1%, or about 2%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100% of the inner surface of the flow channel.

In various embodiments, the solid substrate further comprises the cancer cell or a population thereof adherent to the ECM protein. In various embodiments, the solid substrate further comprises a cell culture adherent to the ECM protein. In further embodiments, the cell culture is a culture of a cancer cell or a population thereof. In some embodiments, the cancer cell is a cancer cell line as disclosed herein. In some embodiments, the cancer cell population comprising one or more cancer cells of various cancer cell line. In some embodiments, the cancer cell is isolated from a biological sample of a subject, such as a biopsy, a tumor biopsy, or a biopsy of a primary tumor. In one embodiment, the tumor biopsy is from a primary tumor. Additionally or alternatively, the subject is suspected of having a metastatic cancer or is suspect of developing a metastatic cancer later. In various embodiment, the cancer cell is an epithelial cancer cell. In various embodiments, the cancer cell is a breast cancer cell, a prostate cancer cell, or a lung cancer cell.

In use, cells from a biopsy are allowed to attach to the extracellular matrix protein layer on the solid substrate within the device. The flow chamber is thereafter sealingly attached to the solid substrate and buffer is pumped through the chamber at a prescribed flow rate to achieve specific shear stresses that detach a subpopulation of cells. The cells contained in the flow through buffer may then be counted and correlated with a survival curve of patient data.

The flow chamber therefore exploits cation concentration differences between tumor and stroma using buffers formulated to mimic the stroma. This provides a test of cell adhesion of metastatic cells, i.e., the "adhesome," in biologically appropriate conditions. As such, detecting metastatic cells in the stroma is a more clinically useful approach to because those cells are disseminating from the tumor; cells in the tumor core itself could also be examined, but given high cation concentrations, their behavior is likely different. The preliminary data provided herein substantiate that adhesive differences between highly adherent versus unsorted metastatic cell lines led to decreased invasive capacity. The device of the present disclosure selects weakly adherent cells and provides evidence to show their enhanced invasive capacity (FIG. 15). Accordingly, validation of weak adhesion strength as a useful physical prognostic indicator of metastasis could provide caregivers with information on the metastatic risk of the primary tumor.

In a further aspect, provided is a method of assessing adhesion strength of a cancer cell or a population thereof. The method comprises, consists essentially of, or consists of culturing a cancer cell, or a population thereof on a solid substrate coated with an extracellular matrix (ECM) protein, such as on a solid substrate of a device as disclosed herein; sealingly attaching the solid substrate to a housing to form a flow channel over the cultured cancer cell, or a population thereof, flowing a shear buffer through the flow channel; collecting the buffer after flowing through the flow channel; and counting the cells within the collected buffer.

In various embodiments, the number of cells within the collected buffer positively correlates to metastatic potential or risk of the cancer cell or population thereof.

In various embodiments, the method further comprises counting the number of cells cultured on the solid substrate (prior to, during or after the culturing step; or prior to, during or after sealing step; or prior to, during or after the flowing step; or prior to, during or after the collecting step). In further embodiments, the percentage of the number of cells in the collected buffer over the total number of cells initially cultured on the solid substrate positively correlates to metastatic potential of the cancer cell or population thereof. In other embodiments, the ratio of the number of cells in the collected buffer versus the number of cells on the solid substrate after the flowing step positively correlates to metastatic potential of the cancer cell or population thereof. In some embodiments, the shear buffer through the flow channel provides a shear stress some cancer cells (i.e., weakly adherent cancer cells) but not all of the cancer cells, such as strongly adherent cancer cell. In some embodiments, the shear stress is about 1 dynes/cm$^2$ to about 2000 dynes/cm$^2$, including any ranges or numbers therebetween, such as about 5 dynes/cm$^2$, or about 10 dynes/cm$^2$, or about 15 dynes/cm$^2$, or about 16 dynes/cm$^2$, or about 17 dynes/cm$^2$, or about 18 dynes/cm$^2$, or about 19 dynes/cm$^2$, or about 20 dynes/cm$^2$, or about 21 dynes/cm$^2$, or about 22 dynes/cm$^2$, or about 23 dynes/cm$^2$, or about 24 dynes/cm$^2$, or about 25 dynes/cm$^2$, or about 26 dynes/cm$^2$, or about 27 dynes/cm$^2$, or about 28 dynes/cm$^2$, or about 29 dynes/cm$^2$, or about 30 dynes/cm$^2$, or about 31 dynes/cm$^2$, or about 32 dynes/cm$^2$, or about 33 dynes/cm$^2$, or about 34 dynes/cm$^2$, or about 35 dynes/cm$^2$, or about 36 dynes/cm$^2$, or about 37 dynes/cm$^2$, or about 38 dynes/cm$^2$, or about 39 dynes/cm$^2$, or about 40 dynes/cm$^2$, or about 41 dynes/cm$^2$, or about 42 dynes/cm$^2$, or about 43 dynes/cm$^2$, or about 44 dynes/cm$^2$, or about 45 dynes/cm$^2$, or about 50 dynes/cm$^2$, or about 55 dynes/cm$^2$, or about 60 dynes/cm$^2$, or about 65 dynes/cm$^2$, or about 70 dynes/cm$^2$, or about 75 dynes/cm$^2$, or about 80 dynes/cm$^2$, or about 85 dynes/cm$^2$, or about 90 dynes/cm$^2$, or about 95 dynes/cm$^2$, or about 100 dynes/cm$^2$, or about 200 dynes/cm$^2$, or about 300 dynes/cm$^2$, or about 400, dynes/cm$^2$, or about 500, dynes/cm$^2$, or about 600 dynes/cm$^2$, or about 700 dynes/cm$^2$, or about 800 dynes/cm$^2$, or about 900 dynes/cm$^2$, or about 1000 dynes/cm$^2$, or about 1500 dynes/cm$^2$, or about 2000 dynes/cm$^2$. In some embodiments, the shear stress may be decided based on the cancer cell type. For example, MDA-MB-231 cells may require a lower shear stress compared to PC-3 and NCI-H1299 cells. Additionally or alternatively, the time period of applying the shear stress to the cultured cells can also be adjusted, such as for about 1 minute to about 1 day including ranges and numbers therebetween, for example, for about 2 minutes, for about 3 minutes, for about 4 minutes, for about 5 minutes, for about 6 minutes, for about 7 minutes, for about 8 minutes, for about 9 minutes, for about 10 minutes, for about 11 minutes, for about 12 minutes, for about 13 minutes, for about 14 minutes, for about 15 minutes, for about 16 minutes, for about 17 minutes, for about 18 minutes, for about 19 minutes, for about 20 minutes, for about 21 minutes, for about 22 minutes, for about 23 minutes, for about 24 minutes, for about 25 minutes, for about 26 minutes, for about 27 minutes, for about 28 minutes, for about 29 minutes, for about 0.5 hour, for about 1 hour, for about 2 hours or longer. Also, exemplified methods of calculating the shear stress ($\tau$) are provided in the Examples, such as by following one of the two equations below as appropriate.

$$\tau = \frac{6\mu Q}{wh^2}$$

where µ is viscosity of the fluid, Q is volumetric flow rate, w is the width of the chamber, and h is the height of the chamber.

$$\tau = \frac{4}{5} r \sqrt{\rho \mu \omega^3}$$

where r is the radial position from the center of the disk, ρ is the buffer density, µ is the buffer viscosity, and ω is the rotational velocity.

In various embodiments, the cancer cell is obtained from a tumor biopsy from a subject. In various embodiments, the cancer cell or a population thereof is isolated from a tumor biopsy of a subject. In various embodiments, the tumor biopsy is from a primary tumor. In various embodiment, the cancer cell is an epithelial cancer cell. In various embodiments, the cancer cell is a breast cancer cell, a prostate cancer cell, or a lung cancer cell.

In yet a further aspect, a method is provided for selecting a therapy for treating cancer metastasis. The method comprises, consists essentially of, or consists of culturing a first cancer cell or a population thereof of a cancer cell line or isolated from a biological sample on a first solid substrate coated with an extracellular matrix (ECM) protein in the presence of the therapy; culturing a second cancer cell or a population thereof of the cancer cell line or isolated from the biological sample on a second solid substrate coated with the extracellular matrix (ECM) protein in the absence of the therapy; sealingly attaching each of the solid substrates to a housing to form a flow channel over the cultured cancer cell or a population thereof, flowing a shear buffer through the flow channels; collecting the buffer after flowing through the flow channels; and counting the cells within the collected buffer. Such method or any step(s) therein can be combined with any other method as disclosed herein.

In various embodiments, less cells counted in the presence of the therapy compared to the one in the absence of the therapy indicates the therapy is suitable for treating cancer metastasis.

Additionally or alternatively, a method as disclosed herein may be used in combination with one or more anti-cancer therapies, such as administering an anti-cancer agent, an ablative therapy, an immunotherapy, cryoablation, thermal ablation, radiotherapy, chemotherapy, radiofrequency ablation, electroporation, alcohol ablation, high intensity focused ultrasound, photodynamic therapy, administration of monoclonal antibodies, or administration of immunotoxins In various embodiments, the ablative therapy does not require invasive surgery. In other embodiments, the ablative therapy comprises, or consists essentially of, or consists of removal of a tumor via surgery.

In another aspect, provided is a method for treating a cancer patient. The method comprises administering to the patient an anti-metastatic cancer therapy. In various embodiments, the patient is diagnosed of having a primary cancer. In various embodiments, the patient has a high metastatic potential or risk. In some embodiments, the patient was selected for the therapy by a method comprising, consisting essentially of, or consisting of determining gene expression of one or more genes, for example in a biological sample of the patient. In various embodiments, the therapy comprises administering to the patient an effective amount of a microtubule-targeting drug, such as nocodazole, paclitaxel, or both. In various embodiments, the patient is selected for the therapy if the biological sample of the patient comprises a cancer cell expressing the one or more genes. In various embodiments, the patient is selected for the therapy if the biological sample of the patient comprises a cancer cell expressing the one or more genes at a higher level compared to a healthy subject or a subject free of the cancer, or a subject free of metastasis of the cancer.

Also provided is a method of determining prognosis of a subject having a cancer. The method comprises, consists essentially of, or consists of determining gene expression of one or more genes in a biological sample of the subject. In various embodiments, the prognosis negatively correlates with the number(s) of expressed gene(s), the level(s) of the gene expression, or both.

Additionally provided is a method of stratifying patients based on patients' metastatic risk. The method comprises, consists essentially of, or consists of determining gene expression of one or more genes in a biological sample of the subject. In various embodiments, the risk level positively correlates with the number(s) of expressed gene(s), the level(s) of the gene expression, or both. In various embodiments, prevention or treatment of cancer metastasis may be applied to the patient having a high metastatic risk. Additionally or alternatively, the patient having a high risk may be further monitored via other methods in order to identify a metastasis, such as via computed tomography (CT), or positron emission tomography (PET)/CT. In various embodiments, the patient having a low metastatic risk may be monitored via the same stratification method with a certain interval, such as every 1 month, every 2 months, every 3 months, every 4 months, every 5 months, every 6 months, or yearly. While other monitoring method(s) may also be used in the patient having a low metastatic risk, the frequency of using the other monitory method(s) may be less frequent compared to a patent having a high metastatic risk.

In yet another aspect, provided is a method comprising, consisting essentially of, or consisting of quantifying or collecting cancer cells displaying one or more of the following features, for example from a biological sample of a subject: a lower adhesion strength compared to the rest of the cells in the cell population or a non-metastatic control; a higher migration speed compared to the rest of the cells in the cell population or a non-metastatic control; an inhibition on migration upon contacting a microtubule-targeting drug; a higher percentage of cell displacement compared to the rest of the cells in the cell population or a non-metastatic control; a higher number of focal adhesions compared to the rest of the cells in the cell population or a non-metastatic control; a higher contractility compared to the rest of the cells in the cell population or a non-metastatic control; a higher invasion compared to the rest of the cells in the cell population or a non-metastatic control; or expression of one or more of the genes. Such method or any step(s) therein can be combined with any other method as disclosed herein.

In a further aspect, provided is a method for determining the metastatic potential of a cancer cell. The method comprises, consists essentially of, or consists of culturing a cancer cell and determining one or more of the following: adhesion strength of the cancer cell; migration speed of the cancer cell; inhibition effect of a microtubule-targeting drug on the migration of the cancer cell; percentage of cell displacement of the cultured cell population; the number of focal adhesions of the cancer cell; contractility of the cancer cell; invasion potential of the cancer cell; or expression of one or more genes. Such method or any step(s) therein can be combined with any other method as disclosed herein.

In various embodiments, the one or more genes are selected from those disclosed in any one or more of Tables 1-3. In further embodiments, the one or more genes are selected from those disclosed in Table 1. In yet further embodiments, the one or more genes are selected from the following genes of Neuroblast Differentiation-Associated Protein AHNAK (AHNAK), A-Kinase Anchoring Protein 13 (AKAP13), A-Kinase Anchoring Protein 9 (AKAP9), ALMS1 Centrosome And Basal Body Associated Protein (ALMS1), APC Regulator Of WNT Signaling Pathway (APC), Assembly Factor For Spindle Microtubules (ASPM), ATM Serine/Threonine Kinase (ATM), Baculoviral IAP Repeat Containing 6 (BIRC6), Bcl2 Modifying Factor (BMF), BRCA2 DNA Repair Associated (BRCA2), BUB1 Mitotic Checkpoint Serine/Threonine Kinase B (BUB1B), Coiled-Coil Domain Containing 88A (CCDC88A), Cyclin A1 (CCNA1), Cyclin B1 (CCNB1), Cyclin B2 (CCNB2), Cyclin F (CCNF), Cell Division Cycle 25B (CDC25B), CDC42 Binding Protein Kinase Alpha (CDC42BPA), CDC42 Effector Protein 2 (CDC42EP2), Cell Division Cycle 45 (CDC45), Cell Division Cycle 6 (CDC6), Centromere Protein E (CENPE), Centromere Protein F (CENPF), Centromere Protein J (CENPJ), Centrosomal Protein 192 (CEP192), Centrosomal Protein 350 (CEP350), Centrosomal Protein 97 (CEP97), Cytoskeleton Associated Protein 2 (CKAP2), Cytoskeleton Associated Protein 5 (CKAP5), Centriolin (CNTRL), DNA Cross-Link Repair 1B (DCLRE1B), Desmoplakin (DSP), Dystonin (DST), Denticleless E3 Ubiquitin Protein Ligase Homolog (DTL), Dynein Cytoplasmic 1 Heavy Chain 1 (DYNC1H1), Dynein Cytoplasmic 2 Heavy Chain 1 (DYNC2H1), E2F Transcription Factor 1 (E2F1), Extra Spindle Pole Bodies Like 1, Separase (ESPL1), Filaggrin (FLG), FERM Domain Containing 6 (FRMD6), Growth Arrest Specific 2 Like 3 (GAS2L3), GTP Binding Protein Overexpressed In Skeletal Muscle (GEM), GEN1 Holliday Junction 5' Flap Endonuclease (GEN1), G Protein Signaling Modulator 2 (GPSM2), G2 And S-Phase Expressed 1 (GTSE1), Histone Deacetylase 4 (HDAC4), HECT And RLD Domain Containing E3 Ubiquitin Protein Ligase 2 (HERC2), Hyaluronan Mediated Motility Receptor (HMMR), Huntingtin (HTT), Protein TALPID3 (KIAA0586), Kinesin Family Member 11 (KIF11), Kinesin Family Member 14 (KIF14), Kinesin Family Member 18A (KIF18A), Kinesin Family Member 18B (KIF18B), Kinesin Family Member 20A (KIF20A), Kinesin Family Member 20B (KIF20B), Kinesin Family Member 4A (KIF4A), Kinetochore Localized Astrin (SPAG5) Binding Protein (KNSTRN), Keratin 17 (KRT17), Keratin 81 (KRT81), Microtubule Actin Crosslinking Factor 1 (MACF1), Microtubule Associated Protein 1B (MAP1B), Minichromosome Maintenance Complex Component 2 (MCM2), Minichromosome Maintenance Complex Component 3 (MCM3), Midasin AAA ATPase 1 (MDN1), Myosin Heavy Chain 15 (MYH15), Myosin VA (MYO5A), Myosin IXA (MYO9A), Neuron Navigator 1 (NAV1), NudE Neurodevelopment Protein 1 (NDE1), NIMA Related Kinase 2 (NEK2), Pro-Apoptotic WT1 Regulator (PAWR), Proliferating Cell Nuclear Antigen (PCNA), Pericentrin (PCNT), Phosphodiesterase 4D Interacting Protein (PDE4DIP), Pseudopodium Enriched Atypical Kinase 1 (PEAK1), Pleckstrin Homology, MyTH4 And FERM Domain Containing H2 (PLEKHH2), Polo Like Kinase 2 (PLK2), Proline And Serine Rich Coiled-Coil 1 (PSRC1), Protein Tyrosine Phosphatase Non-Receptor Type 14 (PTPN14), RAN Binding Protein 2 (RANBP2), RB Binding Protein 6, Ubiquitin Ligase (RBBP6), RCSD Domain Containing 1 (RCSD1), Receptor Accessory Protein 4 (REEP4), Replication Timing Regulatory Factor 1 (RIF1), Serum Amyloid A1 (SAA1), Sodium Channel And Clathrin Linker 1 (SCLT1), SET Domain Containing 2, Histone Lysine Methyltransferase (SETD2), SH3 And PX Domains 2A (SH3PXD2A), Solute Carrier Family 7 Member 11 (SLC7A11), Sperm Associated Antigen 5 (SPAG5), Spectrin Beta, Non-Erythrocytic 1 (SPTBN1), Spectrin Repeat Containing Nuclear Envelope Protein 1 (SYNE1), Spectrin Repeat Containing Nuclear Envelope Protein 2 (SYNE2), Transforming Acidic Coiled-Coil Containing Protein 3 (TACC3), DNA Topoisomerase II Alpha (TOP2A), Tripartite Motif Containing 59 (TRIM59), TTK Protein Kinase (TTK), Ubiquitin Protein Ligase E3 Component N-Recognin 4 (UBR4), or Utrophin (UTRN). In some embodiments, the one or more genes comprises, consists essentially of, or consists of GAS2L3, SYNE2, AKAP9, KIF14, DYNC1H1, or MYO9A. In various embodiments, the one or more of the genes are selected from those listed in FIG. 5D or 5E or both, i.e., ASPM, SYNE2, DST, CENPF, GAS2L3, AKAP9, CENPE, KIF14, DYNC1H1, KIF8A, DYNC2H1, or MYO9A. In various embodiments, the one or more genes are selected from GAS2L3, SYNE2, AKAP9, KIF14, DYNC1H1, or MYO9A. In various embodiments, the one or more genes are associated with microtubule and cytoskeletal organization and binding, such as encoding cytoskeletal components, specifically microtubule-associated proteins, or components linking the cytoskeleton to the nuclear or plasma membranes, or motor proteins, specifically those involved in vesicular transport along microtubules as well as in cytoskeletal contraction.

TABLE 1

Genes linked to highlighted GO terms that were used for TCGA analysis. List of all genes from the ontological terms in FIG. 5 that were included in the TCGA analysis. Genes are shown in alphabetical order

| Gene Name |
| --- |
| AHNAK |
| AKAP13 |
| AKAP9 |
| ALMS1 |
| APC |
| ASPM |
| ATM |
| BIRC6 |
| BMF |
| BRCA2 |
| BUB1B |
| CCDC88A |
| CCNA1 |
| CCNB1 |
| CCNB2 |
| CCNF |
| CDC25B |
| CDC42BPA |
| CDC42EP2 |
| CDC45 |
| CDC6 |
| CENPE |
| CENPF |
| CENPJ |
| CEP192 |
| CEP350 |
| CEP97 |
| CKAP2 |
| CKAP5 |
| CNTRL |
| DCLRE1B |
| DSP |
| DST |
| DTL |
| DYNC1H1 |
| DYNC2H1 |
| E2F1 |
| ESPL1 |
| FLG |
| FRMD6 |
| GAS2L3 |
| GEM |

TABLE 1-continued

Genes linked to highlighted GO terms that were used for TCGA analysis. List of all genes from the ontological terms in FIG. 5 that were included in the TCGA analysis. Genes are shown in alphabetical order Gene Name GEN1
GPSM2
GTSE1
HDAC4
HERC2
HMMR
HTT
KIAA0586
KIF11
KIF14
KIF18A
KIF18B
KIF20A
KIF20B
KIF4A
KNSTRN
KRT17
KRT81
MACF1
MAP18
MCM2
MCM3
MDN1
MYH15
MYOSA
MYO9A
NAV1
NDE1
NEK2
PAWR
PCNA
PCNT
PDE4DIP
PEAK1
PLEKHH2
PLK2
PSRC1
PTPN14
RANBP2
RBBP6
RCSD1
REEP4
RIF1
SAA1
SCLT1
SETD2
SH3PXD2A
SLC7A11
SPAG5
SPTBN1
SYNE1
SYNE2
TACC3
TOP2A
TRIM59
TTK
UBR4
UTRN The genes listed in Table 1 are the most significantly different, i.e., their expression is the most different when comparing weakly vs. strongly adherent cells. Such significant difference is further evidenced by Table 2 and Table 3 below showing the low p value (p-Value) and adjusted p value (p-Adj) comparing weakly vs. strongly adherent cells. Those genes were used in the bioinformatic analyses as detailed in the Examples to define "weakly adherent." The magnitude of their change is important but not required for TCGA analysis. I.e., the altered expression may be upregulated or downregulated, but they are all used to define the cell as "weakly adherent" and differentiate them from other cells.

Table 2 and Table 3 together provide 497 differentially expressed genes between the weakly adherent group and the strongly adherent group. Table 2 lists 333 of them which are upregulated (i.e., increased) in the weakly adherent cells relative to gene expression in strongly adherent cells, and thus having positive values as their Fold Changes. The remaining 164 are listed in Table 3 and downregulated (i.e., decreased) in weakly adherent cells relative to strongly adherent cells, and thus having negative values as their Fold Changes.

TABLE 2

A list of genes, the expression of which is increased in the weakly adherent group compared to the strongly adherent group.

| Name | Description | Fold Change | p-Value | p-Adj |
|---|---|---|---|---|
| ASPM | abnormal spindle microtubule assembly | 2.4626 | 5.14E−35 | 9.23E−31 |
| SYNE2 | spectrin repeat containing, nuclear envelope 2 | 2.2331 | 6.89E−24 | 1.24E−20 |
| CENPE | centromere protein E, 312 kDa | 2.22684 | 1.68E−29 | 7.54E−26 |
| DST | dystonin | 2.07868 | 1.00E−33 | 9.00E−30 |
| AHNAK | AHNAK nucleoprotein | 2.06998 | 9.76E−27 | 3.50E−23 |
| CENPF | centromere protein F, 350/400 kDa | 2.03942 | 2.56E−24 | 5.10E−21 |
| BIRC6 | baculoviral IAP repeat containing 6 | 2.0217 | 7.67E−26 | 1.97E−22 |
| KIAA1109 | KIAA1109 | 1.97366 | 7.78E−22 | 1.27E−18 |
| GAS2L3 | growth arrest-specific 2 like 3 | 1.94286 | 1.06E−15 | 8.66E−13 |
| CEP350 | centrosomal protein 350 kDa | 1.94068 | 7.55E−25 | 1.69E−21 |
| FAT1 | FAT atypical cadherin 1 | 1.88755 | 2.82E−30 | 1.69E−26 |
| SMG1 | SMG1 phosphatidylinositol 3-kinase-related kinase | 1.86104 | 2.50E−18 | 2.99E−15 |
| AKAP9 | A kinase (PRKA) anchor protein 9 | 1.79787 | 2.29E−12 | 1.13E−09 |
| KIF14 | kinesin family member 14 | 1.79605 | 1.40E−13 | 8.40E−11 |
| CASC5 | cancer susceptibility candidate 5 | 1.79305 | 9.46E−18 | 9.43E−15 |
| MKI67 | marker of proliferation Ki-67 | 1.7667 | 9.44E−17 | 8.92E−14 |
| MACF1 | microtubule-actin crosslinking factor 1 | 1.76356 | 1.32E−20 | 1.82E−17 |

TABLE 2-continued

A list of genes, the expression of which is increased in the weakly adherent group compared to the strongly adherent group.

| Name | Description | Fold Change | p-Value | p-Adj |
|---|---|---|---|---|
| MDN1 | midasin AAA ATPase 1 | 1.75985 | 4.63E−15 | 3.32E−12 |
| NAV2 | neuron navigator 2 | 1.75763 | 2.16E−15 | 1.69E−12 |
| KMT2A | lysine (K)-specific methyltransferase 2A | 1.75758 | 1.45E−14 | 9.64E−12 |
| PRKDC | protein kinase, DNA-activated, catalytic polypeptide | 1.75031 | 9.64E−21 | 1.44E−17 |
| TNFAIP8L1 | tumor necrosis factor, alpha-induced protein 8-like 1 | 1.74234 | 5.25E−10 | 1.49E−07 |
| EXPH5 | exophilin 5 | 1.72072 | 1.78E−08 | 3.67E−06 |
| GOLGB1 | golgin B1 | 1.72025 | 5.23E−18 | 5.87E−15 |
| KMT2C | lysine (K)-specific methyltransferase 2C | 1.71435 | 1.54E−11 | 5.77E−09 |
| VPS13B | vacuolar protein sorting 13 homolog B (yeast) | 1.71037 | 8.74E−12 | 3.57E−09 |
| CNTRL | centriolin | 1.70364 | 5.30E−12 | 2.32E−09 |
| HECTD4 | HECT domain containing E3 ubiquitin protein ligase 4 | 1.70303 | 4.84E−15 | 3.34E−12 |
| TRIM59 | tripartite motif containing 59 | 1.67684 | 4.69E−09 | 1.11E−06 |
| HERC1 | HECT and RLD domain containing E3 ubiquitin protein ligase family member 1 | 1.67272 | 2.86E−11 | 1.05E−08 |
| VPS13D | vacuolar protein sorting 13 homolog D (S. cerevisiae) | 1.66139 | 3.68E−12 | 1.69E−09 |
| DYNC1H1 | dynein, cytoplasmic 1, heavy chain 1 | 1.64141 | 6.14E−18 | 6.48E−15 |
| NEURL1B | neuralized E3 ubiquitin protein ligase 1B | 1.63333 | 2.46E−08 | 4.96E−06 |
| PIF1 | PIF1 5'-to-3'' DNA helicase | 1.63252 | 5.79E−08 | 1.06E−05 |
| FAT4 | FAT atypical cadherin 4 | 1.63169 | 4.29E−11 | 1.51E−08 |
| KMT2D | lysine (K)-specific methyltransferase 2D | 1.62647 | 2.95E−12 | 1.39E−09 |
| CENPA | centromere protein A | 1.623 | 1.53E−09 | 4.03E−07 |
| MYCBP2 | MYC binding protein 2, E3 ubiquitin protein ligase | 1.62252 | 2.32E−12 | 1.13E−09 |
| TROAP | trophinin associated protein | 1.6161 | 1.76E−09 | 4.54E−07 |
| HUWE1 | HECT, UBA and WWE domain containing 1, E3 ubiquitin protein ligase | 1.61553 | 1.44E−16 | 1.29E−13 |
| BORA | bora, aurora kinase A activator | 1.61222 | 6.85E−08 | 1.22E−05 |
| CKAP2 | cytoskeleton associated protein 2 | 1.60702 | 2.61E−10 | 7.80E−08 |
| SACS | sacsin molecular chaperone | 1.6034 | 1.01E−09 | 2.70E−07 |
| FRYL | FRY-like | 1.6034 | 2.75E−14 | 1.71E−11 |
| UBR4 | ubiquitin protein ligase E3 component n-recognin 4 | 1.59957 | 1.88E−14 | 1.20E−11 |
| AGR2 | anterior gradient 2, protein disulphide isomerase family member | 1.59854 | 5.52E−07 | 8.06E−05 |
| RNF213 | ring finger protein 213 | 1.5905 | 1.11E−11 | 4.39E−09 |
| TNRC6B | trinucleotide repeat containing 6B | 1.58462 | 3.83E−09 | 9.17E−07 |
| ARL6IP1 | ADP-ribosylation factor-like 6 interacting protein 1 | 1.57779 | 4.88E−11 | 1.69E−08 |
| BOD1L1 | biorientation of chromosomes in cell division 1-like 1 | 1.57439 | 1.19E−12 | 6.09E−10 |
| ATM | ATM serine/threonine kinase | 1.56232 | 1.85E−09 | 4.60E−07 |
| SOGA1 | suppressor of glucose, autophagy associated 1 | 1.5619 | 5.95E−10 | 1.64E−07 |
| KCNQ1OT1 | KCNQ1 opposite strand/antisense transcript 1 (non-protein coding) | 1.55429 | 6.90E−06 | 0.000764 |
| INO80D | INO80 complex subunit D | 1.55348 | 1.51E−06 | 0.000191 |
| USP34 | ubiquitin specific peptidase 34 | 1.55278 | 5.11E−13 | 2.78E−10 |
| CCDC88A | coiled-coil domain containing 88A | 1.55259 | 5.02E−13 | 2.78E−10 |
| VPS13C | vacuolar protein sorting 13 homolog C (S. cerevisiae) | 1.5524 | 4.01E−07 | 6.04E−05 |
| AKAP13 | A kinase (PRKA) anchor protein 13 | 1.54678 | 5.80E−10 | 1.63E−07 |
| VPS13A | vacuolar protein sorting 13 homolog A (S. cerevisiae) | 1.54463 | 3.19E−08 | 6.17E−06 |
| ZBED6 | zinc finger, BED-type containing 6 | 1.54415 | 1.48E−07 | 2.48E−05 |
| UTRN | utrophin | 1.54269 | 1.40E−11 | 5.34E−09 |
| WDFY3 | WD repeat and FYVE domain containing 3 | 1.54012 | 1.01E−10 | 3.18E−08 |
| PRRC2C | proline-rich coiled-coil 2C | 1.53685 | 3.60E−13 | 2.08E−10 |
| MAP1B | microtubule-associated protein 1B | 1.5358 | 7.42E−12 | 3.17E−09 |
| CIT | citron rho-interacting serine/threonine kinase | 1.53532 | 3.67E−10 | 1.08E−07 |
| BMF | Bcl2 modifying factor | 1.53415 | 1.25E−05 | 0.001268 |
| KIF18A | kinesin family member 18A | 1.53336 | 1.25E−08 | 2.65E−06 |
| LOC100288637 | OTU deubiquitinase 7A pseudogene | 1.53325 | 1.85E−07 | 2.99E−05 |
| CKS2 | CDC28 protein kinase regulatory subunit 2 | 1.53117 | 2.29E−08 | 4.67E−06 |
| PSRC1 | proline/serine-rich coiled-coil 1 | 1.52125 | 8.86E−08 | 1.56E−05 |
| SGOL2 | shugoshin-like 2 (S. pombe) | 1.52018 | 1.21E−07 | 2.05E−05 |
| HERC2 | HECT and RLD domain containing E3 ubiquitin protein ligase 2 | 1.51582 | 2.53E−10 | 7.70E−08 |

TABLE 2-continued

A list of genes, the expression of which is increased in the weakly adherent group compared to the strongly adherent group.

| Name | Description | Fold Change | p-Value | p-Adj |
|---|---|---|---|---|
| BRCA2 | breast cancer 2, early onset | 1.51425 | 3.86E−06 | 0.000441 |
| DYNC2H1 | dynein, cytoplasmic 2, heavy chain 1 | 1.51322 | 3.45E−06 | 0.0004 |
| KIF20B | kinesin family member 20B | 1.50171 | 8.66E−09 | 1.94E−06 |
| ASH1L | ash1 (absent, small, or homeotic)-like (Drosophila) | 1.50116 | 5.28E−11 | 1.76E−08 |
| NIPBL | Nipped-B homolog (Drosophila) | 1.49263 | 3.24E−11 | 1.16E−08 |
| USP24 | ubiquitin specific peptidase 24 | 1.49048 | 5.28E−11 | 1.76E−08 |
| CEP97 | centrosomal protein 97 kDa | 1.48771 | 2.56E−07 | 4.03E−05 |
| LINC00641 | long intergenic non-protein coding RNA 641 | 1.48567 | 3.12E−05 | 0.002718 |
| NBEAL1 | neurobeachin-like 1 | 1.48558 | 3.03E−05 | 0.002654 |
| MGA | MGA, MAX dimerization protein | 1.48527 | 3.46E−07 | 5.26E−05 |
| RANBP2 | RAN binding protein 2 | 1.47828 | 5.87E−11 | 1.92E−08 |
| MED13 | mediator complex subunit 13 | 1.4746 | 1.01E−09 | 2.70E−07 |
| TRRAP | transformation/transcription domain-associated protein | 1.47144 | 1.80E−09 | 4.55E−07 |
| AAK1 | AP2 associated kinase 1 | 1.47067 | 7.45E−09 | 1.69E−06 |
| ALMS1 | Alstrom syndrome protein 1 | 1.46854 | 5.86E−08 | 1.06E−05 |
| KIAA0754 | KIAA0754 | 1.4667 | 5.61E−09 | 1.31E−06 |
| ZFHX3 | zinc finger homeobox 3 | 1.46401 | 1.10E−06 | 0.000146 |
| LPP | LIM domain containing preferred translocation partner in lipoma | 1.46187 | 2.27E−06 | 0.000271 |
| FRAS1 | Fraser extracellular matrix complex subunit 1 | 1.46084 | 3.34E−07 | 5.13E−05 |
| ATRX | alpha thalassemia/mental retardation syndrome X-linked | 1.45761 | 1.12E−08 | 2.41E−06 |
| CCNB2 | cyclin B2 | 1.4571 | 5.72E−07 | 8.29E−05 |
| ITPR2 | inositol 1,4,5-trisphosphate receptor, type 2 | 1.45541 | 8.26E−06 | 0.000877 |
| LRRC37A4P | leucine rich repeat containing 37, member A4, pseudogene | 1.45307 | 9.64E−05 | 0.007063 |
| MYO9A | myosin IXA | 1.45306 | 1.52E−06 | 0.000191 |
| CCNA1 | cyclin A1 | 1.44947 | 8.74E−05 | 0.006487 |
| TAOK1 | TAO kinase 1 | 1.44925 | 1.76E−07 | 2.90E−05 |
| KIF20A | kinesin family member 20A | 1.4479 | 0.000156 | 0.010577 |
| NEK2 | NIMA-related kinase 2 | 1.44523 | 0.000173 | 0.011566 |
| BDP1 | B double prime 1, subunit of RNA polymerase III transcription initiation factor IIIB | 1.44458 | 3.28E−07 | 5.08E−05 |
| NAV1 | neuron navigator 1 | 1.44301 | 1.87E−07 | 2.99E−05 |
| HJURP | Holliday junction recognition protein | 1.43673 | 4.41E−07 | 6.54E−05 |
| CKAP5 | cytoskeleton associated protein 5 | 1.43528 | 6.87E−08 | 1.22E−05 |
| CEP192 | centrosomal protein 192 kDa | 1.43518 | 2.70E−08 | 5.32E−06 |
| UBALD2 | UBA-like domain containing 2 | 1.43406 | 4.80E−06 | 0.000542 |
| MUC4 | mucin 4, cell surface associated | 1.43384 | 0.000118 | 0.008443 |
| BRD8 | bromodomain containing 8 | 1.4318 | 3.13E−08 | 6.10E−06 |
| CRYBG3 | beta-gamma crystallin domain containing 3 | 1.43049 | 1.67E−06 | 0.000203 |
| ZNF292 | zinc finger protein 292 | 1.42687 | 1.19E−05 | 0.001223 |
| KIAA2018 | KIAA2018 | 1.42533 | 6.15E−05 | 0.004843 |
| G2E3 | G2/M-phase specific E3 ubiquitin protein ligase | 1.42504 | 1.53E−06 | 0.000191 |
| QSER1 | glutamine and serine rich 1 | 1.42307 | 7.27E−09 | 1.67E−06 |
| NBEA | neurobeachin | 1.41745 | 0.000242 | 0.015376 |
| SYNE1 | spectrin repeat containing, nuclear envelope 1 | 1.41717 | 0.000282 | 0.01725 |
| CCNB1 | cyclin B1 | 1.41651 | 0.00033 | 0.019565 |
| LIFR | leukemia inhibitory factor receptor alpha | 1.41637 | 9.05E−07 | 0.000123 |
| EPHB6 | EPH receptor B6 | 1.41316 | 0.000108 | 0.007842 |
| KIF18B | kinesin family member 18B | 1.40924 | 1.66E−06 | 0.000203 |
| GPSM2 | G-protein signaling modulator 2 | 1.40812 | 2.41E−06 | 0.000286 |
| KNSTRN | kinetochore-localized astrin/SPAG5 binding protein | 1.40489 | 2.37E−05 | 0.002164 |
| LRBA | LPS-responsive vesicle trafficking, beach and anchor containing | 1.40442 | 9.94E−08 | 1.73E−05 |
| CDC25C | cell division cycle 25C | 1.40367 | 6.40E−05 | 0.005019 |
| GEN1 | GEN1 Holliday junction 5' flap endonuclease | 1.40136 | 1.35E−05 | 0.001363 |
| CHD9 | chromodomain helicase DNA binding protein 9 | 1.4005 | 2.82E−05 | 0.002518 |
| SESN3 | sestrin 3 | 1.39917 | 0.000603 | 0.031656 |
| SLC7A11 | solute carrier family 7 (anionic amino acid transporter light chain, xc-system), member 11 | 1.39744 | 3.50E−08 | 6.69E−06 |
| CST1 | cystatin SN | 1.39715 | 4.08E−05 | 0.003426 |
| TMEM71 | transmembrane protein 71 | 1.39663 | 0.000659 | 0.033795 |

TABLE 2-continued

A list of genes, the expression of which is increased in the weakly adherent group compared to the strongly adherent group.

| Name | Description | Fold Change | p-Value | p-Adj |
|---|---|---|---|---|
| BPTF | bromodomain PHD finger transcription factor | 1.39579 | 4.27E−07 | 6.39E−05 |
| WNK3 | WNK lysine deficient protein kinase 3 | 1.39008 | 0.000352 | 0.020519 |
| PRKXP1 | protein kinase, X-linked, pseudogene 1 | 1.3897 | 0.000787 | 0.03825 |
| SPTBN1 | spectrin, beta, non-erythrocytic 1 | 1.38847 | 2.30E−10 | 7.11E−08 |
| ZFHX4 | zinc finger homeobox 4 | 1.38761 | 0.000567 | 0.030183 |
| UBN2 | ubinuclein 2 | 1.38675 | 0.000278 | 0.017143 |
| POU2F1 | POU class 2 homeobox 1 | 1.38419 | 2.30E−05 | 0.002105 |
| TTK | TTK protein kinase | 1.3839 | 3.78E−05 | 0.003214 |
| USP32P2 | ubiquitin specific peptidase 32 pseudogene 2 | 1.38183 | 0.000948 | 0.043733 |
| KIAA0586 | KIAA0586 | 1.37978 | 8.41E−06 | 0.000888 |
| CDC42BPA | CDC42 binding protein kinase alpha (DMPK-like) | 1.37748 | 3.61E−09 | 8.75E−07 |
| PRSS1 | protease, serine, 1 (trypsin 1) | 1.37719 | 0.000964 | 0.044247 |
| KDM5B | lysine (K)-specific demethylase 5B | 1.37695 | 1.23E−06 | 0.000159 |
| SH3PXD2A | SH3 and PX domains 2A | 1.37464 | 1.02E−08 | 2.24E−06 |
| LINC00342 | long intergenic non-protein coding RNA 342 | 1.37464 | 0.000864 | 0.041032 |
| XRN1 | 5′-3′ exoribonuclease 1 | 1.37459 | 7.83E−05 | 0.005903 |
| RAB37 | RAB37, member RAS oncogene family | 1.3737 | 0.000674 | 0.034301 |
| PCNX | pecanex homolog (Drosophila) | 1.37334 | 6.22E−07 | 8.80E−05 |
| AURKA | aurora kinase A | 1.37255 | 0.001243 | 0.054178 |
| ANKRD12 | ankyrin repeat domain 12 | 1.36926 | 7.74E−05 | 0.005867 |
| PLEKHH2 | pleckstrin homology domain containing, family H (with MyTH4 domain) member 2 | 1.36849 | 0.001045 | 0.046884 |
| NF1 | neurofibromin 1 | 1.36758 | 1.63E−05 | 0.001583 |
| MYH15 | myosin, heavy chain 15 | 1.36563 | 0.000999 | 0.045305 |
| GTSE1 | G-2 and S-phase expressed 1 | 1.36237 | 0.000119 | 0.008447 |
| PIKFYVE | phosphoinositide kinase, FYVE finger containing | 1.36125 | 6.82E−06 | 0.00076 |
| NKTR | natural killer cell triggering receptor | 1.36037 | 1.63E−07 | 2.71E−05 |
| PEAK1 | pseudopodium-enriched atypical kinase 1 | 1.36036 | 1.19E−05 | 0.001223 |
| LONRF2 | LON peptidase N-terminal domain and ring finger 2 | 1.36032 | 0.001701 | 0.070683 |
| BMPR2 | bone morphogenetic protein receptor, type II (serine/threonine kinase) | 1.35947 | 9.56E−07 | 0.000129 |
| BUB1B | BUB1 mitotic checkpoint serine/threonine kinase B | 1.35857 | 5.66E−05 | 0.004541 |
| RCSD1 | RCSD domain containing 1 | 1.35658 | 0.000226 | 0.01452 |
| RBBP6 | retinoblastoma binding protein 6 | 1.35621 | 1.62E−06 | 0.0002 |
| DEPDC1 | DEP domain containing 1 | 1.35532 | 0.001839 | 0.075014 |
| ARHGAP11A | Rho GTPase activating protein 11A | 1.35326 | 7.75E−05 | 0.005867 |
| DBF4B | DBF4 zinc finger B | 1.35218 | 0.000173 | 0.011566 |
| LAMA5 | laminin, alpha 5 | 1.35175 | 1.05E−07 | 1.82E−05 |
| CDCA2 | cell division cycle associated 2 | 1.35038 | 8.92E−05 | 0.006588 |
| CDCA8 | cell division cycle associated 8 | 1.34882 | 0.002019 | 0.080895 |
| CHD6 | chromodomain helicase DNA binding protein 6 | 1.34836 | 6.79E−06 | 0.00076 |
| IQGAP3 | IQ motif containing GTPase activating protein 3 | 1.34682 | 1.36E−05 | 0.001363 |
| PLK1 | polo-like kinase 1 | 1.34552 | 0.002414 | 0.091993 |
| SCLT1 | sodium channel and clathrin linker 1 | 1.34408 | 0.000593 | 0.031261 |
| PCNT | pericentrin | 1.34319 | 2.29E−07 | 3.64E−05 |
| ELF3 | E74-like factor 3 (ets domain transcription factor, epithelial-specific) | 1.34242 | 0.002678 | 0.097321 |
| HELZ | helicase with zinc finger | 1.34225 | 5.56E−05 | 0.004514 |
| ALPK1 | alpha-kinase 1 | 1.3397 | 0.00274 | 0.098957 |
| PHIP | pleckstrin homology domain interacting protein | 1.33901 | 4.03E−05 | 0.003395 |
| NDE1 | nudE neurodevelopment protein 1 | 1.33753 | 0.000411 | 0.023303 |
| ATF7IP | activating transcription factor 7 interacting protein | 1.33476 | 4.40E−05 | 0.003658 |
| NLGN1 | neuroligin 1 | 1.33224 | 0.001957 | 0.079126 |
| APC | adenomatous polyposis coli | 1.33101 | 7.38E−05 | 0.005708 |
| ARHGAP11B | Rho GTPase activating protein 11B | 1.329 | 0.003487 | 0.117725 |
| HMMR | hyaluronan-mediated motility receptor (RHAMM) | 1.32822 | 0.000517 | 0.027888 |
| HTT | huntingtin | 1.328 | 1.11E−06 | 0.000146 |
| SETX | senataxin | 1.32738 | 3.96E−06 | 0.00045 |
| POLQ | polymerase (DNA directed), theta | 1.32679 | 0.000204 | 0.013444 |
| SPAG5 | sperm associated antigen 5 | 1.32607 | 0.000181 | 0.011993 |

TABLE 2-continued

A list of genes, the expression of which is increased in the weakly adherent group compared to the strongly adherent group.

| Name | Description | Fold Change | p-Value | p-Adj |
|---|---|---|---|---|
| ATG2B | autophagy related 2B | 1.32481 | 0.000179 | 0.011973 |
| CHD2 | chromodomain helicase DNA binding protein 2 | 1.32454 | 1.81E−06 | 0.00022 |
| RICTOR | RPTOR independent companion of MTOR, complex 2 | 1.32343 | 0.000645 | 0.033495 |
| TANC2 | tetratricopeptide repeat, ankyrin repeat and coiled-coil containing 2 | 1.32328 | 1.90E−05 | 0.001816 |
| DSP | desmoplakin | 1.32279 | 1.25E−06 | 0.000161 |
| CENPJ | centromere protein J | 1.3226 | 0.000442 | 0.024632 |
| LMO7 | LIM domain 7 | 1.31954 | 2.85E−05 | 0.002519 |
| DBF4 | DBF4 zinc finger | 1.31911 | 0.000124 | 0.008743 |
| HDAC4 | histone deacetylase 4 | 1.31797 | 0.000257 | 0.016074 |
| SETD2 | SET domain containing 2 | 1.31692 | 8.08E−06 | 0.000868 |
| CREBRF | CREB3 regulatory factor | 1.31692 | 0.002884 | 0.102707 |
| AGAP6 | ArfGAP with GTPase domain, ankyrin repeat and PH domain 6 | 1.31689 | 0.002973 | 0.10542 |
| KLHL15 | kelch-like family member 15 | 1.31617 | 0.000358 | 0.020771 |
| CDKN3 | cyclin-dependent kinase inhibitor 3 | 1.31578 | 0.000207 | 0.013532 |
| MLLT4 | myeloid/lymphoid or mixed-lineage leukemia; translocated to, 4 | 1.31552 | 1.34E−06 | 0.000171 |
| ATL2 | atlastin GTPase 2 | 1.31549 | 2.10E−05 | 0.001955 |
| DEPDC1B | DEP domain containing 1B | 1.31546 | 0.001035 | 0.046696 |
| EP400 | E1A binding protein p400 | 1.31395 | 4.39E−05 | 0.003658 |
| EP300 | E1A binding protein p300 | 1.31155 | 2.66E−05 | 0.002386 |
| AFF4 | AF4/FMR2 family, member 4 | 1.31115 | 0.000132 | 0.00922 |
| SLCO4A1 | solute carrier organic anion transporter family, member 4A1 | 1.31061 | 0.00348 | 0.117725 |
| ZNF106 | zinc finger protein 106 | 1.31061 | 2.12E−05 | 0.001962 |
| ITPR1 | inositol 1,4,5-trisphosphate receptor, type 1 | 1.30839 | 0.00094 | 0.043586 |
| SPEN | spen family transcriptional repressor | 1.30825 | 1.95E−05 | 0.001848 |
| USP9X | ubiquitin specific peptidase 9, X-linked | 1.30788 | 5.99E−07 | 8.60E−05 |
| NOTCH2 | notch 2 | 1.30684 | 1.82E−07 | 2.98E−05 |
| NMU | neuromedin U | 1.30528 | 0.004084 | 0.131618 |
| REEP4 | receptor accessory protein 4 | 1.30505 | 0.000181 | 0.011993 |
| RNF145 | ring finger protein 145 | 1.30464 | 6.93E−06 | 0.000764 |
| HMGB3 | high mobility group box 3 | 1.3046 | 0.00036 | 0.020771 |
| ESPL1 | extra spindle pole bodies like 1, separase | 1.30402 | 0.000413 | 0.023311 |
| SMC4 | structural maintenance of chromosomes 4 | 1.30313 | 7.08E−05 | 0.005502 |
| PTTG1 | pituitary tumor-transforming 1 | 1.30248 | 0.000146 | 0.010063 |
| HIPK2 | homeodomain interacting protein kinase 2 | 1.30089 | 3.28E−05 | 0.002828 |
| PLCH1 | phospholipase C, eta 1 | 1.30078 | 0.007167 | 0.202263 |
| LINC01000 | long intergenic non-protein coding RNA 1000 | 1.30051 | 0.00026 | 0.016237 |
| CCNF | cyclin F | 1.29997 | 0.000593 | 0.031261 |
| CDCA3 | cell division cycle associated 3 | 1.29997 | 0.000732 | 0.036424 |
| GEM | GTP binding protein overexpressed in skeletal muscle | 1.29989 | 0.000657 | 0.033795 |
| NFIL3 | nuclear factor, interleukin 3 regulated | 1.29977 | 0.001746 | 0.072057 |
| DNHD1 | dynein heavy chain domain 1 | 1.29972 | 0.001524 | 0.064367 |
| SWT1 | SWT1 RNA endoribonuclease homolog (S. cerevisiae) | 1.29944 | 0.007261 | 0.203983 |
| PTPN14 | protein tyrosine phosphatase, non-receptor type 14 | 1.29813 | 3.01E−05 | 0.002649 |
| MIR600HG | MIR600 host gene | 1.29778 | 0.006841 | 0.196191 |
| KIF4A | kinesin family member 4A | 1.29772 | 0.000771 | 0.03782 |
| DMXL2 | Dmx-like 2 | 1.2974 | 0.000794 | 0.03825 |
| UBE2C | ubiquitin-conjugating enzyme E2C | 1.29707 | 0.000449 | 0.024942 |
| LOC100506548 | uncharacterized LOC100506548 | 1.29671 | 0.000343 | 0.020191 |
| JADE2 | jade family PHD finger 2 | 1.29658 | 5.32E−05 | 0.004383 |
| PCF11 | PCF11 cleavage and polyadenylation factor subunit | 1.29625 | 0.000123 | 0.008692 |
| DICER1 | dicer 1, ribonuclease type III | 1.29569 | 7.68E−05 | 0.005867 |
| TET2 | tet methylcytosine dioxygenase 2 | 1.29504 | 0.000745 | 0.036845 |
| JMJD1C | jumonji domain containing 1C | 1.29481 | 7.94E−06 | 0.000859 |
| LOC284454 | uncharacterized LOC284454 | 1.29428 | 0.004097 | 0.131618 |
| SLC5A3 | solute carrier family 5 (sodium/myo-inositol cotransporter), member 3 | 1.29388 | 0.002444 | 0.092965 |
| BUB1 | BUB1 mitotic checkpoint serine/threonine kinase | 1.29307 | 0.00033 | 0.019565 |
| ACBD7 | acyl-CoA binding domain containing 7 | 1.29286 | 0.007192 | 0.20238 |
| KIF2C | kinesin family member 2C | 1.29257 | 0.008152 | 0.220405 |
| CDC25B | cell division cycle 25B | 1.29214 | 8.29E−05 | 0.006225 |
| UBR5 | ubiquitin protein ligase E3 component n-recognin 5 | 1.2919 | 1.56E−05 | 0.001544 |

TABLE 2-continued

A list of genes, the expression of which is increased in the weakly adherent group compared to the strongly adherent group.

| Name | Description | Fold Change | p-Value | p-Adj |
|---|---|---|---|---|
| PRR14L | proline rich 14-like | 1.29141 | 0.000698 | 0.035018 |
| CBL | Cbl proto-oncogene, E3 ubiquitin protein ligase | 1.29042 | 3.41E−05 | 0.002925 |
| LINC01004 | long intergenic non-protein coding RNA 1004 | 1.28982 | 0.003628 | 0.120403 |
| TTBK2 | tau tubulin kinase 2 | 1.28852 | 0.004622 | 0.145553 |
| HNRNPU-AS1 | HNRNPU antisense RNA 1 | 1.28829 | 0.00774 | 0.213083 |
| MYH3 | myosin, heavy chain 3, skeletal muscle, embryonic | 1.28793 | 0.005914 | 0.176936 |
| DZIP3 | DAZ interacting zinc finger protein 3 | 1.28747 | 0.001983 | 0.079983 |
| SLC2A12 | solute carrier family 2 (facilitated glucose transporter), member 12 | 1.28733 | 0.009746 | 0.248516 |
| FSIP2 | fibrous sheath interacting protein 2 | 1.28675 | 0.006647 | 0.193405 |
| PRR11 | proline rich 11 | 1.28662 | 0.000569 | 0.030196 |
| KIF11 | kinesin family member 11 | 1.28636 | 0.000335 | 0.019793 |
| SON | SON DNA binding protein | 1.28618 | 3.20E−06 | 0.000373 |
| METTL7A | methyltransferase like 7A | 1.28552 | 0.009638 | 0.247422 |
| VEGFA | vascular endothelial growth factor A | 1.28533 | 1.25E−05 | 0.001268 |
| TACC3 | transforming, acidic coiled-coil containing protein 3 | 1.28501 | 0.000791 | 0.03825 |
| ASXL2 | additional sex combs like transcriptional regulator 2 | 1.28322 | 9.44E−05 | 0.006946 |
| ZKSCAN8 | zinc finger with KRAB and SCAN domains 8 | 1.28296 | 5.67E−05 | 0.004541 |
| SORL1 | sortilin-related receptor, L(DLR class) A repeats containing | 1.28161 | 0.001574 | 0.06603 |
| TOP2A | topoisomerase (DNA) II alpha | 1.28155 | 0.000892 | 0.042258 |
| RIF1 | replication timing regulatory factor 1 | 1.28134 | 0.000226 | 0.01452 |
| CHD7 | chromodomain helicase DNA binding protein 7 | 1.28068 | 0.000927 | 0.043352 |
| ETV6 | ets variant 6 | 1.28054 | 0.000652 | 0.03372 |
| LPCAT1 | lysophosphatidylcholine acyltransferase 1 | 1.2801 | 1.07E−05 | 0.001112 |
| USP13 | ubiquitin specific peptidase 13 (isopeptidase T-3) | 1.27944 | 0.000163 | 0.010997 |
| ZNF518A | zinc finger protein 518A | 1.27925 | 0.005539 | 0.167668 |
| VANGL1 | VANGL planar cell polarity protein 1 | 1.27889 | 1.57E−05 | 0.001549 |
| ASIC3 | acid sensing (proton gated) ion channel 3 | 1.27836 | 0.004502 | 0.142541 |
| RGS3 | regulator of G-protein signaling 3 | 1.27795 | 0.000665 | 0.033916 |
| GOLGA4 | golgin A4 | 1.27717 | 1.61E−05 | 0.001577 |
| NUF2 | NUF2, NDC80 kinetochore complex component | 1.27682 | 0.000973 | 0.044457 |
| SOX4 | SRY (sex determining region Y)-box 4 | 1.27641 | 0.012531 | 0.29408 |
| CCNA2 | cyclin A2 | 1.27624 | 0.000537 | 0.028858 |
| AGER | advanced glycosylation end product-specific receptor | 1.27487 | 0.012172 | 0.289807 |
| UTP20 | UTP20, small subunit (SSU) processome component, homolog (yeast) | 1.27429 | 2.84E−05 | 0.002519 |
| LOC729218 | uncharacterized LOC729218 | 1.27419 | 0.003577 | 0.119787 |
| ZDBF2 | zinc finger, DBF-type containing 2 | 1.27371 | 0.006808 | 0.195562 |
| AOC3 | amine oxidase, copper containing 3 | 1.27277 | 0.007826 | 0.214499 |
| LCOR | ligand dependent nuclear receptor corepressor | 1.27259 | 0.004745 | 0.148387 |
| NPPA-AS1 | NPPA antisense RNA 1 | 1.27225 | 0.009246 | 0.240551 |
| GPR75 | G protein-coupled receptor 75 | 1.27139 | 0.013212 | 0.302536 |
| FAM83D | family with sequence similarity 83, member D | 1.27135 | 0.01437 | 0.318885 |
| SNAI1 | snail family zinc finger 1 | 1.27079 | 0.007088 | 0.201017 |
| LCORL | ligand dependent nuclear receptor corepressor-like | 1.27053 | 0.003035 | 0.107064 |
| C10orf12 | chromosome 10 open reading frame 12 | 1.26942 | 0.003321 | 0.114229 |
| WNK1 | WNK lysine deficient protein kinase 1 | 1.26885 | 6.11E−05 | 0.004834 |
| ANKRD11 | ankyrin repeat domain 11 | 1.26826 | 4.87E−05 | 0.004028 |
| ARHGEF12 | Rho guanine nucleotide exchange factor (GEF) 12 | 1.26748 | 1.09E−05 | 0.001126 |
| OSER1-AS1 | OSER1 antisense RNA 1 (head to head) | 1.26701 | 0.015011 | 0.327684 |
| C5orf42 | chromosome 5 open reading frame 42 | 1.267 | 0.001177 | 0.051806 |
| TULP4 | tubby like protein 4 | 1.26689 | 0.004616 | 0.145553 |
| SOS1 | son of sevenless homolog 1 (Drosophila) | 1.26656 | 0.00047 | 0.025732 |
| SH3BP5-AS1 | SH3BP5 antisense RNA 1 | 1.26647 | 0.014994 | 0.327684 |
| ARTN | artemin | 1.26619 | 0.006707 | 0.193577 |
| LRP5L | low density lipoprotein receptor-related protein 5-like | 1.26607 | 0.01414 | 0.314933 |
| DMXL1 | Dmx-like 1 | 1.26555 | 0.002532 | 0.094685 |
| TNXB | tenascin XB | 1.26521 | 0.015815 | 0.340007 |

TABLE 2-continued

A list of genes, the expression of which is increased in the weakly adherent group compared to the strongly adherent group.

| Name | Description | Fold Change | p-Value | p-Adj |
|---|---|---|---|---|
| SNN | stannin | 1.26431 | 0.006372 | 0.188459 |
| FAM64A | family with sequence similarity 64, member A | 1.26424 | 0.016754 | 0.349654 |
| INCENP | inner centromere protein antigens 135/155 kDa | 1.26408 | 0.00262 | 0.096219 |
| PIK3C2B | phosphatidylinositol-4-phosphate 3-kinase, catalytic subunit type 2 beta | 1.26379 | 0.016108 | 0.341907 |
| RSBN1 | round spermatid basic protein 1 | 1.26348 | 0.002554 | 0.094781 |
| EGF | epidermal growth factor | 1.26319 | 0.016851 | 0.349654 |
| ZNF155 | zinc finger protein 155 | 1.26286 | 0.009375 | 0.242758 |
| MYEF2 | myelin expression factor 2 | 1.26281 | 0.001994 | 0.080254 |
| APH1B | APH1B gamma secretase subunit | 1.26208 | 0.009288 | 0.241298 |
| DLGAP5 | discs, large (Drosophila) homolog-associated protein 5 | 1.26162 | 0.017118 | 0.35201 |
| LOC90784 | uncharacterized LOC90784 | 1.26115 | 0.00371 | 0.122269 |
| PSD3 | pleckstrin and Sec7 domain containing 3 | 1.26078 | 0.002495 | 0.09428 |
| MYO5A | myosin VA | 1.26045 | 0.000693 | 0.03485 |
| RAPGEFL1 | Rap guanine nucleotide exchange factor (GEF)-like 1 | 1.26005 | 0.017616 | 0.358864 |
| NBPF10 | neuroblastoma breakpoint family, member 10 | 1.26005 | 0.016809 | 0.349654 |
| STAG3L5P-PVRIG2P-PILRB | STAG3L5P-PVRIG2P-PILRB readthrough | 1.25982 | 0.007107 | 0.201237 |
| CEP70 | centrosomal protein 70 kDa | 1.25977 | 0.008905 | 0.233711 |
| GDF15 | growth differentiation factor 15 | 1.25916 | 0.015854 | 0.340046 |
| ZMYM1 | zinc finger, MYM-type 1 | 1.25852 | 0.007777 | 0.213462 |
| GPR87 | G protein-coupled receptor 87 | 1.25833 | 0.018195 | 0.364435 |
| HCG27 | HLA complex group 27 (non-protein coding) | 1.25732 | 0.00594 | 0.177439 |
| REV3L | REV3-like, polymerase (DNA directed), zeta, catalytic subunit | 1.25646 | 0.002523 | 0.094685 |
| KIF23 | kinesin family member 23 | 1.25595 | 0.003042 | 0.107064 |
| ZBTB10 | zinc finger and BTB domain containing 10 | 1.25484 | 0.011608 | 0.280092 |
| TNC | tenascin C | 1.25411 | 0.0014 | 0.060019 |
| BAZ2B | bromodomain adjacent to zinc finger domain, 2B | 1.25405 | 0.00471 | 0.147573 |
| SYNRG | synergin, gamma | 1.25395 | 0.000594 | 0.031261 |
| KLHL24 | kelch-like family member 24 | 1.2538 | 0.019919 | 0.381548 |
| VAMP4 | vesicle-associated membrane protein 4 | 1.25358 | 0.013502 | 0.306433 |
| CENPL | centromere protein L | 1.2535 | 0.001999 | 0.08029 |
| NFAT5 | nuclear factor of activated T-cells 5, tonicity-responsive | 1.25249 | 0.020429 | 0.388078 |

TABLE 3

A list of genes, the expression of which is decreased in the weakly adherent group compared to the strongly adherent group.

| Name | Description | Fold Change | p-Value | p-Adj |
|---|---|---|---|---|
| HELLS | helicase, lymphoid-specific | −1.25042 | 0.002297 | 0.089693 |
| IFIT3 | interferon-induced protein with tetratricopeptide repeats 3 | −1.25044 | 0.001729 | 0.071538 |
| GCH1 | GTP cyclohydrolase 1 | −1.25083 | 0.013932 | 0.312251 |
| CD55 | CD55 molecule, decay accelerating factor for complement (Cromer blood group) | −1.25102 | 7.69E−05 | 0.005867 |
| IRX3 | iroquois homeobox 3 | −1.25125 | 0.005282 | 0.161545 |
| POLD3 | polymerase (DNA-directed), delta 3, accessory subunit | −1.2517 | 0.000312 | 0.018774 |
| CDC45 | cell division cycle 45 | −1.25239 | 0.000275 | 0.017024 |
| NUAK1 | NUAK family, SNF1-like kinase, 1 | −1.25248 | 0.000782 | 0.03816 |
| ABHD5 | abhydrolase domain containing 5 | −1.25249 | 0.000559 | 0.029872 |
| C3HC4 | membrane-associated ring finger (C3HC4) 3, E3 ubiquitin protein ligase | −1.25259 | 0.002305 | 0.089693 |
| LAYN | layilin | −1.25322 | 0.00035 | 0.02045 |
| DUSP10 | dual specificity phosphatase 10 | −1.25332 | 0.002318 | 0.089693 |
| ADAMTS16 | ADAM metallopeptidase with thrombospondin type 1 motif, 16 | −1.25341 | 0.003571 | 0.119787 |

TABLE 3-continued

A list of genes, the expression of which is decreased in the weakly adherent group compared to the strongly adherent group.

| Name | Description | Fold Change | p-Value | p-Adj |
|---|---|---|---|---|
| DTL | denticleless E3 ubiquitin protein ligase homolog (Drosophila) | −1.25404 | 0.000406 | 0.023124 |
| POLE2 | polymerase (DNA directed), epsilon 2, accessory subunit | −1.25415 | 0.001316 | 0.056932 |
| CGN | cingulin | −1.25461 | 0.020133 | 0.383676 |
| FOXQ1 | forkhead box Q1 | −1.25732 | 0.010358 | 0.259213 |
| RGMB | repulsive guidance molecule family member b | −1.25791 | 0.000109 | 0.007874 |
| GNAI1 | guanine nucleotide binding protein (G protein), alpha inhibiting activity polypeptide 1 | −1.2584 | 0.003712 | 0.122269 |
| F3 | coagulation factor III (thromboplastin, tissue factor) | −1.25867 | 3.52E−05 | 0.003007 |
| MARS2 | methionyl-tRNA synthetase 2, mitochondrial | −1.25869 | 0.002632 | 0.096219 |
| WT1 | Wilms tumor 1 | −1.25892 | 0.016002 | 0.341561 |
| PDE4DIP | phosphodiesterase 4D interacting protein | −1.25892 | 0.000468 | 0.025675 |
| ANOS1 | anosmin 1 | −1.25925 | 0.000951 | 0.043791 |
| CHAF1B | chromatin assembly factor 1, subunit B (p60) | −1.25935 | 0.000279 | 0.017181 |
| MYC | v-myc avian myelocytomatosis viral oncogene homolog | −1.25941 | 0.000256 | 0.016069 |
| LINC01547 | long intergenic non-protein coding RNA 1547 | −1.25988 | 0.017557 | 0.358563 |
| SPIN4 | spindlin family, member 4 | −1.26055 | 0.003112 | 0.1087 |
| DCLRE1B | DNA cross-link repair 1B | −1.26095 | 0.00038 | 0.021802 |
| HSPB8 | heat shock 22 kDa protein 8 | −1.26172 | 0.001536 | 0.064569 |
| ALS2CL | ALS2 C-terminal like | −1.26483 | 0.00076 | 0.037389 |
| NNMT | nicotinamide N-methyltransferase | −1.26491 | 0.002306 | 0.089693 |
| DDAH1 | dimethylarginine dimethylaminohydrolase 1 | −1.26514 | 0.000505 | 0.027401 |
| SNHG18 | small nucleolar RNA host gene 18 | −1.26545 | 0.012548 | 0.29408 |
| JAG2 | jagged 2 | −1.26554 | 0.008586 | 0.227661 |
| SAMD1 | sterile alpha motif domain containing 1 | −1.26577 | 0.000693 | 0.03485 |
| ZNF324B | zinc finger protein 324B | −1.26589 | 0.008176 | 0.220655 |
| IL24 | interleukin 24 | −1.26601 | 0.002977 | 0.10542 |
| RND3 | Rho family GTPase 3 | −1.26632 | 6.00E−05 | 0.004765 |
| PLSCR4 | phospholipid scramblase 4 | −1.26714 | 0.013376 | 0.304349 |
| TP73 | tumor protein p73 | −1.26727 | 0.008208 | 0.220902 |
| STYK1 | serine/threonine/tyrosine kinase 1 | −1.2683 | 0.006696 | 0.193577 |
| DENND2A | DENN/MADD domain containing 2A | −1.26949 | 0.01354 | 0.306529 |
| SCG5 | secretogranin V | −1.26976 | 0.010367 | 0.259213 |
| FAM222A | family with sequence similarity 222, member A | −1.27003 | 0.011586 | 0.280092 |
| ATP6V0A4 | ATPase, H+ transporting, lysosomal V0 subunit a4 | −1.27008 | 0.002878 | 0.102707 |
| GTPBP3 | GTP binding protein 3 (mitochondrial) | −1.27048 | 0.000917 | 0.04313 |
| PLK2 | polo-like kinase 2 | −1.27055 | 1.74E−05 | 0.001677 |
| KCNJ15 | potassium channel, inwardly rectifying subfamily J, member 15 | −1.27212 | 0.008557 | 0.227454 |
| GADD45A | growth arrest and DNA-damage-inducible, alpha | −1.27227 | 0.000479 | 0.026094 |
| ATP8B1 | ATPase, aminophospholipid transporter, class I, type 8B, member 1 | −1.27266 | 0.000645 | 0.033495 |
| ADAMTS1 | ADAM metallopeptidase with thrombospondin type 1 motif, 1 | −1.2727 | 0.007623 | 0.211187 |
| CDT1 | chromatin licensing and DNA replication factor 1 | −1.27305 | 0.000125 | 0.008761 |
| KRT17 | keratin 17, type I | −1.27306 | 0.001087 | 0.04828 |
| TNFRSF11B | tumor necrosis factor receptor superfamily, member 11b | −1.27313 | 0.013343 | 0.303977 |
| POLA2 | polymerase (DNA directed), alpha 2, accessory subunit | −1.27414 | 0.000188 | 0.012412 |
| PAWR | PRKC, apoptosis, WT1, regulator | −1.27496 | 0.000234 | 0.014894 |
| ADM | adrenomedullin | −1.2751 | 0.001217 | 0.053151 |
| CDC42EP2 | CDC42 effector protein (Rho GTPase binding) 2 | −1.27537 | 0.000226 | 0.01452 |
| LRRC45 | leucine rich repeat containing 45 | −1.27611 | 0.002165 | 0.085417 |
| TBC1D2 | TBC1 domain family, member 2 | −1.27706 | 0.001141 | 0.050454 |
| GRAMD3 | GRAM domain containing 3 | −1.27983 | 0.000223 | 0.01445 |
| OXTR | oxytocin receptor | −1.28135 | 0.010315 | 0.258635 |
| RIMS2 | regulating synaptic membrane exocytosis 2 | −1.28231 | 0.007475 | 0.208694 |
| S1PR2 | sphingosine-1-phosphate receptor 2 | −1.28241 | 0.011179 | 0.273418 |
| THBS1 | thrombospondin 1 | −1.28257 | 1.81E−05 | 0.001737 |

TABLE 3-continued

A list of genes, the expression of which is decreased in the weakly adherent group compared to the strongly adherent group.

| Name | Description | Fold Change | p-Value | p-Adj |
|---|---|---|---|---|
| TOX | thymocyte selection-associated high mobility group box | −1.2833 | 0.00844 | 0.225465 |
| ZBTB14 | zinc finger and BTB domain containing 14 | −1.28446 | 0.003395 | 0.115877 |
| WDR76 | WD repeat domain 76 | −1.28488 | 0.000114 | 0.008234 |
| MCM3 | minichromosome maintenance complex component 3 | −1.28497 | 7.13E−07 | 1.00E−04 |
| LOC100126784 | uncharacterized LOC100126784 | −1.2858 | 0.010248 | 0.258022 |
| C17orf96 | chromosome 17 open reading frame 96 | −1.28602 | 0.000678 | 0.034385 |
| COL1A2 | collagen, type I, alpha 2 | −1.28782 | 0.009075 | 0.237149 |
| IL32 | interleukin 32 | −1.28812 | 0.000977 | 0.044527 |
| CCDC183-AS1 | CCDC183 antisense RNA 1 | −1.28835 | 0.008986 | 0.235152 |
| IFIT2 | interferon-induced protein with tetratricopeptide repeats 2 | −1.28888 | 0.00104 | 0.046801 |
| FEN1 | flap structure-specific endonuclease 1 | −1.28958 | 7.79E−06 | 0.000848 |
| PCNA | proliferating cell nuclear antigen | −1.28971 | 2.09E−05 | 0.001955 |
| SAA2 | serum amyloid A2 | −1.29352 | 0.007951 | 0.217264 |
| MGLL | monoglyceride lipase | −1.29352 | 5.71E−05 | 0.004554 |
| MB21D2 | Mab-21 domain containing 2 | −1.29458 | 0.003281 | 0.113058 |
| MATN2 | matrilin 2 | −1.29484 | 0.00048 | 0.026094 |
| WTIP | Wilms tumor 1 interacting protein | −1.29486 | 0.001474 | 0.062567 |
| NGF | nerve growth factor (beta polypeptide) | −1.29518 | 0.006763 | 0.19489 |
| DSCC1 | DNA replication and sister chromatid cohesion 1 | −1.29603 | 0.000689 | 0.03485 |
| BMPER | BMP binding endothelial regulator | −1.29704 | 0.00359 | 0.120021 |
| PSG5 | pregnancy specific beta-1-glycoprotein 5 | −1.29813 | 0.002339 | 0.090317 |
| PPP1R13L | protein phosphatase 1, regulatory subunit 13 like | −1.29986 | 0.000254 | 0.015983 |
| CXCR4 | chemokine (C—X—C motif) receptor 4 | −1.30097 | 0.006931 | 0.197819 |
| ZFP36L1 | ZFP36 ring finger protein-like 1 | −1.30102 | 1.02E−06 | 0.000136 |
| MYBL2 | v-myb avian myeloblastosis viral oncogene homolog-like 2 | −1.30271 | 1.97E−05 | 0.001865 |
| GPRC5B | G protein-coupled receptor, class C, group 5, member B | −1.30289 | 0.002762 | 0.098957 |
| PCDH7 | protocadherin 7 | −1.30479 | 0.006159 | 0.183068 |
| CDK5R1 | cyclin-dependent kinase 5, regulatory subunit 1 (p35) | −1.30516 | 0.002301 | 0.089693 |
| VGLL3 | vestigial-like family member 3 | −1.30746 | 0.006093 | 0.181409 |
| FSTL3 | follistatin-like 3 (secreted glycoprotein) | −1.30805 | 8.43E−05 | 0.006308 |
| PSG4 | pregnancy specific beta-1-glycoprotein 4 | −1.30838 | 0.002627 | 0.096219 |
| NCF2 | neutrophil cytosolic factor 2 | −1.30882 | 0.001161 | 0.051206 |
| NOG | noggin | −1.31028 | 0.000228 | 0.014582 |
| LRIG1 | leucine-rich repeats and immunoglobulin-like domains 1 | −1.31097 | 0.000451 | 0.025006 |
| PDCD1LG2 | programmed cell death 1 ligand 2 | −1.31445 | 0.003605 | 0.120108 |
| PROSER2 | proline and serine rich 2 | −1.31471 | 5.59E−05 | 0.00452 |
| CEMIP | cell migration inducing protein, hyaluronan binding | −1.31552 | 0.000136 | 0.009441 |
| ICAM1 | intercellular adhesion molecule 1 | −1.31615 | 0.000116 | 0.008299 |
| KRTAP2-3 | keratin associated protein 2-3 | −1.31769 | 0.00404 | 0.130456 |
| CCNE1 | cyclin E1 | −1.31819 | 0.000269 | 0.016724 |
| PAQR4 | progestin and adipoQ receptor family member IV | −1.32343 | 2.23E−05 | 0.002048 |
| EXO1 | exonuclease 1 | −1.32411 | 9.81E−06 | 0.00103 |
| CDC6 | cell division cycle 6 | −1.3275 | 2.98E−06 | 0.00035 |
| NUAK2 | NUAK family, SNF1-like kinase, 2 | −1.32871 | 0.002531 | 0.094685 |
| FLG | filaggrin | −1.33001 | 0.000322 | 0.019259 |
| G0S2 | G0/G1 switch 2 | −1.33037 | 1.99E−05 | 0.001871 |
| C4BPB | complement component 4 binding protein, beta | −1.33575 | 8.54E−05 | 0.006362 |
| HBEGF | heparin-binding EGF-like growth factor | −1.33845 | 2.85E−07 | 4.44E−05 |
| ALPP | alkaline phosphatase, placental | −1.3407 | 0.002361 | 0.090973 |
| CCDC80 | coiled-coil domain containing 80 | −1.34098 | 3.49E−06 | 0.000402 |
| FGF5 | fibroblast growth factor 5 | −1.34158 | 0.001871 | 0.076172 |
| MCM5 | minichromosome maintenance complex component 5 | −1.34634 | 7.58E−06 | 0.000829 |
| MUSK | muscle, skeletal, receptor tyrosine kinase | −1.34781 | 0.002312 | 0.089693 |
| AMOTL2 | angiomotin like 2 | −1.34866 | 1.95E−06 | 0.000235 |
| SERTAD4 | SERTA domain containing 4 | −1.34905 | 0.000937 | 0.043578 |
| GJB3 | gap junction protein, beta 3, 31 kDa | −1.35059 | 0.001294 | 0.0561 |
| SCARF2 | scavenger receptor class F, member 2 | −1.35214 | 0.001073 | 0.047789 |
| TCF19 | transcription factor 19 | −1.35528 | 2.49E−08 | 4.96E−06 |
| MCM2 | minichromosome maintenance complex component 2 | −1.35843 | 1.11E−07 | 1.89E−05 |

TABLE 3-continued

A list of genes, the expression of which is decreased in the weakly adherent group compared to the strongly adherent group.

| Name | Description | Fold Change | p-Value | p-Adj |
|---|---|---|---|---|
| C4orf26 | chromosome 4 open reading frame 26 | −1.35973 | 0.000665 | 0.033916 |
| INHBA | inhibin, beta A | −1.36417 | 0.000359 | 0.020771 |
| TGFB2 | transforming growth factor, beta 2 | −1.36526 | 6.17E−07 | 8.79E−05 |
| PTX3 | pentraxin 3, long | −1.36995 | 1.63E−05 | 0.001583 |
| E2F1 | E2F transcription factor 1 | −1.38451 | 4.73E−08 | 8.94E−06 |
| SGK1 | serum/glucocorticoid regulated kinase 1 | −1.38967 | 3.85E−05 | 0.003261 |
| UNG | uracil DNA glycosylase | −1.39025 | 5.82E−08 | 1.06E−05 |
| ADAMTSL4 | ADAMTS-like 4 | −1.39188 | 0.000295 | 0.017886 |
| NR2F2 | nuclear receptor subfamily 2, group F, member 2 | −1.39243 | 1.22E−08 | 2.60E−06 |
| DUSP1 | dual specificity phosphatase 1 | −1.39407 | 2.53E−05 | 0.002294 |
| LRRC20 | leucine rich repeat containing 20 | −1.3944 | 2.92E−06 | 0.000345 |
| JPH1 | junctophilin 1 | −1.39615 | 0.000657 | 0.033795 |
| FRMD6 | FERM domain containing 6 | −1.39917 | 1.77E−09 | 4.54E−07 |
| LYPD6 | LY6/PLAUR domain containing 6 | −1.4146 | 0.000125 | 0.008761 |
| SAA1 | serum amyloid A1 | −1.42638 | 8.35E−07 | 0.000114 |
| C6orf132 | chromosome 6 open reading frame 132 | −1.42661 | 5.36E−07 | 7.88E−05 |
| FAM111B | family with sequence similarity 111, member B | −1.42766 | 1.37E−05 | 0.001363 |
| PNMA2 | paraneoplastic Ma antigen 2 | −1.43479 | 1.23E−06 | 0.000159 |
| C3 | complement component 3 | −1.44578 | 5.55E−05 | 0.004514 |
| CXCL1 | chemokine (C—X—C motif) ligand 1 (melanoma growth stimulating activity, alpha) | −1.45138 | 0.000146 | 0.010063 |
| EDN1 | endothelin 1 | −1.46189 | 8.13E−06 | 0.000869 |
| GPRC5A | G protein-coupled receptor, class C, group 5, member A | −1.46836 | 1.01E−12 | 5.32E−10 |
| CPA4 | carboxypeptidase A4 | −1.47813 | 1.06E−06 | 0.000141 |
| CTGF | connective tissue growth factor | −1.48059 | 1.13E−11 | 4.39E−09 |
| MCM6 | minichromosome maintenance complex component 6 | −1.48279 | 4.52E−12 | 2.03E−09 |
| CD274 | CD274 molecule | −1.49297 | 9.25E−09 | 2.05E−06 |
| CLDN1 | claudin 1 | −1.51028 | 2.57E−05 | 0.002314 |
| FST | follistatin | −1.5141 | 8.32E−07 | 0.000114 |
| SERPINE1 | serpin peptidase inhibitor, clade E (nexin, plasminogen activator inhibitor type 1), member 1 | −1.53761 | 8.36E−12 | 3.49E−09 |
| IL6 | interleukin 6 | −1.5478 | 1.37E−08 | 2.86E−06 |
| KRT81 | keratin 81, type II | −1.55907 | 4.44E−10 | 1.28E−07 |
| RGS4 | regulator of G-protein signaling 4 | −1.56204 | 2.94E−09 | 7.23E−07 |
| IL7R | interleukin 7 receptor | −1.58034 | 5.00E−08 | 9.35E−06 |
| CYR61 | cysteine-rich, angiogenic inducer, 61 | −1.58299 | 2.84E−16 | 2.43E−13 |
| SERPINB2 | serpin peptidase inhibitor, clade B (ovalbumin), member 2 | −1.61111 | 7.20E−07 | 0.0001 |
| C3HC4 | membrane-associated ring finger (C3HC4) 4, E3 ubiquitin protein ligase | −1.67978 | 6.35E−11 | 2.03E−08 |
| DKK1 | dickkopf WNT signaling pathway inhibitor 1 | −1.76558 | 3.00E−20 | 3.84E−17 |
| ANKRD1 | ankyrin repeat domain 1 (cardiac muscle) | −1.8296 | 2.00E−26 | 6.00E−23 |
| UCA1 | urothelial cancer associated 1 (non-protein coding) | −1.87425 | 3.77E−15 | 2.82E−12 |

As illustrated in the Examples and Tables 2-3 above, weakly adherent cancer cells display an altered expression of one or more genes as disclosed herein compared to strongly adherent cancer cells. Accordingly, an altered expression (for example, as compared to the average expression of cancer cells optionally of the same cancer type, or alternatively as compared to the expression of a primary cancer optionally of the same cancer type, or alternatively as compared to a non-metastatic cancer cell optionally of the same cancer type, or alternatively as compared to a strongly adherent cancer cell optionally of the same cancer type) of the one or more genes in a cancer cell indicates that the cancer cell is a weakly adherent cell or has a metastatic potential (i.e., metastatic, or having a high risk in developing into a metastatic cancer cell, or having a high risk in developing a metastasis from the cancer cell) or both. Additionally or alternatively, an expression of one or more genes in a cancer cell at a level substantially the same to that of a metastatic cancer cell (optionally of the same cancer type) or alternatively substantially the same to that of a weakly adherent cancer cell (optionally of the same cancer type) also indicates the cancer cell has a metastatic potential, or is a weakly adherent cell, or both.

Accordingly, in various embodiments, an increased expression of one or more genes listed in Table 2 in a cancer cell indicates that the cancer cell has a metastatic potential, or is a weakly adherent cell, or both. Additionally or alternatively, a decreased expression of one or more genes listed in Table 3 in a cancer cell indicates the cancer cell has a metastatic potential, or is a weakly adherent cell, or both. In further embodiments, such altered expression, increased or decreased, may be used in any other embodiments or aspect as disclosed herein, to stratify a patient or select a suitable treatment or therapy for a patient, or both.

Figure 5A:
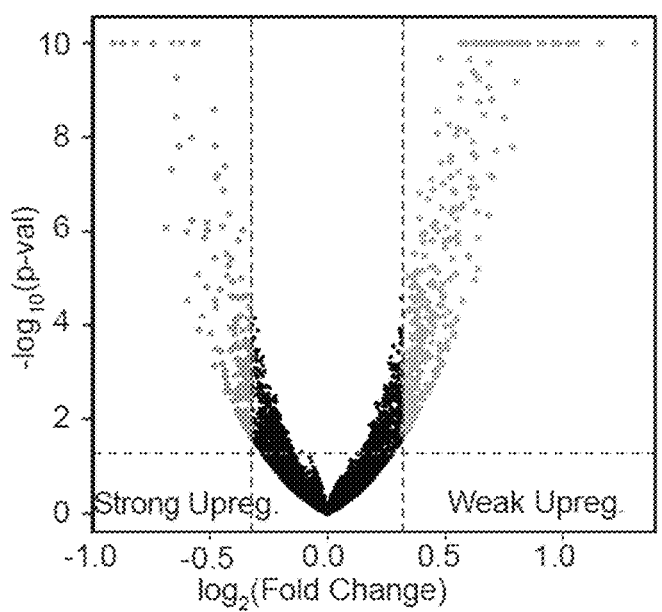
FIGS. 5A-5F are graphical and pictorial diagrams showing RNA-seq identifies intrinsic patterns that indicate structural rather than expression changes in adhesion.
Figure 5B:
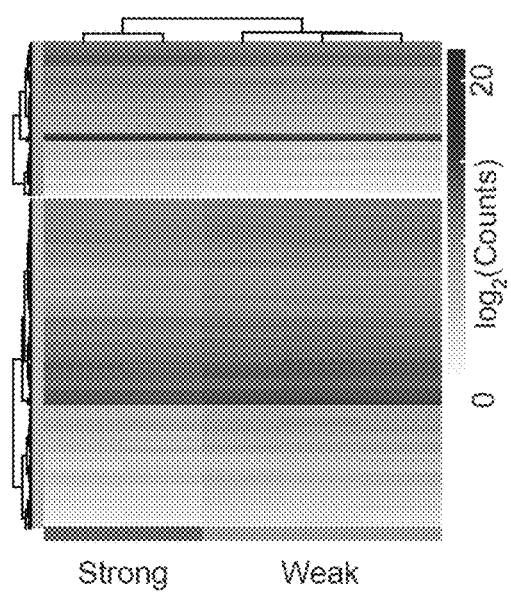
Figure 5C:
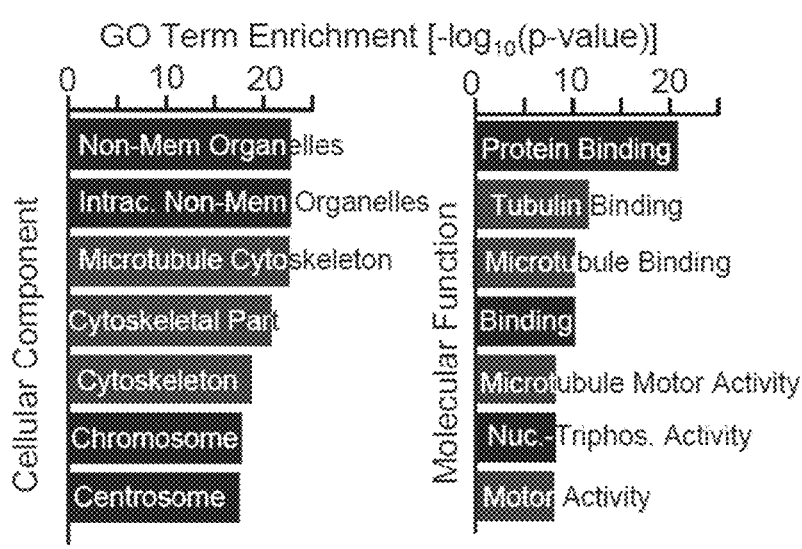
Figure 5D:
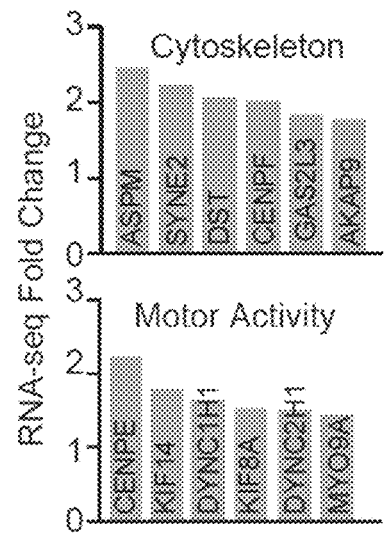
Figure 5E:
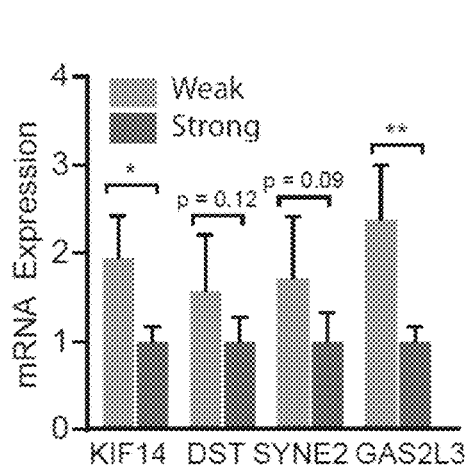

In some embodiments, the expression of a gene as used herein can be quantified as the level of a gene product produced for the gene, such as RNA (for example, an siRNA or a mRNA), a polypeptide, or a protein. For example, as shown in FIG. 5E, an altered gene expression is provided as an increased level of the corresponding mRNA.

In various embodiments, "having a risk" and "having a high risk" are used interchangeably and means having a certain possibility to happen, for example, more than 50%, or more than 60%, or more than 70%, or more that 80%, or more than 90%, or more than 95%, or more than 97%, or more than 99% of possibility to happen.

In various embodiments, an altered expression (such as an increased or decreased expression level) of one or more genes in a cancer cell compared to a control indicates a metastatic cancer cell or a cancer cell having a metastatic potential. In some embodiments, the increase can be upregulated from no expression of the one or more genes at all, i.e., the altered expression is that the gene expression starts. In some embodiments, the decrease can be reduced to no expression of the one or more genes at all, i.e., the altered expression is that the gene expression stops. In some embodiments, the altered expression is an increase if such increase is observed in weakly adherent cancer cells compared to strongly adherent cancer cells. Additionally or alternatively, the altered expression is decrease if such decrease is observed in weakly adherent cancer cells compared to strongly adherent cancer cells. In some embodiments, the control is a primary cancer cell. In some embodiments, the control is a cancer cell free of metastatic risk or potential. Additionally or alternatively, the control is a cancer cell that is not metastatic. In further embodiments, the control cancer cell is of the same origin of the tested cancer cell.

In some embodiments, the biological sample is a tumor biopsy.

In various embodiments, the cancer has metastatic potential.

In various embodiment, the cancer cell is an epithelial cancer cell. In various embodiments, the cancer can be any cancer as disclosed herein, such as a breast cancer, a prostate cancer or a lung cancer.

In yet a further aspect, provided is a composition, a kit or a system comprising one or more of the following: a device as disclosed herein, a probe or an antibody for determining expression of the one or more genes, or an instruction for use.

It would be understand that any embodiment or aspect as disclosed herein may be combined with any other embodiment(s) or aspect(s).

The disclosure further provides diagnostic, prognostic and therapeutic methods, which are based, at least in part, on determination of the identity of a genotype of interest identified herein.

For example, information obtained using the diagnostic assays described herein is useful for determining if a subject is suitable for cancer treatment of a given type. Based on the prognostic information, a doctor can recommend a therapeutic protocol, useful for reducing the malignant mass or tumor in the patient or treat cancer in the individual.

A patient's likely clinical outcome following a clinical procedure such as a therapy or surgery can be expressed in relative terms. For example, a patient having a particular genotype or expression level can experience relatively longer overall survival than a patient or patients not having the genotype or expression level. The patient having the particular genotype or expression level, alternatively, can be considered as likely to survive. Similarly, a patient having a particular genotype or expression level can experience relatively longer progression free survival, or time to tumor progression, than a patient or patients not having the genotype or expression level. The patient having the particular genotype or expression level, alternatively, can be considered as not likely to suffer tumor progression. Further, a patient having a particular genotype or expression level can experience relatively shorter time to tumor recurrence than a patient or patients not having the genotype or expression level. The patient having the particular genotype or expression level, alternatively, can be considered as not likely to suffer tumor recurrence. Yet in another example, a patient having a particular genotype or expression level can experience relatively more complete response or partial response than a patient or patients not having the genotype or expression level. The patient having the particular genotype or expression level, alternatively, can be considered as likely to respond. Accordingly, a patient that is likely to survive, or not likely to suffer tumor progression, or not likely to suffer tumor recurrence, or likely to respond following a clinical procedure is considered suitable for the clinical procedure.

It is to be understood that information obtained using the diagnostic assays described herein can be used alone or in combination with other information, such as, but not limited to, genotypes or expression levels of other genes, clinical chemical parameters, histopathological parameters, or age, gender and weight of the subject. When used alone, the information obtained using the diagnostic assays described herein is useful in determining or identifying the clinical outcome of a treatment, selecting a patient for a treatment, or treating a patient, etc. When used in combination with other information, on the other hand, the information obtained using the diagnostic assays described herein is useful in aiding in the determination or identification of clinical outcome of a treatment, aiding in the selection of a patient for a treatment, or aiding in the treatment of a patient and etc. In a particular aspect, the genotypes or expression levels of one or more genes as disclosed herein are used in a panel of genes, each of which contributes to the final diagnosis, prognosis or treatment.

The methods are useful in the assistance of an animal, a mammal or yet further a human patient. For the purpose of illustration only, a mammal includes but is not limited to a human, a simian, a murine, a bovine, an equine, a porcine or an ovine subject.

Biological Sample Collection and Preparation

The methods and compositions disclosed herein can be used to detect nucleic acids associated with the genetic polymorphisms identified herein. Biological samples can be obtained by standard procedures and can be used immediately or stored, under conditions appropriate for the type of biological sample, for later use. Any liquid or solid biological material obtained from the patient believed to contain nucleic acids comprising the region the polymorphic region can be a suitable sample.

Methods of obtaining test samples are known to those of skill in the art and include, but are not limited to, aspirations, tissue sections, swabs, drawing of blood or other fluids, surgical or needle biopsies.

In some aspects, the biological sample is a tissue or a cell sample. Suitable patient samples in the methods include, but are not limited to, blood, plasma, serum, a biopsy tissue, fine needle biopsy sample, amniotic fluid, plasma, pleural fluid, saliva, semen, serum, tissue or tissue homogenates, frozen or paraffin sections of tissue or combinations thereof. In some aspects, the biological sample comprises, or alternatively consisting essentially of, or yet further consisting of, at least one of a tumor cell, a normal cell adjacent to a tumor, a normal cell corresponding to the tumor tissue type, a blood cell, a peripheral blood lymphocyte, or combinations thereof. In some aspects, the biological sample is an original sample recently isolated from the patient, a fixed tissue, a frozen tissue, a resection tissue, or a microdissected tissue. In some aspects, the biological samples are processed, such as by sectioning of tissues, fractionation, purification, nucleic acid isolation, or cellular organelle separation.

In some embodiments, nucleic acid (DNA or RNA) is isolated from the sample according to any methods known to those of skill in the art. In some aspects, genomic DNA is isolated from the biological sample. In some aspects, RNA is isolated from the biological sample. In some aspects, cDNA is generated from mRNA in the sample. In some embodiments, the nucleic acid is not isolated from the biological sample (e.g., the polymorphism is detected directly from the biological sample).

Detection of Gene Expression

In some aspects, gene expression can be accomplished by hybridization or other methods known in the art, e.g., PCR and similar methods, in some aspects, after isolation of a suitable nucleic acid sample. In some aspects, the gene sequences can be amplified directly from a genomic DNA preparation from the biological sample using PCR, and the sequence composition is determined by sequencing the amplified product (i.e., amplicon). Alternatively, the PCR product can be analyzed following digestion with a restriction enzyme, a method known as PCR-RFLP.

In another embodiment of the disclosure, several nucleic acid probes capable of hybridizing specifically to the nucleic acid containing the gene are attached to a solid phase support, e.g., a "chip" or "microarray." Such gene chips or microarrays can be used to detect genes or gene expression by a number of techniques known to one of skill in the art. In one technique, oligonucleotides are arrayed on a gene chip for determining the DNA sequence by the sequencing by hybridization approach. The probes of the disclosure also can be used for fluorescent detection of a genetic sequence. A probe also can be affixed to an electrode surface for the electrochemical detection of nucleic acid sequences.

In one aspect, "gene chips" or "microarrays" containing probes or primers for the gene of interest are provided alone or in combination with other probes and/or primers. A suitable sample is obtained from the patient extraction of genomic DNA, RNA, or any combination thereof and amplified if necessary. The DNA or RNA sample is contacted to the gene chip or microarray panel under conditions suitable for hybridization of the gene(s) of interest to the probe(s) or primer(s) contained on the gene chip or microarray. The probes or primers can be detectably labeled thereby identifying the polymorphism in the gene(s) of interest. Alternatively, a chemical or biological reaction can be used to identify the probes or primers which hybridized with the DNA or RNA of the gene(s) of interest. The genetic profile of the patient is then determined with the aid of the aforementioned apparatus and methods.

In some aspects, whole genome sequencing, in particular with the "next generation sequencing" techniques, which employ massively parallel sequencing of DNA templates, can be used to obtain genotypes of relevant polymorphisms. Exemplary NGS sequencing platforms for the generation of nucleic acid sequence data include, but are not limited to, Illumina's sequencing by synthesis technology (e.g., Illumina MiSeq or HiSeq System), Life Technologies' Ion Torrent semiconductor sequencing technology (e.g., Ion Torrent PGM or Proton system), the Roche (454 Life Sciences) GS series and Qiagen (Intelligent BioSystems) Gene Reader sequencing platforms.

In some aspects, nucleic acid comprising, or alternatively consisting essentially of, or yet further consisting of the gene is amplified to produce an amplicon. Nucleic acids can be amplified by various methods known to the skilled artisan. Nucleic acid amplification can be linear or exponential. Amplification is generally carried out using polymerase chain reaction (PCR) technologies. Alternative or modified PCR amplification methods can also be used and include, for example, isothermal amplification methods, rolling circle methods, Hot-start PCR, real-time PCR, Allele-specific PCR, Assembly PCR or Polymerase Cycling Assembly (PCA), Asymmetric PCR, Colony PCR, Emulsion PCR, Fast PCR, Real-Time PCR, nucleic acid ligation, Gap Ligation Chain Reaction (Gap LCR), Ligation-mediated PCR, Multiplex Ligation-dependent Probe Amplification, (MLPA), Gap Extension Ligation PCR (GEXL-PCR), quantitative PCR (Q-PCR), Quantitative real-time PCR (QRT-PCR), multiplex PCR, Helicase-dependent amplification, Intersequence-specific (ISSR) PCR, Inverse PCR, Linear-After-The-Exponential-PCR (LATE-PCR), Methylation-specific PCR (MSP), Nested PCR, Overlap-extension PCR, PAN-AC assay, Reverse Transcription PCR(RT-PCR), Rapid Amplification of cDNA Ends (RACE PCR), Single molecule amplification PCR(SMA PCR), Thermal asymmetric interlaced PCR (TAIL-PCR), Touchdown PCR, long PCR, nucleic acid sequencing (including DNA sequencing and RNA sequencing), transcription, reverse transcription, duplication, DNA or RNA ligation, and other nucleic acid extension reactions known in the art. The skilled artisan will understand that other methods can be used either in place of, or together with, PCR methods, including enzymatic replication reactions developed in the future. See, e.g., Saiki, "Amplification of Genomic DNA" in *PCR Protocols*, Innis et al., eds., Academic Press, San Diego, Calif, 13-20 (1990); Wharam, et al., 29(11) *Nucleic Acids Res*, E54-E54 (2001); Hafner, et al., 30(4) *Biotechniques*, 852-6, 858, 860 passim (2001).

In some embodiments, the amplification includes a labeled primer or probe, thereby allowing detection of the amplification products corresponding to that primer or probe. In particular embodiments, the amplification can include a multiplicity of labeled primers or probes; such primers can be distinguishably labeled, allowing the simultaneous detection of multiple amplification products.

In some embodiments, the amplification products are detected by any of a number of methods such as gel electrophoresis, column chromatography, hybridization with a nucleic acid probe, or sequencing the amplicon.

Detectable labels can be used to identify the primer or probe hybridized to a genomic nucleic acid or amplicon. Detectable labels include but are not limited to fluorophores, isotopes (e.g., $^{32}P$, $^{33}P$, $^{35}S$, $^{3}H$, $^{14}C$, $^{125}I$, $^{131}I$) electron-dense reagents (e.g., gold, silver), nanoparticles, enzymes commonly used in an ELISA (e.g., horseradish peroxidase, beta-galactosidase, luciferase, alkaline phosphatase), chemiluminiscent compounds, colorimetric labels (e.g., colloidal gold), magnetic labels (e.g., Dynabeads®), biotin, digoxigenin, haptens, proteins for which antisera or monoclonal antibodies are available, ligands, hormones, oligonucleotides capable of forming a complex with the corresponding oligonucleotide complement.

In one embodiment, a primer or probe is labeled with a fluorophore that emits a detectable signal. The term "fluorophore" as used herein refers to a molecule that absorbs light at a particular wavelength (excitation frequency) and subsequently emits light of a longer wavelength (emission frequency). While a suitable reporter dye is a fluorescent dye, any reporter dye that can be attached to a detection reagent such as an oligonucleotide probe or primer is suitable for use in the methods described. Suitable fluorescent moieties include, but are not limited to, the following fluorophores working individually or in combination: 4-acetamido-4'-isothiocyanatostilbene-2,2'disulfonic acid; acridine and derivatives, e.g., acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodaminexisothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; and tetramethyl rhodamine isothiocyanate (TRITC).

In some aspects, the primer or probe is further labeled with a quencher dye such as Tamra, Dabcyl, or Black Hole Quencher®(BHQ), especially when the reagent is used as a self-quenching probe such as a TaqMan®(U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, PCR Method Appl., 4:357-362; Tyagi et al, 1996, Nature Biotechnology, 14:303-308; Nazarenko et al., 1997, Nucl. Acids Res., 25:2516-2521; U.S. Pat. Nos. 5,866,336 and 6,117,635).

In some aspects, methods for real time PCR use fluorescent primers/probes, such as the TaqMan® primers/probes (Heid, et al., Genome Res 6: 986-994, 1996), molecular beacons, and Scorpion™ primers/probes. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion®™ and TaqMan® technologies are based on the principle of fluorescence quenching and involve a donor fluorophore and a quenching moiety. The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety. The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Forster or fluorescence resonance energy transfer ("FRET"). Quenching by FRET is generally used in TaqMan® primers/probes while proximal quenching is used in molecular beacon and Scorpion™ type primers/probes.

The detectable label can be incorporated into, associated with or conjugated to a nucleic acid primer or probe. Labels can be attached by spacer arms of various lengths to reduce potential steric hindrance or impact on other useful or desired properties. See, e.g., Mansfield, Mol. Cell. Probes (1995), 9:145-156.

Detectable labels can be incorporated into nucleic acid probes by covalent or non-covalent means, e.g., by transcription, such as by random-primer labeling using Klenow polymerase, or nick translation, or, amplification, or equivalent as is known in the art. For example, a nucleotide base is conjugated to a detectable moiety, such as a fluorescent dye, e.g., Cy3™ or Cy5™ and then incorporated into nucleic acid probes during nucleic acid synthesis or amplification. Nucleic acid probes can thereby be labeled when synthesized using Cy3™- or Cy5™-dCTP conjugates mixed with unlabeled dCTP.

Nucleic acid probes can be labeled by using PCR or nick translation in the presence of labeled precursor nucleotides, for example, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides, see, e.g., Henegariu et al., Nat. Biotechnol. (2000), 18:345-348, Nucleic acid probes can be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology can also be used to label proteins by binding to nitrogen and sulfur containing side chains of amino acids. See, e.g., U.S. Pat. Nos. 5,580,990; 5,714,327; and 5,985, 566; and European Patent No. 0539466.

Labeling with a detectable label also can include a nucleic acid attached to another biological molecule, such as a nucleic acid, e.g., an oligonucleotide, or a nucleic acid in the form of a stem-loop structure as a "molecular beacon" or an "aptamer beacon". Molecular beacons as detectable moieties are described; for example, Sokol (*Proc. Natl. Acad. Sci. USA* (1998), 95:11538-11543) synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (Biochemistry (2001), 40:9387-9395), describing a molecular beacon consist of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi, Anal. Biochem. (2001), 294:126-131; Poddar, *Mol. Cell. Probes* (2001), 15:161-167; Kaboev, *Nucleic Acids Res.* (2000), 28:E94. Aptamer beacons can adopt two or more conformations, one of which allows ligand binding. A fluorescence-quenching pair is used to report changes in conformation induced by ligand binding. See also, e.g., Yamamoto et al., *Genes Cells* (2000), 5:389-396; Smirnov et al., *Biochemistry* (2000), 39:1462-1468.

The nucleic acid primer or probe can be indirectly detectably labeled via a peptide. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). A label can also be attached via a second peptide that interacts with the first peptide (e.g., S—S association).

As readily recognized by one of skill in the art, detection of the complex containing the nucleic acid from a sample hybridized to a labeled probe can be achieved through use of a labeled antibody against the label of the probe. In one example, the probe is labeled with digoxigenin and is detected with a fluorescent labeled anti-digoxigenin antibody. In another example, the probe is labeled with FITC, and detected with fluorescent labeled anti-FITC antibody. These antibodies are readily available commercially. In another example, the probe is labeled with FITC, and detected with anti-FITC antibody primary antibody and a labeled anti-anti FITC secondary antibody.

Nucleic acids can be amplified prior to detection or can be detected directly during an amplification step (i.e., "real-time" methods, such as in TaqMan® and Scorpion™ methods). In some embodiments, the target sequence is amplified using a labeled primer such that the resulting amplicon is detectably labeled. In some embodiments, the primer is fluorescently labeled. In some embodiments, the target sequence is amplified and the resulting amplicon is detected by electrophoresis.

With regard to the exemplary primers and probes, those skilled in the art will readily recognize that nucleic acid molecules can be double-stranded molecules and that reference to a particular site on one strand refers, as well, to the corresponding site on a complementary strand. In defining a variant position, allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference can be made to either strand in order to refer to a particular variant position, allele, or nucleotide sequence. Probes and primers, can be designed to hybridize to either strand and detection methods disclosed herein can generally target either strand.

In some embodiments, the primers and probes comprise additional nucleotides corresponding to sequences of universal primers (e.g., T7, M13, SP6, T3) which add the additional sequence to the amplicon during amplification to permit further amplification and/or prime the amplicon for sequencing.

As noted above, the disclosure further provides methods of treating a patient selected by any method of the above embodiments, or identified as likely to experience a more favorable clinical outcome by any of the above methods, following the therapy. In some embodiments, the methods entail administering to the patients such a therapy. The therapy can be any one of the group of: a first line, second line, third line, a fourth line, or a fifth line therapy.

EXAMPLES

The following examples are intended to illustrate but not limit the disclosure.

Briefly, epithelial tumor cell lines were established from lung, breast, and prostate, all of which sorting into weakly/strong adherent groups using the technology as disclosed herein and those weakly adherent cells were more migratory. In addition, unsorted cells when injected into mice formed tumors, and the cells that disseminated from the tumor were more weakly adherent. Further, when pre-sorted by the device, weakly adherent cells formed tumors that are 5× more metastatic than normal cancer cells. These three points show that the technology as disclosed herein is applicable to a wider array of tumor types, and that the cells detected with the technology are indeed the most metastatic and deadly fraction.

Example 1

Migratory Propensity of Metastatic Breast Cancer Cells as a Function of Adhesion Strength MDA-MB231 cells were cultured according to standard ATCC protocols. Initial population adhesion strength was characterized using the spinning-disk shear assay outlined in (23 and 24). The quantitative adhesion strength was determined to be the shear stress at which 50% of the cell population has detached ($\tau_{50}$). The $\tau_{50}$ value was used to calculate the rate of fluid flow through the microfluidic device. To isolate weakly adherent cells, MDA-MB231 cells were seeded onto a fibronectin-coated glass slide at a density of 8000 cells/cm$^2$. The slide was clamped to a polysulphone base plate with an inlet and outlet. Fluid that exits through the outlet is spun down, and the cells are re-suspended in MDA-MB231 growth media and plated on collagen gels (2.4 mg/mL) for migration assays. Cell migration is tracked manually using ImageJ tracking software.

Figure 1B:
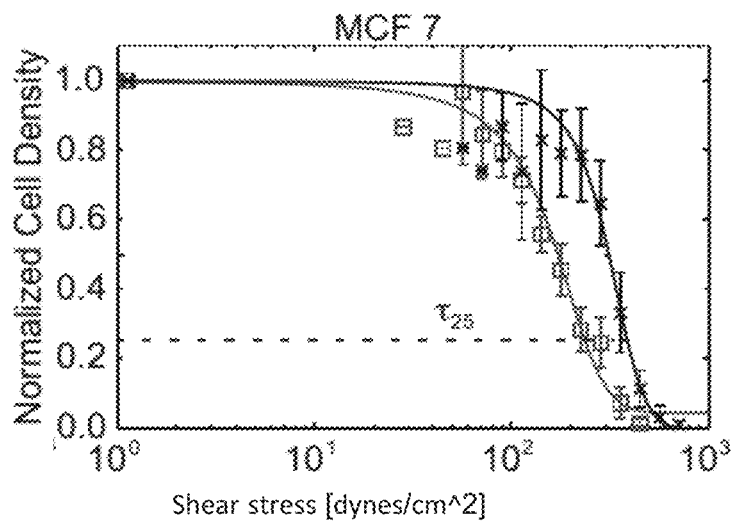
Figure 1C:
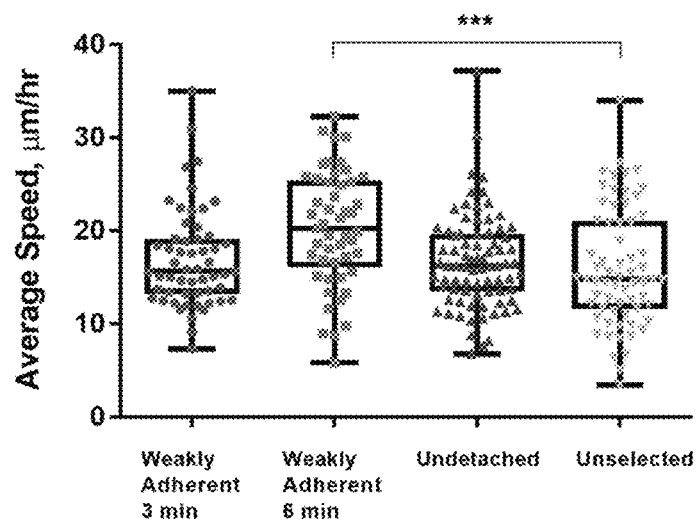

It was shown that metastatic cancer cell lines have lower adhesion strength to fibronectin than their non-metastatic counterparts when exposed to Mg$^{2+}$ and Ca$^{2+}$ concentrations akin to those present in tumor stroma. In contrast, at physiological (serum) concentrations of Mg$^{2+}$ and Ca$^{2+}$, both metastatic and non-metastatic cells have similar adhesion strengths (FIGS. 1A and 1B) (23). The spinning-disk assay was used to select for cells that withstood 45 dynes/cm$^2$ of shear stress without detachment. These strongly adherent cells were significantly less motile than the unselected cell population when migrating on collagen gels (23). To isolate the weakly adherent cells for characterization, a microfluidic chamber was designed that would expose a plate seeded with MDA-MB231 cells to a uniform shear that is controlled by the fluid flow rate through the chamber. Cells were isolated at 30 dynes/cm² after 3 minutes and 6 minutes of exposure to shear, and the total cells isolated were approximately 10-15% of the starting seeded population. The migration of these isolated cell fractions on collagen gels was compared to that of the cells remaining on the plate as well as an unselected control cell population. It was found that the weakly adherent cells exposed to 6 minutes of shear were significantly more motile than the unselected control (FIG. 1C). This indicates that the weakly adherent fraction of the metastatic cell population is likely to have the highest metastatic potential.

Example 2

Materials and Methods

Cell Culture: MDA-MB231 and MCF7 cells were cultured in DMEM, 10% Fetal Bovine Serum (FBS), and 1% antibiotic/antimycotic; MCF10A and MCF10AT cells were cultured in DMEM/F-12, 5% horse serum, 1% penicillin/streptomycin (Pen/Strep), 0.5 µg/ml Hydrocortisone, 20 ng/ml hEGF, 10 µg/ml Insulin, 100 ng/ml Cholera toxin; NCI-H1299 cells were cultured in RPMI, 10% FBS, and 1% Pen/Strep. Products were purchased from Life Technologies. All cells were obtained from ATCC (authenticated by morphology, growth curve, and isoenzyme analysis), verified *mycoplasma* free via PCR, and were not used beyond passage 10.

Parallel plate shear assay: Glass plates (Brain Research Laboratories, Waban MA) were sonicated in 70% ethanol and water. Plates were coated with fibronectin at 2 µg/cm² for 60 minutes and then blocked with 5% bovine serum albumin for 2 hours at 37° C. Plates are then seeded with cells at a density of 5000 cells/cm² and incubated overnight. Components of the parallel plate shear assay (polysulfone base plate, 38 µm thick silicone gasket (SMI), polypropylene luer fixtures (Cole Parmer), ⅛-inch inner diameter tubing (Fisher Scientific)) were assembled and the glass plate was clamped to the base plate containing the inlet and outlet. The inlet tubing was connected to a syringe pump. Shear stress, τ, was calculated using the following equation:

$$\tau = 6\rho Q/wh^2$$

where µ is viscosity of the fluid, Q is volumetric flow rate, w is the width of the chamber, and h is the height of the chamber.

Isolating weakly (WA) and strongly (SA) adherent cells: To test adhesion stability of WA and SA fractions of the population, an intermediate shear stress was firstly determined to detach roughly 40% of cells (~170 dynes/cm² 150 for MDA-MB231 cells). Phosphate buffered saline (PBS) without magnesium and calcium and with 4.5 g/L of dextrose was used to shear cells. Cells were subjected to the intermediate shear stress for 3 minutes to isolate WA cells in the flow-through, which was collected at the outlet. 0.25% Trypsin-EDTA was added to the device to isolate SA cells. Once cells detached, media was pushed through the device to neutralize the trypsin and remove the SA cells. Both populations were then seeded.

To perform the adhesion stability re-mixed population assay, WA and SA cells were isolated at day 0, cultured separately for 24 hours, re-mixed and seeded onto a plate overnight, then re-isolated at 48 hours after the initial isolation.

To isolate the weakest and strongest 2% of the MDA-MB231 cell population for migration assays, the seeded plate was subjected to a low shear stress (28 dynes/cm²) for 3 minutes to isolate WA cells in the flow through from the outlet. The shear stress was then increased to a high shear stress (510 dynes/cm²) for 2 minutes to eliminate intermediate cell fractions. The remaining steps to isolate SA cells are listed above. The weakest MCF10A and MCF10AT cells were isolated using 170 and 130 dynes/cm² of shear stress respectively; the strongest were isolated using 1275 and 595 dynes/cm² respectively.

Co-culture assay: MDA-MB231 and MCF10A cells were trypsinized and resuspended in 25 µM of CellTracker fluorescent probes (Molecular Probes, Life Technologies) in serum-free DMEM: MDA-MB231 in Green CMFDA and MCF10A in Orange CMRA. Cell-dye solutions were incubated at room temperature (RT) for 20 minutes. The cells were then centrifuged and resuspended in MDA-MB231 media. Cells were mixed 50:50 and seeded such that the final seeding density was 5000 cells/cm², then incubated overnight.

Upon isolation of WA and SA cells, both fractions were seeded, incubated overnight, then fixed the following day with 3.7% formaldehyde for 10 minutes. Cells were imaged using a Nikon Eclipse Ti-S microscope at 10× magnification with FITC and Texas Red and counted by color.

Measuring percent detachment versus metastatic capability: MDA-MB231, MCF7, MCF10A, and MCF10AT cells were subjected to 250 dynes/cm² of shear. The detached and adherent fractions were isolated as described and counted to calculate the fraction of cells detached.

Immunofluorescence staining and focal adhesion (FA) analysis: Fixed cells were incubated for 10 minutes at RT with CellMask Deep Red plasma membrane stain (1:1000, Thermo Fisher) in 1 mM $MgCl_2$ solution, followed by incubation for 1 hour at RT with blocking solution of 10% goat serum, 0.1% saponin, 1% bovine serum albumin, 0.03 M glycine in 1 mM $MgCl_2$ solution. Primary paxillin antibody (1:250; ab32084, Abcam) in blocking solution was applied overnight at 4° C. Then, a secondary Alexa Fluor 488-conjugated antibody (1:2000, Invitrogen) in blocking solution was applied for 1 hour at RT, followed by Hoechst 33342 (1:2000, Invitrogen) in DI water for 10 min at RT. The cells were subsequently mounted with Fluoromount-G (Southern Biotech). The samples were imaged with a Zeiss LSM 780 confocal microscope (Zeiss) with a 63× oil immersion objective. A custom-written ImageJ program was used to quantify cell area and FA number and size. All FA metrics were computed across the entire cell to avoid regional biases.

Traction Force Microscopy (TFM): Cell tractions were measured as described and calculated using a custom Matlab routine (27). 2% v/v of 0.2 µm diameter 580/605 FluoSpheres microspheres (Invitrogen) were added to the pre-polymer solution, comprised of 5% acrylamide, 0.06% bis-acrylamide, 1% ammonium persulfate (Fisher), and 0.1% v/v of N,N,N',N'-Tetramethylethylenediamine (VWR International). Gels were prepared in 12 well glass bottom plates (Cellvis), which were precleaned in a UV/Ozone cleaner (ProCleaner™ Plus, Bioforce Nanosciences) and methacrylated to ensure binding of the gel. Collagen was bound to the surface by adding 0.2 mg/ml sulfo-SANPAH and activating with UV light (wavelength 350 nm) for 10 minutes followed by incubation with 0.15 mg/ml type I collagen. Isolated cells were seeded at ~15,000 cells/cm$^2$ on the gels and allowed to adhere for 3 hrs. Brightfield images were taken of each cell prior to obtaining microsphere displacements at 60×. Bead reference positions were then re-obtained after removing the cells with a 10% v/v Triton X solution for 10 minutes. Strain energy was determined from the traction stress map and normalized to cell area.

Western blotting: Weakly and strongly adherent cells were isolated and plated in fibronectin-coated 12-well plates for 3 hours. Cells were lysed with mRIPA supplemented with phosphatase and protease inhibitors as described (28). Protein concentration was measured using a BCA assay. 5 μg protein was mixed with 50 mM DTT, Loading Buffer, and mRIPA, heated at 95° C. for 5 minutes, and loaded into a Bolt 4-12% Bis-Tris Plus gel (Invitrogen) and then run with MES running buffer for 30 min at 200 V. Protein was transferred to a nitrocellulose membrane using an iBlot Cell Transfer Stack (Invitrogen). Membrane was blocked with 5% SeaBlock for 1 hour at RT then incubated overnight at 4° C. with anti-paxillin (Abcam, ab32084), anti-pFAK (Y397) (Abcam, ab81298), anti-FAK (Origene, TA506161), anti-Actin (Abcam, ab8226), and anti-GAPDH (Abcam, ab8245). The membrane was then incubated for 2 hours at RT with AlexaFluor 680 donkey anti-mouse (Life Technologies, A32788) and AlexaFluor 790 donkey anti-rabbit (Life Technologies, A11374) antibodies. The membrane was imaged using a Li-Cor Odyssey CLx and analyzed using Image Studio Lite (Li-Cor).

2D migration assays on collagen gels: 2.4 mg/mL Type I collagen gels were prepared by mixing collagen (Corning) with PBS, DI water, and 1 M NaOH and adjusted to pH 7.0. Gels were added to a 12-well plate and cured at 37° C. for 30 minutes. The weakest and strongest 2% of the cell population were seeded onto the gels and incubated overnight. The cells were imaged with a Nikon Eclipse Ti-S microscope equipped with a temperature- and $CO_2$-controlled stage. Cells were imaged at 10× in brightfield every 15 minutes for 24 hours. The migration data was analyzed via Fiji. The positions were normalized to the starting point and analyzed via a custom MATLAB script to compute instantaneous speed and cell displacement. Cells that divided or did not remain in the frame for 24 hours were not tracked. Cells that interacted with other cells for more than 2 hours were not tracked, as cell-cell interactions artificially slowed cell speed. For MDA-MB231 cell migration under drug treatment, cells were treated with either 0.2 μg/mL nocodazole (Cayman Chemical) or 0.5 μg/mL paclitaxel (LC Laboratories). Cells were imaged the following day for 24 hours and tracked as stated above.

2D migration assays on polyacrylamide gels of varying stiffness: Polyacrylamide gels of low and high stiffness were prepared as described in the TFM methods section, without fluorescent microbeads. The high stiffness prepolymer solution has an identical composition to the gels used for TFM, while the low stiffness prepolymer solution consists of 3% acrylamide and 0.06% bis-acrylamide with all other components identical to the high stiffness gel. Cells were isolated, seeded, and tracked as described.

Preparing spheroids of MDA-MB231 cells: The weakest and strongest 2% of the MDA-MB231 cell population and unselected cells were isolated and seeded in a 12-well plate overnight. Cells were trypsinized and resuspended in 25 μM CellTracker fluorescent probes (Molecular Probes, Life Technologies) as described above. Cells were then centrifuged and resuspended in a solution of 0.25% Methocult in culture media. 2,500 cells (either WA or SA) were added to wells in a 96-well Corning Ultra-Low Attachment Spheroid Microplate (Corning) then incubated for 48 hours.

3D migration assay in collagen gels: Collagen gels were prepared as described above. Spheroids were embedded in a collagen gel solution and added to a 24-well plate. Media was added to the top of the gel, and a time 0 image was captured at 10× magnification with brightfield to obtain initial radius. Embedded spheroids were incubated for 24 hours, after which they were fixed with 3.7% formaldehyde in solution A for 20 minutes. Spheroids were imaged with a Zeiss LSM 780 Confocal Microscope at 10× magnification with the FITC and Texas Red channel. Z-stack images were acquired at 30 μm intervals from the bottom to the top of the spheroid. Maximum intensity projection images were generated and input into a custom Python script to analyze invasive index of spheroid and maximum displacement of cells in the spheroid. Invasive index is defined as:

$$I = \frac{r_{final}}{r_{initial}}$$

where $r_{initial}$ is the radius at time t=0 hours of the spheroid and $r_{final}$ is the radius at time t=24 hours.

RNA sequencing: RNA from WA and SA cells was purified using Qiagen RNeasy Mini Kit (Qiagen, 74104). RNA quality was assessed using TapeStation (Agilent), RNA libraries were prepared using the Illumina TruSeq Stranded RNA, High Throughput Library Prep Kit and sequenced using the Illumina HiSeq 4000 system to generate 50 bp single-end reads. Data was analyzed by Rosalind (rosalind.onramp.bio), with a HyperScale architecture developed by OnRamp BioInformatics, Inc. (San Diego, CA). Reads were trimmed using cutadapt (29). Quality scores were assessed using FastQC (30). Reads were aligned to the Homo sapiens genome build hg19 using STAR (31). Individual sample reads were quantified using HTseq (32) and normalized via Relative Log Expression (RLE) using DESeq2 R library (33). Read Distribution percentages, heatmaps, and sample plots were generated as part of the QC step using RSeQC (34). DEseq2 was also used to calculate fold changes and p-values. Clustering for the differentially expressed gene heatmap was done using the Partitioning Around Medoids method with the fpc R library (35). Functional enrichment analysis of pathways, gene ontology, domain structure and other ontologies was performed using HOMER (36). Enrichment was calculated relative to a set of background genes relevant for the experiment.

Quantitative PCR: RNA from WA and SA cells was purified using Qiagen RNeasy Mini Kit and reverse transcribed using SuperScript III Reverse Transcriptase (ThermoFisher Scientific, 18080093). Quantitative PCR was performed (45 cycles, 95° C. for 15 seconds followed by 60° C. for 1 min) using a 7900HT Fast Real-Time PCR System (Thermo Scientific, 4329001) with the primers listed (Table 4), and iQ SYBR Green Supermix (Bio-Rad Laboratories, 1708880). Target genes were normalized to GAPDH and mRNA quantity was calculated based on a standard curve generated from a fibronectin plasmid.

TABLE 4 qPCR Primers (SEQ ID NOs: 1-12, respectively, in order of appearance))

| Target Gene | Forward | Reverse |
| --- | --- | --- |
| GAS2L3 | AGCCTGCAATTCAAGTATGGTT | TGGTCCGTGTCTGGGAGTC |
| DST | GATOTTAGAGCTCTGCCAGTGTGT | AGTAGOTTCTTTGGCATCATTGAA |
| KIF14 | TGGTGAAATGGCCTGTACAAGT | GGCAACCAGTTAACCOTTTGAG |
| SYNE2 | ACCACCCTATGGAAAGCTACT | CATCTCCCATCTGTCGAAGGC |
| GAPDH | TCGACAGTCAGCCGOATCTTC | ACCAAATCCGTTGACTCCGAC |
| Fibronectin (Standard) | AGGCTTGAACCAACCTACGGA | GCCTAAGCACTGGCACAACAG |

TCGA Dataset Analysis: The TCGA raw data were downloaded from NIH NCI GDC Data portal directly. Corresponding clinical metadata were obtained from a previous publication (37). Only the breast cancer (BRCA) patients with reported negative histological staining for the three markers (Her2, ER, PR) and American Joint Committee on Cancer (AJCC) pathology stages below stage IV were included in the analysis cohort. Patient data were analyzed to determine correlation between gene expression corresponding to weakly adherent or strongly adherent phenotypes and 5-year survival. Patient data were analyzed by normalizing patient gene expression to z-transformed scores with respect to the differentially expressed genes between the weakly adherent and strongly adherent sub-populations. The z-scores were then summed for every patient, and z-score sum-based quantiles were mapped to Strongly Adherent (SA) and Weakly Adherent (WA) categories based on mean gene expression levels. The Kaplan-Meier method was used to create survival plots comparing the 20% of individuals with the lowest score to the 20% with the highest score. The log-rank test was used to determine significance of survival differences between groups. Survival analyses use the Lifelines python library (lifelines.readthedocs.io/en/latest/). Relevant scripts for the analysis of TCGA data are available at: github.com/kec162ucsd/Tumor-Heterogeneity-Adhesion-Strength/.

Statistics: 2D migration assays, 3D spheroid migration assays, and focal adhesion disassembly plots were analyzed using a one-way ANOVA with Tukey test for multiple comparisons. Adhesion stability re-mixed population assay was analyzed with a two-way ANOVA, with Sidak multiple comparison test. All other comparisons were performed using two-tailed unpaired t-test unless otherwise indicated. For all analyses, $*p<0.05$, $p<0.01$, $*p<0.001$, $****p<0.0001$. Data expressed as box-and-whisker plots show all points with the whisker ends corresponding to minimum and maximum values. All other values are expressed as mean+/−standard deviation. Statistical analyses were performed using Prism software.

Data Availability: Data generated in this study was deposited to NCBI under GEO GSE135515 on Aug. 8, 2019. No restrictions on data availability were imposed.

Figure 7A:
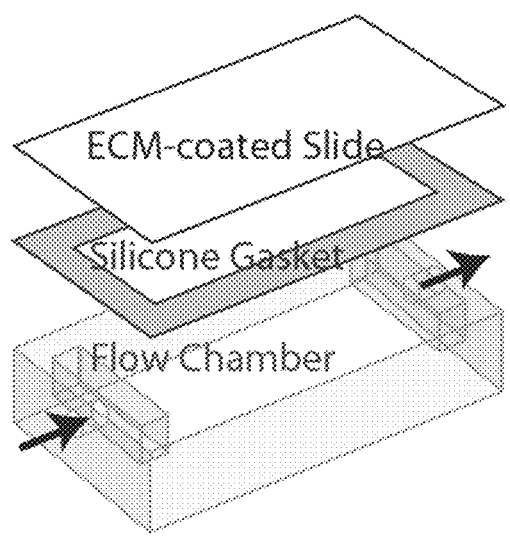
Figure 7C:
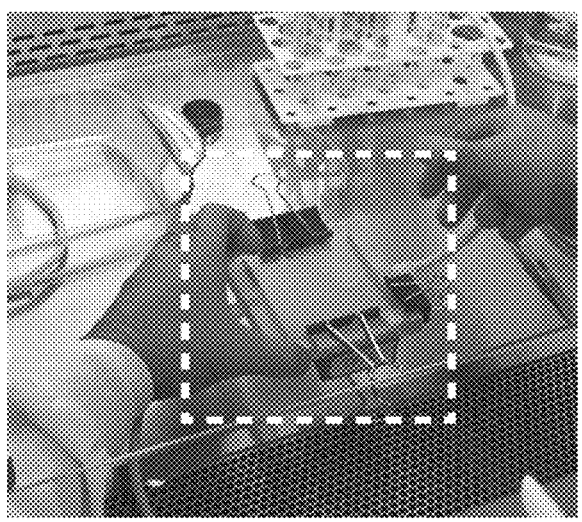

Strongly and weakly adherent phenotypes are maintained post sort. Fabricated is a parallel plate flow chamber that exposes cells to discrete, uniform shear stresses in order to isolate fractions of cells based on adhesion strength and study those cells within a heterogeneous population (FIGS. 7A-7C). To ensure that the application of shear did not change the adhesive heterogeneity of the population, weakly and strongly adherent fractions of MDA-MB231 cells were isolated from a parental cell population by exposing the cell to a shear of 170 dynes/cm$^2$ and stratifying the populations depending on whether they were found in the flow-through or still attached to the device. After sorting, cells were cultured separately, re-mixed, seeded into the device, and subsequently sheared. No significant changes were found between the percent of weakly and strongly adherent cells when tracking cells between days 0 and 2 (FIG. 2A), indicating that the parallel plate shear device assesses, but does not alter, the inherent adhesion heterogeneity of the population.

In order to determine if the adhesion phenotype is stably maintained post isolation, both fractions were isolated from MDA-MB231 cells, cultured separately in either normal or reduced cation media, and then isolated again on the separated fractions. It was found that strongly adherent cells maintained their adherent phenotype 14 days post-isolation, regardless of culture conditions. Weakly adherent cells did not maintain their adhesion phenotype in normal culture media as cells reverted back to their distribution in the parental population; if the selection pressure of low stromal-like cation concentrations was maintained post-isolation, weakly adherent cells were enriched to >70% of the population 6 days post-isolation (FIG. 2B).

Parallel plate flow chamber can distinguish between weakly adherent and strongly adherent cell lines. To test the ability of the flow chamber to select for cells known to have a weaker adhesion strength and as a result their higher metastatic potential, MDA-MB231 (metastatic breast cancer line) and MCF10A (non-malignant breast cell line) cells were seeded in a 50:50 mixture and exposed to a shear stress that should detach the MDA-MB231 cells but not the MCF10A cells (170 dynes/cm$^2$ based on population adhesion assays (23)). The fraction of cells that detached contained 41.7% of the total number of MDA-MB231 cells, while only 0.7% of the total number of MCF10A cells were present in the detached fraction (FIG. 2C), consistent with 10-fold higher adhesion strength of MCF10A vs. MDA-MB231 cells in the absence of cations (23) and suggesting that this assay could distinguish metastatic cells from non-cancerous cells.

In order to link quantitative adhesiveness to metastatic potential, four cell lines of varying metastatic potential were exposed (high metastatic capability: MDA-MB231; low metastatic capability: MCF7 and MCF10A; and H-Ras transformed: MCF10AT, which give rise to invasive carcinomas in vivo (38)) were exposed to 250 dynes/cm$^2$ of shear stress and counted the fraction of detached cells. Consistent with other experimental results shown above, cells with greater tumorigenic and/or metastatic potential had significantly greater detachment at the same shear stress in comparison to cells with lower tumorigenic and/or metastatic potential (FIG. 2D).

Figure 9A:
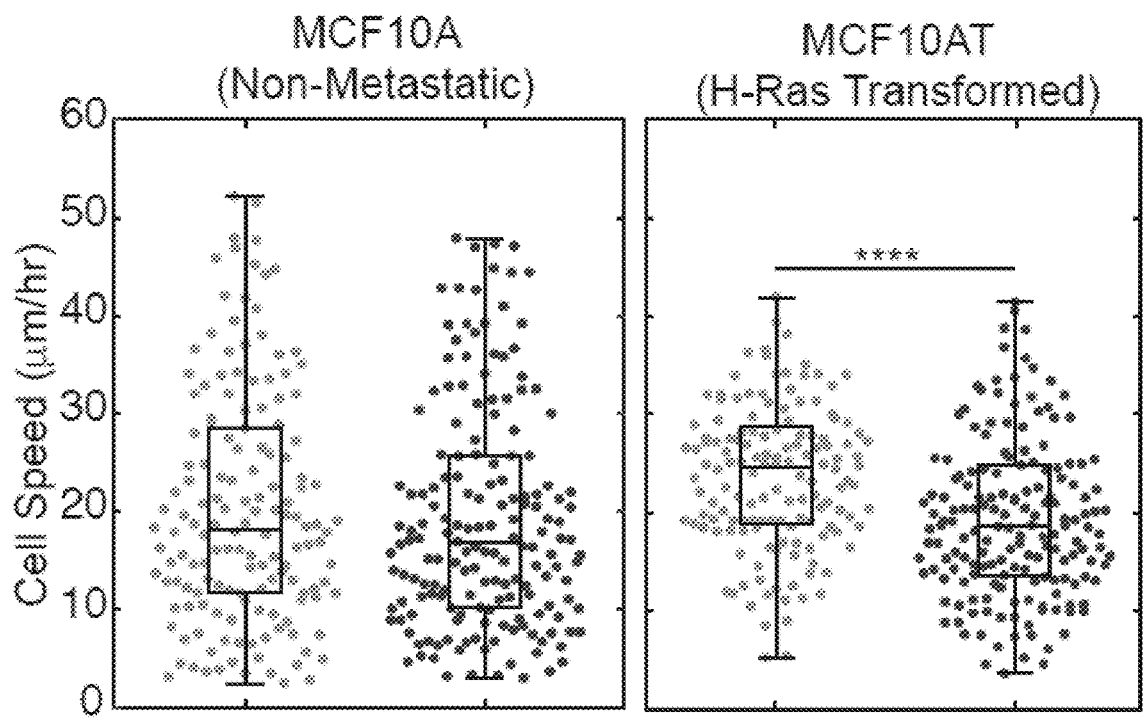
FIGS. 9A and 9B are graphical diagrams showing migratory differences in isogenic MCF10A and MCF10AT cells.
Figure 9B:
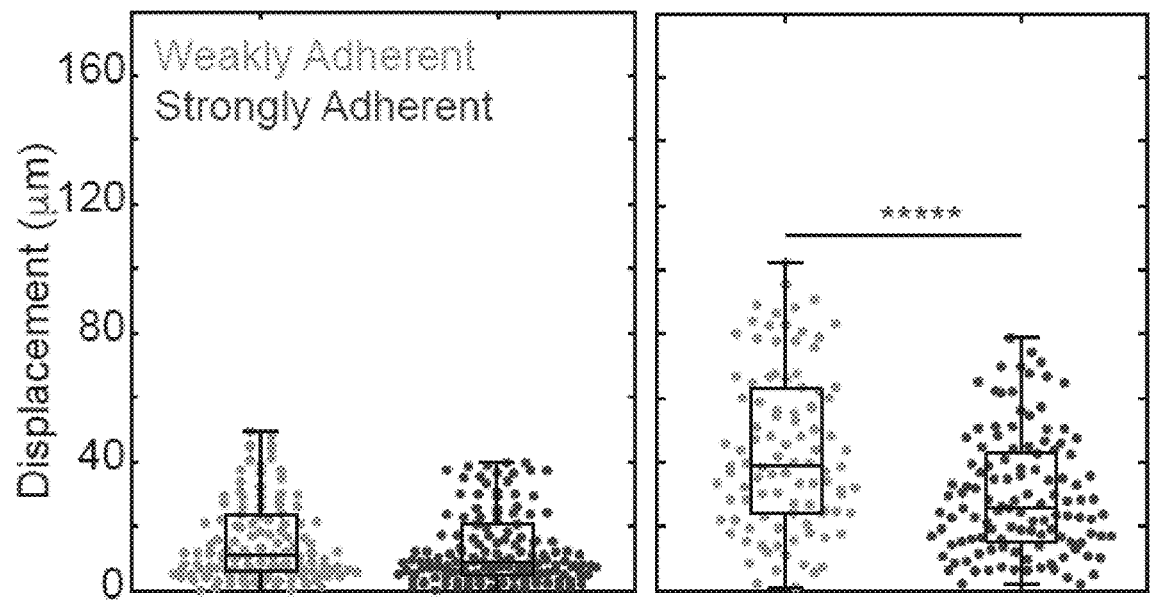

Weakly adherent cells display greater migratory propensity than strongly adherent cells. To assess migration differences in adhesion sorted populations, the ~2% most weakly and most strongly adherent cells of the MDA-MB231 population were isolated using 28 dynes/cm$^2$ and 510 dynes/cm$^2$, respectively and seeded them onto type-I collagen gels. Over 24 hours post-plating, it was found that weakly adherent cells displayed significantly higher average speed than the strongly adherent or unselected (non-sheared) cells (FIG. 3A). Weakly adherent cells also displayed increased total cell displacement than the strongly adherent or unselected cells (FIGS. 3B and 8). Since the adhesion phenotype appears stable, it was further investigated if migratory differences were stable. Weakly and strongly adherent cells along with unselected population were imaged post selection, and then re-imaged 2 days later. No significant differences for any population were observed post selection or later while the weakly adherent fraction maintained its increased migratory propensity (FIG. 3C). The two populations did not exhibit differential proliferation during migration assessments (FIG. 3D), suggesting that higher migration speeds for weakly adherent cells were not the result of proliferation differences. In addition to sorting a metastatic population, sorting fidelity was further demonstrated by directly comparing the ~2% most weakly and strongly adherent of MCF10A and isogenic H-Ras transformed MCF10AT cells. Post-sort on collagen gels, it was observed that the weakly adherent fraction of MCF10AT cells had increased migration speed and displacement relative to its strongly adherent counterpart, while MCF10A cell fractions did not show differences (FIG. 9). These data suggest that heterogeneity in migratory phenotype as a result of selection by adhesion strength is only present in more aggressive cells with increased tumorigenic capability.

Migration can often be affected by matrix properties, and so it was sought to determine if migration differences are intrinsic and therefore persist regardless of environmental changes that could reduce substrate adhesion. Weakly and strongly adherent MDA412 MB231 cells were plated on polyacrylamide gels of low (300 Pa) and high stiffness (1.8 413 kPa) and migration observed for 24 hours. Weakly adherent cells were more migratory than the strongly adherent cells independent of substrate stiffness. However, average speed scaled with substrate stiffness gel for both cell fractions, which indicates that both fractions are mechanically sensitive (FIG. 10). These results indicate that there are cell intrinsic differences independent of environmental changes that could potentially alter substrate adhesion.

Figure 3E:
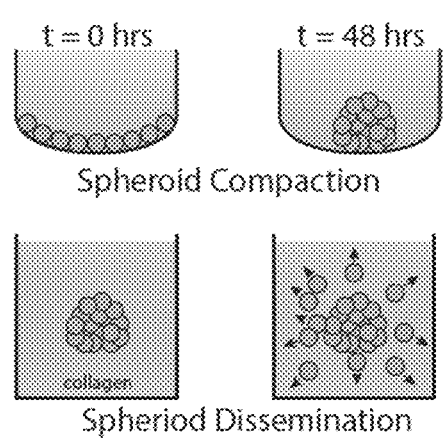
Figure 3F:
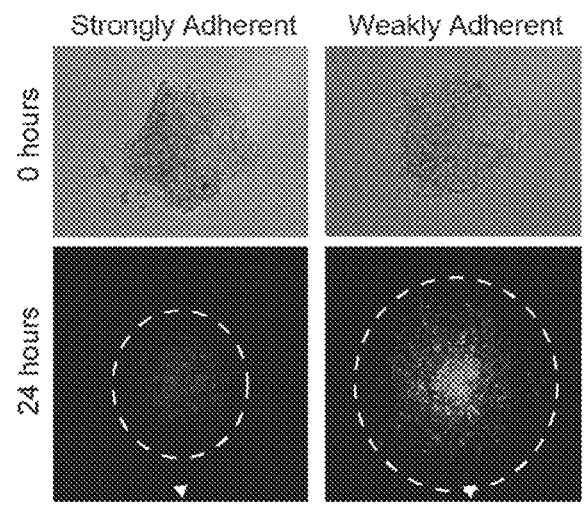
Figure 3G:
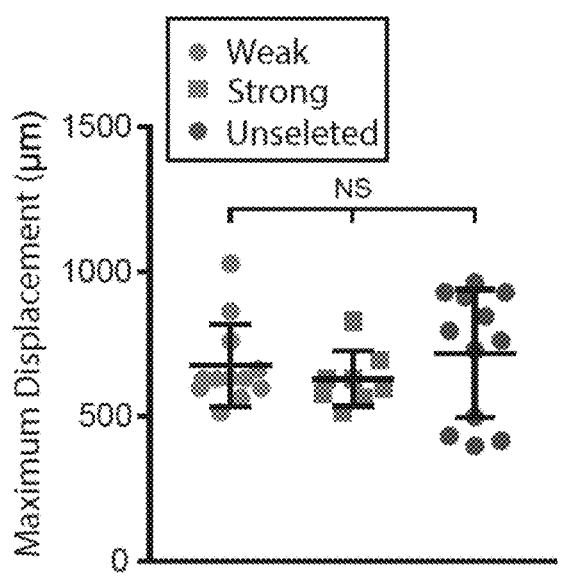
Figure 3H:
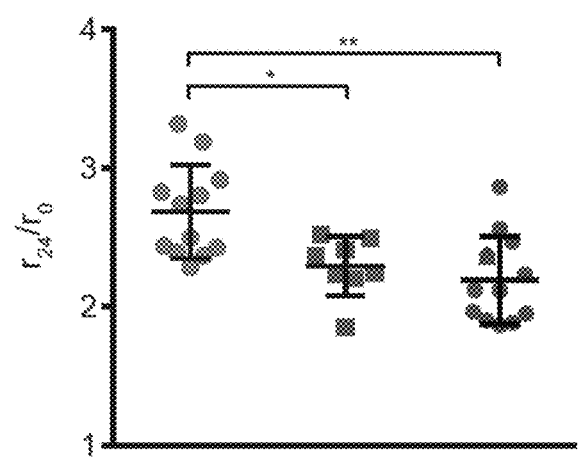

Assays thus far show behaviors in 2D rather than 3D, so the outward migration was assessed from spheroids containing weakly adherent, strongly adherent or unselected cells (FIGS. 3E and 3F). There was no significant difference in maximum cell displacement (FIG. 3G), but the leading edge of weakly adherent cells, i.e., the distance at which the signal is higher than background (FIG. 11), migrated further than strongly adherent and unselected cells, indicated by the significantly higher ratio of final radius to initial radius (FIGS. 3F and 3H). Consistent with 2D migration, these 3D spheroid data bolster the concept that the fraction of tumor cells with the weakest adhesion most represents those with the highest metastatic potential.

Figure 12A:
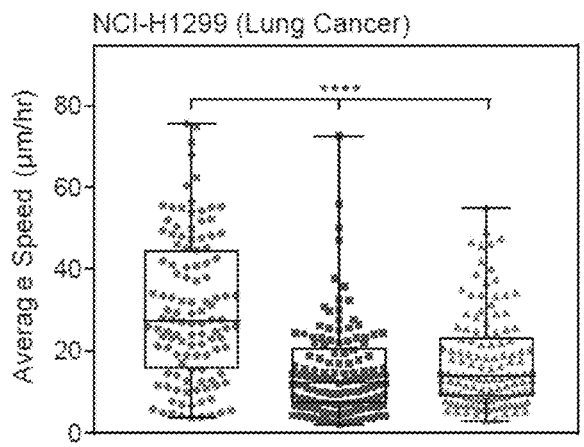
FIGS. 12A and 12B are a series of graphical diagrams showing other epithelial cells populations exhibit migration differences post-sort.
Figure 12B:
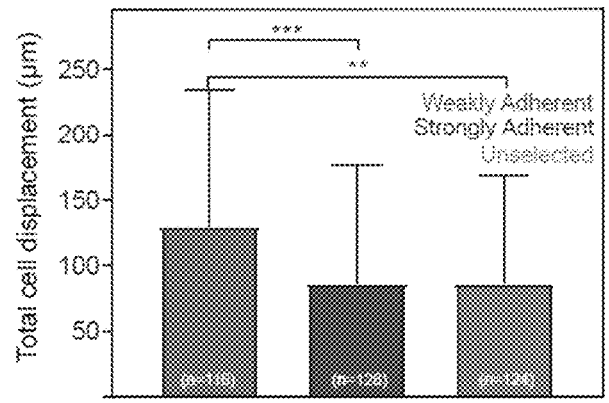

All the cells examined thus far are mammary epithelial, so it was next explored whether cells from other epithelial tumors would exhibit the same cation dependent adhesion sorting and migration phenotype. Weakly and strongly adherent NCI-H1299 metastatic lung cancer cells were isolated and their migration analyzed. As with the metastatic mammary tumor line, weakly adherent metastatic lung cancer cells were more migratory than their strongly adherent counterparts (FIG. 12), suggesting that this behavior may be universal across epithelial tumors.

Figure 4A:
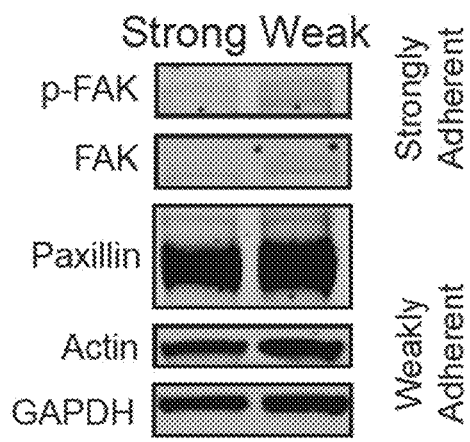
FIGS. 4A-4F are graphical and pictorial diagrams showing adherent phenotypes within a cancer line result from intrinsic adhesion stability and contractility differences.
Figure 4B:
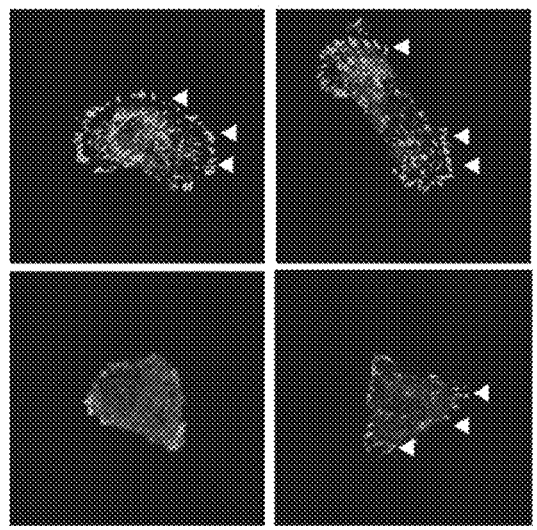
Figure 4C:
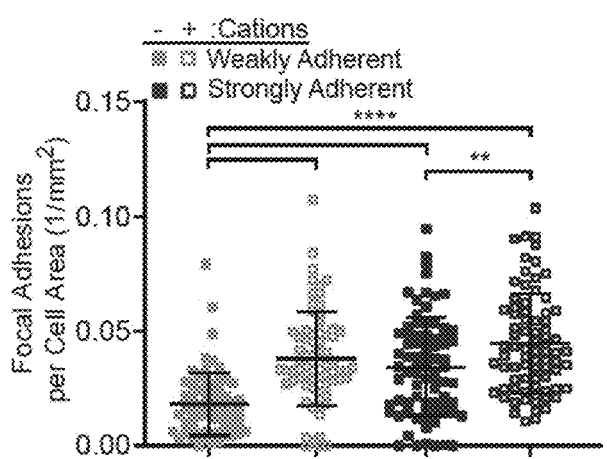
Figure 4D:
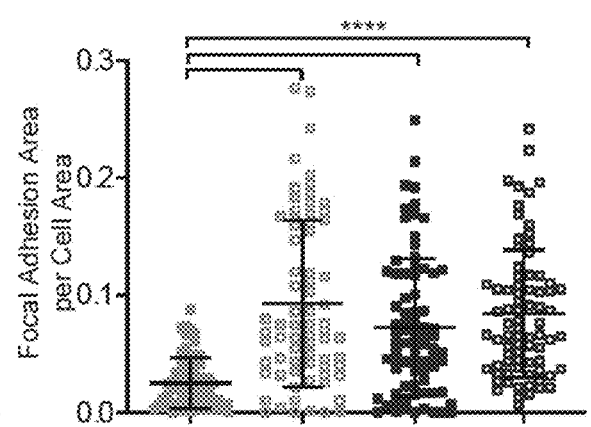
Figure 4E:
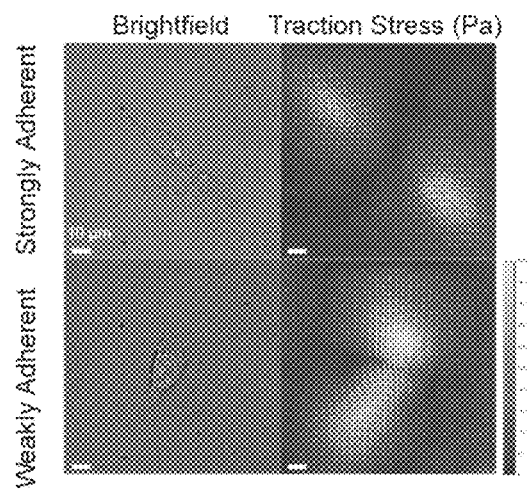
Figure 4F:
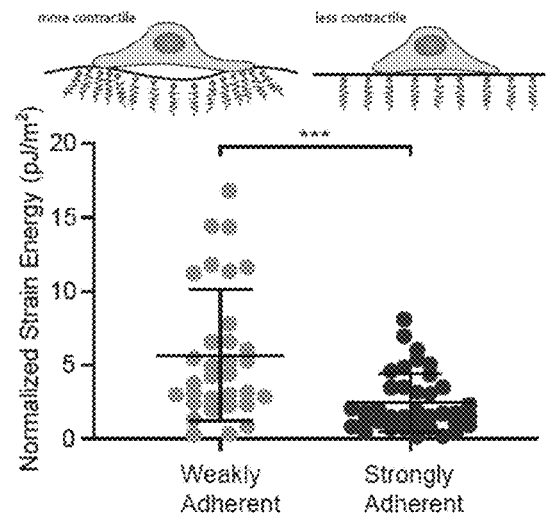
Figure 13A:
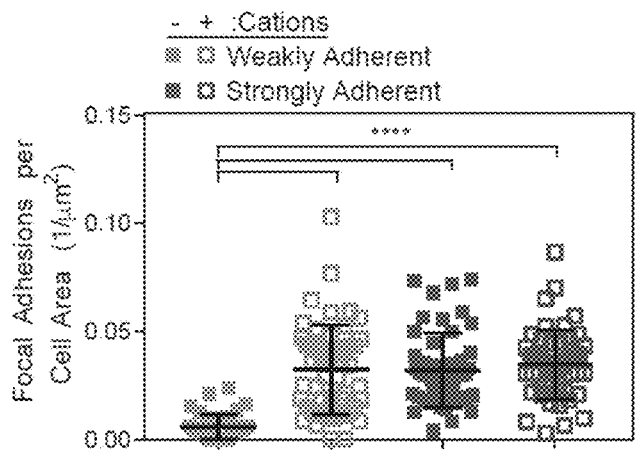
FIGS. 13A and 13B are graphical diagrams showing focal adhesion disassembly in stromal cation conditions.
Figure 13B:
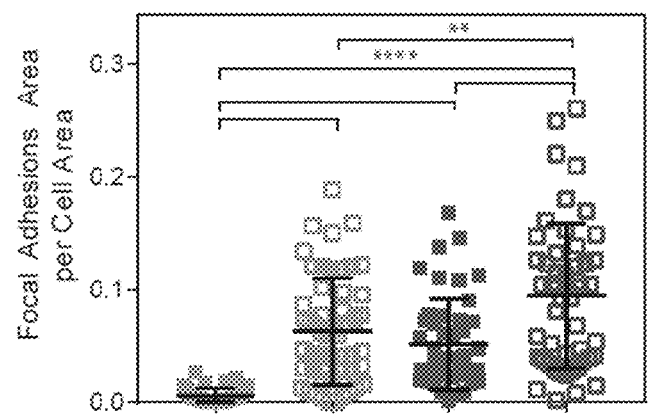

Weakly adherent cells have more labile focal adhesions and are more contractile. Migratory differences between weakly and strongly adherent cells did not result from expression differences in focal adhesion proteins, e.g., pFAK, FAK, paxillin, or actin (FIG. 4A). However, it was previously found that metastatic cells preferentially disassemble their focal adhesions relative to non-metastatic cells when exposed to low cation conditions (23). It was further found as shown in the Examples that the strongly adherent subpopulation of MDA-MB231 cells did not fully disassemble focal adhesions after removal of cations. Conversely, weakly adherent cells disassembled their focal adhesions in the absence of cations on fibronectin (FIGS. 4B-4D) or on type I collagen coated substrates (FIG. 13). These data suggest that weak adhesion could be driven by differential sensitivity to cations and could therefore enhance migration. Similarly, cancer cells that exhibit increased contractility are also more migratory than their less contractile counterparts (39, 40). To ascertain if adhesive state is coupled with contractility differences, traction force microscopy was performed on cells post-sort. Weakly adherent cells were significantly more contractile than their strongly adherent counterparts (FIGS. 4E and 4F), suggesting that weakly adherent cells represent a more aggressive fraction of the population.

Figure 14:
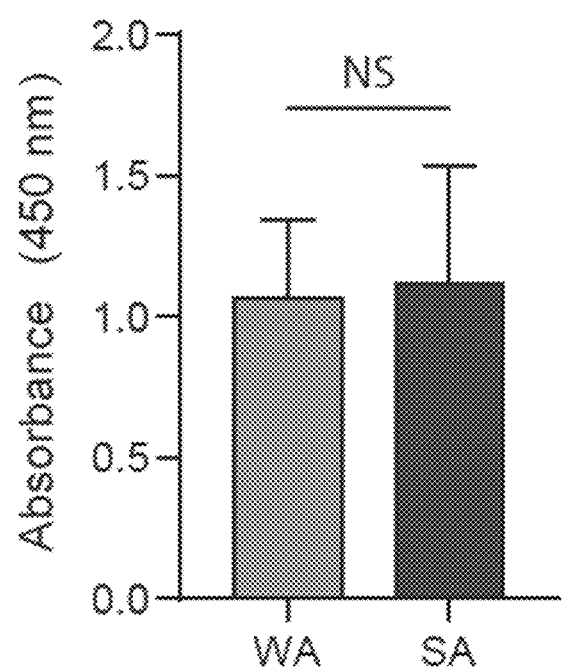
FIG. 14 is a graphical diagram showing that proliferation of post-sort cells is not different. BrdU absorbance is plotted for cells post sort.

Intrinsic transcriptional variation in microtubule proteins contributes to increased migration of weakly adherent cells. Given that populations sorted at the less restrictive 170 dynes/cm$^2$ still remain stable with over 1-2 weeks in culture, and cells sorted at the more restrictive 28 dynes/cm$^2$ show cell intrinsic migration differences independent of environmental changes that are stable for days in culture, it was next interrogated transcriptional differences underlying weakly and strongly adherent phenotypes sorted at 28 dynes/cm$^2$. Stability appears in part because individual populations do not out compete each other, i.e., cell proliferation rates appear similar (FIG. 14). With stable sorting and expansion, differences were assessed through post-sort RNA sequencing. Analyses revealed 500 differentially expressed genes between the sub-populations (FIG. 5A); replicates clustered by sub-population when comparing differentially expressed genes (FIG. 5B). Analysis of genes upregulated in weakly adherent cells demonstrated significant enrichment of gene ontology terms involved in microtubule and cytoskeletal organization and binding (FIG. 5C). Genes in these categories with the most significant expression differences are involved in cytoskeletal components, specifically microtubule-associated proteins. For example, GAS2L3 has been implicated in linking microtubules and actin and results in increased focal adhesion turnover and migration; SYNE2 is also essential for nuclear-cytoskeletal mechano-transduction in invasion and cell contraction (41-43). Components linking the cytoskeleton to the nuclear or plasma membranes were also implicated, e.g., AKAP9, which regulates microtubule movement and is highly expressed in highly metastatic cells (44, 45) (FIG. 5D). There was also significant enrichment in the expression of motor proteins, specifically those involved in vesicular transport along microtubules (KIF14, DYNC1H1) as well as in cytoskeletal contraction (MYO9A) (FIGS. 5C and 5D). KIF14, in particular, is a potent oncogene that is highly expressed in several cancers, particularly breast cancer, and is linked to improved invasiveness and dynamically changing focal adhesions (46, 47). Changes detected through RNA sequencing were validated by qPCR, which confirmed increased expression in weakly adherent cells (FIG. 5E).

Figure 5F:
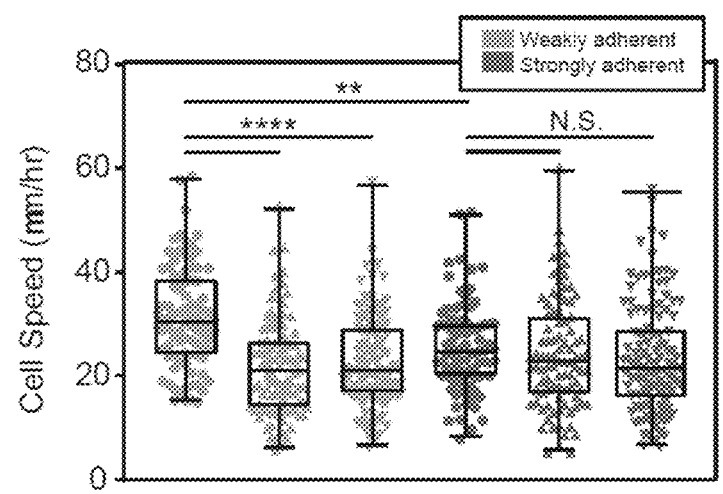

To functionally confirm a link between the upregulated microtubule components in the weakly adherent cells and their subsequent increased migration, both weakly and strongly adherent cells were exposed to either nocodazole or paclitaxel to dissemble or cap microtubules, respectively. When tracking migration, untreated weakly adherent cells had increased average speed compared to untreated strongly adherent cells. However, when treated with either microtubule-targeting drugs, the weakly adherent cells exhibited a significant decrease in average speed, while the strongly adherent cells were unaffected (FIG. 5F). These data suggest that inhibiting the microtubule cytoskeleton preferentially impacts the weakly adherent fraction and points to microtubule-affecting agents as potent therapeutic targets.

Figure 6A:
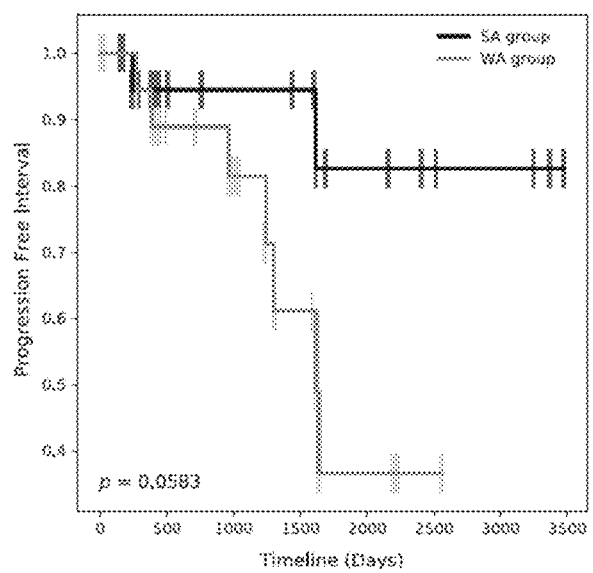
FIGS. 6A and 6B are graphical diagrams showing expression of microtubule-associated genes resembling weakly adherent fraction predicts poor outcome in breast cancer patients.
Figure 6B:
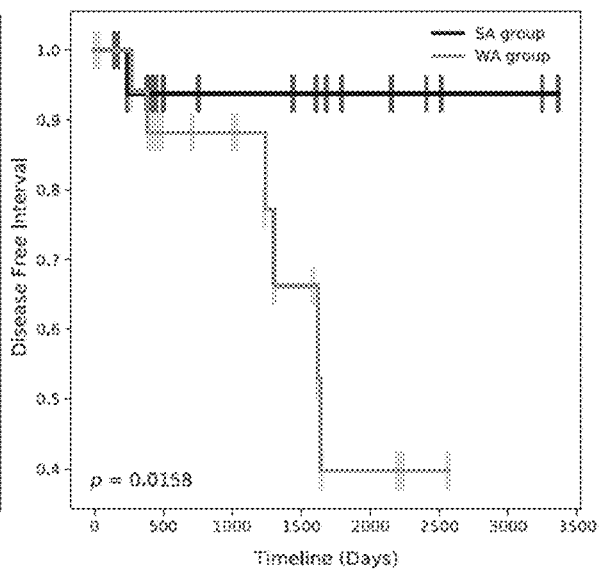

Finally, it was investigated whether differentially expressed genes linked to the highlighted microtubule, cytoskeletal, and microtubule-binding protein ontology terms played a role in human cancer progression. The list of genes was narrowed down to those linked to the highlighted GO terms in FIG. 5C, resulting in 100 genes (Table 1). Using this gene set, the Cancer Genome Atlas (TCGA) breast cancer dataset was then analyzed and restricted to triple-negative breast cancer (TNBC) patients with tumors that ranged from Stage I to III. Compared are patients that had gene expression scores that aligned with the strongly and weakly adherent cells. It was observed that patients with gene expression profiles similar to the weakly adherent cells had decreased progression-free intervals (FIG. 6A) and disease-free intervals (FIG. 6B) compared to patients with gene expression profiles similar to the strongly adherent cells. These data suggest that increased expression of genes associated with microtubule and microtubule-binding proteins, as present in the weakly adherent fraction, could define an "adhesive signature" that results in an increase in metastatic potential and promotes human breast tumor progression.

Example 3

Figures 16A, 16B, 16C:
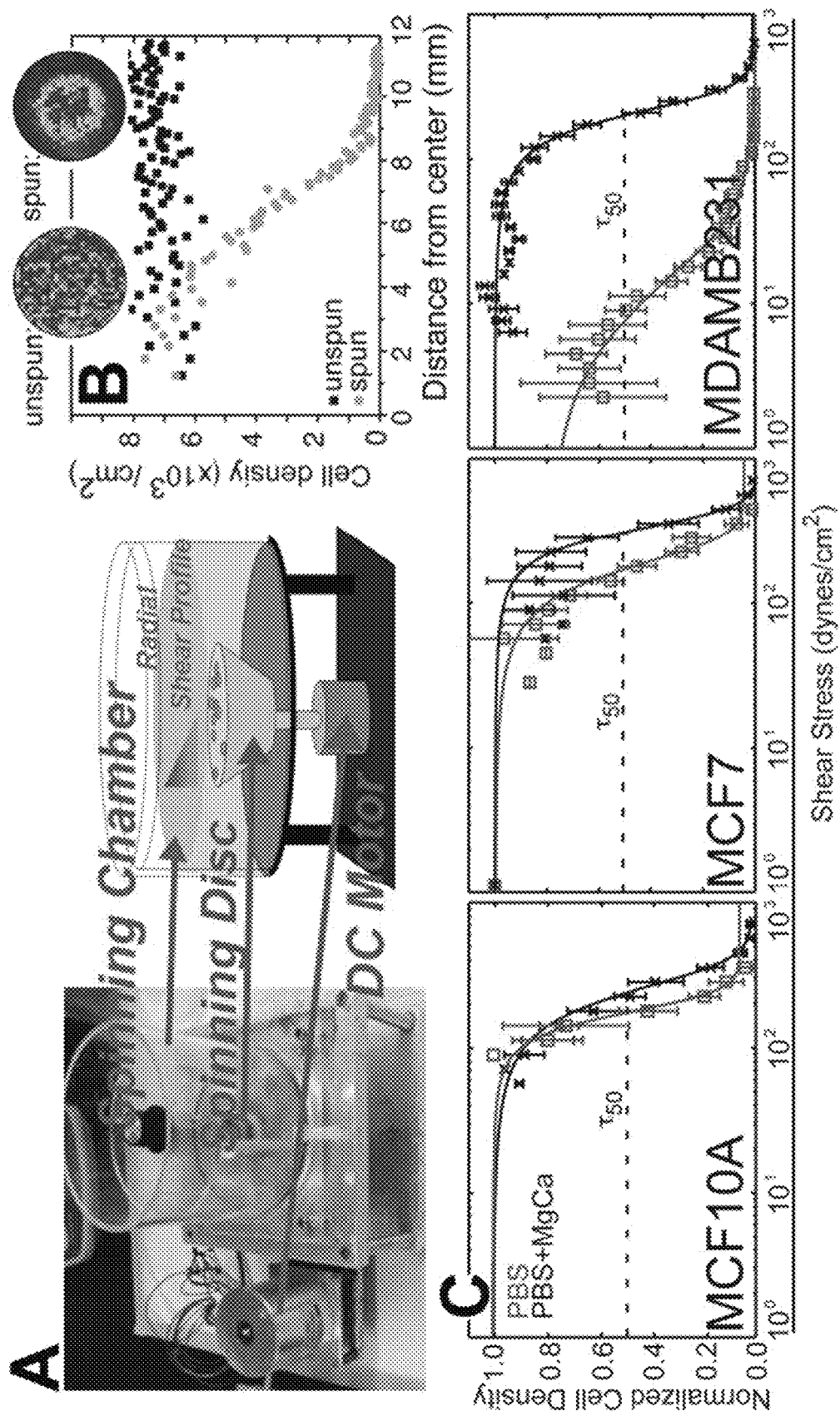
FIGS. 16A-16C demonstrate spinning disc assay.

Substantial heterogeneity also exists in tumors, which may explain why metastases can occur >10 years beyond primary tumor resection.[18] This same heterogeneity was observed within metastatic cancer cell lines.[33, 11] indicate that only human metastatic lines, e.g. FIG. 16C (MDAMB231, MDAMB468, and SUM1315 mammary, PC3 prostate, and NIH-H1299 lung cells), have weaken adhesion in stromal cation concentrations; the change, however, is not uniform.

Figures 17A, 17B, 17C:
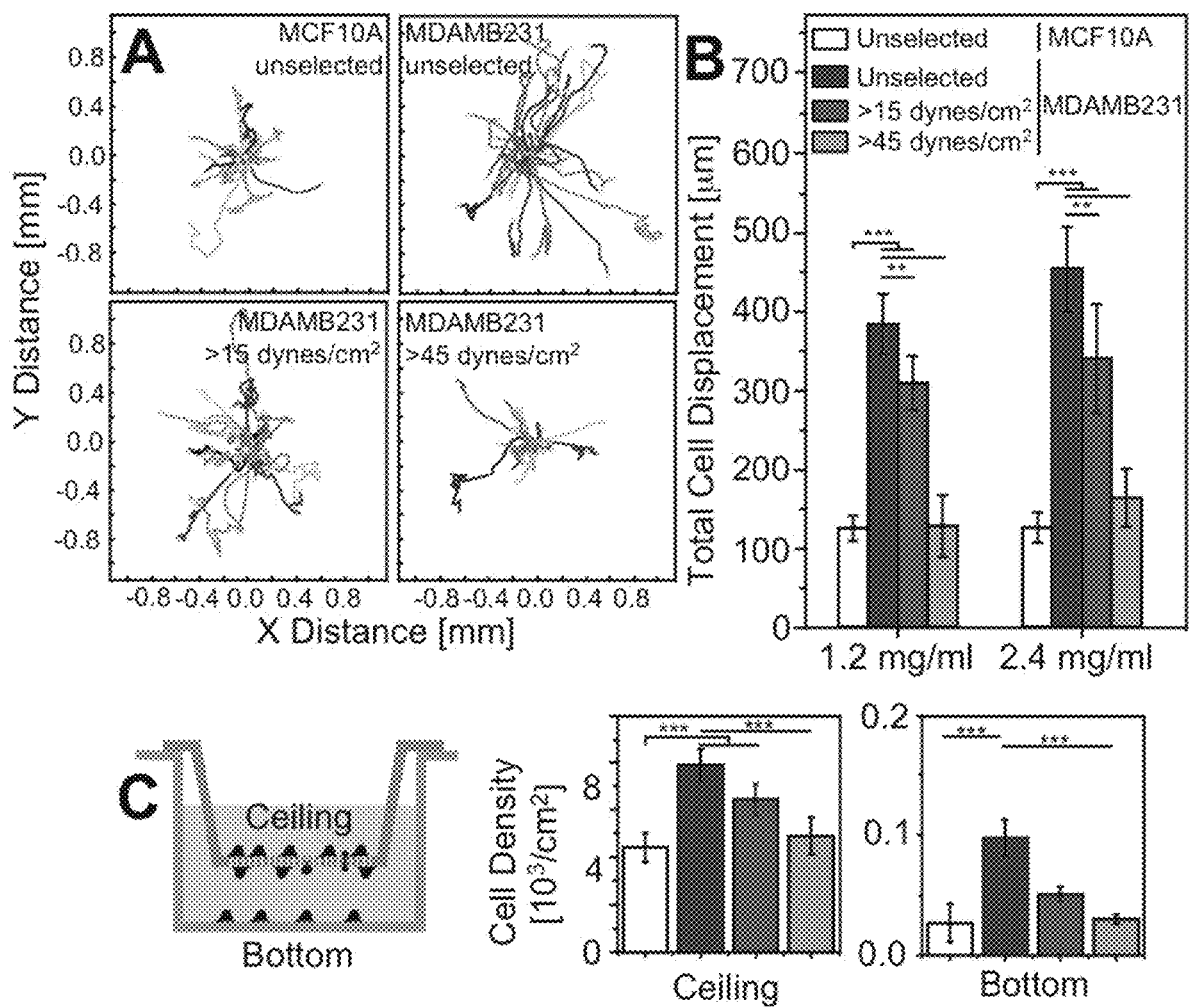
FIGS. 17A-17C provide results of migration and transwell assays with strongly adherent cells.

Cells with less labile focal adhesions and adhesion strength >15 dynes/cm$^2$ exhibit less 3D collagen (FIGS. 17A-17B) and transwell (FIG. 17C) migration than unselected cells. From these data, quantitative results are obtained for the disclosure herein to detect metastasizing cells in the stroma:

(1) <12-hour total time from biopsy receipt to assay or <6-hour from adhesion to assay.
(2) Cell detection despite small volume (<10$^6$ cells) obtained via stromal needle biopsy.
(3) Using a shear threshold appropriate to each line for 5 minutes (e.g. 10 dynes/cm$^2$ for MDAMB231 cells, FIG. 16C), be able to differentiate weakly adherent tumor cells from their stromal counterparts with (i) >90% accuracy and (ii) >90% recovery of weakly adherent cells.
(4) Earlier detection than current blood-based assays as assessed by EpCAM antibody detection.

Weakly adherent cells are collected. Their metastatic capacity is validated. Numbers of collected cells are compared to tumor outcomes. The disclosed technology's performance is compared to a biomarker.

Experimental Approach

Unlike other assays,[1,4,19-26] the approach as disclosed herein employs adhesion strength differences that only subsets of metastatic cell lines exhibit.[11] The technology is validated against the biomarker EpCAM, which is used in the FDA-approved CellSearch technology, using metastatic cell lines and a xenograft mouse model.

Adhesion Strength in Metastatic Cell Lines Correlates with Invasive Capacity: mammary epithelial cell lines of varying metastatic potential were exposed to a range of shear stress to measure their adhesion strength via a spinning disc assay[14,15] (FIG. 16A). Cell density as a function of radial position was assessed and normalized to unspun controls (FIG. 16B). At tumor-like cation concentrations,[12,13] i.e. 0.5 mM Mg$^{2+}$ and 1 mM Ca$^{2+}$ (denoted as PBS+MgCa), non-tumorigenic MCF10A cells, malignant MCF7 cells, and metastatic MDAMB231 cells had similar adhesion strength, i.e. $\tau_{50}$, the shear required to detach 50% of cells (FIG. 16C, black). Stromallike cation levels[12,13] during shear, i.e. 20 M Mg$^{2+}$ and no Ca$^{2+}$ (denoted as PBS), only slightly reduced adhesion strength of MCF10A and MCF7 cells. However with metastatic MDAMB231 cells, adhesion strength was reduced by more than an order of magnitude and was very heterogeneously distributed (FIG. 16C)[11]; adhesion strength homogeneity could be gradually restored with increasing cation concentration and was consistent across other metastatic cells[11], including MDAMB468 and SUM1315 mammary, PC-3 prostate carcinoma, and NIH-H1299 lung cancer cells, but not their non-metastatic counterparts. Adhesion strength was also reduced in H-Ras transformed MCF10A cells, indicating that this difference occurs even with isogenic comparison.

To determine whether adhesive strength can predict invasive behavior, strongly adhering MDAMB231 cells were selected by blocking adhesion to the coverslip center and exposing cells to high shear (either 15 or 45 dynes/cm$^2$) in stromal-like media to select for strongly adherent cells. Minimal 3D migration was observed for MCF10A cells or MDAMB231 cells selected with 45 dynes/cm$^2$ shear. Unselected MDAMB231 cells were significantly more motile (FIGS. 17A-17B), as were other unselected metastatic cells, e.g. MDAMB468, SUM1315, PC-3, and NIH-H1299. Cell invasion, assessed over 48 hours by transwell assay, exhibited an identical trend for MDAMB231 (FIG. 17C) along with the other metastatic lines. These data show that highly adhesive cells appear less migratory and invasive than unselected cells. However these data do not monitor the subpopulation that is likely to be highly metastatic, i.e. weakly adherent cells, thus motivating adhesome technology.

Figures 18A, 18B:
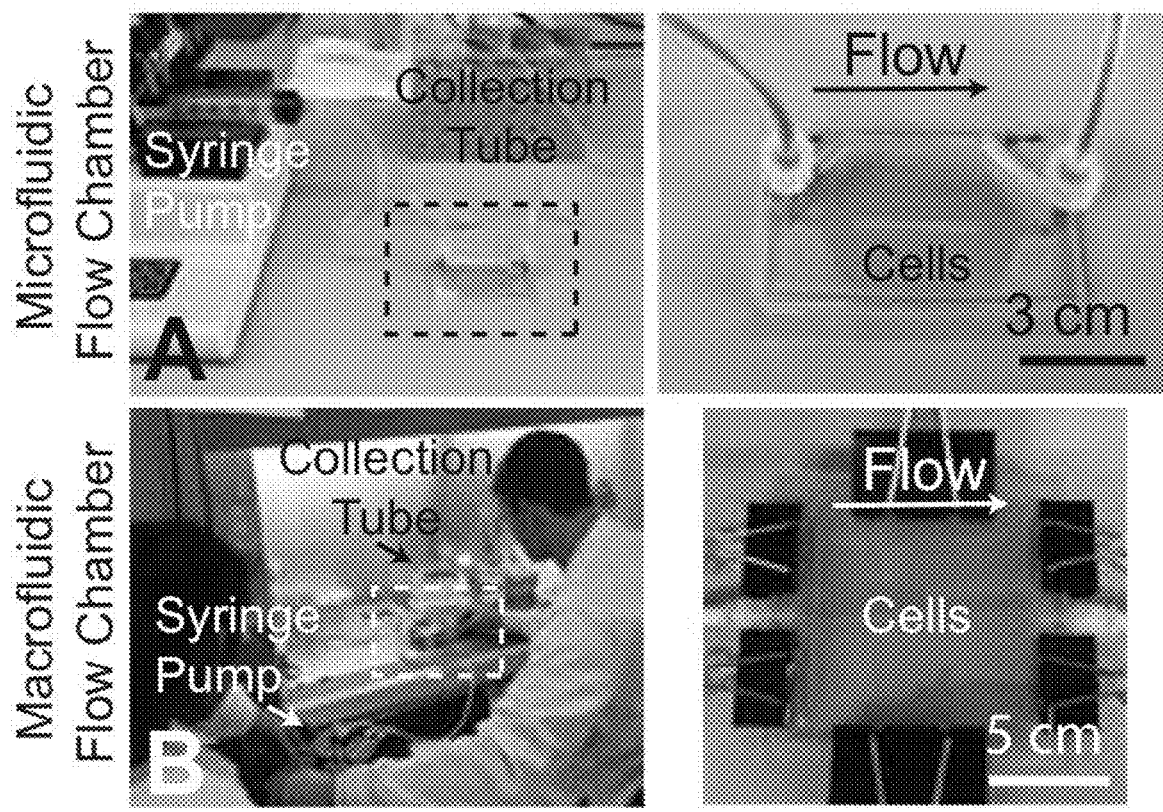
FIGS. 18A-18B show non-limiting examples of adhesome flow chambers.

Adhesome Technology Development: micro- and macro-fluidic flow chambers were developed that could capture weakly adherent cells. Flow within these channels exhibit behavior based on Poiseuille flow.[34] A microfluidic flow chamber is shown in FIG. 18A and was used for experiments where biopsy size could be small, e.g. clinical application, or where the number of cells required for an assay is low. Chambers were fabricated using a reverse casting method. The fluid channel was created with dimensions of 100 μm tall, 4 cm wide, and 3 cm long in PDMS; a built-in inlet and outlet supply and collect cell culture media or shear buffer, i.e. PBS or PBS+MgCa. Cells are attached to an ECM-coated microscope slide that is bonded with the channel. Cells are loaded into the device, cultured for 6 hours, and then sheared for 5 minutes in adhesion buffer (with or without cations). Since the device fits a standard microscope slide, experiments can be performed in massively parallel arrays. Though each device is for a single use, hundreds can be cast off of one master, making it reproducible, cost effective, and high throughput, all of which are important for translation. Cells were seeded at $10^4$ cells/cm$^2$ (total of $1.2 \times 10^5$ cells) because COMSOL fluid dynamics modeling suggest that that density minimizes fluid perturbations from adjacent cells. Flow rates of 0.5 to 45 mL/min driven by a syringe pump provides a range of shear from 1 to 50 dynes/cm$^2$. MDAMB231 cells were isolated using shear of 10 dynes/cm$^2$ for 5 minutes (total volume of 22.5 mL). This should yield the weakest 25% of cells, i.e. $\ll\tau 50$ (FIG. 16C), or $\sim 3 \times 10^4$ cells. Cells are centrifuged, counted, and can used in additional assays (per FIG. 15). A macrofluidic flow chamber was also built (FIG. 18B) for animal model experiments where significant number of cells is required to seed a primary tumor. This fluid channel was machined to have dimensions of 125 μm tall, 7.5 cm wide, and 9 cm long and is made out of autoclaveable polysulfone. $6.8 \times 10^6$ cells are plated to 10×10 cm ECM-coated plates and clamped in place with a rubber gasket to form a seal. Flow rates of 1.5 to 66 mL/min driven by a syringe pump provides a shear range of 1 to 50 dynes/cm$^2$. Again MDAMB231 cells were isolated using shear of 10 dynes/cm$^2$ for 5 minutes (total volume of 66.5 mL) to yield $\sim 1.7 \times 10^5$ cells, which is centrifuged, collected, and injected or analyzed.

Validating the Weakly Adherent but Highly Metastatic Phenotype with Adhesome Technology Improving Recovery of Weak Cells: Knowing how shear affects mammary epithelial cell adhesion strength (FIG. 16C), $1.2 \times 10^5$ cells MDAMB231 and MCF10A cells are cultured in the microfluidic device for 6 hours (milestones 1 and 2), and then switched to stromal-like cation levels, i.e. 20 μM Mg$^{2+}$ [12,13], and then expose cell cultures to shear of 10 (weak) or 45 dynes/cm$^2$ (strong) in the flow chamber. In these conditions, a significant fraction of MDAMB231 but few if any MCF10A cells should detach. Most importantly for validation, these devices can be observed on an inverted optical microscope using bright field to watch cells detach in real time and assess the detection resolution of the assay as disclosed herein. Preliminary assessment of cells recovered from the outflow indicates that no weakly adherent cells are recovered from MCF10A cultured in PBS, but for MDAMB231 cells, $10^4$ cells or 33% of the expected yield (10% of total cells) was recovered. Those cells remaining on the microscope slide represent ~90% of total cells in culture, so cells were not lost post-capture. For cells that are recovered, live/dead staining does not indicate dead cells. Parallel assessment by spinning disc assay[11,14,15] confirms that the weakest 25% of MDAMB231 cells detached at 10 dynes/cm$^2$. However parallel technical replicates of a single sample shows >95% reproducibility in cell recovery (albeit at 33% yield).

To improve capture efficiency of weak cells to >90%, shear exposure time is increased to encourage partially detached cells to completely release given the presence of a significant portion of partially detached cells. Completely eliminating cations from adhesion buffer could also improve detachment by keeping integrins at low affinity. Shear-induced apoptosis is minimized in outflow tracks by minimizing outflow channel shear stress. Lastly, gas exchange was checked and the shear flow by particle velocimetry was validated to identify any sources of fabrication errors with the chamber that could affect capture efficiency.

Figure 19:
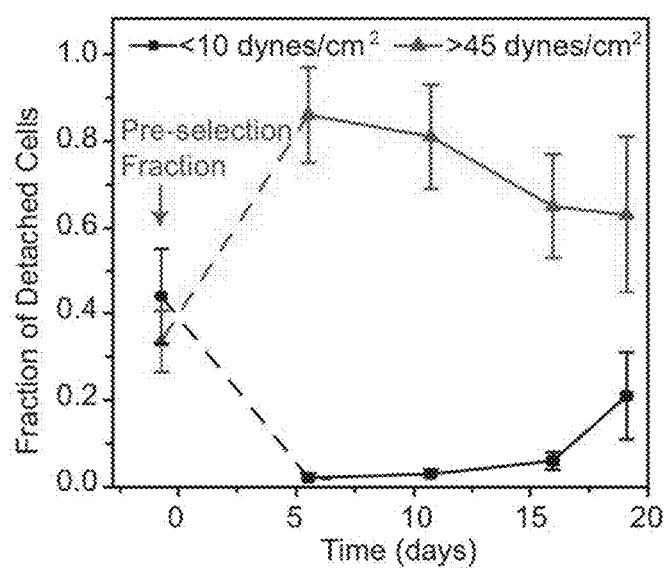
FIG. 19 provides results showing adhesion strength stability. MDAMB231 cells were selected for their strong adhesion using the spinning disc assay,[14] cultured for the indicted number of days, and assessed for the fraction of the population with a given adhesion strength.

Spinning disc data does not suggest that detachment differences could arise from different ECM proteins.[11] All data are confirmed in parallel via the spinning disc assay.[14,15] Once yield has improved for MDAMB231 cells, all other metastatic cell lines are tested from mammary, prostate, and lung tumor lines. In parallel to improving capture efficiency, metastatic capacity of weakly adherent cells is assessed with 3 assays:

(i) Mixed Cell Separation: To more accurately determine that the cells that detach are metastatic, 2 assays are performed. First, MDAMB231 cells in the flow chamber are serially sorted. Cells are plated and sorted after 6 hours. Those cells in the flow through are replated and assessed again after 6 hours to ensure that >90% of the sorted cells detach. Given the stability of strongly adherent phenotypes in the spinning disc assay (FIG. 19), the adhesion strength of the weakly adherent population changes during the assay. >90% of the sorted cells should be recovered in a second run. As a means of validating the 90% accuracy in sorting, unselected MCF10A cells are labeled with the membrane dye DiO and dope membrane dye DiI-labeled MDAMB231 cells at ratios of 0:100, 10:90, 50:50, 90:10, and 100:0. Knowing that only weakly adherent MDAMB231 cells are recovered using 10 dynes/cm$^2$, recovering cells in quantities should be reflective of their mixing ratio, i.e. an MCF10A:MDAMB231 ratio of 50:50 should yield only DiI-labeled cells as measured by flow cytometry] with >95% recovery of the weakly adherent MDAMB231 fraction to ensure the detection sensitivity. Should dye exchange occur and dual-labeled cells observed, cells are transferred with fluorescent proteins. To mimic stroma, NIH3T3 fibroblasts are substituted for MCF10A cells.

Figures 20A, 20B:
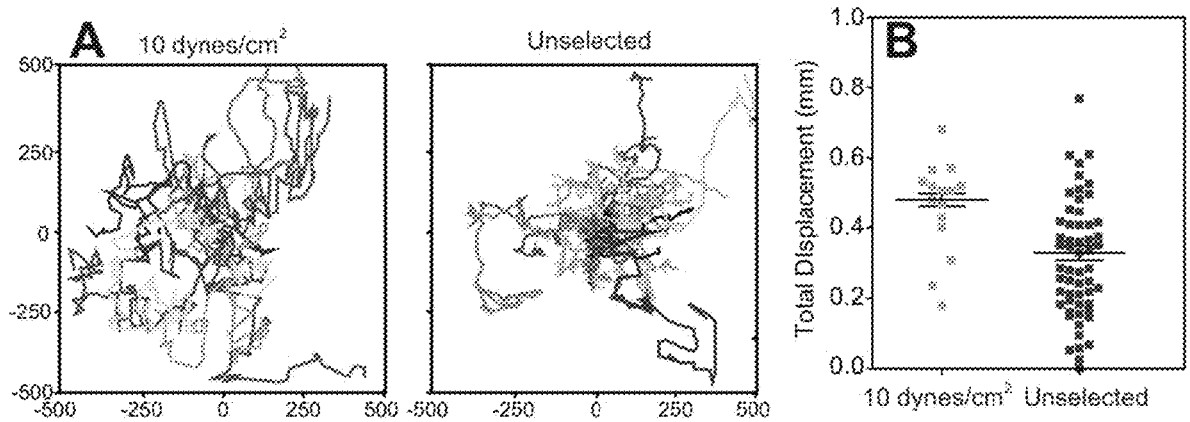
FIGS. 20A-20B provide results showing weakly adherent cell motility.

(ii) Collagen Migration Assay: weakly adherent cells are collected from metastatic cell lines including MDAMB231, MDAMB468, SUM-1315, PC-3, and NIH-H1299 cells via exposure to shear of 10 or 45 dynes/cm$^2$ and collection from the outflow; control unselected cells are also compared. Since analyses are performed in parallel and clonally, low cell numbers are not impede assessment. Weakly adherent cells are mixed with 1.2 and 2.4 mg/mL type I collagen and polymerized in 96 well plates. Cells are mixed at a density of 100 cell/mL with collagen and 10 μL of solution is added to each well using the Bio-Tek Precision Microplate Sample Processor system. Migration is assessed by time-lapse microscopy on a microscope with programmable stage and enclosure for independent CO$_2$ and temperature control. Custom image software run in Metamorph will autofocus to identify cells in bright field and track their centroids over 24 hours as in FIG. 17. Data is analyzed using custom Matlab code[35] to create rose plots of migration and track distance traveled to determine migration persistence. Initial assessment of MDAMB231 cells indicate that weakly adherent cells recovered from the flow chamber are more motile than unselected counterparts (FIG. 20).

(iii) Transwell assay: Weakly adherent cells are seeded onto 96-well plates with transwell permeable supports (8 μm polycarbonate membrane). 1,000 cells/well are seeded on the permeable support, which should be sparse enough to maintain isolated cells (density is adjusted if necessary). After cell attachment on the permeable support, culture media is added to the entire well. Cells are allowed to interact with the transwell and migrate through the membrane for 24 hours before they are fixed and stained. Cells that successfully invaded are counted on the bottom of the permeable support ('ceiling') whereas cells that dropped off the support and adhered to the bottom of the 96-well plate are also counted ('bottom').

Experimental Controls: Non-metastatic human cell lines specific to each tumor type are used as negative controls in the above experiments. Since these cells lines are cation insensitive and strongly adherent, they should neither migrate nor invade substantially. Metastatic MDAMB468 and SUM1315 mammary, PC-3 prostate, and NIH-H1299 lung cells provide additional proof-of-concept data. To compare metastatic and non-metastatic cells isogenically, behavior of H-ras oncogene-transfected MCF10A cells, i.e. MCF10AT, are also be compared[11]. These controls also establish how universal and reproducible this phenotype is.

These data provide evidence across cell lines that shear selection using the adhesome flow chamber isolates weakly adhesive, cation-dependent cells that are more migratory and invasive. Data validate sorting detection limits, accuracy, and efficiency.

Predicting the Capacity of Weakly Adherent Tumor Cells in Stroma to Metastasize In Vivo To prove clinical utility, it is determined if weakly adherent cells have higher de novo metastatic potential than unselected cells in vivo AND that the adhesome flow chamber can detect metastasizing cells in stroma before biomarker assays.

In Vivo Metastasis Assay: Cells are infected with lentivirus to express green fluorescent protein (GFP) prior to isolation and injection to facilitate tracking. Weakly adherent MDAMB231 cells are isolated from the flow through of the microfluidic adhesome device (FIG. 18B) using 10 dynes/cm$^2$ shear. Strongly adherent cells (remaining attached after exposure to 45 dynes/cm$^2$) and unselected cells are used as controls. $10^5$ cells per sample are suspended in 15 μL of Matrigel. Even with the current suboptimal capture efficiency (33%), the macrofluidic chamber is used to isolate a nearly sufficient number of weakly adherent cells (~6×10$^4$ cells) in one run for a mouse. Cells are injected bilaterally into the inguinal (#4) mammary fat pads of 8-week-old female NOD/SCID-beige mice.

Figures 21A, 21B:
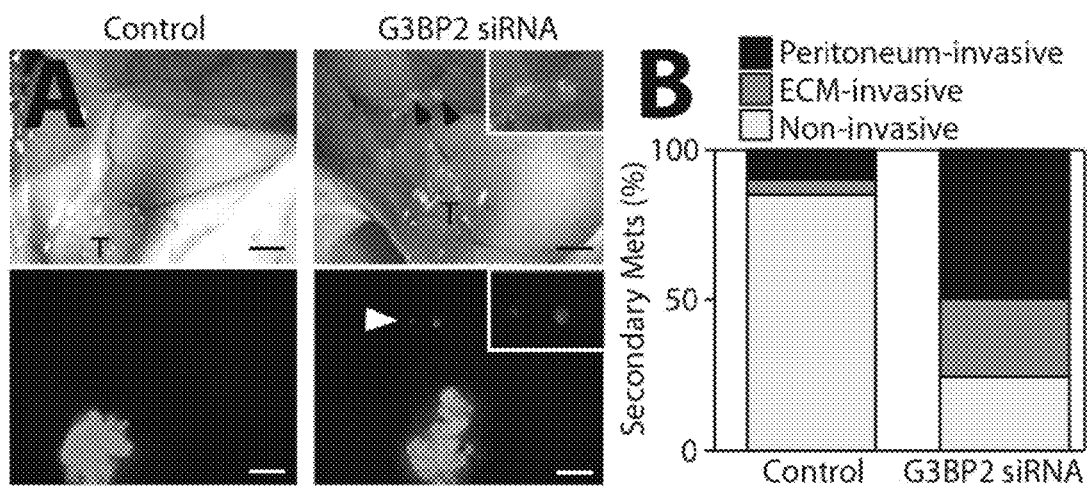
FIGS. 21A-21B provide results of in vivo metastasis assay.

Those performing cell injections are blinded to remove detection bias.[8] Mice per cell isolation type (weakly or strong adherent or unselected) are required to achieve statistical power of 0.8 for a of 0.05. All animals undergo IVIS imaging to verify tumor engraftment and determine the approximate location of primary and secondary tumors using their GFP expression. Mice are euthanized at 7 weeks post implantation, and 3 assays performed to validate clinical utility (see FIG. 15):

(i) Assessing Tumor Burden: Primary and secondary tumors are assessed for weight, size, and morphology using the GFP signal to aide in their identification. Lungs, which are a common site for metastases in this model system,[36] are also assessed for the formation of distant metastases between selected and unselected cell injection groups. Cell injections are limited to MDAMB231 cells to minimize the number of animals needed for proof-of-concept in an in vivo tumor model. Both the Engler and Tlsty labs (see capacity for GFP-labeled MCF10DCIS cells (FIG. 21).[37] While weakly adherent MDAMB231 cells have a higher number of locally (fat padinvasive) and regionally (Peritoneum-invasive) invasive xenograft tumors, other metastatic lines tested above or MCF10DCIS are used to determine if invasion is prevalent among weakly adherent subsets of each line.

Figures 22A, 22B:
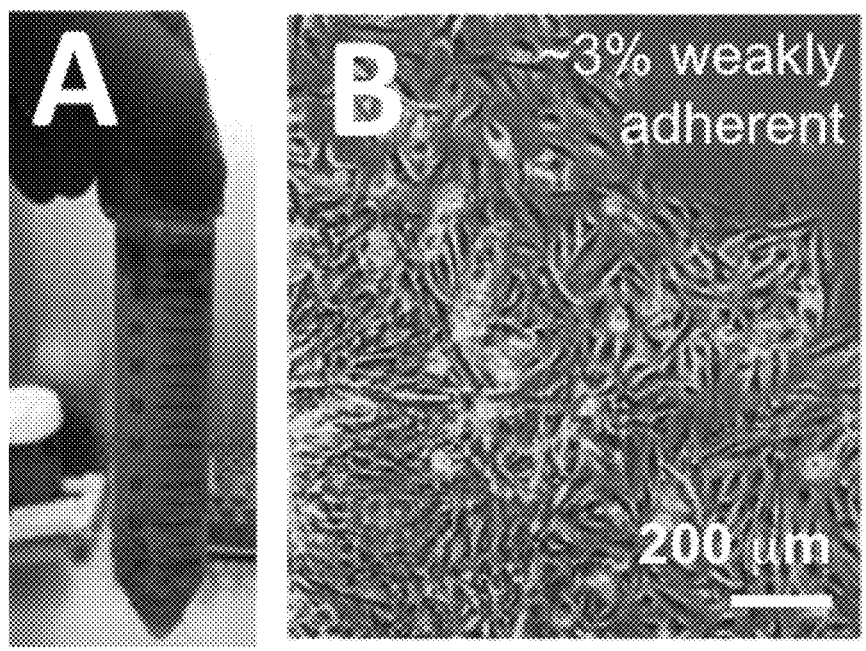
FIGS. 22A-22B show cell recovery from biopsies.

(ii) Stromal Detection via Spinning Assay and Flow Cytometry: In clinic, tumor typing is often performed with needle biopsy. As this is the standard of care, needle biopsy samples of fat pad stroma and peritoneum is performed 2, 4, and 6 weeks post-injection; 16 biopsies are obtained from a regular pattern to prevent regional bias. Biopsy sections are digested with collagenase and hyaluronidase based on previous protocols.[38,39] The single cell suspension is plated on to coverslips for 6 hours. As shown in FIG. 22 from a human needle biopsy, >10$^6$ stromal cells can be recovered and adhere to the device (milestone 2). Thus it is noted that single cell recovery from biopsies is possible and that isolation does not disrupt their adhesion. Cell adhesion strength is assessed for stromal cells of injected animals (or non-injected animals as a negative control) by spinning disc assay to analyze the population. Biopsies containing MDAMB231 cells should show a drop in the adherent cell fraction below 10 dynes/cm$^2$ but no other appreciable cell loss normalized to non-injected controls; stromal fibroblasts have adhesion strength >100 dynes/cm$^2$.[15] Separately the GFP+ stromal fraction is confirmed by flow cytometry, and a small stromal fraction should be GFP+ vs. no positive cells in non-injected animals or those receiving strongly adherent cells. These data should be consistent with experiment (i), i.e. cells detected in the stroma and more tumors resulting for animals injected with weakly adherent cells. As an alternative if more cells are required, analyses can be repeated post-mortem with fat pads for proof-of-concept.

(iii) Stromal Detection via Adhesome Flow Chamber: In addition to broad assessment of adhesome by the spinning disc assay in experiment (ii), the process is repeated with fat pad stroma and peritoneum biopsies, but single cell suspensions are instead be plated onto the adhesome flow chamber for 6 hours. Weakly adherent cells re isolated from the flow through using 10 dynes/cm$^2$ shear, counted, and their GFP+ status confirmed by flow cytometry. Cells that remain adherent are removed by trypsin and their number and GFP status determined by flow cytometry. Again because of strong adhesion by stromal fibroblasts[15] in excess of 100 dynes/cm$^2$, these data should establish that the device has the ability to detect metastatic cells in stroma and that only metastatic cells are present (detection verified by flow cytometry). Further, these data should show the adhesome flow chamber detects weakly adherent cells well in advance of metastases becoming detectable via IVIS and correlates with the number of secondary metastases at 7 weeks. To further confirm that these cells are indeed metastatic if necessary, serial injects of stromal-derived GFP+ cells can be performed or tumor cores biopsied and adhesion strength assessed to validate percentages of metastatic versus non-metastatic tumor cells. In the preliminary assessment of human biopsies in the flow chamber, ~3% detach was noted. Given that an insufficient time has elapsed to determine prognostic value of this percentage of weakly adherent cells in a patient's stroma, it is noted that cell detection of as few as a hundred cell is possible.

Comparison to Biomarker Detection: CellSearch specifically detects extravasated breast cancer cells via EpCAM antibody; >5 circulating tumor cells per 7.5 mL of blood correlates to a 2.6-fold shorter recurrence-free survival time.[40] Since total mouse blood volume is small enough to make CellSearch impractical, stromal and peritoneal biopsies are analyzed by adhesome flow chamber and validated against histological analysis by EpCAM, which is the CellSearch biomarker. The number of GFP+ cells detected in the stroma is compared by adhesome flow chamber to the number of EpCAM+ GFP+ found in histological sections (after extrapolating to an equivalent tissue volume used in the flow chamber).

Stromal detection should show at least an equivalent number of cells between weakly and strongly adherent or unselected cells along with earlier detection based on the migration (FIG. 20). Direct comparisons with recurrence-free survival time using samples from the Breast Program Tissue Core at UCSF (Dr. Tlsty) occur in subsequent awards after proof-of-concept mouse work.

Experimental Controls and Reproducibility: Non-metastatic mammary cell lines, e.g. MCF10A, are used as negative controls should any variance in the outcomes occur]. Experiments are repeated for prostate and lung tumors, e.g. PC-3 and NIH-H1299 cells, respectively, to ensure reproducible results.

These data demonstrate that weakly adherent cells metastasize more frequently and that metastasizing cells can be detected in the stroma via the adhesome flow chamber. These data is benchmarked again data for extravasated cells in the blood.

Example 4

Adhesion Strength and Contractility Enable Metastatic Cells to become Adurotactic Significant changes in cell stiffness, contractility and adhesion, i.e. mechanotype, are observed during a variety of biological processes. Whether cell mechanics merely change as a side effect of or driver for biological processes is still unclear. Here genotypically similar metastatic cancer cells were sorted into strongly adherent (SA) versus weakly adherent (WA) phenotypes to study how contractility and adhesion differences alter the ability of cells to sense and respond to gradients in material stiffness. It was observed that SA cells migrate up a stiffness gradient, or durotax, while WA cells largely ignore the gradient, i.e. adurotax. Biophysical modeling and experimental validation suggest that differences in cell migration and durotaxis between weakly and strongly adherent cells are driven by differences in intra-cellular actomyosin activity. These results provide a direct relationship between cell phenotype and durotaxis and suggest how, unlike other senescent cells, metastatic cancer cells navigate against stiffness gradients.

Durotaxis is a form of directional cell migration in which cells respond to and move towards extracellular regions of increasing stiffness (DuChez et al., 2019; Lo et al., 2000). Durotactic migration has been observed in a large number of migratory cells of mesenchymal lineage and is almost universally reported to occur in both 2D and 3D environments in the direction of increasing stiffness (DuChez et al., 2019; Joaquin et al., 2016; Novikova et al., 2017), with some speculation that it may occur in reverse (Isomursu et al., 2020; Singh et al., 2014). While multi-que migrational responses may occur in vivo (Lara Rodriguez and Schneider, 2013), as the majority of tumors progress, their microenvironment gradually becomes stiffer than the surrounding stroma (Lachowski et al., 2017; McKenzie et al., 2018). This suggests that the ability to move against stiffness gradients seems to be highly relevant at least in some cancers. Therefore, a breakdown in the normal processes regulating durotaxis may contribute to cancer cells developing different sensitivities to stiffness gradients leading to an increase in metastatic potential.

Several mechanisms have been proposed for the molecular basis of durotaxis (Sawada et al., 2006; Sunyer et al., 2016), but how and when these molecular interactions are transduced into a directed force along or against a stiffness gradient is unclear. Computational and mathematical models have bridged gaps in the understanding of how cell mechanics and the microenvironment affect the speed, persistence (Danuser et al., 2013; Holmes and Edelstein-Keshet, 2012; Kim et al., 2018; Mak et al., 2017; Schlüter et al., 2012; Yeoman and Katira, 2018) and emergent behaviors such as durotaxis (Feng et al., 2019; Mak et al., 2015; Novikova et al., 2017; Stefanoni et al., 2011). However, a number of these models make additional a priori assumptions about how intra-cellular processes are differentially affected by stiffness in order to show durotactic behavior (Shatkin et al., 2020). Additionally, co-occurrence of durotaxis, adurotaxis or anti-durotaxis in similar cell populations, as might occur in metastatic tumors, is difficult to explain by current models.

It was hypothesized that mechanotypic heterogeneity across and within cell populations might be responsible for differential durotactic behavior in these populations. In recent work, it was found that adhesion strength acted as a physical marker that sorted isogenic cells into weakly and strongly adhesive cell groups that were more versus less contractile and migratory (Beri et al., 2020), respectively. RNA sequencing further showed transcriptional differences characteristic of distinct mechanotypes that sorted patient outcomes in The Cancer Genome Atlas (TCGA); patients with the weakly adhesive gene signatures relapsed at a rate 2-fold higher than the strongly adhesive gene signatures. Such differences could contribute to durotactic differences not previously observed, and here it shows that mechanotypic differences are the proximate driver for differential rigidity sensing and adurotactic behavior.

Adhesion Dynamics Define an Adurotactic Phenotype

Figures 23A, 23B, 23C, 23D, 23E:
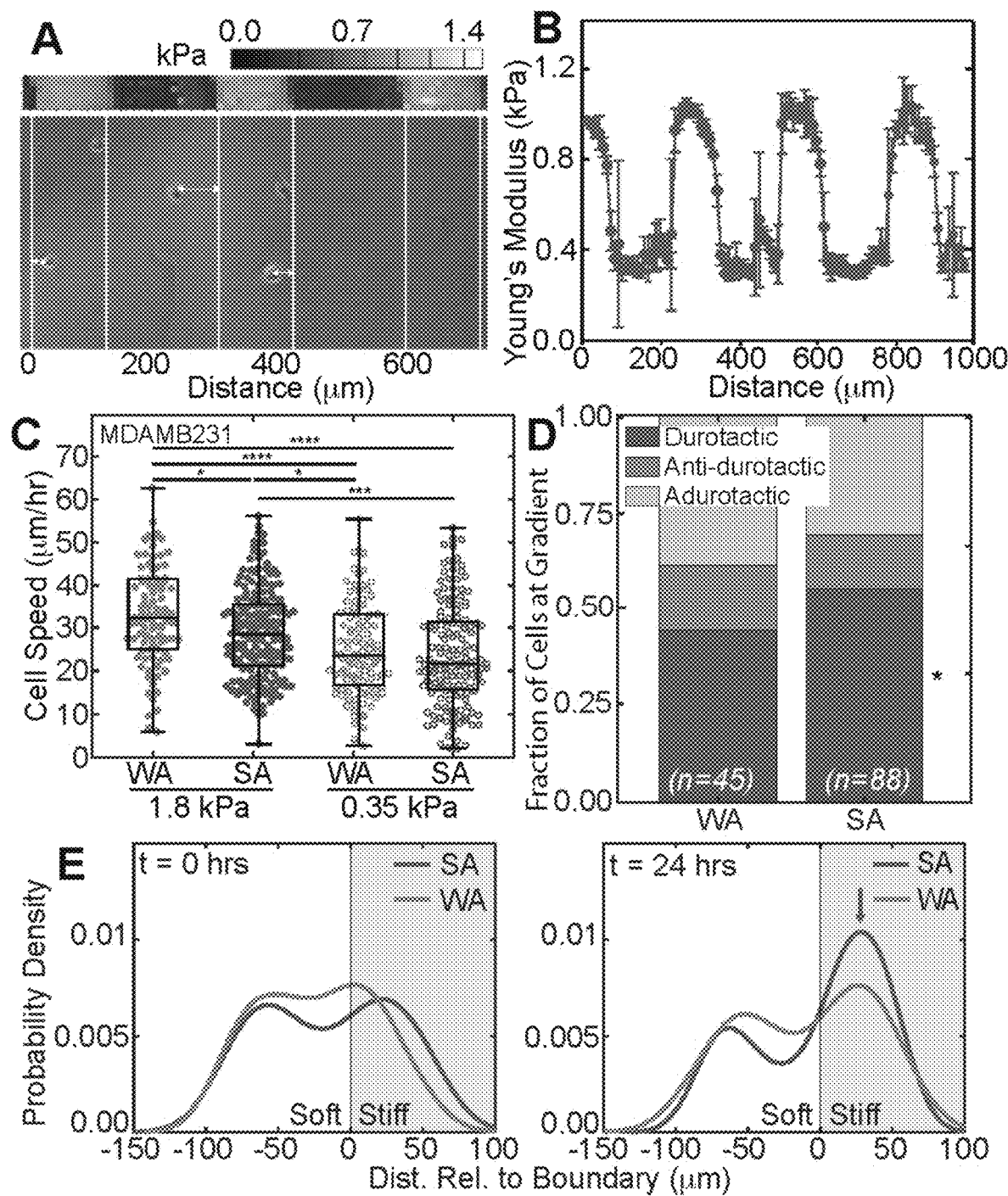
FIGS. 23A-23E show that weakly adherent cells exhibit higher adurotactic behavior.
Figures 24A, 24B, 24C:
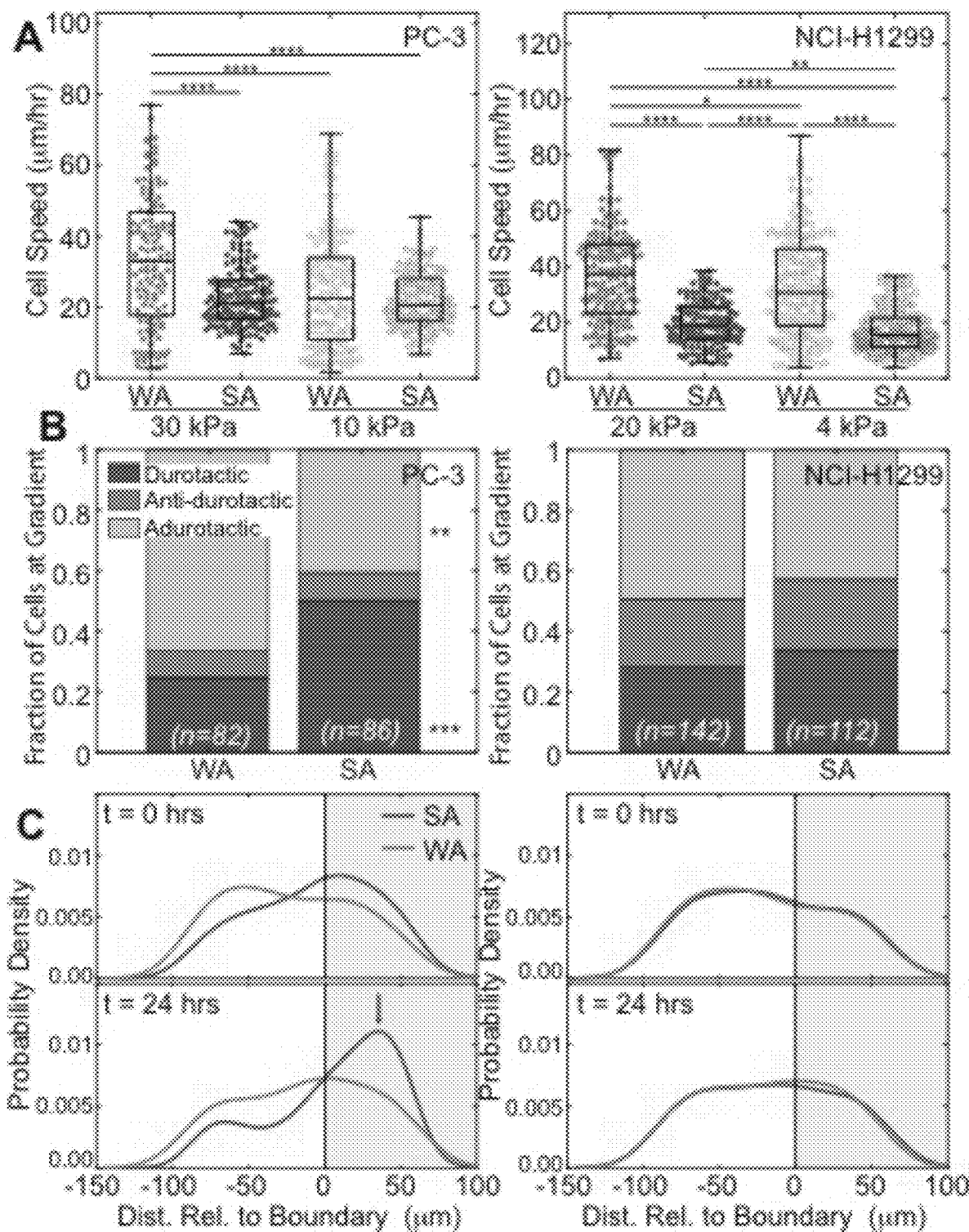
FIGS. 24A-24C show that weakly adherent cells exhibit higher adurotactic behavior, related to FIG. 23.

Here it is reported that weakly adherent populations of various types of cancers cells are significantly less durotactic than their strongly adherent counterparts, potentially explaining how tumor cells migrate down stiffness gradients. Using the parallel plate flow chamber (PPFC) (Beri et al., 2020), cells are isolated based on adhesion strength and seeded onto photopatterned hydrogels with alternating soft and stiff elasticity profiles that match Young's moduli of softer stromal and stiffer tumor ECM for each type of cancer (FIGS. 23A-23B), i.e. 0.3 and 1.5 kPa for mammary (Cox and Erler, 2011; Paszek et al., 2005), 4 and 20 kPa for lung (Burgstaller et al., 2017; Pankova et al., 2019; White, 2015), and 10 and 30 kPa for prostate (Ahn et al., 2010; L. Krupski et al., 2010; Zhai et al., 2010). When cells were plated on these gradients and observed by time-lapse video microscopy (Video now shown), it was found that strongly adherent (SA) cells on average migrate significantly slower than their weakly adherent (WA) counterparts for mammary lung, and prostate cancer cell lines (FIGS. 23C and 24A) on stiff substrates, and slightly slower on softer substrates. Although slower, SA cells for each cell type were more likely to durotax and less likely to undergo adurotaxis than WA subpopulations (FIGS. 23D and 24B); quantitatively, the durotactic odds ratio is calculated as the ratio of the odds that a SA cell is durotactic to the odds that a WA cells is durotactic. It was found that this ratio was between 1.75 and 3 for durotaxis. Conversely for adurotaxis, that ratio was between 0.66 and 0.33 across all cell lines, which indicates that that odds are that SA cells durotax and WA cells adurotax. Consistent with phenotype differences, it was observed accumulation only of the SA cells over 24 hours in culture on patterned substrates as SA cells moved from a random distribution to one biased towards stiffer regions (FIGS. 23E and 24C, and Video not shown). These behaviors again are largely conserved for all cell lines from multiple tumor types, albeit with varying degrees of effect such that accumulation is most robust for a mammary cell line. While the effects are the same, variability may be due in part to inherent mechanotype differences. For example, cells sort into WA and SA subpopulations at different shear stress in the PPFC; lung tumor cells are less adherent overall with the SA fraction sorting at >180 dynes/cm$^2$ while prostate and mammary lines require >500 dynes/cm$^2$ to sort their SA fraction.

Figures 25A, 25B:
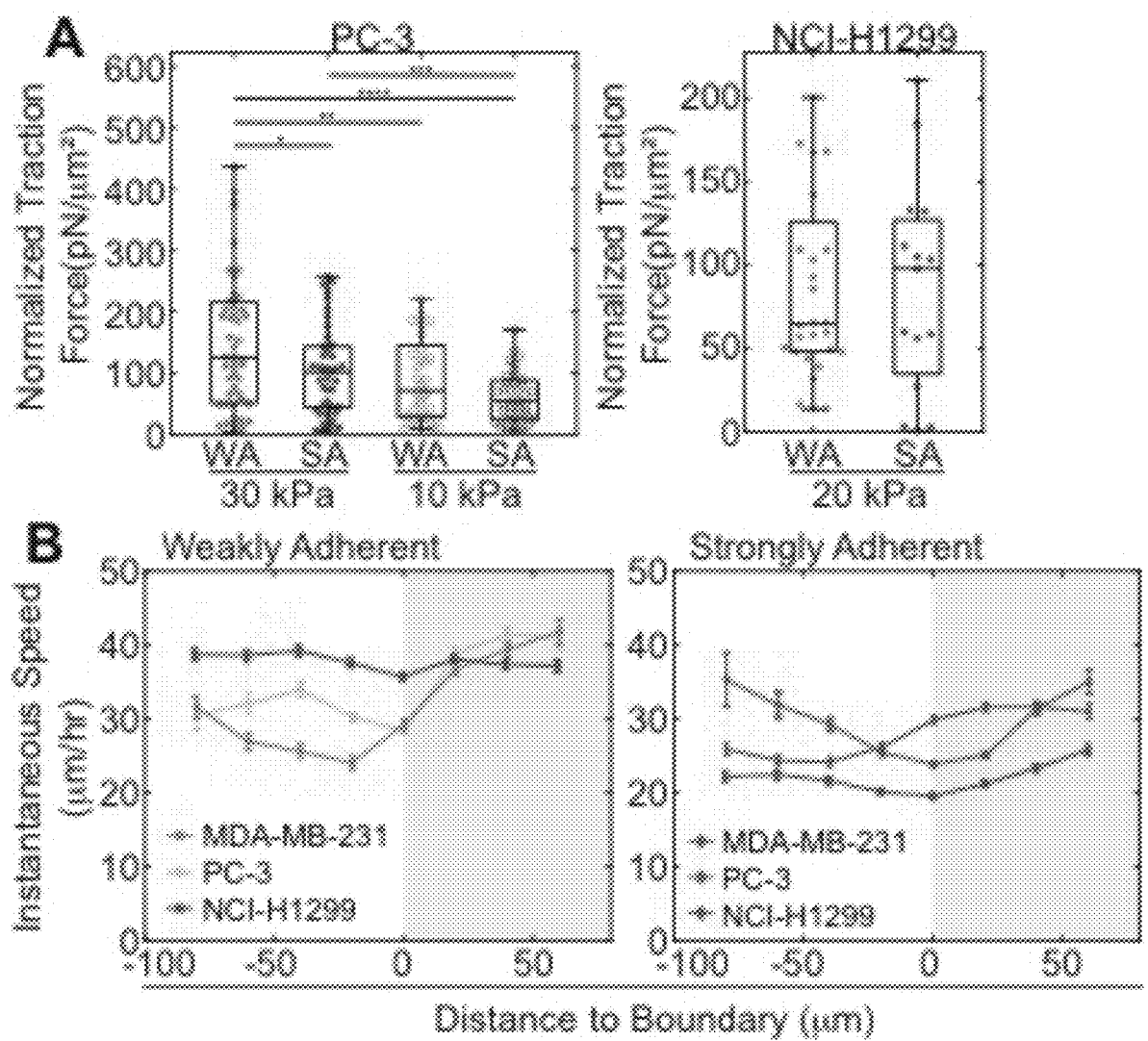
FIGS. 25A-25B show traction forces and instantaneous speed for PC-3 and NCI-H1299 cells, related to FIG. 27.
Figures 26A, 26B, 26C, 26D:
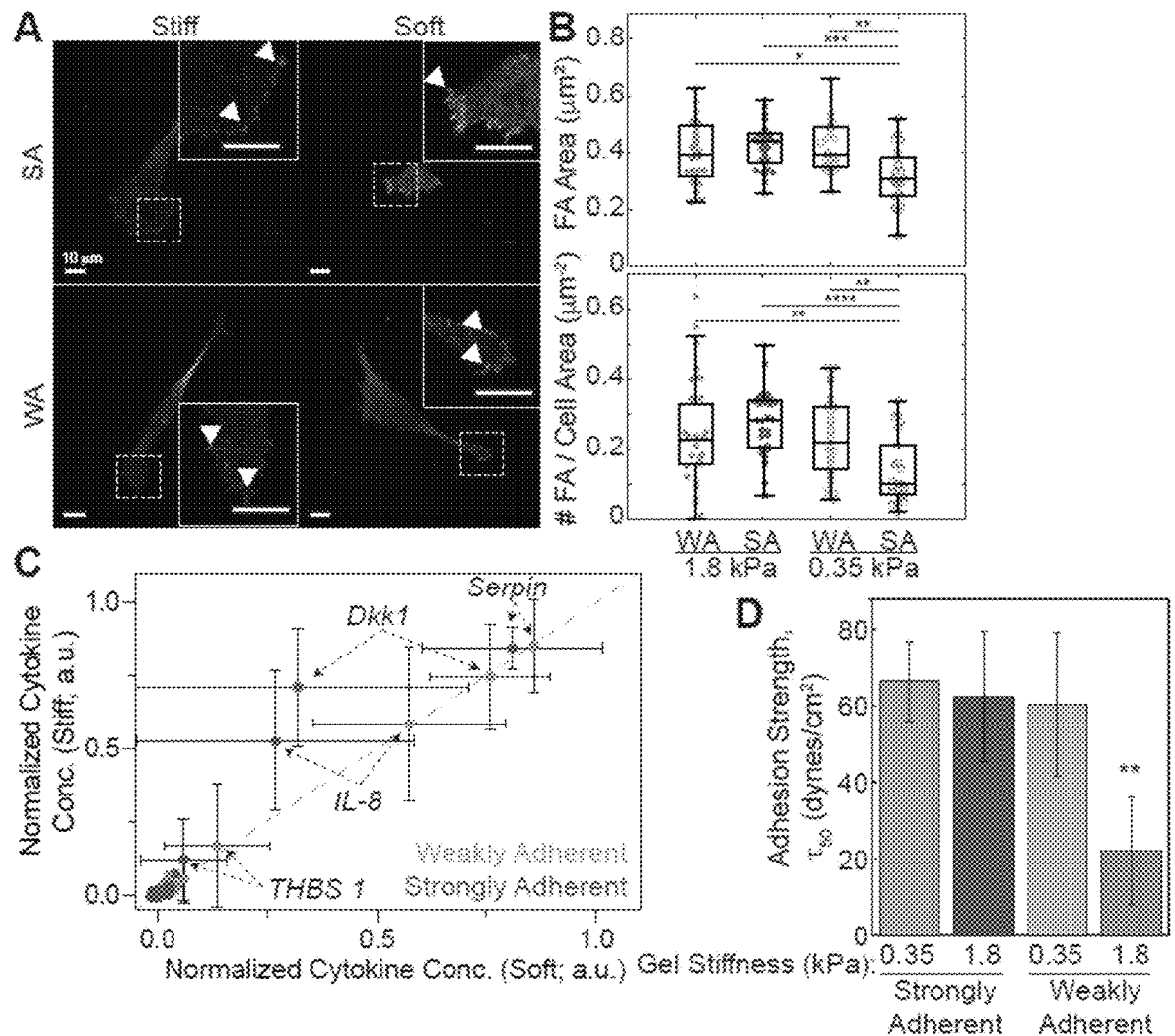
FIGS. 26A-26D show effects of focal adhesions, cytokines, and stiffness on adhesion, related to FIG. 27.

To understand what gives rise to mechanotype, first measured was traction forces across adhesion-sorted cell lines. It was found that weakly adherent tumor cells exhibit higher traction forces—measured for prostate cells lines on both single modulus soft and stiff substrates (FIG. 25A) and for mammary cell lines on single modulus stiff substrates mimicking their fibrotic niche (FIG. 27A); lung is less adherent, and thus it was not observed significant traction differences (FIG. 25A). This general trend, however, may appear counterintuitive: first, that weakly adherent cells generate stronger forces; and second, that cells generating stronger forces show decreased durotaxis and increased adurotaxis. It was noted that as WA cells approached the gradient from either side, their velocities are dependent on distance to the boundary irrespective of the side they are approaching from, while SA cell speed generally increases moving from softer to stiffer substrates (FIG. 25B). This suggests possible traction force redistribution along the cell length for the WA cells as they move across the stiffness gradient. It was also noted that focal adhesion sizes were stiffness dependent for SA cells, while focal adhesion sizes for WA were the similar on either stiffness (FIGS. 26A-26B). These observations suggest that adurotaxis could either arise from a lack of change in balance between adhesion dynamics, redistribution of traction forces across the stiffness gradient, or both. Conversely what does not appear to regulate durotaxis are differences in cytokine expression; blotting of 105 cytokines showed only 4 that were expressed above background and none were differentially expressed (FIG. 26C).

Figures 27A, 27B, 27C, 27D, 27E, 27F, 27G:
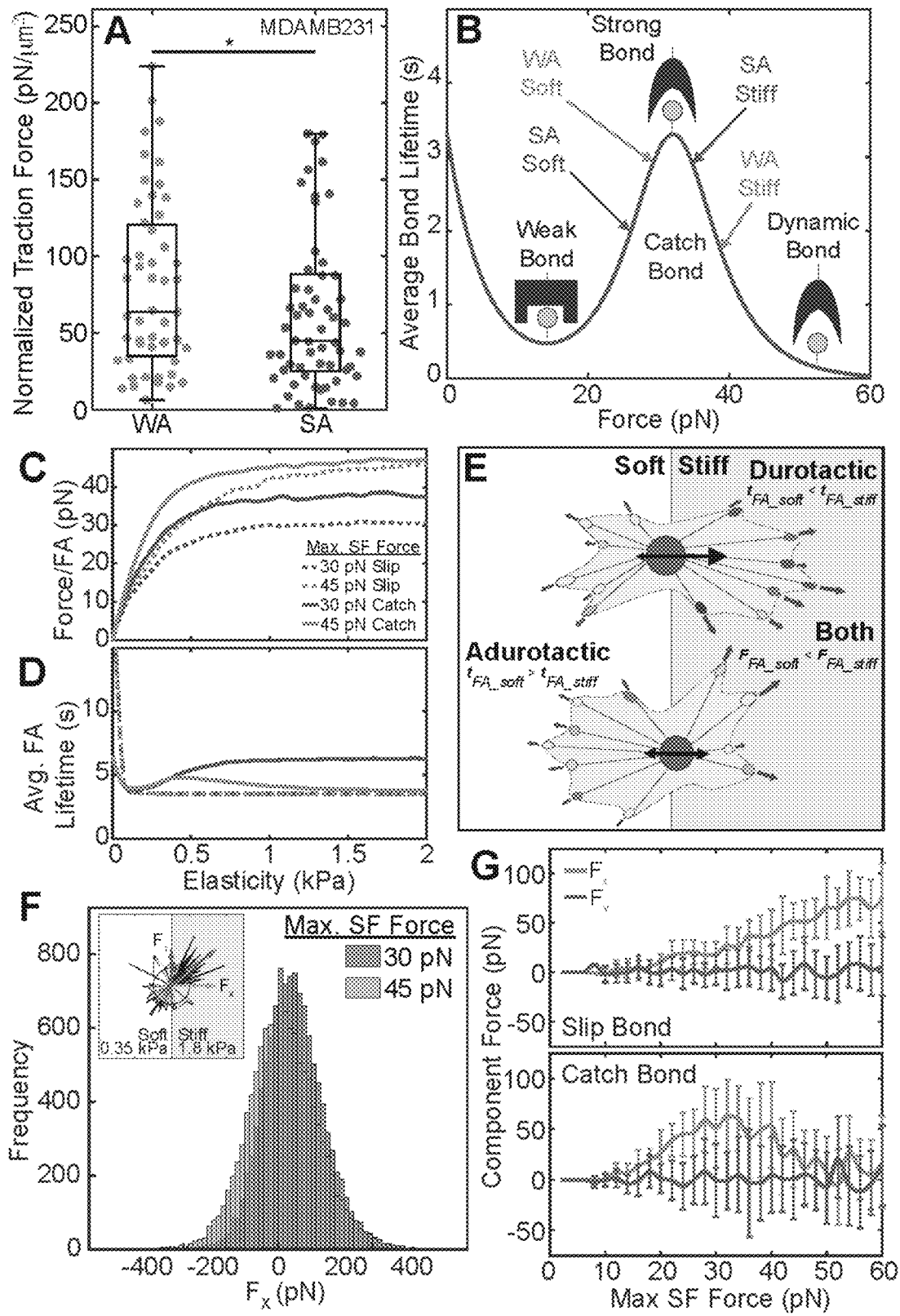
FIGS. 27A-27G show higher forces on catch bonds leads to adurotactic behavior.

To test the above suggestions, a focal adhesion maturation and traction force generation model was utilized dependent on catch bond dynamics between cell adhesion proteins and the substrate (FIG. 27B). In this model, polymerizing actin fibers bind to substrate bound adhesion proteins, mature into actin-myosin stress fibers (SFs) and focal adhesions (FAs) and generate traction forces between the cell and the substrate. The focal adhesions grow/shrink via addition/dissociation of individual integrin-substrate bonds and SF recruitment in a force dependent manner. Stress fibers are limited by the maximum force that each one can generate, i.e. max SF force, and ideally corresponds to the myosin stall force of collectively contracting heads against the actin stress fiber; max SF force is reached exponentially as the stress fiber pulls against the substrate (Schwarz et al., 2006). The substrate stiffness in this model controls the rate of force increase in the stress fibers (equation 5), which in turn alters the force generated in each stress fiber dependent on the associated integrin-substrate adhesion lifetime. The forces driving cell migration are obtained by vectorially summing forces in all the FA bound SFs within the cell at any given instant. Using this model, the effect of integrin catch and slip bonds dynamics (Fusco et al., 2017) was compared on the force per adhesion and on focal adhesion lifetimes as a function of substrate stiffness for cells with different max SF force (assigned from prior observations of SF force (Schwarz et al., 2006)). As a function of substrate stiffness, both catch and slip bonds show increased force per focal adhesion, with catch bonds generating and sustaining higher forces due to bond strengthening and recruitment of secondary stress fibers (FIG. 27C). For focal adhesion lifetimes, lifetimes with slip bond dynamics remained constant across relevant substrate stiffness. For catch bonds however, lower max SF forces saturated focal adhesion lifetimes at higher values whereas higher max SF forces exhibit a small peak near normal mammary stiffness and then drop to saturate at a lower value at higher stiffnesses (FIG. 27D). These data suggest that max-SF force and stiffness-dependent values for FA lifetimes optimize cell migration forces for a given mechanotype. To test the predicted changes in adhesion lifetimes based on substrate stiffness, a range of shear stress was applied to cells cultured on substrates resembling normal and pathological mammary stiffness using a population-based adhesion assay (Boettiger, 2007). It was found that cells selected on glass as weakly but not strongly adherent could modulate their average adhesion strength, become more adherent in softer conditions (FIG. 26D). These results align with model predictions based on catch-bond dynamics between the cell adhesion receptors and the substrate (solid lines in FIG. 27D). Since average FA lifetime is more substrate stiffness-sensitive for weakly adherent cells and identical to strongly adherent cells on softer substrates, these data suggest that weakly adherent cells are less adherent and primed to migrate on stiffer substrates with lower FA lifetimes. These correlations will next be explored in a cell-based model to understand mechanotype mechanisms.

Figures 28A, 28B, 28C, 28D, 28E:
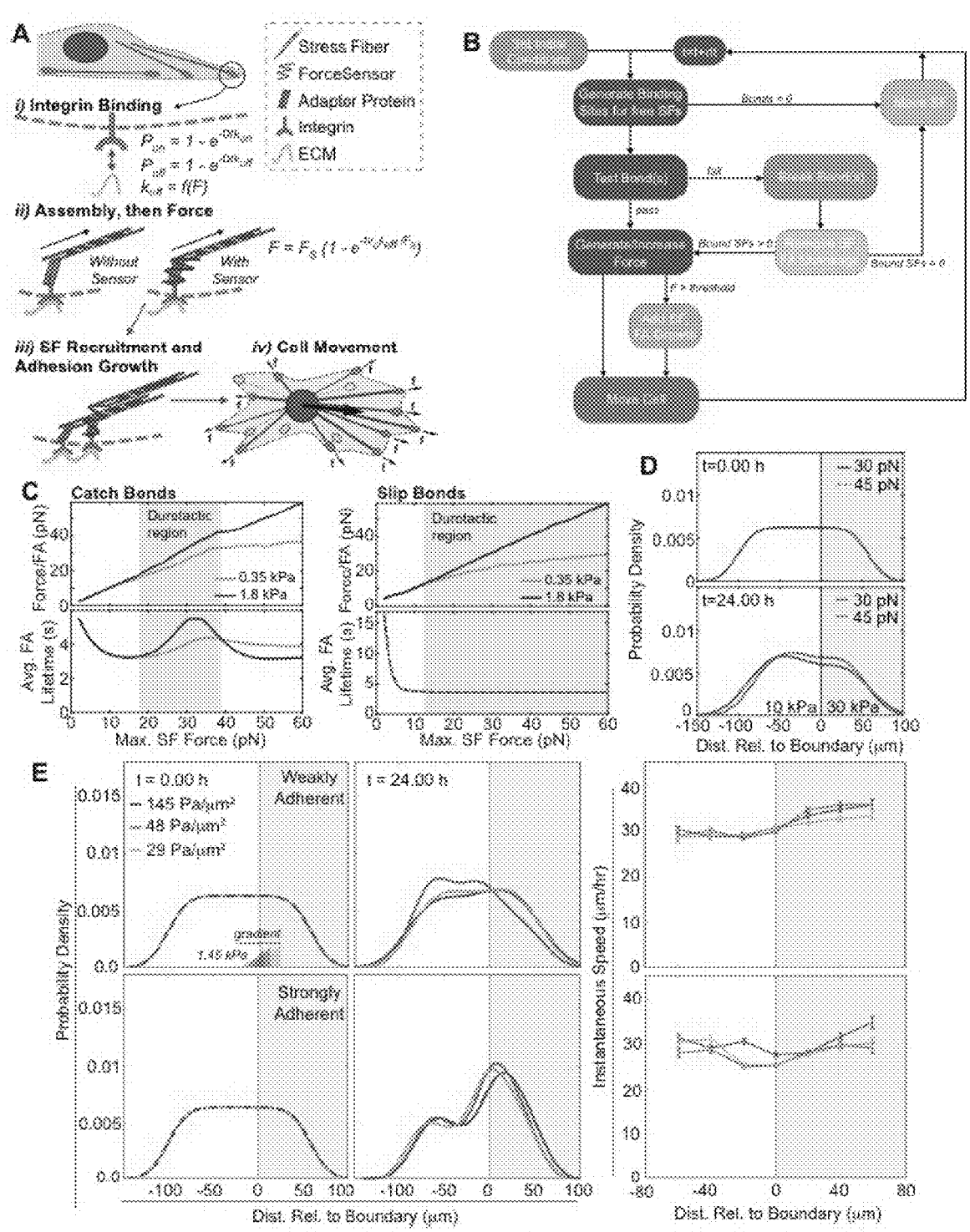
FIGS. 28A-28E provide computational model schematic and its sensitivity to stiffness range and gradient strength, related to FIG. 29.

Actomyosin Contractility Defines Adhesion Phenotype and Explains Migration Behavior In this model framework (FIGS. 28A-28B), a range of max SF forces was compared, finding that 30 pN indeed corresponds to peak bond lifetime at high substrate stiffness but that at higher max SF force, softer substrates experience longer bond lifetimes. It was also found monotonically increasing force per adhesion for catch bonds, consistent with higher traction forces seen experimentally in WA cells (FIG. 27A). Bond lifetimes were insensitive to stiffness for slip bonds while force per adhesion increased monotonically as with catch bonds (FIG. 28C). The relationship between average bond lifetime and substrate elasticity suggests that by increasing max SF force, a scenario could arise in which a cell's catch bonds are more stable adhesions on a softer substrate (FIG. 27E). Stress fibers attached to those adhesion sites would have more time to pull a WA cell in the direction of the softer substrate, balancing numerous shorter-lived forces in focal adhesions on the stiffer region. To illustrate this, a cell was fixed at the step gradient interface and measured force generated parallel ($F_x$) and perpendicular ($F_y$) to the gradient. On average, cells with 30 pN max SF force had a positive $F_x$, indicating that the overall force on the cell is pulling it towards the stiffer substrate, whereas cells with 45 pN max SF force had neutral $F_x$, suggesting the cell would behave adurotactically (FIG. 27F). This scenario requires cell-surface adhesions to behave as catch bonds, which appears reasonable (Kong et al., 2009; Morikis et al., 2017; Zhu and Chen, 2013). It was also note that when slip bond dynamics are used, it results in cells with higher max SF force to durotax (FIG. 27G), which would be at odds with experimental results where WA cells are more contractile but less durotactic than SA cells.

Figures 29A, 29B, 29C, 29D:
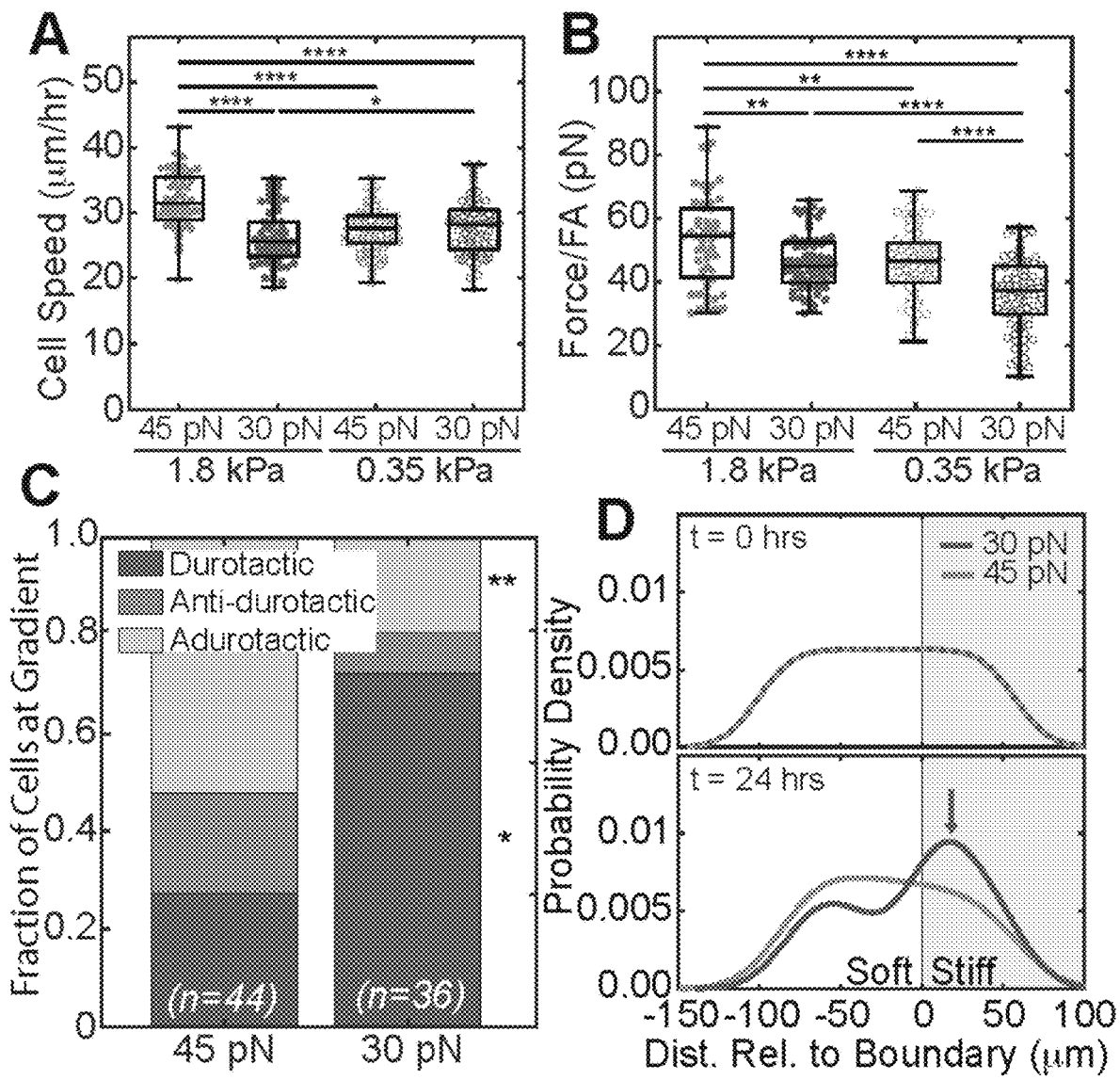
FIGS. 29A-29D provide that differential bond stiffness affect tractions to induce adurotaxis.

The main input required for this model is the max SF force of the WA and SA mammary cells, but with this difference, cell migration speeds and traction forces match experimental observations with the small exception of migration speeds of SA cells on soft substrates, which go up slightly according to the model (FIGS. 29A-29B, Videos not shown). While a fine tuning of other model parameters can fix the disparity, the effect of max SF force was focused here maintaining other parameter values at those commonly found in literature. Additionally, just this difference in max SF force enables the model to correctly predict durotactic differences (FIG. 29C) and the accumulation of SA cells on stiffer substrates versus uniform distribution of WA cells across the gradient over 24 hours for mammary cells (FIG. 29D, Video not shown). Importantly when substrate stiffness is altered to resemble the prostate cancer stiffness gradient (Ahn et al., 2010; L. Krupski et al., 2010; Zhai et al., 2010), mammary cell parameters (Table 5) cause SA cells to not durotax (FIG. 28D). However when substrate stiffness range is maintained, i.e. 0.35 to 1.8 kPa, but the gradient made more shallow, it was not observed changes in cell accumulation on the stiff region of the substrate for SA cells, i.e. they continue to durotax; for WA cells under the same conditions, they still fail to accumulate (FIG. 28E). Thus, it would appear that durotactic and adurotactic behaviors may not be very sensitive to gradient magnitude but rather the mere presence of a gradient.

Adurotactic Phenotype is Titratable by Myosin Activity

Figures 30A, 30B, 30C, 30D, 30E:
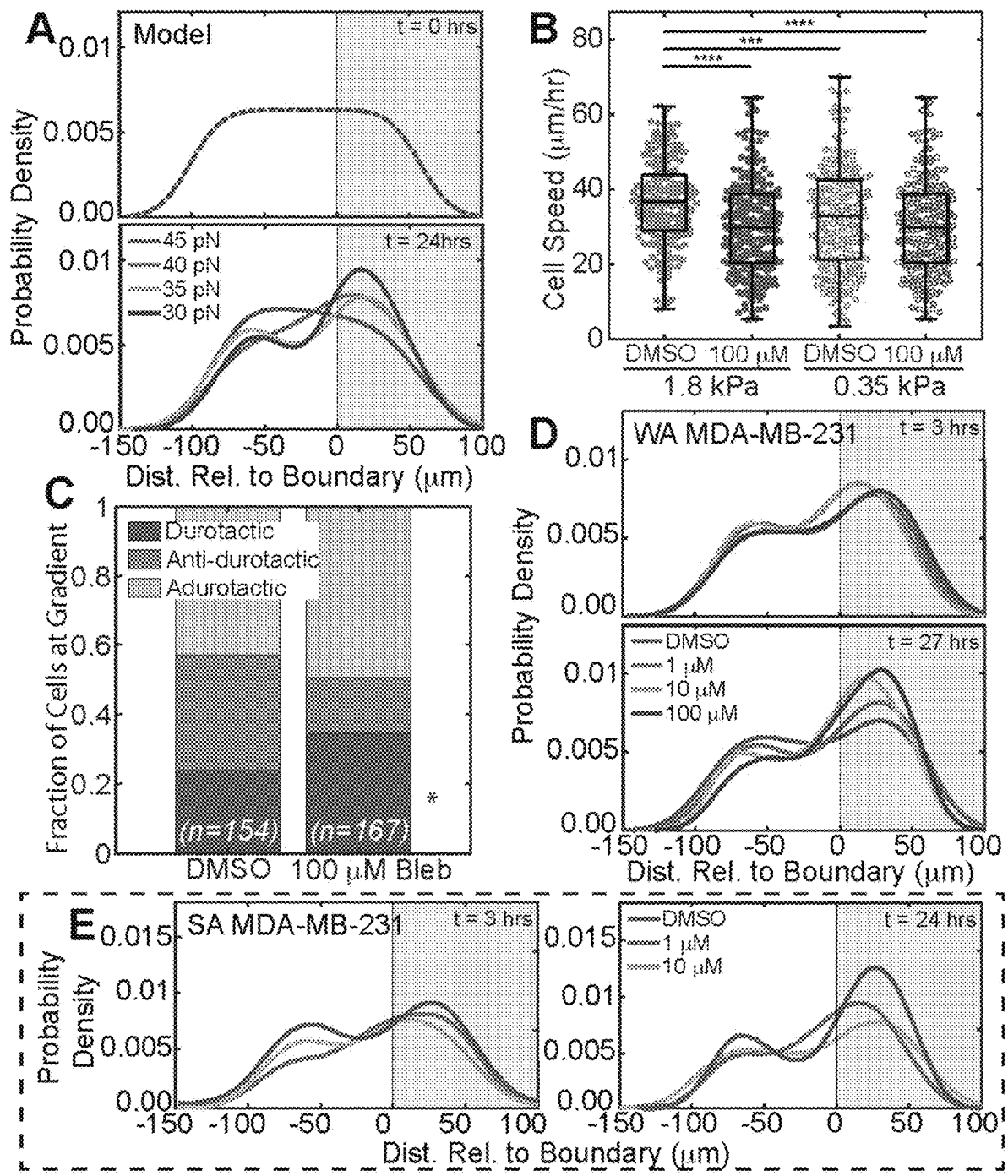
FIGS. 30A-30E provide that tuning contractility modulates adurotaxis in adhesion sorted cells.

The dependence of durotaxis on a change max SF forces implies that the number of active myosin motors per SF filament could affect behavior; prior work suggests that such differences could impart control over cell migration and stiffness (Koenderink et al., 2009). To validate such control in the system, the number of active myosin motors within a cell, was reduced, i.e. SF force, finding that it increases the durotactic tendency of cells as predicted by the model between 30 and 45 pN (FIG. 30A). Furthermore, this was tested experimentally by inhibiting the myosin II activity of WA mammary cells with blebbistatin. Cell speed decreased for blebbistatin treated cells on soft and stiff substrates (FIG. 30B), resulting in similar velocities as untreated SA cells. Furthermore, treated cells are 2-fold more likely to migrate from the soft substrate into the stiff substrate and much less likely to exhibit antidurotactic migration (FIG. 30C). WA mammary cells also showed a dose dependent response to blebbistatin treatment, wherein the WA phenotype became more durotactic, resembling the durotactic behavior of SA cells (FIG. 30D). Conversely, SA mammary cells also showed a dose dependent response to lysophophatidic acid treatment, wherein the SA phenotype became less durotactic, resembling the adurotactic behavior of WA cells (FIG. 30E). These data confirm the suggestion that max SF force, as produced by the number of active myosin motors per SF filament, enables WA cells to exhibit less durotaxis and is a mechanical argument for why WA cells metastasize.

The findings of this work help explain how a metastatic cell's distinct mechanotype correlates to the paradoxical migration down a stiffness gradient that occurs during cancer metastasis. Cancer cells isolated by their adhesion strength from a seemingly isogenic population exhibit consistent behavior across different cell lines from vastly different cancer types; moreover, each cancer type exhibits adurotaxis in their tumor-specific niche, which change dramatically for step gradient strength (between 3- and 5-fold) and gradient range (from 0.3 to 30 kPa). Despite these differences, greater contractility in weakly adherent cells is conserved and led to decreased durotactic behavior that is not directly governed by lack of rigidity sensing, as evidenced by slow down at the gradient boundary. From previous work, RNA sequencing shows a distinct underlying phenotype for weakly vs. strongly adherent cells with differences in cytoskeletal protein expression, which relates to decreased progression-free and disease-free intervals when compared to the gene expression signatures of human patients (Beri et al., 2020). A weakly adherent cell's ability to migrate against stiffness gradients connects this observation to the material properties of the niche, which contribute to its increased metastatic potential.

Computational modeling suggests that mechanotype differences in weakly and strongly adherent cells arises from increased contractility. Furthermore, it demonstrates that catch bonds are a necessary component for the diverging migratory behaviors seen in metastatic cells. Interestingly, catch-bond dynamics have been largely left out of most cell migration and FA dynamics models until recently (Tan et al., 2020). Additionally, the model is able to simulate cells that exhibit both durotaxis and adurotaxis without relying on any a priori assumptions about how rigidity sensing mechanisms are uniquely dependent on substrate stiffness (Novikova et al., 2017). Acto-myosin activity within in single stress fiber largely determines the stress a single bond experiences (Koenderink et al., 2009), with substrate stiffness affecting maximum force loading rate. The biphasic nature of catch bond lifetime allows cancer cells to become more migratory and less durotactic with increased contractility, which likely contributes to the greater metastatic potential as well as sets population stability as observed experimentally (Beri et al., 2020). That being said, while the data suggests a cytoskeletally-driven mechanism, it does not rule out confounding issues from adhesion location, composition, or dynamics.

While material properties change between tumors (Ahn et al., 2010; Burgstaller et al., 2017; Cox and Erler, 2011; L. Krupski et al., 2010; Pankova et al., 2019; Paszek et al., 2005; White, 2015; Zhai et al., 2010) and can be affected by cancer treatment (Miller et al., 2018), it was found that durotactic behavior and migration speed can be tuned by acto-myosin contractility, without any direct tweaks to protein expression levels. This suggests that the differences in migratory behavior are indeed linked directly to cell mechanotype within its niche. This may also explain why drugs that specifically target proteins involved in cell contractility are so effective at reducing invasion and metastasis. Yet tumors are heterogenous and likely contain cells that encompass a range of acto-myosin activities. Additionally, the ECM surrounding tumors show dynamic, non-linear properties which are known to influence the outcome of tumor progression and metastasis (Chaudhuri et al., 2020; Malandrino et al., 2019; Munster et al., 2013). These heterogeneities and tumor plasticity could present some key challenges to drug development. While the current in vitro and in silico models do not focus on these parameters, the results suggest that future metastatic modeling should couple adhesion dynamics, stress fiber considerations and heterogeneity in cellular and ECM mechanics when identifying the lowest effective dose required to prevent metastasis.

Data and Code Availability

The MATLAB code used to track cell migration for brightfield images, analyze focal adhesion immunofluorescence images, simulate cell migration, and test the model is available via Github (github.com/compactmatterlab/Durotaxis). The MATLAB code for adhesion analysis is also available via Github (github.com/englea52/Englerlab).

Experimental Model and Subject Details

Cell Culture

Human metastatic cell lines used in this study include MDA-MB-231 (mammary, female 51 years), PC-3 (prostate, male 62 years), and NCI-H1299 (lung, male 43 years). MDA-MB-231 cells were cultured in DMEM, 10% FBS, and 1% antibiotic/antimycotic; PC-3 cells were cultured in F-12K, 10% FBS, and 1% penicillin/streptomycin; NCI-H1299 cells cultured in RPMI 1640, 10% FBS, and 1% antibiotic/antimycotic. All cells were purchased from ATCC and authenticated by morphology, growth curve, and isoenzyme analysis. PCR was used to verify cultures were free of Mycoplasma, and cells were not used beyond passage 11. Media reagents were purchased from Life Technologies.

Method Details

Fabrication of Step-Gradient Polyacrylamide Gels

A two-step photopolymerization method was used as described previously (Happe et al., 2017) to produce hydrogels with alternating elasticity profiles. Acrylamide concentrations of the prepolymer solutions were modified to obtain elasticities matching that of the tumor and stromal environment of each type of cancer. For breast cancer hydrogels, 3% acrylamide (3.7% for lung, 6.4% for prostate) and 0.4% bis-acrylamide were used for the first prepolymer solution, which was polymerized between a methacrylated 18 mm coverslip and a chlorosilanated glass slide by exposing to ultraviolet light (350 nm) for 5 minutes, using 2-hydroxy-4'-(2-hydroxyethoxy)-2-methylpropiophenone (0.5%) as the photo-initiator. The PA hydrogel was removed from the chlorosilanated glass slide and dehydrated for 1 hour on a hot plate at 30° C. prior to rehydrating with a 2% acrylamide (3.7% for lung, 3.2% for prostate) and 0.4% bis-acrylamide prepolymer solution. The rehydrated gel was again exposed to UV light for 5 min through a high-resolution chrome patterned photomask 200 μm dark stripes and 100 μm clear stripes. The Young's moduli of each region were validated using atomic force microscopy.

The hydrogels were then placed in a 12-well plate on top of 50 μl of 2 mg/ml of collagen I to adhere the coverslip to the bottom of the well. After the collagen polymerized, the gels were immersed in a solution of sulfosuccinimidyl 6-(4'-azido-2'-nitrophenylamino)hexanoate (0.2 mg/ml, Sulfo-SANPAH; Pierce) dissolved in 4-(2-hydroxyethyl)-1-piperazineethanesulfonic acid buffer (pH 8.4, 50 mM) and exposed to UV light (350 nm) for 10 minutes. After washing several times with PBS, the functionalized surface of the gels was coated with collagen I (150 μg/ml) by incubating overnight at 37° C.

Isolating Weakly and Strongly Adherent Cells

Weakly and strongly adherent cells were isolated at varying shear stresses using a parallel plate flow chamber (Beri et al., 2020). To ensure sufficient spacing between individual cells, MDA-MB-231 and NCI-H1299 cells were seeded at ~1800 cells/cm² onto a fibronectin (2 μg/cm²) coated glass plate and incubated overnight. PC-3 cells were found to detach more consistently on a collagen I (1 μg/cm²) coated glass plate and seeded lower at 1500 cells/cm2. For each cell line, PBS free of magnesium and calcium and with 4.5 g/L of dextrose was used to shear cells. Shear stresses used to detach the weakly adherent (WA) population were selected to collect about 20,000 cells at a given flow rate (3 min at 30 dynes/cm² for MDA-MB-231, 3 min at 60 dynes/cm² for PC-3 and NCI-H1299 cells). The strongly adherent (SA) population was collected after washing away the intermediate population at a higher shear stress (2 min 500 at dynes/cm² for MDA-MB-231, 5 min at 300 dynes/cm² for NCI-H1299, and 2 min at 750 dynes/cm² for PC-3), and detaching the remaining SA population using 0.25% trypsin-EDTA. Media was then pumped though the device to neutralize the trypsin and collect the SA cells. Collected cells were then seeded onto hydrogels and allowed to adhere for at least 2 hours prior to imaging.

Population-Based Adhesion Assay

Cells were seeded onto 0.35 and 1.8 kPa hydrogels attached to 25 mm glass coverslips that were functionalized with 10 μg/mL human fibronectin. Cells were seeded at a density ~1,800 cells/cm² to minimize cell-cell contact. Cells attached to coverslips for a minimum of 12 hrs using appropriate cell culture media at which time they were then mounted on a custom-built spinning-disk device (Boettiger, 2007), submerged into temperature-controlled PBS free of magnesium and calcium and with 4.5 g/L of dextrose, and exposed to a range of fluid shear—depending on rotational speed—for 5 min. Once spun, cells were then fixed with 3.7% formaldehyde. Cell nuclei were then stained with 4',6-Diamidino-2-Phenylindole (DAPI, 1:2500) and imaged using a CSU-X1 confocal scanner unit (Yokogawa), QuantEM:512SC camera (Photometrics), and MS-2000-WK multi-axis stage controller (Applied Scientific Instrumentation) on a Nikon Ti-S microscope. Metamorph 7.6 software and a custom-written MATLAB script (https://github.com/englea52/EnglerLab, MathWorks, Natick, MA) was used to stitched together 1500 individual images of nuclei and quantify average cell adhesion, i.e. $\tau_{50}$, which is defined as the shear stress at which 50% of the initial cell population is removed by shear stress. Shear stress was calculated based on equation 1:

$$\tau = \frac{4}{5} r \sqrt{\rho \mu \omega^3} \quad (1)$$

where r is the radial position from the center of the disk, ρ is the buffer density, μ is the buffer viscosity, and ω is the rotational velocity.

2D Migration Assays

Isolated cells were seeded at ~1500 cells/well onto step-gradient gels fixed in a 12-well plate and allowed to adhere for no more than 2 hours to ensure a random distribution across the step-gradient at the start of imaging. The cells were imaged over 24 hours using a Nikon Eclipse Ti-S microscope equipped with a temperature and CO2 controller (Pathology Devices Inc., LiveCell). Images at multiple cell positions were taken in brightfield at 10× every 15 minutes. Cell trajectories were collected and analyzed using a custom MATLAB script (https://github.com/compactmatterlab/Durotaxis, MathWorks, Natick, MA). To prevent biases due to differences in cell division on soft or stiff substrates, daughter cells were excluded in trajectory analysis. From cell trajectories, cell migration was categorized as durotactic, anti-durotactic, or adurotactic, meaning that cells migrated across the substrate stiffness boundary only from soft to stiff, only from stiff to soft, or crossed the boundary multiple times, respectively; cells never approaching the boundary were not categorized. Trajectories were used to determine the distance between each cell and its closest soft-stiff boundary and plot the distribution of cells across the boundary. For cell migrating under drug treatment, cells were treated with either DMSO, 1 µM, 10 µM, or 100 µM (S)-4'-nitro-Blebbistatin (24171, Cayman Chemical Co.) or lysophosphatidic acid and imaged 3 hours after treatment for up to 24 hours.

Traction Force Microscopy

Traction forces were measured as previously described and calculated using a custom MATLAB script (Lo Sardo et al., 2018). Cells were seeded on to single-modulus polyacrylamide hydrogels with an elasticity matching their respective tumor microenvironment. Prepolymer solutions contained 2% (v/v) of 0.2 µm diameter 580/605 FluoSpheres microspheres (Invitrogen). Gels were prepared as previously described (Beri et al., 2020) in 24-well glass bottom plates (Cellvis). Cell were seeded at ~5,000 cells per well and allowed to adhere for at least 3 hours. Brightfield images were taken at 60× to obtain cell areas as measured in ImageJ. Bead images were then captured every minute for 30 minutes. Reference images were then taken after removing the cells with 10% (v/v) Triton X solution. Traction forces were determined from the traction stress map and normalized to cell area.

Computational Modeling

To understand how durotaxis and adurotaxis can occur due to differences in cell contractility and adhesion dynamics, a computational model was built that incorporates focal adhesion formation, stress fiber (SF) mediated force generation, and catch or slip bond dynamics between the cell receptors and surface adhesion sites. This model is described in detail below—

1) A cell is defined by a central point. A random number of stress fibers, obtained from a Poisson distribution with mean $\mu_S\%$, are generated about the central point. Each stress fiber has an initial length equal to the radius of the cell (5 µm) and is oriented radially. The angular distribution of these stress fiber is uniform from 0 to $2\pi$ radian.

2) These stress fibers can then grow in length radially based on the rate of actin polymerization ($v_{act\_L}$ if along the leading edge, defined by a region within $-\pi/2$ and $\pi/2$ radians of the cell migration direction, or $v_{act\_T}$ if in the direction of the trailing edge, a region complimentary to the leading edge) or shrink in length based on the rate of depolymerization ($v_{ret}$). (Initial cell migration direction is picked randomly, though this changes as described in part 7). The stress fibers switch from polymerization to depolymerization sporadically at time intervals generated from an exponential random number based on an average retraction time ($t_{ret}$), while depolymerization stops when the stress fiber reaches a minimum length (assumed to be the cell radius). The polymerizing and depolymerizing stress fibers are free to diffuse angularly about the cell center, with a diffusion coefficient dependent on the length of the SF (Heyes, 2019), equation 2.

$$D_{rot} = \frac{3k_B T in(L/d_{act})}{\pi \eta L^3} \qquad (2)$$

Here $k_B$ is Boltzmann's constant, T is temperature, L is the length of the actin filament, $d_{act}$ is the diameter of an F-actin, and $\eta$ is the viscosity of the cytoplasm.

3) Both polymerizing and depolymerizing SFs can bind to the substrate at their free end and begin to form a focal adhesion via integrin-substrate bonds. This arrests the growth, shrinking and diffusion of the SF. The newly formed ECM-integrin-SF complex may be comprised of solely an adaptor protein (i.e. paxillin (Schaller, 2001), zyxin (Hansen and Kwiatkowski, 2013), etc. (Legate et al., 2006; Wu, 2005; Wu and Dedhar, 2001)), an adapter protein with a stress sensor protein (i.e. vinculin (Grashoff et al., 2010; Rio et al., 2009), talin (Burridge and Guilluy, 2016; Rio et al., 2009)), or branched (i.e. Apr2/3 (Goley and Welch, 2006)) with some combination of adapter and tension sensor proteins. The dynamics of these protein interactions are modeled by first determining the SF-integrin-ECM binding probability, calculated by equation 3, $$P_{on} = 1 - e^{-\Delta t k_{on}} \qquad (3)$$

where $\Delta t$ is the model's timestep and $k_{on}$ is the assembly rate of the SF-integrin-ECM complex. The number of integrins bound to the SF is determined stochastically using the Poisson distribution with an average given by the average number of integrins/F-actin ($\mu_{Int}$). It was assumed that stress fibers with more than one integrin have a branching protein already bound to the SF prior to assembly of the complex. Likewise, each integrin has a certain probability ($P_{tal}$) of being bound to a stress sensor protein prior to complex assembly.

4) Integrin-ECM bonds have a certain probability of unbinding based on the applied load on each bond via the SF and the catch or slip bond dynamics measured experimentally by Kong et al. (Kong et al., 2009) and calculated by equation 4, $$P_{off} = 1 - e^{-\Delta t k_{off}(f)} \qquad (4a)$$

$$k_{off}(f) = [Ae^{-f\xi/K_B T} + (Be^{f\xi/K_B T} + Ce^{-f\xi/K_B T})^{-1}]^{-1} \text{ for catch} \qquad (4b)$$

$$k_{off}(f) = K_0 e^{f/F_b} \text{ for slip} \qquad (4c)$$

where A, B, and C are constants, $\xi$ is the unbinding length, and $f$ is the load on an individual bond. For slip bonds, $K_0$ is the unloaded off rate and $F_b$ is the characteristic bond rupture force (Bangasser and Odde, 2013). When a single SF is bound to multiple integrin-ECM bonds, the SF forces is distributed equally across each of these bonds.

5) The SF force increases exponentially with time based on equation 5, as derived in (Schwarz et al., 2006)

$$F = F_S\left(1 - e^{-v_0 K_{ecm} t/F_S}\right) \qquad (5)$$

where $F_S$ is the max SF force, determined by the myosin motor force ($F_{myo}$) times the number of myosin motors ($\eta_{myo}$). $v_0$ is the myosin sliding velocity and $K_{ecm}$ is the underlying ECM stiffness. The model is based on the linear force velocity relationship of molecular motors such as non-muscle myosin II, (Howard, 2001) and a simple two-spring model. The stiffness of the ECM is converted from the user defined Young's modulus ($E_{stiff}$, $E_{soft}$) by multiplying the modulus with a characteristic length (set to 0.1 µm) based on the order of magnitude for molecular sensing of myosin and related motor protein structures, e.g. thin filaments. The ECM stiffness value is spatially varied to simulate the photopatterned PA gels with a gradient length ($L_{grad}$) of 10 µm between the soft and stiff regions, as determined from AFM measurements. The stiffness of the protein complexes involved in the ECM bond is neglected as they are an order of magnitude stiffer than the underlying substrate.

6) If a tension sensor protein experiences a sufficiently large force ($f > F_{thres}$) it opens actin binding sites for recruiting new SFs (Grashoff et al., 2010; Rio et al., 2009), leading to FA growth and maturation. A new SFs (not one of the existing SFs) will bind to this open site with a given probability determined by equation 6, $$P_{Act} = 1 - e^{-t_{SF} K_{Act}} \tag{6}$$

where $t_{SF}$ is the time the binding site has been open and $K_{Act}$ is the SF binding rate. Number of new SFs that can be recruited is limited by a finite max number of SFs possible in the cell ($n_{SF}$). The new stress fibers are not explicitly simulated as the initial free SFs described in part 2, but are included as newly formed ECM-Integrin-SF complexes described in part 3, within the vicinity of and parallel to the recruiting ECM-Integrin-SF complex.

7) The forces at all bound ECM-Integrin-SF complexes are then summed ($\Sigma F\_$) to get the net force on the cell, which is divided by the friction factor due to bound integrins to calculate the distance the cell will move before the next time step, equation 7.

$$\vec{d} = \Delta t \frac{\sum \vec{F}_i}{n_b \Pi} \tag{7}$$

where F is force the force generated by each SF, $\eta_b$ number of active integrin bonds, and $\Pi$ is the friction factor for an individual bond. The direction of migration also determines the new leading and trailing edges of the cell.

8) SF ends attached to active integrin bonds remain stationary in space as the cell moves. ECM-Integrin-SF complexes deteriorate if all integrin-ECM bonds an SF is attached to are broken. When no ECM-Integrin-SF complexes remain attached in the FA, the FA is dissolved releasing a free SF into the cell. The position of the free SF end is updated with the cell position before the next iteration begins.

9) During any timestep, the dynamics of the free SFs (SFs not bound to integrins) are determined as described in part 2.

Values for each parameter used in this model are shown in Table 5. 24 hours of cell migration was simulated, and the cell position were tracked relative to the soft/stiff boundary as in the time-lapse microscopy images, (Video not shown). The model loops through the flow schematic in FIG. 28A and described in detail above, with each loop comprising a single timestep.

Immunofluorescence Staining and FA Analysis

MDA-MB-231 cells were seeded onto single moduli gels (either 0.48 kPa or 1.8 kPa) and allowed to adhere overnight. Cells were washed with PBS with cations and fixed with 4% paraformaldehyde for 10 minutes. Fixed cells were then stained with deep red cell mask in PBS (1:1000 v/v; Thermofisher Scientific) for 10 minutes. 0.1% TritonX in PBS was used to permeabilize the cells for 10 minutes. Blocking was done with PBS supplemented with FBS (10% v/v, Gemini Bio) for 20 minutes at room temperature. Cells were incubated overnight at 4° C. with primary paxillin antibody (1:500; ab32084, Abcam) in blocking buffer. Gels were then washed with blocking buffer and incubated with secondary Alexa Fluor 488-conjugated antibody (1:500; A11008, Invitrogen) and rhodamine phalloidin (1:3000, R415, Thermofisher Scientific) for 1 hour at room temperature, followed by Hoechst 33342 (1:2000; Invitrogen) in DI water for 10 minutes. Coverslips were then mounted onto slides with Flouromount-G (Southern Biotech). Samples were imaged using a Zeiss LSM 780 confocal microscope (Zeiss) with a 63× oil-immersion objective. A custom MATLAB script was used to measure cell area and size and number of focal adhesions.

Cytokine Antibody Array

Media was analyzed using the Proteome Profiler Human XL Cytokine Array (R&D Systems). Briefly, membranes were blocked for 1 hour using array buffer, and media was then combined with array buffer overnight at 4° C. with rocking. Membranes were washed, incubated with the antibody cocktail diluted for 1 hour, washed, and incubated with streptavidin-HRP for 30 minutes, and finally treated with chemiluminescent reagent mix; membranes were exposed to film and imaged. Pixel quantification was performed in ImageJ and normalized to positive and loading controls. Conditioned media for SA and WA cells on 0.35 and 1.8 kPa substrates were normalized to internal loading control spots and plotted against each other.

Quantification and Statistical Analysis

Comparisons for migration speeds and traction forces were done using a two-tailed unpaired t-test or one-way ANOVA with Tukey test for multiple comparisons for the indicated comparisons where appropriate and as indicated. Categorical comparisons for durotactic, anti-durotactic, and adurotactic cells were done using a Fisher's exact test using definitions from the 2D migration assay section of this manuscript; again, durotactic cells were defined as cells that are on the soft region at the start of the time lapse and migrated to the stiff in the 24 hours of imaging, and vice versa for anti-durotactic. Adurotactic cells were defined as cells that crossed the boundary at some point during imaging and returned to the substrate they started on. Probability density estimations were calculated using MATLAB's kernel smoothing function and plotted to visualize cell distributions at the start of imaging (t=0 h) and after 24 hours of imaging (t=24 h). The theoretical optimum bandwidth for the kernel smoothing function was used to generate reasonably smooth curves. Despite potential errors near the edges of the bounded region (−57.5 to 85 μm of the boundary), to reduce sensitivity to sampling error, an unbounded KDE was used. This does not affect the cell density estimation near the stiffness gradient. P-values for all analyses, *, $P<0.05$; , $P<0.01$; *, $P<0.001$; and ****, $P<0.0001$. Outliers were removed only in plotting using MATLAB's quartiles method, so box-and-whisker plots remove points outside the whisker ends, defined by 1.5 interquartile ranges above the upper quartile or below the lower quartile. Other error bars were expressed as mean±SD. Statistical analyses were done using MATLAB.

Movies were generated showing migration of cells on hydrogels with stiffness gradients, Related to FIG. 23; migration of anti-durotactic cell on hydrogels with stiffness gradients, Related 610 to FIG. 23; migration of adurotactic cells on hydrogels with stiffness gradients, Related to FIG. 23; weakly adherent cells exhibit higher adurotactic behavior, Related to FIG. 23; Durotaxis model for Bond Stall Force of 30 pN, Related to FIG. 29; Durotaxis model for Bond Stall Force of 45 pN, Related to FIG. 29; Durotaxis model indicates that Bond Stall Force drives adurotactic behavior, Related to FIG. 29 (data now shown).

TABLE 5

Model parameters for the cell durotaxis model. Parameters are listed in order of appearance in methods section. Note that for some figure, $E_{stiff}$ and $E_{soft}$ were changed as indicated.

| Parameter | Description | Value | Source |
|---|---|---|---|
| $\mu_{SF}$ | Average assembly sites/cell | Adjustable, 50 | (Elosegui-Artola et al., 2014) |
| $V_{act\_L}$ | Actin assembly, trailing edge | 0.2 μm s$^{-1}$ | (Pollard, 1986; Prahl et al., 2020; Vavylonis et al., 2005) |
| $V_{act\_T}$ | Actin assembly, trailing edge | 0.1 μm s$^{-1}$ | (Pollard, 1986; Prahl et al., 2020; Vavylonis et al., 2005) |
| $V_{ret}$ | Actin disassembly velocity | 0.5 μm s$^{-1}$ | (Vavylonis et al., 2005) |
| $t_{ret}$ | Retraction Time | 10 s | (Bosgraaf and Van Haastert, 2009b, 2009a) |
| $D_{rot}$ | Rotational diffusion constant of F-actin | Calculated, s$^{-1}$ | |
| $k_B$ | Boltzmann's constant | 1.3806E−23 kg m$^2$ s$^{-2}$ K$^{-1}$ | |
| T | Temperature | 310.15K | |
| L | Length of actin filament | Calculated, μm | |
| $d_{act}$ | Diameter of Actin | 7 nm | (Cooper, 2000) |
| η | Cytoplasm (water) viscosity @ 37 C | 0.0006913 Pa s | |
| $K_{on}$ | Integrin-SF assembly rate | 0.1 s$^{-1}$ | (Bidone et al., 2019; Vicente-Manzanares et al., 2009) |
| $\mu_{int}$ | Average Integrins/F-actin | 1 | (Blystone, 2004) |
| $P_{tal}$ | Probability of force-sensor protein | 0.7 | (Himmel et al., 2009) |
| $k_{off}$ | Unbinding rate | Calculated, s$^{-1}$ | |
| A | Fitting constant | 3.309 | |
| B | Fitting constant | 0.0003942 | |
| C | Fitting constant | 58.19 | |
| ζ | Unbinding length | 0.7959 nm | (Kong et al., 2009) |
| $k_0$ | Unloaded off rate | | |
| $F_b$ | Bond rupture force | | |
| $F_s$ | Max filament force | $F_{myo} \times n_{myo}$ | |
| $F_{myo}$ | Myosin Motor Force | 2 pN | (Molloy et al., 1995) |
| $n_{myo}$ | # of Myosin Motors/F-actin | Adjustable, 10-25 | (Cooper and Hausman, 2007) |
| $V_0$ | Myosin sliding velocity | 1 μm s$^{-1}$ | (Brizendine et al., 2015) |
| $K_{ECM}$ | ECM stiffness | ECM modulus × 0.1 μmlength scale typical for myosin sensing | |
| $E_{stiff}$ | Young's modulus, Stiff | 1800 Pa, Measured experimentally | |
| $E_{soft}$ | Young's modulus, Soft | 350 Pa, Measured experimentally | |
| $L_{grad}$ | Gradient Length | 10 μm, from AFM measurements | |
| $F_{thres}$ | Force sensor threshold | 1 pN | (Grashoff et al., 2010; Rio et al., 2009) |
| $K_{act}$ | Actin-Talin assembly rate | 1 s$^{-1}$ | (Tapia-Rojo et al., 2020) |
| $n_{SF}$ | Maximum SFs/FA | Adjustable, 100 | (Prahl et al., 2020) |
| Π | Bond friction factor | 2 × 10$^{-5}$ kg s$^{-1}$ | (Pompe et al., 2011) |

Example 5

The disclosure in the above Examples as well as in Beri et al, 2020 (Cancer Res. 2020 Feb. 15; 80(4):901-911. Epub 2019 Dec. 19.) established a method and a device to sort cells based on adhesion strength. It also established that breast and lung prostate cancer cell populations, when sorted by adhesion, would stratify their ability to migrate (weakest being most migratory). Finally, it showed that the transcriptional profile of the most weakly adherent breast cancer cell population, when mapped into triple negative breast cancer patient outcomes from The Cancer Genome Atlas (TCGA), corresponds to statistically shorter disease free and progression free intervals.

Figures 31A, 31B, 31C:
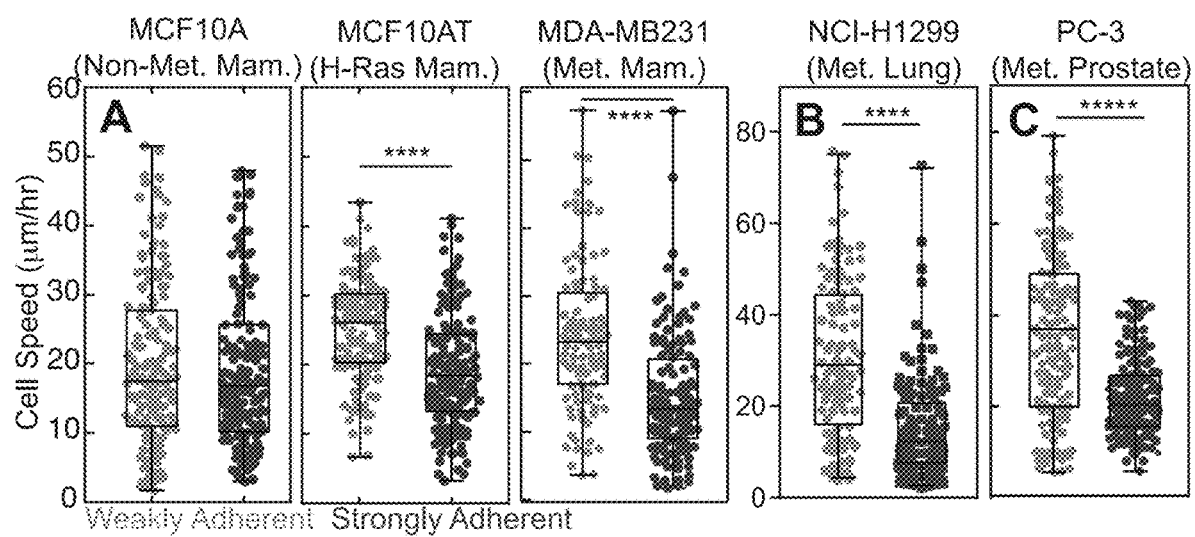
FIGS. 31A-31C provide migration speed of adhesion-sorted cells.

Example 4 uses the technology as disclosed herein to sort cells and then look at their ability to migrate in vitro on gradients of stiffness that mirror breast, prostate, and lung cancer. Example 4 further extends the use to the separation technology to a prostate cancer cells, which shows faster migration for the more weakly adherent prostate cancer cell population. All data sets are shown in FIG. 31 for clarity; when sorted for adhesion strength, non-metastatic breast cells do not show differential migration (MCF10A; FIG. 31A, left). When an oncogene is turned on, i.e. H-Ras, the cells sort and migration stratifies (FIG. 31A, middle) along with metastatic cells (FIG. 31A, right). Lung and prostate also show this pattern (FIGS. 31B-31C).

These data broaden the link between adhesion and migration, but do not address invasion in vivo. Thus, unsorted, metastatic cells were injected into the 4$^{th}$ inguinal mammary fat pad of nude mice. Tumors were resected after 6 weeks. Tumor cells were sorted (which had been marked by GFP expression) and it was determined if those cells that migrated out were strongly or weakly adherent to their environment (FIG. 32A). When comparing tumor and stroma, there were more injected cells in the tumor than had migrated out (FIG. 32B). However, those cells migrating out of the tumor were more weakly adherent (FIG. 32C). When computing the tumor:stroma adhesion strength ration per animal, it was found that stromal cells are ~50% less adhesive (FIG. 32D). These data confirm that those cells most likely to migrate out of a tumor are weakly adherent.

Figures 33A, 33B, 33C, 33D, 33E, 33F:
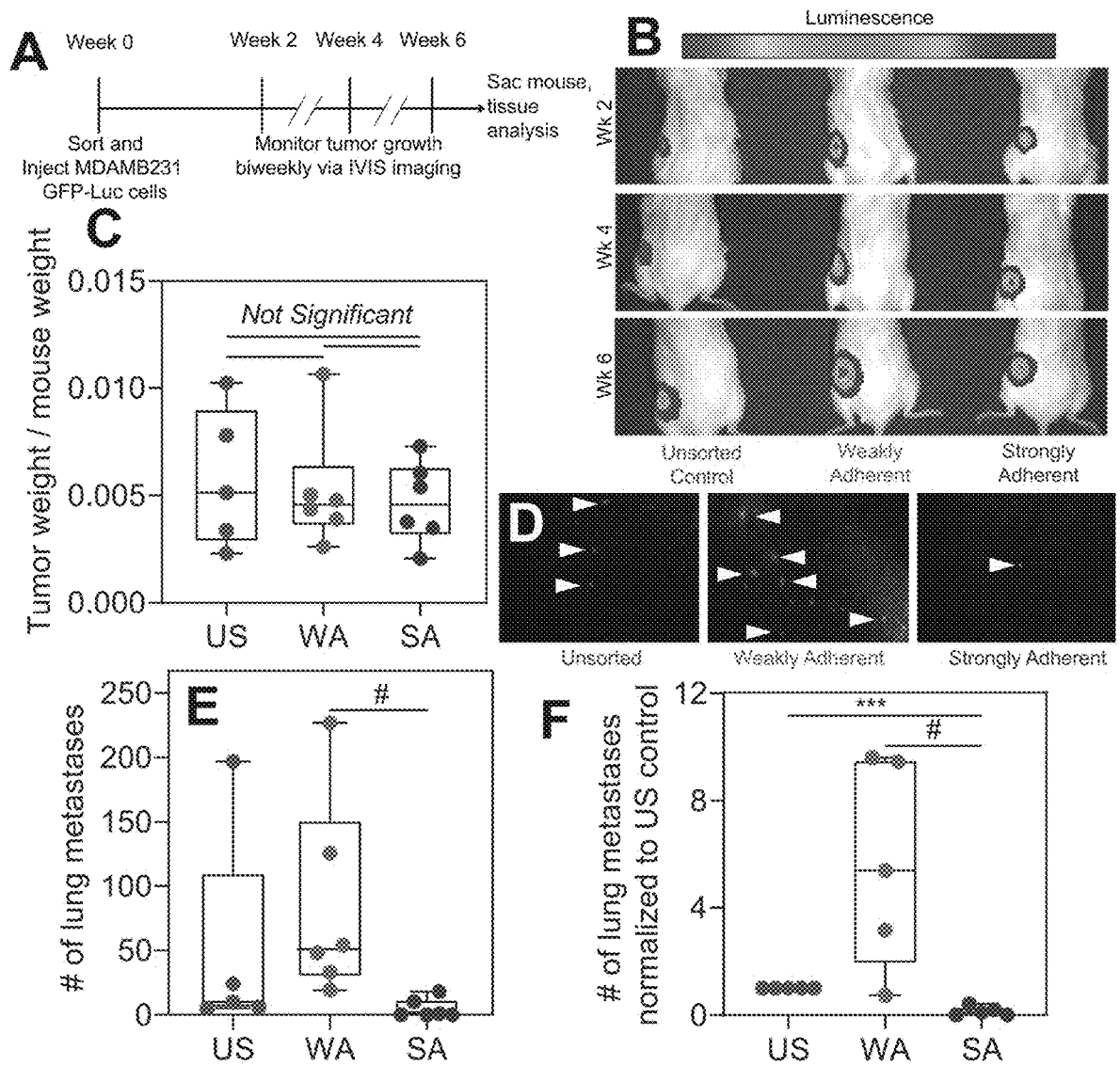
FIGS. 33A-33F provide that weakly adherent cells metastasize more than strongly adherent or unsorted MDMBA231 cells.

Since unsorted cells showed that a portion of the tumor could disseminate and they were more weakly adherent, if raises the question of whether tumors composed exclusively of weakly adherent cells metastasize more frequently. Thus, adhesion sorting was performed with the device as disclosed herein to yield weakly adherent, strongly adherent, and unselected populations of mammary cells (MDAMB231). Cells were injected into the 4$^{th}$ inguinal mammary fat pad. The animals were non-invasively imaged (IVIS) for 6 weeks. Finally the lungs were excised for analysis post-mortem (FIG. 33A). Up through 6 weeks post injection, IVIS imaging showed tumors growing (FIG. 33B). At 6 weeks, tumors were excised, showing no changes in growth as a result of adhesion selection using the device as disclosed herein (FIG. 33C). However consistent with the hypothesis as proposed herein about weakly adherent cells being detrimental to patient outcomes, it was observed that when tumors were comprised of only weakly adherent cells, breast cancer metastasized to the lungs more frequently for weakly adherent cells, whereas for strongly adherent cells, they almost never did (FIGS. 33D-33F); unsorted cells exhibited intermediate metastatic potential consistent with containing both populations but not exclusively one or the other.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

Although the disclosure has been described with reference to the above examples, it will be understood that modifications and variations are encompassed within the spirit and scope of the disclosure. Accordingly, the disclosure is limited only by the following claims.

REFERENCES

The following references are hereby incorporated by reference in their entireties.

REFERENCE LIST #1 FOR THOSE CITED DOCUMENTS REFERENCED AS NUMBERS IN BRACKETS WITHIN THE SPECIFICATION

1. P. S. Steeg, Targeting metastasis. Nature Reviews Cancer 16, 201-218 (2016).
2. S. R. L., M. K. D., J. Ahmedin, Cancer statistics, 2018. CA: A Cancer Journal for 587 Clinicians 68, 7-30 (2018).
3. E. Quintana et al., Efficient tumour formation by single human melanoma cells. Nature 589 456, 593 (2008).
4. K. Polyak, Heterogeneity in breast cancer. The Journal of Clinical Investigation 121, 591 3786-3788 (2011).
5. X.-x. Sun, Q. Yu, Intra-tumor heterogeneity of cancer cells and its implications for cancer treatment. Acta Pharmacologica Sinica 36, 1219 (2015).
6. Y. Liu et al., Lack of correlation of stem cell markers in breast cancer stem cells. British Journal Of Cancer 110, 2063 (2014).
7. C. Alibert, B. Goud, J. B. Manneville, Are cancer cells really softer than normal cells? 597 Biology of the Cell 109, 167-189 (2017).
8. J. S. Dudani, D. R. Gossett, H. T. K. Tse, D. Di Carlo, Pinched-flow hydrodynamic stretching of single-cells. Lab on a Chip 13, 3728-3734 (2013).
9. D. R. Gossett et al., Hydrodynamic stretching of single cells for large population mechanical phenotyping. Proceedings of the National Academy of Sciences of the United States of America 109, 7630-7635 (2012).
10. D. P. Qi et al., Screening cell mechanotype by parallel microfiltration. Scientific Reports 5, (2015).
11. K. D. Nyberg et al., The physical origins of transit time measurements for rapid, single cell mechanotyping. Lab on a Chip 16, 3330-3339 (2016).
12. P. Beri et al., Biomaterials to model and measure epithelial cancers. Nature Reviews Materials, (2018).
13. A. J. Ridley et al., Cell migration: integrating signals from front to back. Science 302, 1704-1709 (2003).
14. P. DiMilla, J. Stone, J. Quinn, S. Albelda, D. Lauffenburger, Maximal migration of human smooth muscle cells on fibronectin and type IV collagen occurs at an intermediate attachment strength. The Journal of Cell Biology 122, 729-737 (1993).
15. K. Bijian et al., Targeting focal adhesion turnover in invasive breast cancer cells by the purine derivative reversine. British Journal of Cancer 109, 2810-2818 (2013).
16. I. Indra et al., An in vitro correlation of mechanical forces and metastatic capacity. Physical Biology 8, (2011).
17. N. E. Reticker-Flynn et al., A combinatorial extracellular matrix platform identifies cell extracellular matrix interactions that correlate with metastasis. Nature Communications 3, 1122 (2012).
18. C. M. Yates, H. M. McGettrick, G. B. Nash, G. E. Rainger, in Metastasis Research Protocols, M. Dwek, U. Schumacher, S. A. Brooks, Eds. (Springer New York, New York, NY, 2014), pp. 57-75.
19. C. P. Palmer et al., Single cell adhesion measuring apparatus (SCAMA): application to cancer cell lines of different metastatic potential and voltage-gated Na+ channel expression. European Biophysics Journal 37, 359-368 (2008).
20. A. J. Garcia, N. D. Gallant, Stick and grip. Cell Biochemistry and Biophysics 39, 61-73 (2003).
21. M. Veiseh et al., Cellular heterogeneity profiling by hyaluronan probes reveals an invasive but slow-growing breast tumor subset. Proceedings of the National Academy of Sciences 111, E1731-E1739 (2014).
22. Piyush B. Gupta et al., Stochastic State Transitions Give Rise to Phenotypic Equilibrium in Populations of Cancer Cells. Cell 146, 633-644 (2011).
23. Fuhrmann, A., et al. Biophysical Journal 112.4 (2017): 736-745.
24. A. Fuhrmann, J. Li, S. Chien, A. J. Engler, Cation Type Specific Cell Remodeling Regulates Attachment Strength. PLOS ONE 9, e102424 (2014).
25. M. H. Seltzer, F. E. Rosato, M. J. Fletcher, Serum and tissue magnesium levels in human breast carcinoma. J Surg Res 10, 159-162 (1970).
26. M. H. Seltzer, F. E. Rosato, M. J. Fletcher, Serum and tissue calcium in human breast carcinoma. Cancer Res 30, 615-616 (1970).
27. V. Lo Sardo et al., Unveiling the Role of the Most Impactful Cardiovascular Risk Locus through Haplotype Editing. Cell 175, 1796-1810.e1720 (2018).
28. A. Kumar et al., Mechanical activation of noncoding-RNA-mediated regulation of disease-associated phenotypes in human cardiomyocytes. Nature Biomedical Engineering 3, 137-146 (2019).
29. M. Martin, Cutadapt removes adapter sequences from high-throughput sequencing reads. 2011 17, 3 (2011).
30. S. Andrews. (2010) FAST QC: A quality control tool for high throughput sequence data. www.bioinformatics.babraham.ac.uk/projects/fastqc/
31. A. Dobin et al., STAR: ultrafast universal RNA-seq aligner. Bioinformatics 29, 15-21 (2012).
32. S. Anders, P. T. Pyl, W. Huber, HTSeq—a Python framework to work with high throughput sequencing data. Bioinformatics 31, 166-169 (2014).
33. M. I. Love, W. Huber, S. Anders, Moderated estimation of fold change and dispersion for RNA-seq data with DESeq2. Genome Biology 15, 550 (2014).
34. L. Wang, S. Wang, W. Li, RSeQC: quality control of RNA-seq experiments. Bioinformatics 28, 2184-2185 (2012).
35. C. Hennig. Cran-package fpc. cran.r-project.org/web/packages/fpc/
36. S. Heinz et al., Simple Combinations of Lineage-Determining Transcription Factors Prime cis-Regulatory Elements Required for Macrophage and B Cell Identities. Molecular Cell 38, 576-589 (2010).
37. J. Liu et al., An Integrated TCGA Pan-Cancer Clinical Data Resource to Drive High-Quality Survival Outcome Analytics. Cell 173, 400-416.e411 (2018).
38. H. G. H., W. S. R., MCF-10AT: A Model for Human Breast Cancer Development. The Breast Journal 5, 122-129 (1999).
39. C. T. Mierke et al., Vinculin facilitates cell invasion into three-dimensional collagen matrices. The Journal of biological chemistry 285, 13121-13130 (2010).
40. C. M. Kraning-Rush, J. P. Califano, C. A. Reinhart-King, Cellular traction stresses increase with increasing metastatic potential. PloS one 7, e32572-e32572 (2012).
41. M. J. Stroud, R. A. Kammerer, C. Ballestrem, Characterization of G2L3 (GAS2-like 3), a new microtubule- and actin-binding protein related to spectraplakins. The Journal of biological chemistry 286, 24987-24995 (2011).
42. P. Friedl, K. Wolf, J. Lammerding, Nuclear mechanics during cell migration. Current Opinion in Cell Biology 23, 55-64 (2011).
43. A. Jayo et al., Fascin Regulates Nuclear Movement and Deformation in Migrating Cells. Developmental Cell 38, 371-383 (2016).
44. N. Kumar, S. Gupta, S. Dabral, S. Singh, S. Sehrawat, Role of exchange protein directly activated by cAMP (EPAC1) in breast cancer cell migration and apoptosis. Molecular and Cellular Biochemistry 430, 115-125 (2017).
45. M.-H. Yang et al., MALAT1 promotes colorectal cancer cell proliferation/migration/invasion via PRKA kinase anchor protein 9. Biochimica et Biophysica Acta (BBA)-Molecular Basis of Disease 1852, 166-174 (2015).
46. S. M. Ahmed et al., KIF14 negatively regulates Rap1a-Radil signaling during breast cancer progression. The Journal of Cell Biology 199, 951-967 (2012).
47. B. L. Thériault et al., Transcriptional and Epigenetic Regulation of KIF14 Overexpression in Ovarian Cancer. PLOS ONE 9, e91540 (2014).
48. L. Mi et al., The metastatic suppressor NDRG1 inhibits EMT, migration and invasion through interaction and promotion of caveolin-1 ubiquitylation in human colorectal cancer cells. Oncogene 36, 4323 (2017).
49. J. Hu, A. S. Verkman, Increased migration and metastatic potential of tumor cells expressing aquaporin water channels. The FASEB Journal 20, 1892-1894 (2006).
50. J. K. Slack et al., Alterations in the focal adhesion kinase/Src signal transduction pathway correlate with increased migratory capacity of prostate carcinoma cells. Oncogene 20, 1152 (2001).
51. M. C. Frame, V. J. Fincham, N. O. Carragher, J. A. Wyke, v-SRC'S hold over actin and cell adhesions. Nature Reviews Molecular Cell Biology 3, 233 (2002).
52. G. W. McLean et al., The role of focal-adhesion kinase in cancer—a new therapeutic opportunity. Nature Reviews Cancer 5, 505 (2005).
53. R. Feng et al., Targeting the Microtubular Network as a New Antimyeloma Strategy. Molecular Cancer Therapeutics 10, 1886-1896 (2011).

REFERENCE LIST #2 FOR THOSE DOCUMENTS REFERENCED BY SUPERSCRIPTED NUMBERS WITHIN THE SPECIFICATION

[1] Weigelt, B., Peterse, J. L. & van't Veer, L. J. Breast cancer metastasis: markers and models. Nat Rev Cancer 5, 591-602, doi:10.1038/nrc1670 (2005).
[2] Gallardo, E. et al. miR-34a as a prognostic marker of relapse in surgically resected non-small-cell lung cancer. Carcinogenesis 30, 1903-1909, doi:10.1093/carcin/bgp219 (2009).
[3] Zelefsky, M. J. et al. High-dose intensity modulated radiation therapy for prostate cancer: early toxicity and biochemical outcome in 772 patients. Int J Radiat Oncol Biol Phys 53, 1111-1116 (2002).
[4] Liu, Y. et al. Lack of correlation of stem cell markers in breast cancer stem cells. Br J Cancer 110, 2063-2071, doi:10.1038/bjc.2014.105 (2014).
[5] Wirtz, D., Konstantopoulos, K. & Searson, P. C. The physics of cancer: the role of physical interactions and mechanical forces in metastasis. Nat Rev Cancer 11, 512-522, doi:10.1038/nrc3080 (2011).

[6] Physical Sciences—Oncology Centers, N. et al. A physical sciences network characterization of nontumorigenic and metastatic cells. Scientific reports 3, 1449, doi:10.1038/srep01449 (2013).

[7] Bijian, K. et al. Targeting focal adhesion turnover in invasive breast cancer cells by the purine derivative reversine. Br J Cancer 109, 2810-2818, doi:10.1038/bjc.2013.675 (2013).

[8] Palmer, C. P. et al. Single cell adhesion measuring apparatus (SCAMA): application to cancer cell lines of different metastatic potential and voltage-gated Na+ channel expression. Eur Biophys J 37, 359-368, doi:10.1007/s00249-007-0219-2 (2008).

[9] Reticker-Flynn, N. E. et al. A combinatorial extracellular matrix platform identifies cellextracellular matrix interactions that correlate with metastasis. Nature communications 3, 1122, doi:10.1038/ncomms2128 (2012).

[10] Fischer, E. G. et al. Tumor cell adhesion and migration supported by interaction of a receptorprotease complex with its inhibitor. J Clin Invest 104, 1213-1221, doi:10.1172/JCI7750 (1999).

[10] Fuhrmann, A., Banisadr, A., Beri, P., Tlsty, T. D. & Engler, A. J. Metastatic State of Cancer Cells May Be Indicated by Adhesion Strength. Biophys J 112, 736-745, doi:10.1016/j.bpj.2016.12.038 (2017).

[12] Seltzer, M. H., Rosato, F. E. & Fletcher, M. J. Serum and tissue magnesium levels in human breast carcinoma. J Surg Res 10, 159-162 (1970).

[13] Seltzer, M. H., Rosato, F. E. & Fletcher, M. J. Serum and tissue calcium in human breast carcinoma. Cancer Res 30, 615-616 (1970).

[14] Boettiger, D. Quantitative measurements of integrin-mediated adhesion to extracellular matrix. Methods Enzymol. 426, 1-25 (2007).

[15] Fuhrmann, A., Li, J., Chien, S. & Engler, A. J. Cation type specific cell remodeling regulates attachment strength. PLoS One 9, e102424, doi:10.1371/journal.pone.0102424 (2014).

[16] Taneja, P. et al. Classical and Novel Prognostic Markers for Breast Cancer and their Clinical Significance. Clin Med Insights Oncol 4, 15-34 (2010).

[17] Mehlen, P. & Puisieux, A. Metastasis: a question of life or death. Nat Rev Cancer 6, 449-458, doi:10.1038/nrc1886 (2006).

[18] Niravath, P. & Osborne, C. K. in Diseases of the Breast (eds J. R. Harris, M. E. Lippman, M. Morrow, & C. K Osborne) Ch. 31, 488-494 (Lippincott Williams & Wilkins, 2014).

[19] Wang, C. et al. Evaluation of CD44 and CD133 as cancer stem cell markers for colorectal cancer. Oncol Rep 28, 1301-1308, doi:10.3892/or.2012.1951 (2012).

[20] Sahlberg, S. H., Spiegelberg, D., Glimelius, B., Stenerlow, B. & Nestor, M. Evaluation of cancer stem cell markers CD133, CD44, CD24: association with AKT isoforms and radiation resistance in colon cancer cells. PLoS One 9, e94621, doi:10.1371/journal.pone.0094621 (2014).

[21] Vizio, B. et al. Comparative evaluation of cancer stem cell markers in normal pancreas and pancreatic ductal adenocarcinoma. Oncol Rep 27, 69-76, doi:10.3892/or.2011.1461 (2012).

[22] Alix-Panabieres, C. et al. Detection and characterization of putative metastatic precursor cells in cancer patients. Clin Chem 53, 537-539, doi:10.1373/clinchem.2006.079509 (2007).

[23] Kemper, K. et al. The AC133 epitope, but not the CD133 protein, is lost upon cancer stem cell differentiation. Cancer Res 70, 719-729, doi:10.1158/0008-5472.CAN-09-1820 (2010).

[24] Ricci-Vitiani, L. et al. Identification and expansion of human colon-cancer-initiating cells. Nature 445, 111-115, doi:10.1038/nature05384 (2007).

[25] Medema, J. P. Cancer stem cells: the challenges ahead. Nat Cell Biol 15, 338-344, doi:10.1038/ncb2717 (2013).

[26] Tse, H. T. et al. Quantitative diagnosis of malignant pleural effusions by single-cell mechanophenotyping. Sci Transl Med 5, 212ra163, doi:10.1126/scitranslmed.3006559 (2013).

[27] Mach, A. J., Kim, J. H., Arshi, A., Hur, S. C. & Di Carlo, D. Automated cellular sample preparation using a Centrifuge-on-a-Chip. Lab Chip 11, 2827-2834, doi:10.1039/c1lc20330d (2011).

[28] Lafrenie, R. M., Buchanan, M. R. & Orr, F. W. Adhesion molecules and their role in cancer metastasis. Cell biophysics 23, 3-89 (1993).

[29] Arbiser, J. L. et al. Isolation of mouse stromal cells associated with a human tumor using differential diphtheria toxin sensitivity. Am J Pathol 155, 723-729, doi:10.1016/S0002-9440(10)65171-1 (1999).

[30] Kansy, B. A. et al. The bidirectional tumor—mesenchymal stromal cell interaction promotes the progression of head and neck cancer. Stem Cell Res Ther 5, 95, doi:10.1186/scrt484 (2014).

[31] Nasulewicz, A. et al. Magnesium deficiency inhibits primary tumor growth but favors metastasis in mice. Biochim Biophys Acta 1739, 26-32, doi:10.1016/j.bbadis.2004.08.003 (2004).

[32] Dai, Q. et al. Blood magnesium, and the interaction with calcium, on the risk of high-grade prostate cancer. PLoS One 6, e18237, doi:10.1371/journal.pone.0018237 (2011).

[33] Gupta, P. B. et al. Stochastic state transitions give rise to phenotypic equilibrium in populations of cancer cells. Cell 146, 633-644, doi:10.1016/j.cell.2011.07.026 (2011).

[34] Lu, H. et al. Microfluidic shear devices for quantitative analysis of cell adhesion. Anal Chem 76, 5257-5264, doi:10.1021/ac049837t (2004).

[35] Huth, J. et al. TimeLapseAnalyzer: multi-target analysis for live-cell imaging and time-lapse microscopy. Comput Methods Programs Biomed 104, 227-234, doi:10.1016/j.cmpb.2011.06.002 (2011).

[36] Yang, J. et al. Twist, a master regulator of morphogenesis, plays an essential role in tumor metastasis. Cell 117, 927-939, doi:10.1016/j.cell.2004.06.006 (2004).

[37] Wei, S. C. et al. Matrix stiffness drives Epithelial-Mesenchymal Transition and tumor metastasis through a Twist1-G3BP2 mechanotransduction pathway. Nature Cell Biology 17, 678-688 (2015).

[38] Labarge, M. A., Garbe, J. C. & Stampfer, M. R. Processing of human reduction mammoplasty and mastectomy tissues for cell culture. J Vis Exp, doi:10.3791/50011 (2013).

[39] Lee, M. C. et al. Single-cell analyses of transcriptional heterogeneity during drug tolerance transition in cancer cells by RNA sequencing. Proc Natl Acad Sci USA 111, E4726-4735, doi:10.1073/pnas.1404656111 (2014).

[40] Cristofanilli, M. et al. Circulating tumor cells, disease progression, and survival in metastatic breast cancer. N Engl J Med 351, 781-791, doi:10.1056/NEJMoa040766 (2004).

REFERENCE LIST #3 FOR THOSE REFERENCES CITED BY THEIR AUTHORS ACROSS THE SPECIFICATION

Ahn, B.-M., Kim, J., Ian, L., Rha, K.-H., and Kim, H.-J. (2010). Mechanical property characterization of prostate cancer using a minimally motorized indenter in an ex vivo indentation experiment. Urology 76, 1007-1011.

Bangasser, B. L., and Odde, D. J. (2013). Master equation-based analysis of a motor-clutch model for cell traction force. Cell Mol Bioeng 6, 449-459.

Beri, P., Popravko, A., Yeoman, B. M., Kumar, A., Chen, K., Hodzic, E., Chiang, A., Banisadr, A., Placone, J., Carter, H., et al. (2020). Cell adhesiveness serves as a biophysical marker for metastatic potential| Cancer Research. Cancer Research 80, 901-911.

Bidone, T. C., Skeeters, A. V., Oakes, P. W., and Voth, G. A. (2019). Multiscale model of integrin adhesion assembly. PLOS Computational Biology 15, e1007077.

Blystone, S. D. (2004). Integrating an integrin: a direct route to actin. Biochimica et Biophysica Acta (BBA)-Molecular Cell Research 1692, 47-54.

Boettiger, D. (2007). Quantitative Measurements of Integrin-Mediated Adhesion to Extracellular Matrix. In Methods in Enzymology, (Academic Press), pp. 1-25.

Bosgraaf, L., and Van Haastert, P. J. M. (2009a). The Ordered Extension of Pseudopodia by Amoeboid Cells in the Absence of External Cues. PLoS ONE 4.

Bosgraaf, L., and Van Haastert, P. J. M. (2009b). Navigation of Chemotactic Cells by Parallel Signaling to Pseudopod Persistence and Orientation. PLoS ONE 4, e6842.

Brizendine, R. K., Alcala, D. B., Carter, M. S., Haldeman, B. D., Facemyer, K. C., Baker, J. E., and Cremo, C. R. (2015). Velocities of unloaded muscle filaments are not limited by drag forces imposed by myosin cross-bridges. PNAS 112, 11235-11240.

Burgstaller, G., Oehrle, B., Gerckens, M., White, E. S., Schiller, H. B., and Eickelberg, O. (2017). The instructive extracellular matrix of the lung: basic composition and alterations in chronic lung disease. European Respiratory Journal 50.

Burridge, K., and Guilluy, C. (2016). Focal adhesions, stress fibers and mechanical tension. Exp Cell Res 343, 14-20.

Chaudhuri, O., Cooper-White, J., Janmey, P. A., Mooney, D. J., and Shenoy, V. B. (2020). Effects of extracellular matrix viscoelasticity on cellular behaviour. Nature 584, 535-546.

Cooper, G. M. (2000). Structure and Organization of Actin Filaments. The Cell: A Molecular Approach. 2nd Edition.

Cooper, G. M., and Hausman, R. E. (2007). The Cell: A Molecular Approach (ASM Press).

Cox, T. R., and Erler, J. T. (2011). Remodeling and homeostasis of the extracellular matrix: implications for fibrotic diseases and cancer. Disease Models & Mechanisms 4, 165-178.

Danuser, G., Allard, J., and Mogilner, A. (2013). Mathematical Modeling of Eukaryotic Cell Migration: Insights Beyond Experiments. Annu Rev Cell Dev Biol 29, 501-528.

DuChez, B. J., Doyle, A. D., Dimitriadis, E. K., and Yamada, K. M. (2019). Durotaxis by Human Cancer Cells. Biophysical Journal 116, 670-683.

Elosegui-Artola, A., Jorge-Penas, A., Moreno-Arotzena, O., Oregi, A., Lasa, M., Garcia-Aznar, J. M., Juan-Pardo, E. M. D., and Aldabe, R. (2014). Image Analysis for the Quantitative Comparison of Stress Fibers and Focal Adhesions. PLOS ONE 9, e107393.

Feng, J., Levine, H., Mao, X., and Sander, L. M. (2019). Cell motility, contact guidance, and durotaxis. Soft Matter 15, 4856-4864.

Fusco, S., Panzetta, V., and Netti, P. A. (2017). Mechanosensing of substrate stiffness regulates focal adhesions dynamics in cell. Meccanica 52, 3389-3398.

Goley, E. D., and Welch, M. D. (2006). The ARP2/3 complex: an actin nucleator comes of age. Nature Reviews Molecular Cell Biology 7, 713-726.

Grashoff, C., Hoffman, B. D., Brenner, M. D., Zhou, R., Parsons, M., Yang, M. T., McLean, M. A., Sligar, S. G., Chen, C. S., Ha, T., et al. (2010). Measuring mechanical tension across vinculin reveals regulation of focal adhesion dynamics. Nature 466, 263-266.

Hansen, M. D. H., and Kwiatkowski, A. V. (2013). Chapter One—Control of Actin Dynamics by Allosteric Regulation of Actin Binding Proteins. In International Review of Cell and Molecular Biology, K. W. Jeon, ed. (Academic Press), pp. 1-25.

Happe, C. L., Tenerelli, K. P., Gromova, A. K., Kolb, F., and Engler, A. J. (2017). Mechanically patterned neuromuscular junctions-in-a-dish have improved functional maturation. MBoC 28, 1950-1958.

Heyes, D. M. (2019). Translational and rotational diffusion of rod shaped molecules by molecular dynamics simulations. J. Chem. Phys. 150, 184503.

Himmel, M., Ritter, A., Rothemund, S., Pauling, B. V., Rottner, K., Gingras, A. R., and Ziegler, W. H. (2009). Control of High Affinity Interactions in the Talin C Terminus. J Biol Chem 284, 13832-13842.

Holmes, W. R., and Edelstein-Keshet, L. (2012). A Comparison of Computational Models for Eukaryotic Cell Shape and Motility. PLoS Comput Biol 8.

Howard, J. (2001). Mechanics of Motor Proteins and the Cytoskeleton (Sunderland, Mass: Sinauer Associates, Publishers).

Isomursu, A., Park, K.-Y., Hou, J., Cheng, B., Shamsan, G., Fuller, B., Kasim, J., Mahmoodi, M. M., Lu, T. J., Genin, G. M., et al. (2020). Negative durotaxis: cell movement toward softer environments. BioRxiv 2020.10.27.357178.

Joaquin, D., Grigola, M., Kwon, G., Blasius, C., Han, Y., Perlitz, D., Jiang, J., Ziegler, Y., Nardulli, A., and Hsia, K. J. (2016). Cell migration and organization in three-dimensional in vitro culture driven by stiffness gradient. Biotechnology and Bioengineering 113, 2496-2506.

Kim, M.-C., Silberberg, Y. R., Abeyaratne, R., Kamm, R. D., and Asada, H. H. (2018). Computational modeling of three-dimensional ECM-rigidity sensing to guide directed cell migration. PNAS 201717230.

Koenderink, G. H., Dogic, Z., Nakamura, F., Bendix, P. M., MacKintosh, F. C., Hartwig, J. H., Stossel, T. P., and Weitz, D. A. (2009). An active biopolymer network controlled by molecular motors. Proc. Natl. Acad. Sci. U.S.A. 106, 15192-15197.

Kong, F., Garcia, A. J., Mould, A. P., Humphries, M. J., and Zhu, C. (2009). Demonstration of catch bonds between an integrin and its ligand. J Cell Biol 185, 1275-1284.

L. Krupski, T., Gundersen, C., Carson, W. C., Moskaluk, C., Harper, J., and Gerling, G. J. (2010). Assessing mechanical properties of benign and malignant prostate tissue. JCO 28, e15109-e15109.

Lachowski, D., Cortes, E., Pink, D., Chronopoulos, A., Karim, S. A., P. Morton, J., and del Rio Hernindez, A. E. (2017). Substrate Rigidity Controls Activation and Durotaxis in Pancreatic Stellate Cells. Scientific Reports 7, 1-12.

Lara Rodriguez, L., and Schneider, I. C. (2013). Directed cell migration in multi-cue environments. Integr Biol (Camb) 5, 1306-1323.

Legate, K. R., Montanez, E., Kudlacek, O., and Fassler, R. (2006). ILK, PINCH and parvin: the tIPP of integrin signalling. Nat. Rev. Mol. Cell Biol. 7, 20-31.

Lo, C. M., Wang, H. B., Dembo, M., and Wang, Y. L. (2000). Cell movement is guided by the rigidity of the substrate. Biophys J 79, 144-152.

Lo Sardo, V., Chubukov, P., Ferguson, W., Kumar, A., Teng, E. L., Duran, M., Zhang, L., Cost, G., Engler, A. J., Urnov, F., et al. (2018). Unveiling the Role of the Most Impactful Cardiovascular Risk Locus through Haplotype Editing. Cell 175, 1796-1810.e20.

Mak, M., Kim, T., Zaman, M. H., and Kamm, R. D. (2015). Multiscale mechanobiology: computational models for integrating molecules to multicellular systems. Integr Biol (Camb) 7, 1093-1108.

Mak, M., Anderson, S., McDonough, M. C., Spill, F., Kim, J. E., Boussommier-Calleja, A., Zaman, M. H., and Kamm, R. D. (2017). Integrated Analysis of Intracellular Dynamics of MenaINV Cancer Cells in a 3D Matrix. Biophysical Journal 112, 1874-1884.

Malandrino, A., Trepat, X., Kamm, R. D., and Mak, M. (2019). Dynamic filopodial forces induce accumulation, damage, and plastic remodeling of 3D extracellular matrices. PLOS Computational Biology 15, e1006684.

McKenzie, A. J., Hicks, S. R., Svec, K. V., Naughton, H., Edmunds, Z. L., and Howe, A. K. (2018). The mechanical microenvironment regulates ovarian cancer cell morphology, migration, and spheroid disaggregation. Scientific Reports 8, 1-20.

Miller, J. P., Borde, B. H., Bordeleau, F., Zanotelli, M. R., LaValley, D. J., Parker, D. J., Bonassar, L. J., Pannullo, S. C., and Reinhart-King, C. A. (2018). Clinical doses of radiation reduce collagen matrix stiffness. APL Bioengineering.

Molloy, J. E., Burns, J. E., Kendrick-Jones, J., Tregear, R. T., and White, D. C. S. (1995). Movement and force produced by a single myosin head. Nature 378, 209-212.

Morikis, V. A., Chase, S., Wun, T., Chaikof, E. L., Magnani, J. L., and Simon, S. I. (2017). Selectin catch-bonds mechanotransduce integrin activation and neutrophil arrest on inflamed endothelium under shear flow. Blood 130, 2101-2110.

Munster, S., Jawerth, L. M., Leslie, B. A., Weitz, J. I., Fabry, B., and Weitz, D. A. (2013). Strain history dependence of the nonlinear stress response of fibrin and collagen networks. Proc Natl Acad Sci USA 110, 12197-12202.

Novikova, E. A., Raab, M., Discher, D. E., and Storm, C. (2017). Persistence-driven durotaxis: Generic, directed motility in rigidity gradients. Phys Rev Lett 118, 078103.

Pankova, D., Jiang, Y., Chatzifrangkeskou, M., Vendrell, I., Buzzelli, J., Ryan, A., Brown, C., and O'Neill, E. (2019). RASSF1A controls tissue stiffness and cancer stem-like cells in lung adenocarcinoma. EMBO J 38.

Paszek, M. J., Zahir, N., Johnson, K. R., Lakins, J. N., Rozenberg, G. I., Gefen, A., Reinhart-King, C. A., Margulies, S. S., Dembo, M., Boettiger, D., et al. (2005). Tensional homeostasis and the malignant 770 phenotype. Cancer Cell 8, 241-254.

Pollard, T. D. (1986). Rate constants for the reactions of ATP- and ADP-actin with the ends of actin filaments. J Cell Biol 103, 2747-2754.

Pompe, T., Kaufmann, M., Kasimir, M., Johne, S., Glorius, S., Renner, L., Bobeth, M., Pompe, W., and Werner, C. (2011). Friction-Controlled Traction Force in Cell Adhesion. Biophys J 101, 1863-1870.

Prahl, L. S., Stanslaski, M. R., Vargas, P., Piel, M., and Odde, D. J. (2020). Predicting Confined 1D Cell Migration from Parameters Calibrated to a 2D Motor-Clutch Model. Biophysical Journal 118, 1709-1720.

Rio, A. del, Perez-Jimenez, R., Liu, R., Roca-Cusachs, P., Fernandez, J. M., and Sheetz, M. P. (2009). Stretching Single Talin Rod Molecules Activates Vinculin Binding. Science 323, 638-641.

Sawada, Y., Tamada, M., Dubin-Thaler, B. J., Cherniavskaya, O., Sakai, R., Tanaka, S., and Sheetz, M. P. (2006). Force Sensing by Extension of the Src Family Kinase Substrate, p130Cas. Cell 127, 1015-1026.

Schaller, M. D. (2001). Paxillin: a focal adhesion-associated adaptor protein. Oncogene 20, 6459-6472.

Schliter, D. K., Ramis-Conde, I., and Chaplain, M. A. J. (2012). Computational Modeling of Single-Cell Migration: The Leading Role of Extracellular Matrix Fibers. Biophys J 103, 1141-1151.

Schwarz, U. S., Erdmann, T., and Bischofs, I. B. (2006). Focal adhesions as mechanosensors: The two-spring model. Biosystems 83, 225-232.

Shatkin, G., Yeoman, B., Birmingham, K., Katira, P., and Engler, A. J. (2020). Computational models of migration modes improve our understanding of metastasis. APL Bioengineering 4, 041505.

Singh, S. P., Schwartz, M. P., Lee, J. Y., Fairbanks, B. D., and Anseth, K. S. (2014). A peptide functionalized poly (ethylene glycol) (PEG) hydrogel for investigating the influence of biochemical and biophysical matrix properties on tumor cell migration. Biomater Sci 2, 1024-1034.

Stefanoni, F., Ventre, M., Mollica, F., and Netti, P. A. (2011). A numerical model for durotaxis. Journal of Theoretical Biology 280, 150-158.

Sunyer, R., Conte, V., Escribano, J., Elosegui-Artola, A., Labernadie, A., Valon, L., Navajas, D., Garcia-Aznar, J. M., Munoz, J. J., Roca-Cusachs, P., et al. (2016). Collective cell durotaxis emerges from long-range intercellular force transmission. Science 353, 1157-1161.

Tan, S. J., Chang, A. C., Anderson, S. M., Miller, C. M., Prahl, L. S., Odde, D. J., and Dunn, A. R. (2020). Regulation and dynamics of force transmission at individual cell-matrix adhesion bonds. Science Advances 6, eaax0317.

Tapia-Rojo, R., Alonso-Caballero, A., and Fernandez, J. M. (2020). Direct observation of a coil-to-helix contraction triggered by vinculin binding to talin. Science Advances 6, eaaz4707.

Vavylonis, D., Yang, Q., and O'Shaughnessy, B. (2005). Actin polymerization kinetics, cap structure, and fluctuations. PNAS 102, 8543-8548.

Vicente-Manzanares, M., Choi, C. K., and Horwitz, A. R. (2009). Integrins in cell migration—the actin connection. J Cell Sci 122, 199-206.

White, E. S. (2015). Lung Extracellular Matrix and Fibroblast Function. Ann Am Thorac Soc 12, S30-S33.

Wu, C. (2005). PINCH, N(i)ck and the ILK: network wiring at cell-matrix adhesions. Trends Cell Biol. 15, 460-466.

Wu, C., and Dedhar, S. (2001). Integrin-linked kinase (ILK) and its interactors. J Cell Biol 155, 505-510.

Yeoman, B. M., and Katira, P. (2018). A stochastic algorithm for accurately predicting path persistence of cells migrating in 3D matrix environments. PLOS ONE 13, e0207216.

Zhai, L., Madden, J., Foo, W.-C., Mouraviev, V., Polascik, T. J., Palmeri, M. L., and Nightingale, K. R. (2010). Characterizing the stiffness of Human Prostates using Acoustic Radiation Force. Ultrason Imaging 32, 201-213.

Zhu, C., and Chen, W. (2013). Catch Bonds of Integrin/Ligand Interactions. In Single-Molecule Studies of Proteins, A. F. Oberhauser, ed. (New York, NY: Springer), pp. 77-96.

Although the disclosure has been described with reference to the above example, it will be understood that modifications and variations are encompassed within the spirit and scope of the disclosure. Accordingly, the invention is limited only by the following claims.

What is claimed is:

1. A method of assessing adhesion strength and metastatic potential of a heterogeneous population of cancer cells, the method comprising:
   (a) culturing the heterogeneous population of cancer cells on a solid substrate coated with an extracellular matrix (ECM) protein;
   (b) sealingly attaching the solid substrate to a housing to form a flow channel over the population of cancer cells such that the housing is in fluid communication with a fluid inlet and fluid outlet;
   (c) flowing a shear buffer through the flow channel such that a subpopulation of cells of the heterogeneous population of cancer cells having a first adhesion strength are dislodged from the ECM by the shear buffer;
   (d) collecting the shear buffer containing the subpopulation of cells with a collection chamber in fluid communication with the fluid outlet after flowing through the flow channel; and
   (e) counting the subpopulation of cells within the collected buffer of (d).

2. The method of claim 1, wherein the number of the subpopulation of cells within the collected buffer correlates to the adhesion strength of the cancer cell population.

3. The method of claim 1, further comprising: (f) counting the number of cells cultured on the solid substrate in step (a) or after step (c), and determining the percentage of cell number in the collected buffer over the total number of cells initially cultured on the solid substrate, or determining the ratio of the number of the subpopulation of cells in the collected buffer versus the number of cells on the solid substrate after the step of (c), wherein the percentage or ration of cells correlates to adhesion strength of the cancer cell population.

4. The method of claim 1, wherein the heterogenous cancer cell population is isolated from a tumor biopsy of a subject.

5. The method of claim 4, wherein the tumor biopsy is from a primary tumor.

6. The method of claim 1, wherein the heterogenous cancer cell population comprises a population from the group of: breast cancer cells, prostate cancer cells, or lung cancer cells.

7. The method of claim 1, further comprising determining the gene expression of one or more genes associated with metastasis in the subpopulation of cells.

8. The method of claim 7, the one or more genes are selected from Neuroblast Differentiation-Associated Protein AHNAK (AHNAK), A-Kinase Anchoring Protein 13 (AKAP13), A-Kinase Anchoring Protein 9 (AKAP9), ALMS1 Centrosome And Basal Body Associated Protein (ALMS1), APC Regulator Of WNT Signaling Pathway (APC), Assembly Factor For Spindle Microtubules (ASPM), ATM Serine/Threonine Kinase (ATM), Baculoviral IAP Repeat Containing 6 (BIRC6), Bcl2 Modifying Factor (BMF), BRCA2 DNA Repair Associated (BRCA2), BUB1 Mitotic Checkpoint Serine/Threonine Kinase B (BUB1B), Coiled-Coil Domain Containing 88A (CCDC88A), Cyclin A1 (CCNA1), Cyclin B1 (CCNB1), Cyclin B2 (CCNB2), Cyclin F (CCNF), Cell Division Cycle 25B (CDC25B), CDC42 Binding Protein Kinase Alpha (CDC42BPA), CDC42 Effector Protein 2 (CDC42EP2), Cell Division Cycle 45 (CDC45), Cell Division Cycle 6 (CDC6), Centromere Protein E (CENPE), Centromere Protein F (CENPF), Centromere Protein J (CENPJ), Centrosomal Protein 192 (CEP192), Centrosomal Protein 350 (CEP350), Centrosomal Protein 97 (CEP97), Cytoskeleton Associated Protein 2 (CKAP2), Cytoskeleton Associated Protein 5 (CKAP5), Centriolin (CNTRL), DNA Cross-Link Repair 1B (DCLRE1B), Desmoplakin (DSP), Dystonin (DST), Denticleless E3 Ubiquitin Protein Ligase Homolog (DTL), Dynein Cytoplasmic 1 Heavy Chain 1 (DYNC1H1), Dynein Cytoplasmic 2 Heavy Chain 1 (DYNC2H1), E2F Transcription Factor 1 (E2F1), Extra Spindle Pole Bodies Like 1, Separase (ESPL1), Filaggrin (FLG), FERM Domain Containing 6 (FRMD6), Growth Arrest Specific 2 Like 3 (GAS2L3), GTP Binding Protein Overexpressed In Skeletal Muscle (GEM), GEN1 Holliday Junction 5' Flap Endonuclease (GEN1), G Protein Signaling Modulator 2 (GPSM2), G2 And S-Phase Expressed 1 (GTSE1), Histone Deacetylase 4 (HDAC4), HECT And RLD Domain Containing E3 Ubiquitin Protein Ligase 2 (HERC2), Hyaluronan Mediated Motility Receptor (HMMR), Huntingtin (HTT), Protein TALPID3 (KIAA0586), Kinesin Family Member 11 (KIF11), Kinesin Family Member 14 (KIF14), Kinesin Family Member 18A (KIF18A), Kinesin Family Member 18B (KIF18B), Kinesin Family Member 20A (KIF20A), Kinesin Family Member 20B (KIF20B), Kinesin Family Member 4A (KIF4A), Kinetochore Localized Astrin (SPAG5) Binding Protein (KNSTRN), Keratin 17 (KRT17), Keratin 81 (KRT81), Microtubule Actin Crosslinking Factor 1 (MACF1), Microtubule Associated Protein 1B (MAP1B), Minichromosome Maintenance Complex Component 2 (MCM2), Minichromosome Maintenance Complex Component 3 (MCM3), Midasin AAA ATPase 1 (MDN1), Myosin Heavy Chain 15 (MYH15), Myosin VA (MYOSA), Myosin IXA (MYO9A), Neuron Navigator 1 (NAV1), NudE Neurodevelopment Protein 1 (NDE1), NIMA Related Kinase 2 (NEK2), Pro-Apoptotic WT1 Regulator (PAWR), Proliferating Cell Nuclear Antigen (PCNA), Pericentrin (PCNT), Phosphodiesterase 4D Interacting Protein (PDE4DIP), Pseudopodium Enriched Atypical Kinase 1 (PEAK1), Pleckstrin Homology, MyTH4 And FERM Domain Containing H2 (PLEKHH2), Polo Like Kinase 2 (PLK2), Proline And Serine Rich Coiled-Coil 1 (PSRC1), Protein Tyrosine Phosphatase Non-Receptor Type 14 (PTPN14), RAN Binding Protein 2 (RANBP2), RB Binding Protein 6, Ubiquitin Ligase (RBBP6), RCSD Domain Containing 1 (RCSD1), Receptor Accessory Protein 4 (REEP4), Replication Timing Regulatory Factor 1 (RIF1), Serum Amyloid A1 (SAA1), Sodium Channel And Clathrin Linker 1 (SCLT1), SET Domain Containing 2, Histone Lysine Methyltransferase (SETD2), SH3 And PX Domains 2A (SH3PXD2A), Solute Carrier Family 7 Member 11 (SLC7A11), Sperm Associated Antigen 5 (SPAG5), Spectrin Beta, Non-Erythrocytic 1 (SPTBN1), Spectrin Repeat Containing Nuclear Envelope Protein 1 (SYNE1), Spectrin Repeat Containing Nuclear Envelope Protein 2 (SYNE2), Transforming Acidic Coiled-Coil Containing Protein 3 (TACC3), DNA Topoisomerase II Alpha (TOP2A), Tripartite Motif Containing 59 (TRIM59), TTK Protein Kinase (TTK), Ubiquitin Protein Ligase E3 Component N-Recognin 4 (UBR4), or Utrophin (UTRN).

9. The method of claim 7, wherein the one or more genes are selected from GAS2L3, SYNE2, AKAP9, KIF14, DYNC1H1, or MYO9A.

\* \* \* \* \*

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agcctgcaat tcaagtatgg tt                                              22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tggtccgtgt ctgggagtc                                                  19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatcttacag ctctgccagt gtgt                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtagcttct ttggcatcat tgaa                                            24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggtgaaatg gcctgtacaa gt                                              22

<210> SEQ ID NO 6
<211> LENGTH: 22
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 6
ggcaaccagt taaccctttg ag                                              22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
accaccctat ggaaagctac t                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catctcccat ctgtcgaagg c                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcgacagtca gccgcatctt c                                               21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
accaaatccg ttgactccga c                                               21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aggcttgaac caacctacgg a                                               21

<210> SEQ ID NO 12
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 12
gcctaagcac tggcacaaca g                                              21
```